US012503422B2

(12) United States Patent
Oniciu et al.

(10) Patent No.: US 12,503,422 B2
(45) Date of Patent: Dec. 23, 2025

(54) GEMCABENE, PHARMACEUTICALLY ACCEPTABLE SALTS THEREOF, COMPOSITIONS THEREOF AND METHODS OF USE THEREFOR

(71) Applicant: NeuroBo Pharmaceuticals, Inc., Boston, MA (US)

(72) Inventors: Daniela Carmen Oniciu, Gainesville, FL (US); Charles Larry Bisgaier, Ann Arbor, MI (US); José Rui Gomes, Basel (CH); Stefan Heckhoff, Loerrach (DE)

(73) Assignee: NeuroBo Pharmaceuticals, Inc., Boston, MA (US)

( * ) Notice: Subject to any disclaimer, the term of this patent is extended or adjusted under 35 U.S.C. 154(b) by 926 days.

(21) Appl. No.: 17/583,081

(22) Filed: Jan. 24, 2022

(65) Prior Publication Data

US 2022/0332672 A1 Oct. 20, 2022

Related U.S. Application Data

(63) Continuation of application No. 16/402,853, filed on May 3, 2019, now abandoned, which is a continuation (Continued)

(51) Int. Cl.

*C07C 51/43* (2006.01)
*A61K 9/20* (2006.01)

(Continued)

(52) U.S. Cl.

CPC ............ *C07C 62/08* (2013.01); *A61K 9/2018* (2013.01); *A61K 9/2054* (2013.01);

(Continued)

(58) Field of Classification Search

CPC ......... C07C 62/08; C07C 51/43; C07C 51/47; C07C 59/305; A61K 9/2018;

(Continued)

(56) References Cited

U.S. PATENT DOCUMENTS 2,033,909 A 3/1936 Cox et al.
4,691,034 A 9/1987 Sanderson et al.

(Continued)

FOREIGN PATENT DOCUMENTS

CA 1197242 11/1985
CN 1182415 A 5/1998

(Continued)

OTHER PUBLICATIONS

Office Action for U.S. Appl. No. 14/942,765, mailed Sep. 21, 2017, 41 pages.

(Continued)

*Primary Examiner* — Matthew P Coughlin
*Assistant Examiner* — Ashli Ariana Chicks
(74) *Attorney, Agent, or Firm* — Sterne, Kessler, Goldstein & Fox P.L.L.C.

(57) ABSTRACT

This present invention provides gemcabene pharmaceutically acceptable salts having a PSD90 of 35 μm to about 90 μm, methods for purifying crude gemcabene, pharmaceutically acceptable salts of purified gemcabene, pharmaceutical compositions of a gemcabene pharmaceutically acceptable salt and therapeutic and prophylactic methods useful for various conditions, including dyslipidemia.

8 Claims, 59 Drawing Sheets

Specification includes a Sequence Listing.

Related U.S. Application Data of application No. 15/956,172, filed on Apr. 18, 2018, now abandoned.

(60) Provisional application No. 62/584,576, filed on Nov. 10, 2017, provisional application No. 62/569,358, filed on Oct. 6, 2017, provisional application No. 62/486,728, filed on Apr. 18, 2017, provisional application No. 62/486,822, filed on Apr. 18, 2017.

(51) Int. Cl.

| | |
|---|---|
| ***A61K 31/194*** | (2006.01) |
| ***C07C 51/47*** | (2006.01) |
| ***C07C 59/305*** | (2006.01) |
| ***C07C 62/08*** | (2006.01) |

(52) U.S. Cl.
CPC ............ *A61K 31/194* (2013.01); *C07C 51/43* (2013.01); *C07C 51/47* (2013.01); *C07C 59/305* (2013.01)

(58) Field of Classification Search
CPC ....... A61K 9/2054; A61K 31/194; A61P 3/06; A61P 1/16; A61P 1/18; A61P 3/00; A61P 9/00; A61P 11/00; A61P 19/00; A61P 29/00
See application file for complete search history.

(56) References Cited

U.S. PATENT DOCUMENTS

| | | | |
|---|---|---|---|
| 5,133,974 | A | 7/1992 | Paradissis et al. |
| 5,166,174 | A | 11/1992 | Ueno et al. |
| 5,648,387 | A | 7/1997 | Bisgaier et al. |
| 6,410,802 | B1 | 6/2002 | Dasseux et al. |
| 6,500,457 | B1 | 12/2002 | Midha et al. |
| 6,861,555 | B2 | 3/2005 | Ando et al. |
| 6,909,014 | B2 | 6/2005 | Dasseux et al. |
| 7,510,729 | B2 | 3/2009 | Kolter et al. |
| 7,777,071 | B2 | 8/2010 | Goel |
| 8,563,761 | B2 | 10/2013 | Armand et al. |
| 9,486,446 | B2 | 11/2016 | KurasaWa et al. |
| 9,849,104 | B2 | 12/2017 | Bisgaier et al. |
| 10,227,285 | B2 | 3/2019 | Oniciu et al. |
| 2003/0119912 | A1 | 6/2003 | Ando et al. |
| 2004/0137054 | A1 | 7/2004 | Hager et al. |
| 2004/0142035 | A1 | 7/2004 | Chang et al. |
| 2004/0167229 | A1 | 8/2004 | Bakker-Arkema et al. |
| 2004/0192771 | A1 | 9/2004 | Dasseux et al. |
| 2005/0004196 | A1 | 1/2005 | Kowala |
| 2005/0101572 | A1 | 5/2005 | Goel |
| 2007/0116758 | A1 | 5/2007 | Dafna et al. |
| 2008/0069873 | A1 | 3/2008 | Pearnchob et al. |
| 2008/0241240 | A1 | 10/2008 | Kim et al. |
| 2009/0036414 | A1 | 2/2009 | Du et al. |
| 2009/0208539 | A1 | 8/2009 | Penhasi et al. |
| 2009/0220611 | A1 | 9/2009 | Dargelas et al. |
| 2009/0220613 | A1 | 9/2009 | Odidi et al. |
| 2009/0226515 | A1 | 9/2009 | Schmitt et al. |
| 2010/0015220 | A1 | 1/2010 | Wetterau et al. |
| 2010/0196569 | A1 | 8/2010 | Scanlin et al. |
| 2010/0247639 | A1 | 9/2010 | Ravishankar et al. |
| 2011/0171112 | A1 | 7/2011 | Arrmand et al. |
| 2012/0164221 | A1 | 6/2012 | Bova et al. |
| 2012/0165411 | A1 | 6/2012 | Bisgaier |
| 2013/0109699 | A1 | 5/2013 | Ohata et al. |
| 2013/0123354 | A1 | 5/2013 | Currie et al. |
| 2013/0273157 | A1 | 10/2013 | Ishii et al. |
| 2014/0154313 | A1 | 6/2014 | Counts et al. |
| 2014/0371314 | A1 | 12/2014 | Bar-Tana |
| 2015/0005386 | A1 | 1/2015 | Bisgaier |
| 2015/0094303 | A1 | 4/2015 | Bachovchin et al. |
| 2015/0283202 | A1 | 10/2015 | Shailubhai |
| 2016/0137584 | A1 | 5/2016 | Oniciu et al. |
| 2017/0158601 | A9 | 6/2017 | Oniciu et al. |
| 2018/0194713 | A1 | 7/2018 | Oniciu et al. |
| 2018/0297929 | A1 | 10/2018 | Oniciu et al. |
| 2018/0325825 | A1 | 11/2018 | Oniciu et al. |
| 2019/0008779 | A1 | 1/2019 | Oniciu et al. |

FOREIGN PATENT DOCUMENTS

| | | | | |
|---|---|---|---|---|
| CN | 104127391 A | 11/2014 | | |
| CN | 105434391 A | 3/2016 | | |
| EA | 015519 B1 | 8/2011 | | |
| EP | 2604256 A1 | 6/2013 | | |
| JP | 2003-520835 | 7/2003 | | |
| JP | 2006-501238 | 1/2006 | | |
| JP | 2007-500690 | 1/2007 | | |
| JP | 2015-503588 | 2/2015 | | |
| RU | 2008118974 | 12/2009 | | |
| RU | 2404767 C1 | 11/2010 | | |
| RU | 2491070 C2 | 8/2013 | | |
| SU | 324740 A3 | 12/1971 | | |
| WO | WO 1996/030328 | 10/1996 | | |
| WO | WO-9630328 A1 | * | 10/1996 | ................ A61P 3/06 |
| WO | WO 2000/059855 | 10/2000 | | |
| WO | WO 2001/055078 | 8/2001 | | |
| WO | WO 2002/030922 | 4/2002 | | |
| WO | WO 2003/004470 | 1/2003 | | |
| WO | WO 2003/088962 | 10/2003 | | |
| WO | WO 2004/017952 | 3/2004 | | |
| WO | WO 2004/045596 | 6/2004 | | |
| WO | WO 2005/009431 | 2/2005 | | |
| WO | WO 2007 /058664 | 5/2007 | | |
| WO | WO 2008/018877 | 2/2008 | | |
| WO | WO 2008/106901 | 9/2008 | | |
| WO | WO 2009/024889 | 2/2009 | | |
| WO | WO 2009/135949 | 11/2009 | | |
| WO | WO 2009/140341 | 11/2009 | | |
| WO | WO 2012/002919 | 1/2012 | | |
| WO | WO 2012/117071 | 9/2012 | | |
| WO | WO 2013/084237 | 6/2013 | | |
| WO | WO 2016/077832 | 5/2016 | | |
| WO | WO 2017/079755 | 5/2017 | | |
| WO | WO 2018/195163 | 10/2018 | | |

OTHER PUBLICATIONS

Office Action for U.S. Appl. No. 14/942,765, mailed Feb. 8, 2018, 39 pages.
Office Action for U.S. Appl. No. 14/942,765, mailed May 2, 2017, 36 pages.
Office Action for U.S. Appl. No. 14/942,765, mailed Sep. 20, 2016, 30 pages.
Office Action for U.S. Appl. No. 14/942,765, mailed Sep. 4, 2018, 30 pages.
International Search Report and Written Opinion for International Application No. PCT/US2015/060917, mailed May 13, 2016, 13 pages.
International Search Report and Written Opinion for International Application No. PCT/US2016/060849, mailed Mar. 13, 2017, 21 pages.
International Preliminary Report on Patentability for International Application No. PCT/US2016/060849, dated May 8, 2018, 17 pages.
International Search Report and Written Opinion for International Application No. PCT/US2018/028113, mailed Jun. 21, 2018, 9 pages.
Office Action for U.S. Appl. No. 15/977,226, mailed Dec. 14, 2018, 35 pages.
International Search Report and Written Opinion for International Application No. PCT/US2018/032351, mailed Aug. 8, 2018, 9 pages.
6.2 Direct Alkylation of Simple Enolates (Online), Retrieved from the Internet: <URL:http://chem.yonsei.ac.kr/chem/upload/CHE6402-01/119665643430625.pdf>, Aug. 2010, 9 pages.
Amer, A, “What is a simple way to convert an ester into carboxylic acid?” (Online), Feb. 19, 2014, Retrieved from the Internet: Apr. 17, 2017, 1 page.

(56) References Cited

OTHER PUBLICATIONS

Ballantyne, C. M. et al., "Effect of Ezetimibe Coadministered With Atorvastatin in 628 Patients WithPrimary Hypercholesterolemia. A Prospective, Randomized, Double-Blind Trial." Circulation, 2003;107:2409-2415.
Bhasin, R. K. et al., "Design & Development of Atorvastatin Orally Disintegrating Tablets & Their Evaluationby Electronic Tongue," Drug Development & Delivery [Online], Retrieved from the Internet: <URL:http://www.drug-dev.com/Main/Back-Issues/Design-Development-of-Atorvastatin-Orally-Disinteg-446.aspx>,Apr. 2012.
Billecke, S. et al., "Human serum paraoxonase (PON1) isozymes Q and R hydrolyze lactones and cycliccarbonate esters," Drug Metabolism and Disposition, vol. 28, No. 11, pp. 1335-1342 (2000).
Bisgaier, C. L. et al., "A novel compound that elevates high density lipoprotein and activates theperoxisome proliferator activated receptor," Journal of Lipid Research, 39:17-30 ( 1998).
Blonk, M. et al., "Pharmacokinetic Drug-Drug Interaction Study Between Raltegravir and Atorvastatin 20 mgin Healthy Volunteers," J Acquir Immune Defic Syndr 2015;69:44-51.
Boyd, R. A. et al., "Atorvastatin coadministration may increase digoxin concentrations by inhibition ofintestinal P-glycoprotein-mediated secretion," Journal of Clinical Pharmacology, 2000; 40:91-98.
Castaneda, P. S. et al., "Design and evaluation of a transdermal patch with atorvastatin," Farmacia,2017, vol. 65, No. 6, pp. 908-916.
Chemguide, Hydrolysing Esters (Online), (2004), Retrieved from the Internet: <http://www.chemguide.co.uk/organicprops/esters/hydrolysis.html>, Retrieved from the Internet on: Aug. 25, 2016, 4 pages.
Bisgaier, C. L. et al., "125: 328104r Preparation of terminal carboxy or tetrazole group-containing dialkylethers as anticholesteremics and antidiabetics," Chemical Abstracts, 23-Aliphatic Compounds 328108, vol. 125, No. 25, p. 1337 (1996).
Clayden, "Alkylation of Enolates," Chapter 26, pp. 663-688 (2008).
Clayden, "Nucleophilic Substitution at Saturated Carbon," Chapter 15, p. 348 (2012).
Clayden et al., Organic Chemistry, Chapter 25: Alkylation of Enolates, pp. 588-589 (2012).
Di Stasi, S. L. et al., "Effects of Statins on Skeletal Muscle: A Perspective for Physical Therapists," PhysTher. Oct. 2010; 90(10): 1530-1542.
Dressman, J. B., "Comparison of canine and human gastrointestinal physiology," Pharmaceutical Research, vol. 3, No. 3, 1986, pp. 123-131.
Fallingborg, J. et al., "pH-Profile and regional transit times of the normal gut measured by aradiotelemetry device," Aliment Pharmacol Ther., Dec. 1989, 3(6)605-613.
Gite, S. et al., "Development and Validation of a Discriminating Dissolution Method for Atorvastatin Delayed-Release Nanoparticles Using a Flow-Through Cell: A Comparative Study Using USP Apparatus 4 and 1,"Dissolution Technologies, 23(2):14-20; May 2016.
Gleiter, R. et al. "Synthesis of 5,5, 10, 10-Tetramethyl-1-oxacyclotridecane-6,7,8,9-tetrone—on theMechanism of the Rubottom Reaction," Liebigs Annalen, vol. 1995, Issue 9, Aug. 1995, pp. 1655-1661.
Gomez-Bombarelli, R., et al. "Mechanisms of Lactone Hydrolysis in Acidic Conditions," The Journal ofOrganic Chemistry, 2013, vol. 78, pp. 6880-6889.
Gomez-Bombarelli, R., et al. "Mechanisms of Lactone Hydrolysis in Neutral and Alkaline Conditions," TheJournal of Organic Chemistry, 2013, vol. 78, pp. 6868-6879.
Hajir, M. et al., "Stable amorphous calcium oxalate: synthesis and potential intermediate inbiomineralization," Chem. Commun. 2014, 50:6534-6536.
Hayashi, K. et al., "Studies on angiotensin converting enzyme inhibitors. II. Syntheses and angiotensinconverting enzyme inhibitory activities of carboxyethylcarbamoyl-1,2,3,4-tetrahydroisoquinoline-3-carboxylicacid derivatives," Chemical and Pharmaceutical Bulletin, vol. 31, No. 10, pp. 3553-3561 (1983).
Hermann, M. et al., "Exposure of atorvastatin is unchanged but lactone and acid metabolites are increasedseveral-fold in patients with atorvastatin-induced myopathy," Clin. Pharmacol. Ther. 2006;79(6):532-539.
Ireland, R. E. et al., "132. Diels-Alder Approach to Highly Functionalized Tertiary a-Hydroxy Ketones: ANovel Route to the Hexahydrobenzofuran Portion of the Avermectins and Milbemycins," Helv. Chim. Acta1986, 69:1273-1286.
Kakurkin, N. P. et al., "Solutions in the Calcium Oxide-Ethylene Glycol-Water System," ISSN 1070-4272, Russian Journal of Applied Chemistry, 2007, vol. 80, No. 5, pp. 722-725, Pleiades Publishing, Ltd., 2007.Original Russian Text, N.P. Kakurkin, A.O. Kirillov, V.V. Shcherbakov, 2007, published in Zhurnal PrikladnoiKhimii, 2007, vol. 80, No. 5, DD. 743-746.
Kantola, T. et al., "Effect of itraconazole on the pharmacokinetics of atorvastatin," Clin. Pharmacol. Ther.,1998, 64:58-65.
Kearney, A. S. et al., "The interconversion kinetics, equilibrium, and solubilities of the lactone andhydroxyacid forms of the HMG-COA reductase inhibitor, Cl-981," Pharmaceutical Research, vol. 10, No. 10,1993, pp. 1461-1465.
Khare, A. R. et al., "Swelling/deswelling of anionic copolymer gels," Biomaterials 16 (1995) 559-567.
Konig, J. et al., "Localization and Genomic Organization of a New HepatocellularOrganic Anion Transporting Polypeptide," The Journal of Biological Chemistry, vol. 275, No. 30, Jul. 28, 2000, pp. 23161-23168.
Kot Ame, R. N. et al., "Formulation and Evaluation of Microspheres of Atorvastatin Calcium by ParticleEngineering Through Spherical Crystalisation," Research Journal of Pharmaceutical, Biological and ChemicalSciences, Jul.-Sep. 2013, vol. 4, Issue 3, pp. 1460-1468.
Kumar, N. et al., "Atorvastatin calcium encapsulated eudragit nanoparticles with enhanced oralbioavailability, safety and efficacy profile," Pharmaceutical Development and Technology, Mar. 2017;22(2): 156-167. doi: 10.3109/10837450.2015.1108983. EpubNov. 11, 2015.
Lennernas, H., "Clinical Pharmacokinetics of Atorvastatin," Clin Pharmacokinet 2003; 42( 13): 1141-1160.
Lew, G., "Effect of Particle Size on Dissolution and Gastrointestinal Absorption Rates of Pharmaceuticals, "American Journal of Pharmacy and the Sciences Supporting Public Health, 135:78-92 (Mar. 1963).
"Making Soap—Saponification," Aug. 29, 2003, 3 pages.
McShane, M. et al., "An Oral, Rising, Multiple-Dose Tolerance, Pharmacokinetic, and PharmacodynamicStudy of Gemcabene in Healthy Volunteers," Gemphire Therapeutics Inc., Poster, ATVB May 2016, Nashville, TN, Abstract No. 482 Presentation No. 427, 1 page.
MIT Department of Chemistry X-Ray Diffraction Facility, "Growing Quality Crystals," (Online), (2004),Retrieved from the Internet: <URL: http://web.mit.edu/x-ray/cystallize.html>, Retrieved on Sep. 1, 2016,5 pages.
Mudie, D. M. et al., "Physiological Parameters for Oral Delivery and In vitro Testing," Mol Pharm. Oct. 4, 2010; 7(5): 1388-1405. doi: 10.1021/mp100149j.
Mueller, R. et al., "Long Hydrocarbon Chain Ether Diols and Ether Diacids That Favorably Alter LipidDisorders in Vivo," J. Med. Chem. 2004, 47(21):5183-5197.
Narayanan, V. S. et al., "Design and evaluation of bi-layer drug delivery system of atorvastatin andglipizide," Int. J. Chem. Sci.: 7(3), 2009, 1802-1816.
Pang, K. S., "Modeling of intestinal drug absorption: roles of transporters and metabolic enzymes (for theGillette review series)," Drug Metabolism and Disposition, vol. 31, No. 12, 2003, pp. 1507-1519.
Pasanen, M. K. et al., "Different Effects of SLCO1 B1 Polymorphism on the Pharmacokinetics of Atorvastatinand Rosuvastatin," Clinical Pharmacology & Therapeutics, vol. 82, No. 6, Dec. 2007, pp. 726-733.
Prueksaritanont, T. et al., "Glucuronidation of Statins in Animals and Humans: A Novel Mechanism ofStatin Lactonization," Drug Metabolism and Disposition May 2002, 30(5):505-512; DOI:https://doi.org/10.1124/dmd.30.5.505.

(56) References Cited

OTHER PUBLICATIONS

Schwindeman, J. A et al., "Safe handling of organolithium compounds in the laboratory," Chemical Healthand Safety, vol. 9, Issue 3, May/Jun. 2002, pp. 6-11.
Shanmukaraj, D. et al., "Boron Esters as Tunable Anion Carriers for Non-Aqueous BatteriesElectrochemistry," J. Am. Chem. Soc. 2010, 132(9):3055-3062.
Sisido, K. et al., "Condensation oft-Butyl Esters with Organic Halides in the Presence of Alkali Amides," J.Am. Chem. Soc., 81(21):5817-5819 (Nov. 1959).
Skottheim, I. B. et al., "Atorvastatin Metabolite Measurements as a Diagnostic Tool for Statin-InducedMyopathy," Mol. Diagn. Ther. 2011:15(4): 221-227.
Srivastava, R. A K et al., "Gemcabene, a first-in-class lipid-lowering agent in late- stage development, down-regulates acute-phase C-reactive protein via C/EBP-o-mediated transcriptional mechanism," Molecularand Cellular Biochemistry, https://doi.org/10.1007/s11010-018-3353-5, published online: Apr. 11, 2018, 17pages.
Taylor, E. P., "30. Synthetic Neuromuscular Blocking Agents. Part II. Bis(quaternary Ammonium Salts)derived from Laudanosine," J. Chem. Soc. (Resumed), 1952, Issue 0, 142-145.
Vitthal, K. V. et al., "Melt extrusion based solid dispersions for enhanced solubility and physical stability ofatorvastatin calcium," International Journal of Biopharmaceutics, 2016; 7(1): 35-47.
Weber, E, "Neutralliganden mit Tensidstruktur—Synthase, Komplexierung, lonentransfer," Liebigs Ann.Chem., D 1983, pp. 770-801.
Wu, X. et al., "Atorvastatin transport in the Caco-2 cell model: contributions of P-glycoprotein and protonmonocarboxylicacid co-transporter," Pharmaceutical Research, Feb. 2000, vol. 17, No. 2, pp. 209-215.
Wuts, P. G. M. et al., Chapter 5. Protection for the Carboxyl Group, In: Greene's Protective Groups inOrganic Synthesis, Fourth Edition, John Wiley & Sons, Inc., Published online Apr. 10, 2006, pp. 582-588.
Yang, J. et al., "Kilogram-Scale Synthesis of bis(6-Hydroxy-5,5-Dimethylhexyl)ether (ESP24232), a NovelLipid Lowering Agent," Organic Preparations and Procedures International, The New Journal for OrganicSynthesis, vol. 36(6): 587-596 (2004); Received Aug. 26, 2004, Accepted Nov. 10, 2004, Published online: Feb. 11, 2009.
Zhang, T., "Physiologically based pharmacokinetic modeling of disposition and drug-drug interactions foratorvastatin and its metabolites," European Journal of Pharmaceutical Sciences 77 (2015) 216-229.
Dalko, P. I. et al., "Stereoselective Synthesis of Quaternary Benzylic Carbons Using C2 Symmetriclmidazolines and Tetrahydrofuran as Electrophile," J. Org. Chem., 1998, vol. 63, No. 23, pp. 8107-8117.
The fourth series of Experimental Chemistry 22, Organic Synthesis IV, Acid, Amino Acid, and Peptide, 1994, 2nd issue, pp. 6-11.
Assmus, M. et al., "Accurate GI targeting with EUDRAGIT FS 30 D/L 30 D-55 mixtures," Evonik Industries, [Online], 2008. Retrieved from the Internet: <URL:http://www.pharmapolymers.com/pharmapolymers/MCMSbase/Pages/ProvideResource.aspx?respath=/NR/rdonlyres/32DOD09C-18F5-47 AO-AFFA-0030E84F9C57/O/CRS2008 AccurateGIT argetingwithEUDRAGITFS30DandL30D55mixtures.pdf>, 1 page.
DeBunne, A. et al., "Development and in vitro evaluation of an enteric-coated multiparticulate drug deliverysystem for the administration of piroxicam to dogs," European Journal of Pharmaceutics andBiopharmaceutics, 54(3):343-348 (Nov. 2002).
Dreu, R. et al., "Development of a multiple-unit tablet containing enteric-coated pellets," PharmaceuticalDevelopment and Technology, 16(2):118-126 (Apr. 2011).
Fyles, T. M. et al., "Solid-phase synthesis of a library of linear oligoester ion- channels," Organic &Biomolecular Chemistry, vol. 7, pp. 725-732 (2009).
Oniciu, D. C. et al., "Long hydrocarbon chain diols and diacids with central ether or ketone moieties thatfavorably alter lipid disorders," Pharmazie, 61(2):157-165 (2006).
Watson, T. G. et al., "Long-Acting Contraceptive Agents: Esters of Norethisterone with a- and/or ~-ChainBranching," Steroids, vol. 41, No. 3 (Mar. 1983) pp. 255-266.
Zhang, Y. et al., "The preparation of carbon-14 and tritium radiolabeled PD-72953," Journal of LabelledCompounds and Radiopharmaceuticals, vol. 50, Issue 5-6 (2007) pp. 602-604.
Gemcabene, PubChem CID: 157692, Aug. 2005, 1 page.
Extended European Search report for European Application No. 18788278.2, mailed Sep. 17, 2020, 10 pages.
Stein, E. et al., "Efficacy and safety of gemcabene as add-on to stable statin therapy in hypercholesterolemic patients", Journal of Clinical Lipidology, 2016, 10: 1212-1222.
Brittain H G: "Developing an Appropriate Salt Form for an Active Pharmaceutical Ingredient | American Pharmaceutical Review—The Review of American Pharmaceutical Business & Technology", American Pharmaceutical Review, Jan. 12, 2009, XP055109646.
Bastin R J, et al., "Salt Selection and Optimisation for Pharmaceutical New Chemical Entities", Organic Process Research and Development, Jan. 1, 2000, vol. 4, No. 5, pp. 427-435, XP008154792.

* cited by examiner

*Gemcabene calcium salt hydrate Crystal Form 1 (PSD90 = 52 μm)

*Gemcabene calcium salt hydrate Crystal Form 1 (PSD90 = 52 μm)

| Parameter (mean ± SD) | Vehicle in Normal (n=8) | Vehicle in NASH (n=8) | Gemcabene* 30 mg/kg (n=8) | Gemcabene* 100 mg/kg (n=8) | Gemcabene* 300 mg/kg (n=8) | Telmisartan 10 mg/kg (n=7) |
|---|---|---|---|---|---|---|
| Sirius red-positive area (%) | 0.19 ± 0.03 | 0.84 ± 0.12 | 0.56 ± 0.18 | 0.53 ± 0.18 | 0.59 ± 0.16 | 0.48 ± 0.09 |

*Gemcabene calcium salt hydrate Crystal Form 1 (PSD90 = 52 μm)

GEM = gemcabene calcium salt hydrate Crystal Form 1 (PSD90 = 52 μm); GEM 30 indicates 30 mg/kg of gemcabene calcium salt hydrate Crystal Form 1 (PSD90 = 52 μm)

SEQUENCE LISTING

```
<160> NUMBER OF SEQ ID NOS: 60

<210> SEQ ID NO 1
<211> LENGTH: 19
<212> TYPE: DNA
<213> ORGANISM: Mus sp.

<400> SEQUENCE: 1

ttccaggctt tgggcatca                                        19


<210> SEQ ID NO 2
<211> LENGTH: 24
<212> TYPE: DNA
<213> ORGANISM: Mus sp.

<400> SEQUENCE: 2

atgttcagca tgttcagcag tgtg                                  24
```

<210> SEQ ID NO 3
<211> LENGTH: 19
<212> TYPE: DNA
<213> ORGANISM: Mus sp.

<400> SEQUENCE: 3
tatggcccag accctcaca 19

<210> SEQ ID NO 4
<211> LENGTH: 24
<212> TYPE: DNA
<213> ORGANISM: Mus sp.

<400> SEQUENCE: 4
ggagtagaca aggtacaacc catc 24

<210> SEQ ID NO 5
<211> LENGTH: 19
<212> TYPE: DNA
<213> ORGANISM: Mus sp.

<400> SEQUENCE: 5
gcatccacgt gttggctca 19

<210> SEQ ID NO 6
<211> LENGTH: 23
<212> TYPE: DNA
<213> ORGANISM: Mus sp.

<400> SEQUENCE: 6
ctccagccta ctcattggga tca 23

<210> SEQ ID NO 7
<211> LENGTH: 22
<212> TYPE: DNA
<213> ORGANISM: Mus sp.

<400> SEQUENCE: 7
aagagcatcc gacactgctg ac 22

<210> SEQ ID NO 8
<211> LENGTH: 24
<212> TYPE: DNA
<213> ORGANISM: Mus sp.

<400> SEQUENCE: 8
agcacagcct gaatagccac atac 24

<210> SEQ ID NO 9
<211> LENGTH: 20
<212> TYPE: DNA
<213> ORGANISM: Mus sp.

<400> SEQUENCE: 9
tgagccctgc tcagcaaaga 20

<210> SEQ ID NO 10
<211> LENGTH: 21
<212> TYPE: DNA
<213> ORGANISM: Mus sp.

<400> SEQUENCE: 10
gaggacctga tccgtccaca a 21

<210> SEQ ID NO 11
<211> LENGTH: 24
<212> TYPE: DNA
<213> ORGANISM: Mus sp.

<400> SEQUENCE: 11
gggacagctt agcctctaca ccaa 24

<210> SEQ ID NO 12
<211> LENGTH: 21
<212> TYPE: DNA
<213> ORGANISM: Mus sp.

<400> SEQUENCE: 12
gactggtacg ggccacaaga a 21

<210> SEQ ID NO 13
<211> LENGTH: 22
<212> TYPE: DNA
<213> ORGANISM: Mus sp.

<400> SEQUENCE: 13
gagaccagca gtctttgctc ca 22

<210> SEQ ID NO 14
<211> LENGTH: 22
<212> TYPE: DNA
<213> ORGANISM: Mus sp.

<400> SEQUENCE: 14
ggagctgctc agttcaactc ca 22

<210> SEQ ID NO 15
<211> LENGTH: 19
<212> TYPE: DNA
<213> ORGANISM: Mus sp.

<400> SEQUENCE: 15
accgctgggt tcctgaaag 19

<210> SEQ ID NO 16
<211> LENGTH: 22
<212> TYPE: DNA
<213> ORGANISM: Mus sp.

<400> SEQUENCE: 16
tcaggcacat ccatagacag ca 22

<210> SEQ ID NO 17
<211> LENGTH: 20
<212> TYPE: DNA
<213> ORGANISM: Mus sp.

<400> SEQUENCE: 17
gcaagttcag ctgcctgcaa 20

<210> SEQ ID NO 18
<211> LENGTH: 23
<212> TYPE: DNA
<213> ORGANISM: Mus sp.

<400> SEQUENCE: 18
atgccgtgga tgaactgagg taa 23

<210> SEQ ID NO 19
<211> LENGTH: 22
<212> TYPE: DNA
<213> ORGANISM: Mus sp.

<400> SEQUENCE: 19
accactgctc aggtccactg tc 22

<210> SEQ ID NO 20
<211> LENGTH: 22
<212> TYPE: DNA
<213> ORGANISM: Mus sp.

<400> SEQUENCE: 20
gctgtcacta tcccggagtt ca 22

<210> SEQ ID NO 21
<211> LENGTH: 25
<212> TYPE: DNA
<213> ORGANISM: Mus sp.

<400> SEQUENCE: 21
atgtgggact ttgtgctatc tccag 25

<210> SEQ ID NO 22
<211> LENGTH: 20
<212> TYPE: DNA
<213> ORGANISM: Mus sp.

<400> SEQUENCE: 22
agttcagtgc ccgccagttc 20

<210> SEQ ID NO 23
<211> LENGTH: 22
<212> TYPE: DNA
<213> ORGANISM: Mus sp.

<400> SEQUENCE: 23
tgaccttcat cccagagcct tc 22

<210> SEQ ID NO 24
<211> LENGTH: 20
<212> TYPE: DNA
<213> ORGANISM: Mus sp.

<400> SEQUENCE: 24
ggcatgagcg ggtatccatc 20

<210> SEQ ID NO 25
<211> LENGTH: 22
<212> TYPE: DNA
<213> ORGANISM: Mus sp.

<400> SEQUENCE: 25
ggatgacagg cttgcagcta tg 22

<210> SEQ ID NO 26
<211> LENGTH: 20
<212> TYPE: DNA
<213> ORGANISM: Mus sp.

<400> SEQUENCE: 26
ggaacgtaag tcgccggatg 20

<210> SEQ ID NO 27
<211> LENGTH: 22
<212> TYPE: DNA
<213> ORGANISM: Mus sp.

<400> SEQUENCE: 27
gaagcgggac tctgtcctca ag 22

<210> SEQ ID NO 28
<211> LENGTH: 22
<212> TYPE: DNA
<213> ORGANISM: Mus sp.

<400> SEQUENCE: 28
cagcagctga gccacctgta tc 22

<210> SEQ ID NO 29
<211> LENGTH: 25
<212> TYPE: DNA
<213> ORGANISM: Mus sp.

<400> SEQUENCE: 29
ctaagtagcg tgcaggagtc cgata 25

<210> SEQ ID NO 30
<211> LENGTH: 24
<212> TYPE: DNA
<213> ORGANISM: Mus sp.

<400> SEQUENCE: 30
cagaagccgg tgaacttgtc agta 24

<210> SEQ ID NO 31
<211> LENGTH: 24
<212> TYPE: DNA
<213> ORGANISM: Mus sp.

<400> SEQUENCE: 31
ggtgcttgag gaccataaat gaga 24

<210> SEQ ID NO 32
<211> LENGTH: 22
<212> TYPE: DNA
<213> ORGANISM: Mus sp.

<400> SEQUENCE: 32
gcacgtgcag ttggttaagg ac 22

<210> SEQ ID NO 33
<211> LENGTH: 21
<212> TYPE: DNA
<213> ORGANISM: Mus sp.

<400> SEQUENCE: 33
gtgacctcat tgcctgtgac c 21

<210> SEQ ID NO 34
<211> LENGTH: 24
<212> TYPE: DNA
<213> ORGANISM: Mus sp.

<400> SEQUENCE: 34
ttaagcacca gacttcaccc agac 24

<210> SEQ ID NO 35
<211> LENGTH: 21
<212> TYPE: DNA
<213> ORGANISM: Mus sp.

<400> SEQUENCE: 35
gataacctgg atgccgtcgt g 21

<210> SEQ ID NO 36
<211> LENGTH: 25
<212> TYPE: DNA
<213> ORGANISM: Mus sp.

<400> SEQUENCE: 36
cttcacgctc ttgagacttt ggttc 25

<210> SEQ ID NO 37
<211> LENGTH: 22
<212> TYPE: DNA
<213> ORGANISM: Mus sp.

<400> SEQUENCE: 37
tggacgttat attgggccgt tc 22

<210> SEQ ID NO 38
<211> LENGTH: 23
<212> TYPE: DNA
<213> ORGANISM: Mus sp.

<400> SEQUENCE: 38
gtagggcatg ggtcaccagt aag 23

<210> SEQ ID NO 39
<211> LENGTH: 19
<212> TYPE: DNA
<213> ORGANISM: Mus sp.

<400> SEQUENCE: 39
ttccaggctt tgggcatca 19

<210> SEQ ID NO 40
<211> LENGTH: 24
<212> TYPE: DNA
<213> ORGANISM: Mus sp.

<400> SEQUENCE: 40
atgttcagca tgttcagcag tgtg 24

<210> SEQ ID NO 41
<211> LENGTH: 21
<212> TYPE: DNA
<213> ORGANISM: Mus sp.

<400> SEQUENCE: 41
caacgatgat gcacttgcag a 21

<210> SEQ ID NO 42
<211> LENGTH: 25
<212> TYPE: DNA
<213> ORGANISM: Mus sp.

<400> SEQUENCE: 42
ctccaggtag ctatggtact ccaga 25

<210> SEQ ID NO 43
<211> LENGTH: 22
<212> TYPE: DNA
<213> ORGANISM: Mus sp.

<400> SEQUENCE: 43
tccaggatga ggacatgagc ac 22

<210> SEQ ID NO 44
<211> LENGTH: 23
<212> TYPE: DNA
<213> ORGANISM: Mus sp.

<400> SEQUENCE: 44
gaacgtcaca caccagcagg tta 23

<210> SEQ ID NO 45
<211> LENGTH: 18
<212> TYPE: DNA
<213> ORGANISM: Mus sp.

<400> SEQUENCE: 45
tgcacccaaa ccgaagtc 18

<210> SEQ ID NO 46
<211> LENGTH: 20
<212> TYPE: DNA
<213> ORGANISM: Mus sp.

<400> SEQUENCE: 46
gtcagaagcc agcgttcacc 20

<210> SEQ ID NO 47
<211> LENGTH: 23
<212> TYPE: DNA
<213> ORGANISM: Mus sp.

<400> SEQUENCE: 47
gccaagggtt gacttcaaga aca 23

<210> SEQ ID NO 48
<211> LENGTH: 21
<212> TYPE: DNA
<213> ORGANISM: Mus sp.

<400> SEQUENCE: 48
aggctcctcc tttccaggtc a 21

<210> SEQ ID NO 49
<211> LENGTH: 24
<212> TYPE: DNA
<213> ORGANISM: Mus sp.

<400> SEQUENCE: 49
gcctgtacgg gatcatactg gttc 24

<210> SEQ ID NO 50
<211> LENGTH: 24
<212> TYPE: DNA

<213> ORGANISM: Mus sp.

<400> SEQUENCE: 50
ccagagcgct ggtcatgtag taga 24

<210> SEQ ID NO 51
<211> LENGTH: 25
<212> TYPE: DNA
<213> ORGANISM: Mus sp.

<400> SEQUENCE: 51
agaggctata gctgggagca gaaac 25

<210> SEQ ID NO 52
<211> LENGTH: 21
<212> TYPE: DNA
<213> ORGANISM: Mus sp.

<400> SEQUENCE: 52
gcaagggcta acattccagc a 21

<210> SEQ ID NO 53
<211> LENGTH: 25
<212> TYPE: DNA
<213> ORGANISM: Mus sp.

<400> SEQUENCE: 53
aaagactggt attcaagaac cctca 25

<210> SEQ ID NO 54
<211> LENGTH: 23
<212> TYPE: DNA
<213> ORGANISM: Mus sp.

<400> SEQUENCE: 54
cctctgttat aaacggcaga gca 23

<210> SEQ ID NO 55
<211> LENGTH: 24
<212> TYPE: DNA
<213> ORGANISM: Mus sp.

<400> SEQUENCE: 55
ctctacttgg gaccaagacc atga 24

<210> SEQ ID NO 56
<211> LENGTH: 24
<212> TYPE: DNA
<213> ORGANISM: Mus sp.

<400> SEQUENCE: 56
ccattgagat tggaatggct acag 24

<210> SEQ ID NO 57
<211> LENGTH: 24
<212> TYPE: DNA
<213> ORGANISM: Mus sp.

<400> SEQUENCE: 57
cgggacactg tacggagact acaa 24

<210> SEQ ID NO 58
<211> LENGTH: 21

-continued

```
<212> TYPE: DNA
<213> ORGANISM: Mus sp.

<400> SEQUENCE: 58

gtggccagtg agagcccata a                                               21


<210> SEQ ID NO 59
<211> LENGTH: 24
<212> TYPE: DNA
<213> ORGANISM: Mus sp.

<400> SEQUENCE: 59

tgtgacttcc acatcctgaa acaa                                            24


<210> SEQ ID NO 60
<211> LENGTH: 20
<212> TYPE: DNA
<213> ORGANISM: Mus sp.

<400> SEQUENCE: 60

gcaccgtggg cacaacttac                                                 20
```

GEMCABENE, PHARMACEUTICALLY ACCEPTABLE SALTS THEREOF, COMPOSITIONS THEREOF AND METHODS OF USE THEREFOR

CROSS-REFERENCE TO RELATED APPLICATIONS

This application is a continuation of U.S. application Ser. No. 16/402,853, filed May 3, 2019, which is a continuation of 15/956,172, filed Apr. 18, 2018, which claims the benefit of U.S. Provisional Application No. 62/486,728, filed Apr. 18, 2017, U.S. Provisional Application No. 62/486,822, filed Apr. 18, 2017, U.S. Provisional Application No. 62/569,358, filed Oct. 6, 2017, and U.S. Provisional Application No. 62/584,576, filed Nov. 10, 2017, the disclosure of each of which is incorporated by reference herein in its entirety.

DESCRIPTION OF THE TEXT FILE SUBMITTED ELECTRONICALLY

The content of the electronically submitted sequence listing (Name: 4194_0170008_Sequencelisting_ST25, Size: 9,143 bytes; and Date of Creation:) is incorporated herein by reference in its entirety.

FIELD OF THE INVENTION

This invention provides pharmaceutically acceptable salts of 6-(5-carboxy-5-methyl-hexyloxy)-2,2-dimethyl-hexanoic acid ("gemcabene"), wherein the pharmaceutically acceptable salts have a PSD90 ranging from 35 μm to about 90 μm as measured by laser light diffraction, and compositions comprising (i) an effective amount of a pharmaceutically acceptable salt of gemcabene, wherein the pharmaceutically acceptable salt has a PSD90 ranging from 35 μm to about 90 μm as measured by laser light diffraction, and (ii) a pharmaceutically acceptable carrier or vehicle. This invention further provides methods for purifying crude gemcabene, comprising dissolving the crude gemcabene in in heptane to provide a heptane solution of the crude gemcabene and cooling the heptane solution to a temperature ranging from 10° C. to 15° C. to precipitate gemcabene. The invention further provides pharmaceutically acceptable salts of gemcabene as synthesized or purified by the methods of the invention. The pharmaceutically acceptable salts of gemcabene and compositions thereof are useful for treating or preventing liver disease or an abnormal liver condition, a disorder of lipoprotein or glucose metabolism, a cardiovascular or related vascular disorder, a disease caused by fibrosis (such as liver fibrosis), or a disease associated with inflammation (such as liver inflammation).

BACKGROUND

Elevated levels of low-density lipoprotein cholesterol (LDL-C) and triglycerides are associated with mixed dyslipidemia including type IIb hyperlipidemia. Type IIb is characterized by elevation of apolipoprotein B, very low-density lipoprotein cholesterol (VLDL-C), intermediate density lipoprotein cholesterol (IDL), and small dense low-density lipoprotein (LDL) levels, in addition to elevation in LDL-C and triglyceride levels.

Individuals with mixed dyslipidemia including individuals with type IIb hyperlipidemia have an increased rate of developing a cardiovascular disease and those individual with familial combined hyperlipidemia (FCHL) have a high incidence of premature coronary artery disease. Familial hyperlipidemias can be classified according to the Fredrickson classification, which is based on the pattern of lipoprotein migration in electrophoresis or ultracentrifugation. In addition, type IIb patients have a high risk of developing non-alcoholic fatty liver disease (NAFLD) and non-alcoholic steatosis hepatitis (NASH), which are forms of fatty liver that can develop due to hepatic triglyceride overproduction and accumulation. NAFLD is strongly associated with features of metabolic syndrome, including obesity, insulin resistance, type-2 diabetes mellitus, and dyslipidemia. NASH can cause the liver to swell and become damaged. NASH tends to develop in people who are overweight or obese, or have diabetes, or mixed dyslipidemia, or high cholesterol or high triglycerides or an inflammatory condition. NASH is marked by hepatocyte ballooning and liver inflammation, which can lead to liver damage and progress to scarring and irreversible changes, similar to the damage caused by heavy alcohol use.

NAFLD, NASH or fatty liver can lead to metabolic complications including elevation of liver enzymes, fibrosis, cirrhosis, hepatocellular carcinoma, and liver failure. Liver failure is life-threatening and therefore there is a need to develop therapies to delay development, prevent formation or reverse the condition of a fatty liver, such as in type IIb patients and other patients at risk for, or present with fatty liver disease.

Current treatment options for type IIb hyperlipidemia are limited. While statins are very effective at lowering LDL-C, in general they are not very effective at also lowering triglyceride concentrations. Further, high dose statin therapy is often not well tolerated because it can cause muscle pain (myalgia) and increase patient's risk for serious muscle toxicity, such as rhabdomyolysis. Also, commonly used triglyceride lowering agents that are given in combination with statins are not well-tolerated. Fibrates when given with statins are known to have drug-drug interactions resulting in increased statin blood drug levels and present an increased safety risk. Indeed, the interaction of the statin, Baychol (Cerivastatin) with the fibrate, gemfibrozil resulted severe muscle toxicity and deaths, and raised safety concerns that resulted in the removal of Baychol from the market. Fibrates are associated with myalgia and an increased risk of muscle toxicity, fish oil needs to be taken multiple times daily, and is associated with a fish oil aftertaste, burping or regurgitation, and niacin causes flushing particularly when administered in combination with statins.

Thus, there is a need for a safe and efficacious treatment for type IIb hyperlipidemia which can lower one or both LDL-C concentrations and triglyceride concentrations, treatment or prevention of liver disease or an abnormal liver condition, a disorder of lipoprotein or glucose metabolism, a cardiovascular or related vascular disorder, a disease caused by increased levels of fibrosis, or a disease associated with increased inflammation, with minimal risks or side effects.

Further, a pharmaceutically acceptable salt of gemcabene having a PSD90 of less than 30 μm can be difficult to handle due to its low density and/or increased electrostatic properties. Without bound to any theory, particles having low density and/or high electrostatic properties render tableting these particles difficult, particularly in manufacturing processes.

SUMMARY OF THE INVENTION

The present invention provides pharmaceutically acceptable salts of gemcabene, the pharmaceutically acceptable salts having a particle size distribution characterized by a PSD90 ranging from 35 μm to about 90 μm as measured by laser light diffraction and providing a plasma gemcabene $AUC_{(0-24)}$ ranging from about 200 μg·hr/mL at steady state to about 6000 μg·hr/mL at steady state when administered to a human subject at a dose of about 50 mg/day to about 900 mg/day.

The present invention still further provides pharmaceutically acceptable salts of gemcabene, the pharmaceutically acceptable salts having a PSD90 ranging from 35 μm to about 90 μm as measured by laser light diffraction and providing a plasma gemcabene $AUC_{last}$ ranging from about 50 μg·hr/mL to about 7500 μg·hr/mL after a single dose administration of about 50 mg to about 900 mg to a human subject.

The present invention still further provides methods for purifying crude gemcabene, wherein the crude gemcabene comprises no more than 1% w/w of 2,2,7,7-tetramethyl-octane-1,8-dioic acid as determined by high-performance liquid chromatography, comprising: dissolving the crude gemcabene in heptane to provide a heptane solution of the crude gemcabene; and cooling the heptane solution to a temperature ranging from 10° C. to 15° C. to precipitate gemcabene, wherein the gemcabene comprises 0.5% w/w or less of 2,2,7,7-tetramethyl-octane-1,8-dioic acid by area as determined by high-performance liquid chromatography.

The present invention still further provides gemcabene purified by the methods of the present invention.

The present invention still further provides pharmaceutically acceptable salts of gemcabene prepared from the gemcabene purified by the methods of the present invention.

A gemcabene pharmaceutically acceptable salt disclosed herein is a "compound of the invention".

The present invention still further provides compositions comprising an effective amount of a compound of the invention, and a pharmaceutically acceptable carrier or vehicle (each composition being a "composition of the invention").

The present invention still further provides methods for treating or preventing a liver disease or an abnormal liver condition, comprising administering to a subject in need thereof an effective amount of a compound of the invention.

The present invention still further provides methods for treating or preventing a disorder of lipoprotein metabolism, comprising administering to a subject in need thereof an effective amount of a compound of the invention.

The present invention still further provides methods for reducing in a subject's blood plasma or blood serum the subject's total cholesterol concentration, low-density lipoprotein cholesterol concentration, low-density lipoprotein concentration, very low-density lipoprotein cholesterol concentration, very low-density lipoprotein concentration, non-HDL cholesterol concentration, non-HDL concentration, apolipoprotein B concentration, triglyceride concentration, apolipoprotein C-III concentration, C-reactive protein concentration, fibrinogen concentration, lipoprotein(a) concentration, interleukin-6 concentration, angiopoietin-like protein 3 concentration, angiopoietin-like protein 4 concentration, PCSK9 concentration, or serum amyloid A concentration, comprising administering to a subject in need thereof an effective amount of a compound of the invention.

The present invention still further provides methods for elevating in the subject's blood plasma or blood serum the subject's high-density lipoprotein cholesterol concentration, high-density lipoprotein concentration, high-density cholesterol triglyceride concentration, adiponectin concentration or apolipoprotein A-I concentration, comprising administering to a subject in need thereof an effective amount of a compound of the invention.

The present invention still further provides methods for treating or preventing thrombosis, a blood clot, a primary cardiovascular event, a secondary cardiovascular event, progression to nonalcoholic fatty liver disease, nonalcoholic steatohepatitis, liver cirrhosis hepatocellular carcinoma, liver failure, pancreatitis, pulmonary fibrosis or hyperlipoproteinemia type IIB, comprising administering to a subject in need thereof an effective amount of a compound of the invention.

The present invention still further provides methods for reducing a subject's risk of developing thrombosis, a blood clot, a primary cardiovascular event, a secondary cardiovascular event, progression to nonalcoholic fatty liver disease, nonalcoholic steatohepatitis, liver cirrhosis, hepatocellular carcinoma, liver failure, pancreatitis, pulmonary fibrosis or hyperlipoproteinemia type IIB, comprising administering to a subject in need thereof an effective amount of a compound of the invention.

The present invention still further provides methods of reducing or inhibiting progression of fibrosis, steatosis, ballooning or inflammation in the liver of a subject, comprising administering to a subject in need thereof an effective amount of a compound of the invention.

The present invention still further provides methods for reducing post-prandial lipemia or preventing prolonged post-prandial lipemia, comprising administering to a subject in need thereof an effective amount of a compound of the invention.

The present invention still further provides methods for reducing a fibrosis score or a nonalcoholic fatty liver disease activity score in a subject, comprising administering to a subject in need thereof an effective amount of a compound of the invention.

The present invention still further provides methods for stabilizing, regressing, or maintaining a fibrosis score or a nonalcoholic fatty liver disease activity score in a subject, comprising administering to a subject in need thereof an effective amount of a compound of the invention.

The present invention still further provides methods for slowing the progression of a fibrosis score or a nonalcoholic fatty liver disease activity score in a subject, comprising administering to a subject in need thereof an effective amount of a compound of the invention.

The present invention still further provides methods for reducing a fat content in a liver of a subject, comprising administering to a subject in need thereof an effective amount of a compound of the invention.

The present invention still further provides methods for treating or preventing a disorder of glucose metabolism, comprising administering to a subject in need thereof an effective amount of a compound of the invention.

The present invention still further provides methods for treating or preventing a cardiovascular disorder or a related vascular disorder, comprising administering to a subject in need thereof an effective amount of a compound of the invention.

The present invention still further provides methods for treating or preventing inflammation, comprising administering to a subject in need thereof an effective amount of a compound of the invention.

The present invention still further provides methods for preventing or reducing the risk of developing pancreatitis, comprising administering to a subject in need thereof an effective amount of a compound of the invention.

The present invention still further provides methods for treating or preventing a pulmonary disorder, comprising administering to a subject in need thereof an effective amount of a compound of the invention.

The present invention still further provides methods for treating or preventing musculoskeletal discomfort, comprising administering to a subject in need thereof an effective amount of a compound of the invention.

The present invention still further provides methods for lowering a subject's LDL-C concentration, comprising administering to a subject in need thereof an effective amount of a compound of the invention.

DETAILED DESCRIPTION OF THE INVENTION

Figure 1A:
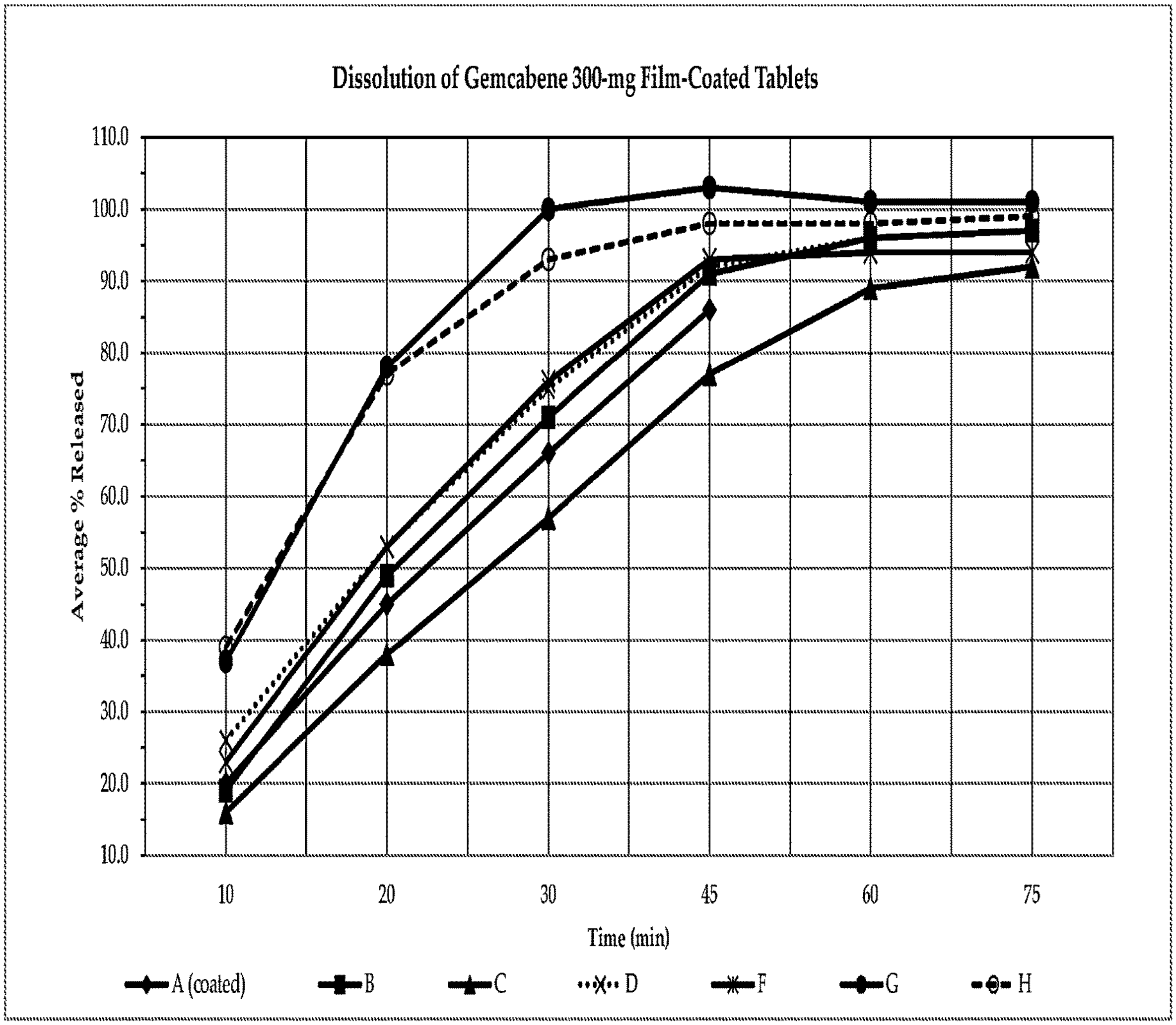
FIG. 1A is a line graph showing a dissolution profile of gemcabene from a composition of the invention in the form of a film-coated tablet.

The present invention provides compounds of the invention. In some embodiments, the compound of the invention is gemcabene calcium salt. In some embodiments, the compound of the invention is gemcabene calcium salt hydrate. In some embodiment, the compound of the invention is amorphous or crystalline pharmaceutically acceptable salt of gemcabene. Gemcabene has been previously described, e.g., in U.S. Pat. No. 5,648,387, which is hereby incorporated by reference in its entirety. Various gemcabene calcium salt hydrates have been previously described, e.g., in U.S. Pat. No. 6,861,555, which is hereby incorporated by reference in its entirety.

The present invention further provides compositions of the invention. In some embodiments, the compositions of the invention further comprise an additional pharmaceutically active agent. In other embodiments, the compositions of the invention further comprise two or more additional pharmaceutically active agents. The compositions of the invention are useful for treating or preventing various diseases including liver disease or an abnormal liver condition, a disorder of lipoprotein or glucose metabolism, a cardiovascular or related vascular disorder, a disease caused by increased levels of fibrosis, or a disease associated with increased inflammation. The invention further provides methods for treating or preventing liver disease or an abnormal liver condition, a disorder of lipoprotein or glucose metabolism, a cardiovascular or related vascular disorder, a disease caused by increased levels of fibrosis, or a disease associated with increased inflammation, comprising administering to a subject in need thereof an effective amount of a compound of the invention.

Each of the therapeutic or prophylactic methods disclosed herein is a "therapeutic or prophylactic method of the invention".

A compound of the invention has a PSD90 ranging from 35 μm to about 90 μm. In some embodiments, the compound of the invention has a PSD90 ranging from 35 μm to about 85 μm. In some embodiments, the compound of the invention has a PSD90 ranging from 35 μm to about 80 μm. In some embodiments, the compound of the invention has a PSD90 ranging from 35 μm to about 75 μm. In some embodiments, the compound of the invention has a PSD90 ranging from 40 μm to about 75 μm. In some embodiments, the compound of the invention has a PSD90 ranging from 45 μm to about 75 μm. In some embodiments, the compound of the invention has a PSD90 ranging from 50 μm to about 75 μm. In some embodiments, the compound of the invention has a PSD90 ranging from 45 μm to 75 μm. In some embodiments, the compound of the invention has a PSD90 ranging from 50 μm to 75 μm.

In some embodiments, the compounds of the invention have a dissolution profile having a value of at least 80% in pH 5.0 potassium acetate buffer at 37° C.±5° C. in no more than 45 minutes as measured by high-performance liquid chromatography using a detection wavelength of 210 nm. In some embodiments, the compound of the invention has a dissolution profile having a value of at least 85% in no more than 45 minutes. In some embodiments, the compound of the invention has a dissolution profile having a value of at least 90% in no more than 45 minutes.

In some embodiments the compounds of the invention have a dissolution profile having a n value of at least 70% in pH 5.0 potassium acetate buffer at 37° C.±5° C. in no more than 30 minutes as measured by high-performance liquid chromatography using a detection wavelength of 210 nm.

In some embodiments, the compound of the invention is a gemcabene calcium salt. In other embodiments, the compound of the invention is a gemcabene calcium salt hydrate. In some embodiments, the compound of the invention is an amorphous solid. In some embodiments, the compound of the invention is a crystalline polymorph. In some embodiments, the compound of the invention is gemcabene calcium salt hydrate Crystal Form 1. In other embodiments, the compound of the invention is gemcabene calcium salt hydrate Crystal Form 2. In other embodiments, the compound of the invention is gemcabene calcium salt hydrate Crystal Form C1. In other embodiments, the compound of the invention is gemcabene calcium salt hydrate Crystal Form C2. In other embodiments, the compound of the invention is gemcabene calcium salt hydrate Crystal Form C3. In some embodiments, the compound of the invention is an amorphous gemcabene calcium salt. In some embodiments, the compound of the invention is an amorphous gemcabene calcium salt hydrate.

In some embodiments, the compound of the invention has a water content of about 2% w/w to about 5% w/w of the compound of the invention. In other embodiments, the compound of the invention has the water content of about 2% w/w to about 4% w/w. In some embodiments, the water content is about 3% w/w to about 5% w/w. In other embodiments, the water content is about 3% w/w to about 4% w/w.

In some embodiments, the compound of the invention is a gemcabene calcium salt solvate. In some embodiments, the compound of the invention is a gemcabene calcium salt alcohol solvate. In some embodiments, the compound of the invention is a gemcabene calcium salt ethanol solvate. In some embodiments, the compound of the invention is a gemcabene calcium salt n-propyl solvate. In some embodiments, the compound of the invention is a gemcabene calcium salt isopropyl solvate. In some embodiments, the compound of the invention is a gemcabene calcium salt methanol solvate. In some embodiments, the compound of the invention is a gemcabene calcium salt n-butyl solvate.

In some embodiments, the compound of the invention has an ethanol content of about 0% w/w to about 0.5% w/w of the compound of the invention. In some embodiments, the compound of the invention has an ethanol content of about 0.5% w/w to about 8% w/w of the compound of the invention.

In some embodiments, the composition of the invention is in a form of a tablet or a capsule. In some embodiments, the composition of the invention further comprises an effective amount of an additional pharmaceutically active agent. In other embodiments, the composition of the invention further comprises an effective amount of two or more additional pharmaceutically active agents.

In some embodiments, the additional pharmaceutically active agent is a statin. In some embodiments, the statin is atorvastatin, simvastatin, pravastatin, rosuvastatin, fluvastatin, lovastatin, pitavastatin, mevastatin, dalvastatin, dihydrocompactin, or cerivastatin, or a pharmaceutically acceptable salt thereof. In some embodiments, the pharmaceutically acceptable salt of the statin is a calcium salt. In some embodiments, the statin is atorvastatin calcium.

Other illustrative additional pharmaceutically active agents include, but are not limited to, a lipid lowering agent, a PCSK9 (proprotein convertase subtilisin/kexin type 9) inhibitor, a cholesterol absorption inhibitor, an ACC (acetyl-CoA carboxylase) inhibitor, an ApoC-III (apolipoprotein C-III) inhibitor, an ApoB (apolipoprotein B) synthesis inhibitor, an ANGPTL 3 (angiopoietin-like protein 3) inhibitor, an ANGPTL 4 (angiopoietin-like protein 4) inhibitor, an ANGPTL 8 (angiopoietin-like protein 8) inhibitor, an ACL (adenosine triphosphate citrate lyase) inhibitor, a microsomal transfer protein inhibitor, a fenofibric acid, a fish oil, a fibrate, a thyroid hormone beta receptor agonist, a farnesoid X receptor (FXR), a CCR2/CCR5 (C—C chemokine receptor types 2 (CCR2) and 5 (CCR5)) inhibitor or antagonist, a caspase protease inhibitor, an ASK-1 (Apoptosis signal-regulating kinase 1) inhibitor, a galectin-3 protein, a NOX (Nicotinamide adenine dinucleotide phosphate oxidase) inhibitor, an ileal bile acid transporter, a PPAR (peroxisome proliferator-activated receptor) agonist, a PPAR dual agonist, a pan-PPAR agonist, a sodium-glucose co-transporter 1 or 2 (SGLT1 or SGLT2) inhibitor, a dipeptidyl peptidase 4 (DPP4) inhibitor, a fatty acid synthase (FAS) inhibitor, a toll-like receptor antagonist, a thyroid hormone receptor-beta (THR-β) agonist, a liver-directed, selective THR-β agonist, an ACO1 modulator, a 1-mieloperoxidase inhibitor, a 1-ketohexokinase (1-KHK) inhibitor, an oxidative stress inhibitor, a fibroblast growth factor 21 (FGF21) or 19 (FGF19) inhibitor, a transforming growth factor beta-1 (TGF-β1) agonist, a hepatic de novo lipogenesis (DNL) inhibitor, an enoyl CoA hydratase inhibitor, a cholesterol 7-alpha hydroxylase (Cyp7A1) agonist, a Collagen Type 3 inhibitor, and a CETP (cholesterylester transfer protein) inhibitor. In some embodiments, the additional pharmaceutically active agent is ezetimibe.

In some embodiments, the additional pharmaceutically active agent is a contraceptive agent. As used herein, a "contraceptive agent" refers to any pharmaceutically active agent that promotes the prevention of conception, impregnation, or implantation or prevents or reduces the likelihood of pregnancy. In some embodiments, the contraceptive agent is one or both of ethinyl estradiol and norethindrone. In some embodiments, the contraceptive agent is a combination of ethinyl estradiol and norethindrone. In some embodiments, the contraceptive agent is estrogen, an estrogen derivative, progestin or a progestin derivative.

The present invention provides methods for treating or preventing a liver disease or an abnormal liver condition, comprising administering to a subject in need thereof an effective amount of a compound of the invention. Illustrative liver diseases or abnormal liver conditions include, but are not limited to, nonalcoholic fatty liver disease, nonalcoholic steatohepatitis, alcoholic steatohepatitis, cirrhosis, inflammation, fibrosis, partial fibrosis, primary biliary cirrhosis, primary sclerosing cholangitis, liver failure, hepatocellular carcinoma, liver cancer, hepatic steatosis, hepatocyte ballooning, hepatic lobular inflammation, and hepatic triglyceride accumulation. In some embodiments, the liver disease or liver condition is nonalcoholic fatty liver disease or nonalcoholic steatohepatitis.

The present invention provides methods for treating or preventing an abnormal fibrosis of an internal organ of a subject, comprising administering to a subject in need thereof an effective amount of a compound of the invention. In some embodiments, the abnormal fibrosis of an internal organ is in a human subject.

The present invention provides methods for treating or preventing a disease or an abnormal condition generated by an inflammatory response of an organ in a subject, comprising administering to a subject in need thereof an effective amount of a compound of the invention. In some embodiments, the inflammatory response is in an internal organ. In some embodiments, the subject is a human.

The present invention provides methods for treating or preventing a disorder of lipoprotein metabolism, comprising administering to a subject in need thereof an effective amount of a compound of the invention. Illustrative disorders of lipoprotein metabolism include, but are not limited to, dyslipidemia, dyslipoproteinemia, mixed dyslipidemia, atherosclerotic cardiovascular disease (ASCVD), type IIb hyperlipidemia, familial combined hyperlipidemia, familial hypercholesterolemia, familial chylomicronemia syndrome, hypertriglyceridemia, dysbetalipoproteinemia, lipoprotein overproduction, lipoprotein deficiency, elevation of total cholesterol, elevation of low-density lipoprotein cholesterol concentration, elevation of very low-density lipoprotein cholesterol concentration, elevation of non-HDL cholesterol concentration, elevation of apolipoprotein B concentration, elevation of apolipoprotein C-III concentration, elevation of C-reactive protein concentration, elevation of fibrinogen concentration, elevation of lipoprotein(a) concentration, elevation of interleukin-6 concentration, elevation of angiopoietin-like protein 3 concentration, elevation of angiopoietin-like protein 4 concentration, elevation of serum amyloid A concentration, elevation of PCSK9, increased risk of thrombosis, increased risk of a blood clot, low HDL-cholesterol concentration, elevation of low-density lipoprotein concentration, elevation of very low-density lipoprotein concentration, elevation of triglyceride concentration, prolonged post-prandial lipemia, lipid elimination in bile, a metabolic disorder, phospholipid elimination in bile, oxysterol elimination in bile, abnormal bile production, peroxisome proliferator activated receptor-associated disorder, hypercholesterolemia, hyperlipidemia and visceral obesity. In some embodiments, the disorder of lipoprotein metabolism is mixed dyslipidemia, atherosclerotic cardiovascular disease (ASCVD), type IIb hyperlipidemia, or familial combined hyperlipidemia. In some embodiments, the disorder of lipoprotein metabolism is familial hypercholesterolemia.

The present invention provides methods for reducing a subject's total cholesterol, low-density lipoprotein cholesterol concentration, very low-density lipoprotein cholesterol concentration, non-HDL cholesterol concentration, apolipoprotein B concentration, apolipoprotein C-III concentration, C-reactive protein concentration, fibrinogen concentration, lipoprotein(a) concentration, interleukin-6 concentration, angiopoietin-like protein 3 concentration, angiopoietin-like protein 4 concentration, serum amyloid A concentration, PCSK9 concentration, low-density lipoprotein concentration, very low-density lipoprotein concentration, or triglyceride concentration, comprising administering to a subject in need thereof, an effective amount of a compound of the invention. In some embodiments, the present invention provides methods for reducing a subject's triglyceride concentration or LDL-cholesterol, comprising administering to a subject in need thereof, an effective amount of a compound of the invention.

The present invention provides methods for reducing a subject's cholesterol-rich remnant ApoB-lipoprotein or triglyceride-rich remnant ApoB-lipoprotein concentration in the subject's blood serum or plasma, comprising administering to a subject in need thereof an effective amount of a compound of the invention. In some embodiments, the present invention provides methods for reducing a subject's cholesterol- and triglyceride-rich remnant ApoB-lipoproteins (C-TRLs) in the subject's plasma, comprising administering to a subject in need thereof, an effective amount of a compound of the invention.

The present invention provides methods for increasing hepatic clearance of cholesterol-rich remnant ApoB-lipoprotein or triglyceride-rich remnant ApoB-lipoprotein in a subject, comprising administering to a subject in need thereof, an effective amount of a compound of the invention. In some embodiments, the present invention provides methods for enhancing or increasing hepatic clearance of C-TRLs in a subject, comprising administering to a subject in need thereof, an effective amount of a compound of the invention. Without bound to any theory, fast hepatic clearance of C-TRLs lead to less cholesterol deposition (less plaque buildup) in arteries. Thus, increasing hepatic clearance of cholesterol-rich remnant ApoB-lipoprotein, triglyceride-rich remnant ApoB-lipoprotein, or C-TRLs can be useful in treating or preventing cardiovascular diseases including atherosclerosis.

The present invention provides methods for reducing a subject's risk of thrombosis or blood clot, comprising administering to a subject in need thereof an effective amount of a compound of the invention.

The present invention provides methods for treating or preventing a disorder of glucose metabolism, comprising administering to a subject in need thereof an effective amount of a compound of the invention. Illustrative disorders of glucose metabolism include, but are not limited to, insulin resistance, impaired glucose tolerance, impaired fasting glucose (concentration in blood), diabetes mellitus, familial partial lipodystrophy, lipodystrophy, obesity, peripheral lipoatrophy, diabetic nephropathy, diabetic retinopathy, renal disease, and septicemia. In some embodiments, obesity is central obesity.

The present invention provides methods for treating or preventing an atherometabolic syndrome, comprising administering to a subject in need thereof an effective amount of a compound of the invention. In some embodiments, the present invention provides methods for reducing a subject's risk of developing an atherometabolic syndrome, comprising administering to a subject in need thereof, an effective amount of a compound of the invention. Atherometabolic syndrome, like type 2 diabetes, increases plasma levels of cholesterol- and triglyceride-rich remnant ApoB-lipoproteins (C-TRLs). In some embodiments, atherometabolic syndrome includes metabolic syndrome, which can be defined by a cluster of symptoms that include abdominal obesity, impaired glucose tolerance, dyslipidemia, and raised blood pressure. In some embodiments, atherometabolic syndrome includes one or more conditions associated with increased risk of cardiovascular disease or one or more conditions associated with increased blood pressure, increased LDL-C, lowered HDL-C, and/or increased blood sugar level.

The present invention provides methods for treating or preventing a cardiovascular disorder or a related vascular disorder, comprising administering to a subject in need thereof an effective amount of a compound of the invention. Illustrative cardiovascular disorders or related vascular disorders include, but are not limited to, arteriosclerosis, atherosclerosis, hypertension, coronary artery disease, myocardial infarction, arrhythmia, atrial fibrillation, heart valve disease, heart failure, cardiomyopathy, myopathy, pericarditis, impotence, and a thrombotic disorder.

The present invention provides methods for treating or preventing a C-reactive protein-related disorder, comprising administering to a subject in need thereof an effective amount of a compound of the invention. In some embodiments, the C-reactive protein related disorder is inflammation, ischemic necrosis, or a thrombotic disorder.

The present invention provides methods for treating or preventing disorders related to modulating inflammation markers or C-reactive proteins, comprising administering to a subject in need thereof an effective amount of a compound of the invention. In some embodiments, the disorder related to modulating inflammation markers or C-reactive proteins is inflammation, ischemic necrosis, or a thrombotic disorder.

The present invention provides methods for treating or preventing Alzheimer's disease, comprising administering to a subject in need thereof an effective amount of a compound of the invention.

The present invention provides methods for treating or preventing Parkinson's disease, comprising administering to a subject in need thereof an effective amount of a compound of the invention.

The present invention provides methods for treating or preventing pancreatitis, comprising administering to a subject in need thereof an effective amount of a compound of the invention. The present invention provides methods for preventing or reducing the risk of developing pancreatitis, comprising administering to a subject in need thereof an effective amount of a compound of the invention.

The present invention provides methods for treating or preventing pulmonary disorder, comprising administering to a subject in need thereof an effective amount of a compound of the invention. In some embodiments, the pulmonary disorder is chronic obstructive pulmonary disease or an idiopathic pulmonary fibrosis.

The present invention provides methods for treating or preventing musculoskeletal discomfort, comprising administering to a subject in need thereof an effective amount of a compound of the invention. In some embodiments, the musculoskeletal discomfort is myalgia. In another embodiment, the musculoskeletal discomfort is myositis.

The present invention provides methods for treating or preventing a sulfatase-2-related disorder, comprising administering to a subject in need thereof an effective amount of a compound of the invention. In some embodiments, the sulfatase-2-related disorder is a hepatic sulfatase-2-related disorder. In some embodiments, the sulfatase-2-related disorder is a disorder of lipogenesis or lipid modulation.

Examples of disorders of lipogenesis include, but are limited to, diabetes and related conditions, obesity, hepatic steatosis, non-alcoholic steatohepatitis, cancer, cardiovascular disease (hypertriglyceridemia), and skin disorders.

Examples of disorders of lipid modulation include, but are not limited to, elevated total cholesterol, elevated low-density lipoprotein cholesterol (LDL-C), elevated apolipoprotein B (Apo B), elevated triglyceride and elevated non-high-density lipoprotein cholesterol.

The present invention provides methods for downregulating hepatic sulfatase-2 expression in a subject, comprising administering to a subject in need thereof an effective amount of a compound of the invention.

The present invention provides methods for treating or preventing an ApoC-III related disorder, comprising administering to a subject in need thereof an effective amount of a compound of the invention. In some embodiments, the ApoC-III related disorder is a disorder of lipogenesis or lipid modulation, described herein.

The present invention provides methods for treating or preventing an ACC1-related disorder, comprising administering to a subject in need thereof an effective amount of a compound of the invention. In some embodiments, the ACC1-related disorder is a disorder of lipogenesis or lipid modulation, described herein.

The present invention provides methods for treating or preventing an ADH-4-related disorder, comprising administering to a subject in need thereof an effective amount of a compound of the invention. In some embodiments, the ADH-4-related disorder is a disorder of lipogenesis or lipid modulation, described herein.

The present invention provides methods for treating or preventing a TNF-α-related disorder, comprising administering to a subject in need thereof an effective amount of a compound of the invention. In some embodiments, the TNF-α-related disorder is inflammation.

The present invention provides methods for treating or preventing a MCP-1-related disorder, comprising administering to a subject in need thereof an effective amount of a compound of the invention. In some embodiments, the MCP-1-related disorder is inflammation.

The present invention provides methods for treating or preventing a MIP-1β-related disorder, comprising administering to a subject in need thereof an effective amount of a compound of the invention. In some embodiments, the MIP-1β-related disorder is inflammation.

The present invention provides methods for treating or preventing a CCR5-related disorder, comprising administering to a subject in need thereof an effective amount of a compound of the invention. In some embodiments, the CCR5-related disorder is inflammation.

The present invention provides methods for treating or preventing a CCR2-related disorder, comprising administering to a subject in need thereof an effective amount of a compound of the invention. In some embodiments, the CCR2-related disorder is inflammation.

The present invention provides methods for treating or preventing a NF-κB-related disorder, comprising administering to a subject in need thereof an effective amount of a compound of the invention. In some embodiments, the NF-κB-related disorder is inflammation.

The present invention provides methods for treating or preventing a TIMP-1-related disorder, comprising administering to a subject in need thereof an effective amount of a compound of the invention. In some embodiments, the TIMP-1-related disorder is fibrosis. In some embodiments, the fibrosis is hepatic fibrosis.

The present invention provides methods for treating or preventing a MMP-2-related disorder, comprising administering to a subject in need thereof an effective amount of a compound of the invention. In some embodiments, the MMP-2-related disorder is hepatic carcinogenesis or cancer.

In some embodiments, the therapeutic or prophylactic methods of the invention further comprise administering an effective amount of an additional pharmaceutically active agent. In some embodiments, the therapeutic or prophylactic methods of the invention further comprise administering an effective amount of two or more additional pharmaceutically active agent. In some embodiments, the additional pharmaceutically active agent is a statin. In some embodiments, the statin is atorvastatin, simvastatin, pravastatin, rosuvastatin, fluvastatin, lovastatin, pitavastatin, mevastatin, dalvastatin, dihydrocompactin, or cerivastatin or a pharmaceutically acceptable salt thereof. In some embodiments, the statin is atorvastatin calcium.

Illustrative additional pharmaceutically active agents are as disclosed herein. In some embodiments, the additional pharmaceutically active agent is a human hormone FGF19.

Definitions

The term "about" when immediately preceding a numerical value means±up to 20% of the numerical value. For example, "about" a numerical value means±up to 20% of the numerical value, in some embodiments, ±up to 19%, ±up to 18%, ±up to 17%, ±up to 16%, ±up to 15%, ±up to 14%, ±up to 13%, ±up to 12%, ±up to 11%, ±up to 10%, ±up to 9%, ±up to 8%, ±up to 7%, ±up to 6%, ±up to 5%, ±up to 4%, ±up to 3%, ±up to 2%, ±up to 1%, ±up to less than 1%, or any other value or range of values therein.

A "subject" is a human or non-human mammal, e.g., a bovine, horse, feline, canine, rodent, or non-human primate. The human can be a male or female, child, adolescent or adult. The female can be premenarcheal or postmenarcheal.

As used herein, the "gemcabene" (United States Adopted Name) has the chemical name 6-(5-carboxy-5-methyl-hexyloxy)-2,2-dimethyl-hexanoic acid, which is also known as 6-(5-carboxy-5-methyl-hexyloxy)-2,2-dimethylhexanoic acid or 6,6'-oxybis(2,2-dimethylhexanoic acid), and has the structure:

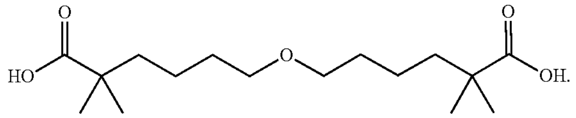 [SMILES: CC(C)(CCCCOCCCCC(C)(C)C(=O)O)C(=O)O]

As used herein, "gemcabene calcium salt" has the structure:

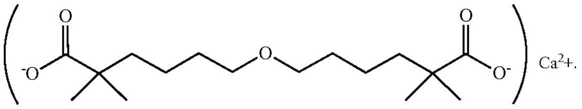

Illustrative pharmaceutically acceptable salts of a basic compound include those of an inorganic or organic acid, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, or carbonic acid. In some embodiments, examples of inorganic or organic acids suitable to form an acid addition salt, include but are not limited to, hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc.

Illustrative pharmaceutically acceptable salts of an acidic compound, e.g., gemcabene, include alkali metal salts, (e.g., lithium, sodium and potassium salts), alkaline earth metal salts (e.g., calcium and magnesium salts), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. In some embodiments, a pharmaceutically acceptable salt derived from inorganic bases include, but are not limited to, the sodium, potassium, lithium, ammonium, calcium, magnesium, iron, zinc, copper, manganese, aluminum salts and the like. Pharmaceutically acceptable salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

An "effective amount" when used in connection with a compound of the invention means an amount of the compound of the invention that, when administered to a subject for treating or preventing a disorder or abnormal condition, is effective to treat or prevent the disorder or abnormal condition, alone or in combination with an additional pharmaceutically active agent.

An "effective amount" when used in connection with an additional pharmaceutically active agent means an amount of the additional pharmaceutically active agent that, when administered to a subject for treating or preventing a disorder or abnormal condition, is effective to treat or prevent the disorder or abnormal condition, alone or in combination with a compound of the invention.

All weight percentages (i.e., "% by weight" and "wt. %" and w/w) referenced herein, unless otherwise indicated, are relative to the total weight of the mixture or composition, as the case can be.

As used herein, "$D_{90}$" or "PSD90", means that 90% of the particles of a compound of the invention have a diameter that is less than the indicated diameter. For example, a $D_{90}$ or a PSD90 of 75 μm means that 90% of the cumulative volume of the particles of the indicated compound of the invention have a diameter that is less than 75 μm. Similarly, as used herein, "$D_{50}$" or "PSD50", means that 50% of the cumulative volume of the particles of a compound of the invention have a diameter that is less than the indicated diameter. Also, as used herein, "$D_{10}$" or "PSD10", means that 10% of the cumulative volume of the particles of a compound of the invention have a diameter that is less than the indicated diameter.

As used herein, an "immediate-release" composition refers to a composition of the invention that releases at least 75% (by weight) of a compound of the invention within one hour of administration to a subject. In some embodiments, an immediate-release composition of the invention releases at least 75% by weight, at least 80% by weight, at least 85% by weight, or at least 90% by weight of a compound of the invention within 45 minutes of administration to a subject.

As used herein, "$AUC_{(0-24)}$" refers to area under the plasma concentration-time curve from time 0 to 24 hours following a compound's administration.

As used herein, "$AUC_{last}$", which is synonymous with "$AUC_{(0\text{-}tldc)}$", "$AUC_{(0\text{-}tlqc)}$", "$AUC_{(0\text{-}tc)}$", and "$AUC_{(0\text{-}t)}$", refers to area under the plasma concentration-time curve from time 0 to the last detectable concentration of a compound following its administration. As used herein, "baseline plasma or blood serum LDL-C" refers to plasma or blood serum LDL-C of a subject as measured prior to administration of the compound of the invention.

As used herein, a subject "on a stable dose" of a lipid-lowering medication, drug or agent, such as a statin, refers to a subject that has been taking the same dose of lipid-lowering medication (e.g., statins) for a period of time in which the subject's blood serum or plasma concentration of LDL-C has stabilized. As used herein, "stabilized" means that a new steady state level of LDL-C in the subject's blood serum or plasma concentration has been achieved at a time after beginning the lipid-lowering medication and remains relatively constant from day today within reasonable margins (±15%) of the new steady state level.

As used herein, a "statin therapy" refers to a treatment where a subject is administered a statin. In some embodiment, the subject is "undergoing statin therapy", i.e., being administered with a statin. In some embodiments, the stain therapy is maximally tolerated statin therapy. In some embodiments, the statin therapy is ineffective to treat or prevent a disease or condition as disclosed herein. In some embodiments, the statin therapy is ineffective to lower the subject's LDL-C concentration, lower the subject's triglyceride concentration, or raise the subject's HDL-C concentration to a normal value or to the subject's goal value. As used herein, "maximally tolerated statin therapy" refers to therapeutic regimen comprising the administration of daily dose of a statin that is the maximally tolerated dose for a particular subject "Maximally tolerated dose" means the highest dose of statin that can be administered to a subject without causing unacceptable adverse side effects in the subject.

As used herein, "a subject with homozygous familial hypercholesterolemia (HoFH)" or "an HoFH subject" is a subject determined to have HoFH by genetic confirmation or clinical diagnosis. A subject with HoFH (1) has a genetic confirmation of two mutant alleles at the LDL-receptor, apolipoprotein B, PCSK9 or the LDL-RAP1 (LDL-receptor adaptor protein 1) gene locus. For example, the subject may have paired or same (homozygous) or two unpaired or dissimilar (compound homozygous or compound heterozygous) mutations at alleles on the LDL-receptor, apolipoprotein B, PCSK9, or the LDL-RAP1 gene locus; or (2) is clinically determined to have (a) untreated LDL-C>500 mg/dL (12.92 mmol/L) or treated LDL-C≥300 mg/dL (7.76 mmol/L) together with either appearance of cutaneous or tendinous xanthoma before 10 years of age, or evidence of heterozygous familial hypercholesterolemia in both parents, or (b) LDL-C>300 mg/dL (7.76 mmol/L) on maximally tolerated lipid-lowering drug therapy. The clinically diagnosis (phenotypic) is only indicative of HoFH, but there are some subjects that does not meet the clinical LDL-C limitations (e.g., subjects have LDL-C≤500 mg/dL or LDL-C<300 mg/dL) yet have HoFH by genetic confirmation. Similarly, subjects can be clinically diagnosed as having HoFH but not by genetic confirmation.

As used herein, "a subject with heterozygous familial hypercholesterolemia (HeFH)" or "an HeFH subject" is a subject determined to have HeFH by genetic confirmation or clinical diagnosis. A subject with HeFH is clinically determined to have LDL-C≥190 mg/dL.

Genotype analysis for each of four genes is not commonly conducted as the analysis is lengthy, expensive and interpretations of results are controversial. For example, polymorphic changes in DNA that result in a single amino acid or small changes may result in little or no functional change in the protein, but this genetic variation is considered a "mutation" or "varian" of the predominant gene in the population. The loose interpretation of functional activity does not allow precision in genetic classification. Furthermore, other genetic and environmental factors result in phenotypic variation. For the above reasons, in medical practice, the classification of familial hypercholesterolemia, and more specifically homozygous familial hypercholesterolemia, is generally based on clinical interpretation. The clinical interpretation is sometimes supported by follow-up gene sequence analysis for both alleles of the LDL-receptor, apolipoprotein B, PCSK9 and LDL-RAP1 for the subject and if feasible the parents, siblings, and other relatives.

TABLE A

| Examples of Genetic Inheritance and Terminology of Familial Hypercholesterolemia | | | | | | |
|---|---|---|---|---|---|---|
| | | Genes Inherited from Mother | | | | |
| | Mutation | None | LDL-R (Position 1) | LDL-R (Position 2) | ApoB (Position 1) | LDL-R (Position 1) plus ApoB (Position 1) |
| Genes Inherited from Father | None | Normal | Heterozygous | Heterozygous | Heterozygous | Compound Heterozygous |
| | LDL-R (Position 1) | Heterozygous | Homozygous | Compound Homozygous | Compound Heterozygous | Homozygous |
| | LDL-R (Position 2) | Heterozygous | Compound Homozygous | Homozygous | Compound Heterozygous | Compound Homozygous |
| | ApoB (Position 1) | Heterozygous | Compound Heterozygous | Compound Heterozygous | Homozygous | Homozygous |
| | LDL-R (Position 1) plus ApoB (Position 1) | Compound Heterozygous | Homozygous | Compound Homozygous | Homozygous | Double Homozygous |

Particle Size Distribution

In some embodiments, the PSD90 of the compounds of the invention is achieved by reducing the particles' size, e.g., by micronizing or milling. In some embodiments, the micronizing or milling is achieved using a pinmill. In some embodiments, the micronizing or milling is achieved using a Fitzmill.

In some embodiments, the compounds of the invention have a PSD90 ranging from 35 μm to about 90 μm. In some embodiments, the compounds of the invention have a PSD90 ranging from 36 μm to about 90 μm. In some embodiments, the compounds of the invention have a PSD90 ranging from 37 μm to about 90 μm. In some embodiments, the compounds of the invention have a PSD90 ranging from 38 μm to about 90 μm. In some embodiments, the compounds of the invention have a PSD90 ranging from 39 μm to about 90 μm. In some embodiments, the compounds of the invention have a PSD90 ranging from 40 μm to about 90 μm.

In some embodiments, the compounds of the invention have a PSD90 ranging from 35 μm to about 85 μm. In some embodiments, the compounds of the invention have a PSD90 ranging from 36 μm to about 85 μm. In some embodiments, the compounds of the invention have a PSD90 ranging from 37 μm to about 85 μm. In some embodiments, the compounds of the invention have a PSD90 ranging from 38 μm to about 85 μm. In some embodiments, the compounds of the invention have a PSD90 ranging from 39 μm to about 85 μm. In some embodiments, the compounds of the invention have a PSD90 ranging from 40 μm to about 85 μm.

In some embodiments, the compounds of the invention have a PSD90 ranging from 35 μm to about 80 μm. In some embodiments, the compounds of the invention have a PSD90 ranging from 36 μm to about 80 μm. In some embodiments, the compounds of the invention have a PSD90 ranging from 37 μm to about 80 μm. In some embodiments, the compounds of the invention have a PSD90 ranging from 38 μm to about 80 μm. In some embodiments, the compounds of the invention have a PSD90 ranging from 39 μm to about 80 μm. In some embodiments, the compounds of the invention have a PSD90 ranging from 40 μm to about 80 μm.

In some embodiments, the compounds of the invention have a PSD90 ranging from 35 μm to about 75 μm. In some embodiments, the compounds of the invention have a PSD90 ranging from 36 μm to about 75 μm. In some embodiments, the compounds of the invention have a PSD90 ranging from 37 μm to about 75 μm. In some embodiments, the compounds of the invention have a PSD90 ranging from 38 μm to about 75 μm. In some embodiments, the compounds of the invention have a PSD90 ranging from 39 μm to about 75 μm. In some embodiments, the compounds of the invention have a PSD90 ranging from 40 μm to about 75 μm.

In other embodiments, the compounds of the invention have a PSD90 ranging from 45 μm to about 90 μm. In other embodiments, the compounds of the invention have a PSD90 ranging from 45 μm to about 85 μm. In other embodiments, the compounds of the invention have a PSD90 ranging from 45 μm to about 80 μm. In other embodiments, the compounds of the invention have a PSD90 ranging from 45 μm to about 75 μm.

In some embodiments, the compounds of the invention have a PSD90 ranging from 50 μm to about 90 μm. In some embodiments, the compounds of the invention have a PSD90 ranging from 50 μm to about 85 μm. In some embodiments, the compounds of the invention have a PSD90 ranging from 50 μm to about 80 μm. In some embodiments, the compounds of the invention have a PSD90 ranging from 50 μm to about 75 μm.

In some embodiments, the compounds of the invention have a PSD90 of 35 μm, 36 μm, 37 μm, 38 μm, 39 μm, 40 μm, 41 μm, 42 μm, 43 μm, 44 μm, 45 μm, 46 μm, 47 μm, 48 μm, 49 μm, 50 μm, 51 μm, 52 μm, 53 μm, 54 μm, 55 μm, 56 μm, 57 μm, 58 μm, 59 μm, 60 μm, 61 μm, 62 μm, 63 μm, 64 μm, 65 μm, 66 μm, 67 μm, 68 μm, 69 μm, 70 μm, 71 μm, 72 μm, 73 μm, 74 μm, 75 μm, 76 μm, 77 μm, 78 μm, 79 μm, 80 μm, 81 μm, 82 μm, 83 μm, 84 μm, 85 μm, 86 μm, 87 μm, 88 μm, 89 μm, 90 μm, or a value ranging from and to any of these diameters.

In some embodiments, the compounds of the invention have a PSD90 of about 44 μm, about 45 μm, about 46 μm, about 47 μm, about 48 μm, about 49 μm, about 50 μm, about 51 μm, about 52 μm, about 53 μm, about 54 μm, about 55 μm, about 56 μm, about 57 μm, about 58 μm, about 59 μm, about 60 μm, about 61 μm, about 62 μm, about 63 μm, about 64 μm, about 65 μm, about 66 μm, about 67 μm, about 68 μm, about 69 μm, about 70 μm, about 71 μm, about 72 μm, about 73 μm, about 74 μm, about 75 μm, about 76 μm, about 77 μm, about 78 μm, about 79 μm, about 80 μm, about 81 μm, about 82 μm, about 83 μm, about 84 μm, about 85 μm, about 86 μm, about 87 μm, about 88 μm, about 89 μm, about 90 μm, or a value ranging from and to any of these diameters.

Without being bound by theory, the compounds of the invention having a PSD90 of about 50 μm to about 62 μm particularly enable compressed tablet formulation with desired properties such as high drug loading, good compressibility, fast dissolution profile, and minimal to no cracking.

In some embodiments, the particle size distribution and the PSD90 of a compound of the invention is determined by the laser light diffraction particle size distribution analysis. The particle size distribution is determined in accordance with the Fraunhofer light diffraction method. In this method, a coherent laser beam passes through the sample and the resulting diffraction pattern is focused on a multi-element detector. Since the diffraction pattern depends, among other parameters, on particle size, the particle size distribution can be calculated based on the measured diffraction pattern of the sample. The method is described in more detail in USP38-NF33, <429> Light Diffraction Measurement of Particle Size.

Dissolution Profiles

In some embodiments, the compound of the invention has a dissolution profile characterized by its (% dissolution) over time. For example, the dissolution profile can have a (% dissolution) value of at least 80% in 45 minutes or less in pH 5.0 potassium acetate buffer at 37° C.±5° C. as measured by high-performance liquid chromatography using a detection wavelength of 210 nm. In some embodiments, the compound of the invention is a calcium salt. In some embodiments, the calcium salt is a calcium salt hydrate. In some embodiments, the compound of the invention is an amorphous solid. In some embodiments, the compound of the invention is a crystalline polymorph. In some embodiments, the calcium salt hydrate is calcium salt hydrate Crystal Form 1. In some embodiments, the calcium salt hydrate is calcium salt hydrate Crystal Form 2. In other embodiments, the compound of the invention is gemcabene calcium salt hydrate Crystal Form C3. In other embodiments, the compound of the invention is gemcabene calcium salt hydrate Crystal Form C2. In other embodiments, the compound of the invention is gemcabene calcium salt hydrate Crystal Form C1.

In some embodiments, the compound of the invention is a calcium salt solvate. In some embodiments, the calcium salt solvate is a calcium salt ethanol solvate.

In some embodiments, a compound of the invention has a dissolution profile characterized by % dissolution value of at least 85% gemcabene in 45 minutes or less in pH 5.0 potassium acetate buffer at 37° C.±5° C. and as measured by high-performance liquid chromatography using a detection wavelength of 210 nm. In some embodiments, a compound of the invention has a dissolution profile characterized by % dissolution value of at least 90% gemcabene in 45 minutes or less in pH 5.0 potassium acetate buffer at 37° C.±5° C. and as measured by high-performance liquid chromatography using a detection wavelength of 210 nm. See Example 13 for detailed method of determining % dissolution values.

In some embodiments, a compound of the invention has a dissolution profile characterized by % dissolution value of at least 80%, at least 81%, at least 82%, at least 83%, at least 85%, at least 86%, at least 87%, at least 88%, at least 89%, at least 90%, at least 91%, at least 92%, at least 93%, at least 94%, or at least 95%, or any value ranging from these percentages (e.g., 85%-90% dissolution), in 45 minutes or less in pH 5.0 potassium acetate buffer at 37° C.±5° C. and as measured by high-performance liquid chromatography using a detection wavelength of 210 nm.

In some embodiments, the compound of the invention has a dissolution profile characterized by % dissolution value of at least 70% in 30 minutes or less in pH 5.0 potassium acetate buffer at 37° C.±5° C. as measured by high-performance liquid chromatography using a detection wavelength of 210 nm. In some embodiments, the pharmaceutically acceptable salt is a calcium salt. In some embodiments, the calcium salt is a calcium salt hydrate. In some embodiments, the compound of the invention is an amorphous solid. In some embodiments, the compound of the invention is a crystalline polymorph. In some embodiments, the calcium salt hydrate is calcium salt hydrate Crystal Form 1. In some embodiments, the calcium salt hydrate is calcium salt hydrate Crystal Form 2. In some embodiments, the calcium salt hydrate is calcium salt hydrate Crystal Form C3. In some embodiments, the calcium salt hydrate is calcium salt hydrate Crystal Form C2. In some embodiments, the calcium salt hydrate is calcium salt hydrate Crystal Form C1.

TABLE B

Summary of illustrative polymorphic forms of gemcabene calcium

| | Crystal Form 1 | Crystal Form 2 | Crystal Form C3 | Gemcabene calcium salt ethanol solvate | Amorphous |
|---|---|---|---|---|---|
| Appearance | White solid | White solid | White solid | White solid | White solid |
| Thermal Analysis (TGA/DTA) | A weight loss of 3.6% is noted in the TGA up to 180° C. Single endothermic event at onset 133° C. (peak at 153° C.) by DTA. | A weight loss of 3.6 wt. % is noted in the TGA up to approximately 200° C. | A weight loss of 5.5% in noted by TGA up to approximately 200° C. | A weight loss of 4.8% is noted by TGA up to approximately 160° C. Single endothermic event at onset 110° C. (peak at 137° C.) by DTA. | A weight loss of 3.1 wt. % is noted by TGA up to approximately 150° C. |
| Thermal Analysis (DSC) | N/A | A single exotherm at onset 49° C. (peak 62° C.), followed by a single endotherm at onset 176° C. (peak 194° C.) are observed by DSC. | A single endotherm at onset 31° C. (peak 35° C.), followed by a single endotherm at onset 150° C. (peak 167° C.) are observed by DSC. | N/A | No thermal events are noted in the DSC. |

TABLE B-continued

Summary of illustrative polymorphic forms of gemcabene calcium

| | Crystal Form 1 | Crystal Form 2 | Crystal Form C3 | Gemcabene calcium salt ethanol solvate | Amorphous |
|---|---|---|---|---|---|
| Residual Solvent (GC) | Ethanol - 1100 ppm | Ethanol - 288 ppm | Ethanol - 76070 ppm | Ethanol - 28628 ppm t-Butyl methyl ether - 511 ppm | N/A |
| Moisture Content (KF) | Average 3.5% w/w | Average 3.1% w/w | Average 2.1% w/w | N/A | Average 2.6% w/w |
| % Gemcabene[1] (HPLC/CAD) | 87.52% (w/w %) | 89.57% (w/w %) | 83.98% (w/w %) | 90.51% (w/w %) | 88.85% (w/w %) |
| Particle Size (PSD) | D10 = 8.9 μm D50 = 24.3 μm D90 = 44.1 μm | D10 = 5.0 μm D50 = 14.4 μm D90 = 38.2 μm | D10 = 8.8 μm D50 = 20.4 μm D90 = 44.3 μm | D10 = 3.3 μm D50 = 31.8 μm D90 = 85.0 μm | D10 = 5.2 μm D50 = 26.4 μm D90 = 60.3 μm |

[1]% Gemcabene indicates percent by weight which is attributed to gemcabene conjugate base component, which excludes the weight of calcium or water content.
TGA = thermogravimetric analysis;
DTA = differential thermal analysis;
DSC = differential scanning calorimetry;
GC = gas chromatography;
KF = Karl-Fisher;
HPLC/CAD = high -performance liquid chromatography with charged aerosol detector;
PSD = particle size distribution In some embodiments, a compound of the invention has a dissolution profile characterized by % dissolution value of at least 85% in 45 minutes or less in pH 5.0 potassium acetate buffer at 37° C.±5° C. as measured by high-performance liquid chromatography using a detection wavelength of 210 nm. In some embodiments, a compound of the invention has a dissolution profile characterized by % dissolution value of at least 90% gemcabene in 45 minutes or less in pH 5.0 potassium acetate buffer at 37° C.±5° C. as measured by high-performance liquid chromatography using a detection wavelength of 210 nm.

In some embodiments, a compound of the invention has a dissolution profile characterized by % dissolution value of, at least 70%, at least 71%, at least 72%, at least 73%, at least 74%, or at least 75%, or a value ranging from and to any of these percentages, in 30 minutes or less in pH 5.0 potassium acetate buffer at 37° C.±5° C. as measured by high-performance liquid chromatography using a detection wavelength of 210 nm.

In some embodiments, a compound of the invention comprises an amorphous form or a crystalline form of gemcabene or a pharmaceutically acceptable salt thereof having a dissolution profile comprising a value of (1) at least 80% in pH 5.0 potassium acetate buffer at 37° C.±5° C. in no more than 45 minutes as measured by high-performance liquid chromatography using a detection wavelength of 210 nm and (2) at least 70% in pH 5.0 potassium acetate buffer at 37° C.±5° C. in no more than 30 minutes as measured by high-performance liquid chromatography using a detection wavelength of 210 nm.

The present invention further provides a pharmaceutically acceptable salt of gemcabene, the pharmaceutically acceptable salt having (a) a PSD90 ranging from 40 μm to about 75 μm as measured by laser light diffraction and (b) a dissolution profile characterized by a % dissolution value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm.

In some embodiments, the dissolution profile is measured using the composition of the invention. In some embodiments, the dissolution profile of a compound of the invention is measured using a composition of the invention that is in the form of a tablet. In some embodiments, the tablet is a compressed tablet. In some embodiment, the compressed tablet is a film-coated compressed tablet.

In some embodiments, the dissolution profile of a compound of the invention is measured using a composition of the invention that is in the form of a capsule.

Water and Ethanol Contents

In some embodiments, the compound of the invention has a water content of about 1% w/w to about 6% w/w of the compound of the invention. In some embodiments, the compound of the invention has a water content of about 2% w/w to about 5% w/w of the compound of the invention. In some embodiments, the water content of the compound of the invention is about 2% w/w to about 5%, about 2% w/w to about 4% w/w, about 3% w/w to about 5% w/w, or about 3% w/w to about 4% w/w of the compound of the invention, or a value ranging from and to any of these percent by weight values. In some embodiments, the water content of the compound of the invention is about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, or about 5.0% by weight of the compound of the invention. In other embodiments, the water content of the compound of the invention is about 3.4%, about 3.5%, about 3.6%, or about 3.7% by weight of the compound of the invention.

In some embodiments, the compound of the invention has an ethanol content of about 0% w/w to about 0.5% w/w of the compound of the invention. In some embodiments, the ethanol content of the compound of the invention is about 0.0%, about 0.1%, about 0.2%, about 0.3%, about 0.4%, or about 0.5% by weight of the compound of the invention.

In some embodiments, a compound of the invention has an ethanol content that is less than about 5000 ppm of the compound of the invention. In some embodiments, a compound of the invention has an ethanol content that is less than about 4000 ppm of the compound of the invention. In some embodiments, a compound of the invention has an ethanol content that is less than about 3000 ppm of the compound of the invention. In some embodiments, a compound of the invention has an ethanol content that is less than about 2000 ppm of the compound of the invention. In some embodiments, the ethanol content is less than about 500 ppm, less than about 600 ppm, less than about 700 ppm, less than about 800 ppm, less than about 900 ppm, less than about 1000 ppm, less than about 1100 ppm, less than about 1200 ppm, less than about 1300 ppm, less than about 1400 ppm, less than about 1500 ppm, less than about 1600 ppm, less than about 1700 ppm, less than about 1800 ppm, less than about 1900 ppm, or less than about 2000 ppm, of the compound of the invention.

In some embodiments, the compound of the invention has an ethanol content of about 0.5% w/w to about 8% w/w of the compound of the invention. In some embodiment, the compound of the invention is an ethanol solvate having an ethanol content of about 0.5% w/w to about 8% w/w of the compound of the invention. In some embodiments, the ethanol content of the compound of the invention is about 0.5%, about 0.6%, about 0.7%, about 0.8%, about 0.9%, about 1.0% by, about 1.1%, about 1.2%, about 1.3%, about 1.4%, about 1.5%, about 1.6%, about 1.7%, about 1.8%, about 1.9%, 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, or about 8.0%, weight of the compound of the invention.

In some embodiments, a compound of the invention has an ethanol content is about 20,000 ppm to about 40,000 ppm of the compound of the invention. In some embodiments, a compound of the invention is an ethanol solvate having an ethanol content is about 20,000 ppm to about 40,000 ppm of the compound of the invention. In some embodiments, a compound of the invention has an ethanol content that is about 20,000 ppm, about 21,000 ppm, about 22,000 ppm, about 23,000 ppm, about 24,000 ppm, about 25,000 ppm, about 26,000 ppm, about 27,000 ppm, about 28,000 ppm, about 29,000 ppm, about 30,000 ppm, about 31,000 ppm, about 32,000 ppm, about 33,000 ppm, about 34,000 ppm, about 35,000 ppm, about 36,000 ppm, about 37,000 ppm, about 38,000 ppm, about 39,000 ppm, about 40,000 ppm of the compound of the invention. In some embodiments, a compound of the invention has an ethanol content that is about 28,000 ppm, about 28,100 ppm, about 28,200 ppm, about 28,300 ppm, about 28,400 ppm, about 28,500 ppm, about 28,600 ppm, about 28,700 ppm, about 28,800 ppm, or about 28,900 ppm of the compound of the invention.

Pharmacokinetics

In some embodiments, a steady state plasma concentration of gemcabene in a subject is achieved within about 5-20 days following the start of repeated dose administration of the compound of the invention or following increase in daily dosing of the compound of the invention. In some embodiments, a steady state plasma concentration of gemcabene in a subject is achieved within about 14 days following the start of repeated dose administration of the compound of the invention or following increase in daily dosing of the compound of the invention. In some embodiments, the steady state is achieved within 5, 6, 7, 8, 9, 10, 11, 12, 13, 14, or 15 days following the start of daily administration of the compound of the invention at a dose of about 50 mg/day to about 900 mg/day or following the increase in daily dose of the compound of the invention to a dose of about 50 mg/day to about 900 mg/day.

The present invention provides compounds of the invention having a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm, and providing a plasma gemcabene $AUC_{(0-24)}$ ranging from about 200 μg·hr/mL at steady state to about 6000 μg·hr/mL at steady state when administered to a human subject at a dose of about 50 mg/day to about 900 mg/day.

The present invention provides pharmaceutically acceptable salts of gemcabene, the pharmaceutically acceptable salts having (a) a particle size distribution characterized by a PSD90 ranging from 40 μm to about 75 μm as measured by laser light diffraction (b) a dissolution profile characterized by a % dissolution value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm; and providing a plasma gemcabene $AUC_{(0-24)}$ ranging from about 200 μg·hr/mL at steady state to about 6000 μg·hr/mL at steady state when administered to a human subject at a dose of about 50 mg to about 900 mg.

In some embodiments, the compound of the invention provides a plasma gemcabene $AUC_{(0-24)}$ ranging from about 200 μg·hr/mL at steady state to about 6000 μg·hr/mL at steady state when administered to a human subject at a dose of about 50 mg/day to about 900 mg/day. In some embodiments, the compound of the invention provides a plasma gemcabene $AUC_{(0-24)}$ ranging from about 250 μg·hr/mL at steady state to about 6000 μg·hr/mL at steady state when administered to a human subject at a dose of about 50 mg/day to about 900 mg/day. In some embodiments, the compound of the invention provides a plasma gemcabene $AUC_{(0-24)}$ ranging from about 250 μg·hr/mL at steady state to about 5750 μg·hr/mL at steady state when administered to a human subject at a dose of about 50 mg/day to about 900 mg/day. In some embodiments, the compound of the invention provides a plasma gemcabene $AUC_{(0-24)}$ ranging from about 300 μg·hr/mL at steady state to about 5500 μg·hr/mL at steady state when administered to a human subject at a dose of about 50 mg/day to about 900 mg/day.

In some embodiments, the compound of the invention provides a plasma gemcabene $AUC_{(0-24)}$ ranging from 200 μg·hr/mL at steady state to 6000 μg·hr/mL at steady state when administered to a human subject in an amount that is molar equivalent to about 50 mg of gemcabene per day to about 900 mg of gemcabene per day. In some embodiments, the compound of the invention provides a plasma gemcabene $AUC_{(0-24)}$ ranging from 250 μg·hr/mL at steady state to 6000 μg·hr/mL at steady state when administered to a human subject in an amount that is molar equivalent to about 50 mg of gemcabene per day to about 900 mg of gemcabene per day. In some embodiments, the compound of the invention provides a plasma gemcabene $AUC_{(0-24)}$ ranging from 250 μg·hr/mL at steady state to 5750 μg·hr/mL at steady state when administered to a human subject in an amount that is molar equivalent to about 50 mg of gemcabene per day to about 900 mg of gemcabene per day. In some embodiments, the compound of the invention provides a plasma gemcabene $AUC_{(0-24)}$ ranging from 300 μg·hr/mL at steady state to 5500 μg·hr/mL at steady state when administered to a human subject in an amount that is molar equivalent to about 50 mg of gemcabene per day to about 900 mg of gemcabene per day.

In some embodiments, the compound of the invention provides a plasma gemcabene $AUC_{(0-24)}$ of about 200 μg·hr/mL, about 250 μg·hr/mL, about 300 μg·hr/mL, about 350 μg·hr/mL, about 400 μg·hr/mL, about 450 μg·hr/mL, about 500 μg·hr/mL, about 550 μg·hr/mL, about 600 μg·hr/mL, about 650 μg·hr/mL, about 700 μg·hr/mL, about 750 μg·hr/mL, about 800 μg·hr/mL, about 850 μg·hr/mL, about 900 μg·hr/mL, about 950 μg·hr/mL, about 1000 μg·hr/mL, about 1100 μg·hr/mL, about 1200 μg·hr/mL, about 1300 μg·hr/mL, about 1400 μg·hr/mL, about 1500 μg·hr/mL, about 1600 μg·hr/mL, about 1700 μg·hr/mL, about 1800 μg·hr/mL, about 1900 μg·hr/mL, about 2000 μg·hr/mL, about 2100 μg·hr/mL, about 2200 μg·hr/mL, about 2300 μg·hr/mL, about 2400 μg·hr/mL, about 2500 μg·hr/mL, about 2600 μg·hr/mL, about 2700 μg·hr/mL, about 2800 μg·hr/mL, about 2900 μg·hr/mL, about 3000 μg·hr/mL, about 3100 μg·hr/mL, about 3200 μg·hr/mL, about 3300 μg·hr/mL, about 3400 μg·hr/mL, about 3500 μg·hr/mL, about 3600 μg·hr/mL, about 3700 μg·hr/mL, about 3800 μg·hr/mL, about 3900 μg·hr/mL, about 4000 μg·hr/mL, about 4100 μg·hr/mL, about 4200 μg·hr/mL, about 4300 μg·hr/mL, about 4400 μg·hr/mL, about 4500 μg·hr/mL, about 4600 μg·hr/mL, about 4700 μg·hr/mL, about 4800 μg·hr/mL, about 4900 μg·hr/mL, about 5000 μg·hr/mL, about 5100 μg·hr/mL, about 5200 μg·hr/mL, about 5300 μg·hr/mL, about 5400 μg·hr/mL, about 5500 μg·hr/mL, about 5600 μg·hr/mL, about 5700 μg·hr/mL, about 5800 μg·hr/mL, about 5900 μg·hr/mL, or about 6000 μg·hr/mL at steady state when administered to a human subject at a dose of about 50 mg/day to about 900 mg/day, or when administered to a human subject in an amount that is molar equivalent to about 50 mg of gemcabene per day to about 900 mg gemcabene per day.

In some embodiments, the compound of the invention provides a plasma gemcabene $AUC_{(0-24)}$ ranging from about 200 μg·hr/mL at steady state to about 6000 μg·hr/mL at steady state or from about 250 μg·hr/mL at steady state to about 6000 μg·hr/mL at steady state when administered to a human subject at a dose of about 50 mg/day, about 60 mg/day, about 70 mg/day, about 80 mg/day, about 90 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day, about 200 mg/day, about 210 mg/day, about 220 mg/day, about 230 mg/day, about 240 mg/day, about 250 mg/day, about 260 mg/day, about 270 mg/day, about 280 mg/day, about 290 mg/day, 300 mg/day, about 310 mg/day, about 320 mg/day, about 330 mg/day, about 340 mg/day, about 350 mg/day, about 360 mg/day, about 370 mg/day, about 380 mg/day, about 390 mg/day, 400 mg/day, about 410 mg/day, about 420 mg/day, about 430 mg/day, about 440 mg/day, about 450 mg/day, about 460 mg/day, about 470 mg/day, about 480 mg/day, about 490 mg/day, 500 mg/day, about 510 mg/day, about 520 mg/day, about 530 mg/day, about 540 mg/day, about 550 mg/day, about 560 mg/day, about 570 mg/day, about 580 mg/day, about 590 mg/day, 600 mg/day, about 610 mg/day, about 620 mg/day, about 630 mg/day, about 640 mg/day, about 650 mg/day, about 660 mg/day, about 670 mg/day, about 680 mg/day, about 690 mg/day, 700 mg/day, about 710 mg/day, about 720 mg/day, about 730 mg/day, about 740 mg/day, about 750 mg/day, about 760 mg/day, about 770 mg/day, about 780 mg/day, about 790 mg/day, 800 mg/day, about 810 mg/day, about 820 mg/day, about 830 mg/day, about 840 mg/day, about 850 mg/day, about 860 mg/day, about 870 mg/day, about 880 mg/day, about 890 mg/day, or about 900 mg/day.

In some embodiments, the compound of the invention provides a plasma gemcabene $AUC_{(0-24)}$ ranging from 200 μg·hr/mL at steady state to 6000 μg·hr/mL at steady state or from 250 μg·hr/mL at steady state to 6000 μg·hr/mL at steady state when administered to a human subject in an amount that is molar equivalent to about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, 300 mg, about 310 mg, about 320 mg, about 330 mg, about 340 mg, about 350 mg, about 360 mg, about 370 mg, about 380 mg, about 390 mg, 400 mg, about 410 mg, about 420 mg, about 430 mg, about 440 mg, about 450 mg, about 460 mg, about 470 mg, about 480 mg, about 490 mg, 500 mg, about 510 mg, about 520 mg, about 530 mg, about 540 mg, about 550 mg, about 560 mg, about 570 mg, about 580 mg, about 590 mg, 600 mg, about 610 mg, about 620 mg, about 630 mg, about 640 mg, about 650 mg, about 660 mg, about 670 mg, about 680 mg, about 690 mg, 700 mg, about 710 mg, about 720 mg, about 730 mg, about 740 mg, about 750 mg, about 760 mg, about 770 mg, about 780 mg, about 790 mg, 800 mg, about 810 mg, about 820 mg, about 830 mg, about 840 mg, about 850 mg, about 860 mg, about 870 mg, about 880 mg, about 890 mg, or about 900 mg of gemcabene per day.

In some embodiments, the compound of the invention provides a plasma gemcabene $AUC_{(0-24)}$ ranging from about 200 μg·hr/mL at steady state to about 1000 μg·hr/mL at steady state when administered to a human subject at a dose of about 50 mg/day or in an amount that is molar equivalent to about 50 mg of gemcabene per day. In some embodiments, the compound of the invention provides a plasma gemcabene $AUC_{(0-24)}$ ranging from about 200 μg·hr/mL at steady state to about 500 μg·hr/mL at steady state when administered to a human subject at a dose of about 50 mg/day or in an amount that is molar equivalent to about 50 mg of gemcabene per day.

In some embodiments, the compound of the invention provides a plasma gemcabene $AUC_{(0-24)}$ ranging from about 300 μg·hr/mL at steady state to about 1500 μg·hr/mL at steady state when administered to a human subject at a dose of about 150 mg/day or in an amount that is molar equivalent to about 150 mg of gemcabene per day. In some embodiments, the compound of the invention provides a plasma gemcabene $AUC_{(0-24)}$ ranging from about 500 μg·hr/mL at steady state to about 1200 μg·hr/mL at steady state when administered to a human subject at a dose of about 150 mg/day or in an amount that is molar equivalent to about 150 mg of gemcabene per day.

In some embodiments, the compound of the invention provides a plasma gemcabene $AUC_{(0-24)}$ ranging from about 500 μg·hr/mL at steady state to about 2500 μg·hr/mL at steady state when administered to a human subject at a dose of about 300 mg/day or in an amount that is molar equivalent to about 300 mg of gemcabene per day. In some embodiments, the compound of the invention provides a plasma gemcabene $AUC_{(0-24)}$ ranging from about 1000 μg·hr/mL at steady state to about 2000 μg·hr/mL at steady state when administered to a human subject at a dose of about 300 mg/day or in an amount that is molar equivalent to about 300 mg of gemcabene per day.

In some embodiments, the compound of the invention provides a plasma gemcabene $AUC_{(0-24)}$ ranging from about 750 μg·hr/mL at steady state to about 3250 μg·hr/mL at steady state when administered to a human subject at a dose of about 450 mg/day or in an amount that is molar equivalent to about 450 mg of gemcabene per day. In some embodiments, the compound of the invention provides a plasma gemcabene $AUC_{(0-24)}$ ranging from about 1250 μg·hr/mL at steady state to about 3000 μg·hr/mL at steady state when administered to a human subject at a dose of about 450 mg/day or in an amount that is molar equivalent to about 450 mg of gemcabene per day.

In some embodiments, the compound of the invention provides a plasma gemcabene $AUC_{(0-24)}$ ranging from about 1500 μg·hr/mL at steady state to about 5000 μg·hr/mL at steady state when administered to a human subject at a dose of about 600 mg/day or in an amount that is molar equivalent to about 600 mg of gemcabene per day. In some embodiments, the compound of the invention provides a plasma gemcabene $AUC_{(0-24)}$ ranging from about 1500 μg·hr/mL at steady state to about 4500 μg·hr/mL at steady state when administered to a human subject at a dose of about 600 mg/day or in an amount that is molar equivalent to about 600 mg of gemcabene per day. In some embodiments, the compound of the invention provides a plasma gemcabene $AUC_{(0-24)}$ ranging from 2000 μg·hr/mL at steady state to 4000 μg·hr/mL at steady state when administered to a human subject at a dose of about 600 mg/day or in an amount that is molar equivalent to about 600 mg of gemcabene per day.

In some embodiments, the compound of the invention provides a plasma gemcabene $AUC_{(0-24)}$ ranging from about 3000 μg·hr/mL at steady state to about 6000 μg·hr/mL at steady state when administered to a human subject at a dose of about 900 mg/day or in an amount that is molar equivalent to about 900 mg of gemcabene per day. In some embodiments, the compound of the invention provides a plasma gemcabene $AUC_{(0-24)}$ ranging from 3250 μg·hr/mL at steady state to about 5750 μg·hr/mL at steady state when administered to a human subject at a dose of about 900 mg/day or in an amount that is molar equivalent to about 900 mg of gemcabene per day.

In some embodiments, the compound of the invention provides a plasma gemcabene $AUC_{(0-24)}$ ranging from about 500 μg·hr/mL at steady state to about 6000 μg·hr/mL at steady state when administered to a human subject at a dose ranging from about 300 mg/day to about 900 mg/day or in an amount that is molar equivalent in a range from about 300 mg to about 900 mg of gemcabene per day. In some embodiments, the compound of the invention provides a plasma gemcabene $AUC_{(0-24)}$ ranging from about 1500 μg·hr/mL at steady state to about 5250 μg·hr/mL at steady state when administered to a human subject at a dose ranging from about 450 mg/day to about 750 mg/day or in an amount that is molar equivalent in a range from about 450 mg to about 750 mg of gemcabene per day. In some embodiments, the compound of the invention provides a plasma gemcabene $AUC_{(0-24)}$ ranging from about 1500 μg·hr/mL at steady state to about 5250 μg·hr/mL at steady state when administered to a human subject at a dose ranging from about 500 mg/day to about 700 mg/day or in an amount that is molar equivalent in a range from about 500 mg to about 700 mg of gemcabene per day.

The present invention provides compounds of the invention having a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm, and providing a plasma gemcabene $AUC_{last}$ ranging from about 50 μg·hr/mL to about 7500 μg·hr/mL after a single dose administration of about 50 mg to about 900 mg to a human subject.

The present invention provides a pharmaceutically acceptable salt of gemcabene, the pharmaceutically acceptable salt having (a) a PSD90 ranging from 40 μm to about 75 μm as measured by laser light diffraction and (b) a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm, and providing a plasma gemcabene $AUC_{last}$ ranging from about 50 μg·hr/mL to about 7500 μg·hr/mL after a single dose administration of about 50 mg to about 900 mg to a human subject.

In some embodiments, the compound of the invention provides a plasma gemcabene $AUC_{last}$ ranging from about 50 μg·hr/mL to about 7500 μg·hr/mL after a single dose administration of about 50 mg to about 900 mg. In some embodiments, the compound of the invention provides a plasma gemcabene $AUC_{last}$ ranging from about 150 μg·hr/mL to about 5750 μg·hr/mL after a single dose administration of about 50 mg to about 900 mg. In some embodiments, the compound of the invention provides a plasma gemcabene $AUC_{last}$ ranging from about 400 μg·hr/mL to about 5500 μg·hr/mL after a single dose administration of about 50 mg to about 900 mg. In some embodiments, the compound of the invention provides a plasma gemcabene $AUC_{last}$ ranging from about 500 μg·hr/mL to about 5250 μg·hr/mL after a single dose administration of about 50 mg to about 900 mg.

In another embodiment, the compound of the invention provides a plasma gemcabene $AUC_{last}$ ranging from about 50 μg·hr/mL to about 7500 μg·hr/mL after a single dose administration of the compound of the invention in an amount that is molar equivalent to about 50 mg of gemcabene to about 900 mg of gemcabene. In another embodiment, the compound of the invention provides a plasma gemcabene $AUC_{last}$ ranging from about 150 μg·hr/mL to about 5750 μg·hr/mL after a single dose administration of the compound of the invention in an amount that is molar equivalent to about 50 mg of gemcabene to about 900 mg of gemcabene. In another embodiment, the compound of the invention provides a plasma gemcabene $AUC_{last}$ ranging from about 400 μg·hr/mL to about 5500 μg·hr/mL after a single dose administration of the compound of the invention in an amount that is molar equivalent to about 50 mg of gemcabene to about 900 mg of gemcabene. In another embodiment, the compound of the invention provides a plasma gemcabene $AUC_{last}$ ranging from about 500 μg·hr/mL to about 5250 μg·hr/mL after a single dose administration of the compound of the invention in an amount that is molar equivalent to about 50 mg of gemcabene to about 900 mg of gemcabene. In another embodiment, the compound of the invention provides a plasma gemcabene $AUC_{last}$ ranging from about 500 μg·hr/mL to about 5500 μg·hr/mL after a single dose administration of the compound of the invention in an amount that is molar equivalent to about 50 mg of gemcabene to about 900 mg of gemcabene.

In some embodiments, the compound of the invention provides a plasma gemcabene $AUC_{last}$ of about 50 μg·hr/mL, about 100 μg·hr/mL, about 150 μg·hr/mL, about 200 μg·hr/mL, about 250 μg·hr/mL, about 300 μg·hr/mL, about 350 μg·hr/mL, about 400 μg·hr/mL, about 450 μg·hr/mL, about 500 μg·hr/mL, about 550 μg·hr/mL, about 600 μg·hr/mL, about 650 μg·hr/mL, about 700 μg·hr/mL, about 750 μg·hr/mL, about 800 μg·hr/mL, about 850 μg·hr/mL, about 900 μg·hr/mL, about 950 μg·hr/mL, about 1000 μg·hr/mL, about 1100 μg·hr/mL, about 1200 μg·hr/mL, about 1300 μg·hr/mL, about 1400 μg·hr/mL, about 1500 μg·hr/mL, about 1600 μg·hr/mL, about 1700 μg·hr/mL, about 1800 μg·hr/mL, about 1900 μg·hr/mL, about 2000 μg·hr/mL, about 2100 μg·hr/mL, about 2200 μg·hr/mL, about 2300 μg·hr/mL, about 2400 μg·hr/mL, about 2500 μg·hr/mL, about 2600 μg·hr/mL, about 2700 μg·hr/mL, about 2800 μg·hr/mL, about 2900 μg·hr/mL, about 3000 μg·hr/mL, about 3100 μg·hr/mL, about 3200 μg·hr/mL, about 3300 μg·hr/mL, about 3400 μg·hr/mL, about 3500 μg·hr/mL, about 3600 μg·hr/mL, about 3700 μg·hr/mL, about 3800 μg·hr/mL, about 3900 μg·hr/mL, about 4000 μg·hr/mL, about 4100 μg·hr/mL, about 4200 μg·hr/mL, about 4300 μg·hr/mL, about 4400 μg·hr/mL, about 4500 μg·hr/mL, about 4600 μg·hr/mL, about 4700 μg·hr/mL, about 4800 μg·hr/mL, about 4900 μg·hr/mL, about 5000 μg·hr/mL, about 5100 μg·hr/mL, about 5200 μg·hr/mL, about 5300 μg·hr/mL, about 5400 μg·hr/mL, about 5500 μg·hr/mL, about 5600 μg·hr/mL, about 5700 μg·hr/mL, about 5800 μg·hr/mL, about 5900 μg·hr/mL, about 6000 μg·hr/mL, about 6100 μg·hr/mL, about 6200 μg·hr/mL, about 6300 μg·hr/mL, about 6400 μg·hr/mL, about 6500 μg·hr/mL, about 6600 μg·hr/mL, about 6700 μg·hr/mL, about 6800 μg·hr/mL, about 8900 μg·hr/mL, about 7000 μg·hr/mL, about 7100 μg·hr/mL, about 7200 μg·hr/mL, about 7300 μg·hr/mL, about 7400 μg·hr/mL, about 7500 μg·hr/mL, after a single dose administration of about 50 mg to about 900 mg, or after single administration of the compound of the present invention in an amount that is molar equivalent to about 50 mg of gemcabene to about 900 mg gemcabene.

In some embodiments, the compound of the invention provides a plasma gemcabene $AUC_{last}$ ranging from about 50 μg·hr/mL to about 7500 μg·hr/mL after a single administration of about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, 300 mg, about 310 mg, about 320 mg, about 330 mg, about 340 mg, about 350 mg, about 360 mg, about 370 mg, about 380 mg, about 390 mg, 400 mg, about 410 mg, about 420 mg, about 430 mg, about 440 mg, about 450 mg, about 460 mg, about 470 mg, about 480 mg, about 490 mg, 500 mg, about 510 mg, about 520 mg, about 530 mg, about 540 mg, about 550 mg, about 560 mg, about 570 mg, about 580 mg, about 590 mg, 600 mg, about 610 mg, about 620 mg, about 630 mg, about 640 mg, about 650 mg, about 660 mg, about 670 mg, about 680 mg, about 690 mg, 700 mg, about 710 mg, about 720 mg, about 730 mg, about 740 mg, about 750 mg, about 760 mg, about 770 mg, about 780 mg, about 790 mg, 800 mg, about 810 mg, about 820 mg, about 830 mg, about 840 mg, about 850 mg, about 860 mg, about 870 mg, about 880 mg, about 890 mg, or about 900 mg.

In some embodiments, the compound of the invention provides a plasma gemcabene $AUC_{last}$ ranging from about 50 μg·hr/mL to about 7500 μg·hr/mL after a single administration of the compound of the invention in an amount that is molar equivalent to about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, 300 mg, about 310 mg, about 320 mg, about 330 mg, about 340 mg, about 350 mg, about 360 mg, about 370 mg, about 380 mg, about 390 mg, 400 mg, about 410 mg, about 420 mg, about 430 mg, about 440 mg, about 450 mg, about 460 mg, about 470 mg, about 480 mg, about 490 mg, 500 mg, about 510 mg, about 520 mg, about 530 mg, about 540 mg, about 550 mg, about 560 mg, about 570 mg, about 580 mg, about 590 mg, 600 mg, about 610 mg, about 620 mg, about 630 mg, about 640 mg, about 650 mg, about 660 mg, about 670 mg, about 680 mg, about 690 mg, 700 mg, about 710 mg, about 720 mg, about 730 mg, about 740 mg, about 750 mg, about 760 mg, about 770 mg, about 780 mg, about 790 mg, 800 mg, about 810 mg, about 820 mg, about 830 mg, about 840 mg, about 850 mg, about 860 mg, about 870 mg, about 880 mg, about 890 mg, or about 900 mg of gemcabene.

In some embodiments, the compound of the invention provides a plasma gemcabene $AUC_{last}$ ranging from about 50 μg·hr/mL to about 750 μg·hr/mL after single administration to a human subject at a dose of about 50 mg or in an amount that is molar equivalent to about 50 mg of gemcabene. In some embodiments, the compound of the invention provides a plasma gemcabene $AUC_{last}$ ranging from about 100 μg·hr/mL to about 500 μg·hr/mL after single administration to a human subject at a dose of about 50 mg or in an amount that is molar equivalent to about 50 mg of gemcabene.

In some embodiments, the compound of the invention provides a plasma gemcabene $AUC_{last}$ ranging from about 100 μg·hr/mL to about 1250 μg·hr/mL after single dose administration to a human subject at a dose of about 150 mg or in an amount that is molar equivalent to about 150 mg of gemcabene. In some embodiments, the compound of the invention provides a plasma gemcabene $AUC_{last}$ ranging from about 200 μg·hr/mL to about 1000 μg·hr/mL after single dose administration to a human subject at a dose of about 150 mg or in an amount that is molar equivalent to about 150 mg of gemcabene.

In some embodiments, the compound of the invention provides a plasma gemcabene $AUC_{last}$ ranging from about 500 μg·hr/mL to about 2250 μg·hr/mL after single dose administration to a human subject at a dose of about 300 mg or in an amount that is molar equivalent to about 300 mg of gemcabene. In some embodiments, the compound of the invention provides a plasma gemcabene $AUC_{(0-24)}$ ranging from about 750 μg·hr/mL to about 2000 μg·hr/mL after single dose administration to a human subject at a dose of about 300 mg or in an amount that is molar equivalent to about 300 mg of gemcabene.

In some embodiments, the compound of the invention provides a plasma gemcabene $AUC_{last}$ ranging from about 1000 μg·hr/mL to about 4000 μg·hr/mL after single dose administration to a human subject at a dose of about 600 mg or in an amount that is molar equivalent to about 600 mg of gemcabene. In some embodiments, the compound of the invention provides a plasma gemcabene $AUC_{last}$ ranging from about 1500 μg·hr/mL to about 3500 μg·hr/mL after single dose administration to a human subject at a dose of about 600 mg or in an amount that is molar equivalent to about 600 mg of gemcabene. In some embodiments, the compound of the invention provides a plasma gemcabene $AUC_{last}$ ranging from about 1750 μg·hr/mL to about 3750 μg·hr/mL after single administration to a human subject at a dose of about 600 mg or in an amount that is molar equivalent to about 600 mg of gemcabene.

In some embodiments, the compound of the invention provides a plasma gemcabene $AUC_{last}$ ranging from about 2500 μg·hr/mL to about 6000 μg·hr/mL after single dose administration to a human subject at a dose of about 900 mg or in an amount that is molar equivalent to about 900 mg of gemcabene. In some embodiments, the compound of the invention provides a plasma gemcabene $AUC_{last}$ ranging from about 2750 μg·hr/mL to about 5500 μg·hr/mL after single dose administration to a human subject at a dose of about 900 mg or in an amount that is molar equivalent to about 900 mg of gemcabene.

In some embodiments, the compound of the invention provides a plasma gemcabene $AUC_{last}$ ranging from about 500 μg·hr/mL to about 5500 μg·hr/mL after single dose administration to a human subject at a dose of about 300 mg to about 900 mg or in an amount that is molar equivalent to about 300 mg to about 900 mg of gemcabene. In some embodiments, the compound of the invention provides a plasma gemcabene $AUC_{last}$ ranging from about 750 μg·hr/mL to about 5000 μg·hr/mL after single dose administration to a human subject at a dose of about 450 mg to about 750 mg or in an amount that is molar equivalent to about 450 mg to about 750 mg of gemcabene. In some embodiments, the compound of the invention provides a plasma gemcabene $AUC_{last}$ ranging from about 1000 μg·hr/mL to about 4500 μg·hr/mL after single dose administration to a human subject at a dose of about 500 mg to about 700 mg or in an amount that is molar equivalent to about 500 mg to about 700 mg of gemcabene.

In some embodiments, the compound of the invention provides reduction in a human subject's baseline plasma or blood serum low-density lipoprotein cholesterol (LDL-C) by about 1% to about 80% when administered to a human subject at a dose of about 50 mg/day to about 900 mg/day. In some embodiments, the compound of the invention provides reduction in a human subject's baseline plasma or blood serum LDL-C by about 5% to about 75% when administered to a human subject at a dose of about 50 mg/day to about 900 mg/day. In some embodiments, the compound of the invention provides reduction in a human subject's baseline plasma or blood serum LDL-C by about 10% to about 75% when administered to a human subject at a dose of about 50 mg/day to about 900 mg/day. In some embodiments, the compound of the invention provides reduction in a human subject's baseline plasma or blood serum LDL-C by about 15% to about 70% when administered to a human subject at a dose of about 50 mg/day to about 900 mg/day. In some embodiments, the compound of the invention provides reduction in a human subject's baseline plasma or blood serum LDL-C by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% when administered to a human subject at a dose of about 50 mg/day to about 900 mg/day.

In some embodiments, the compound of the invention provides reduction in a human subject's baseline plasma or blood serum LDL-C by at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, or at least about 80%, when administered to a human subject at a dose of about 50 mg/day to about 900 mg/day.

In some embodiments, the compound of the invention provides reduction in a human subject's baseline plasma or blood serum total cholesterol by about 1% to about 80%, including all subranges therein, when administered to a human subject at a dose of about 50 mg/day to about 900 mg/day.

In some embodiments, the compound of the invention provides reduction in a human subject's baseline plasma or blood serum LDL-C by about 1% to about 80% when administered to a human subject in an amount that is molar equivalent to about 50 mg to about 900 mg gemcabene per day. In some embodiments, the compound of the invention provides reduction in a human subject's baseline plasma or blood serum LDL-C by about 5% to about 75%, about 10% to about 75%, or about 15% to about 70%, when administered to a human subject in an amount that is molar equivalent to about 50 mg to about 900 mg gemcabene per day. In some embodiments, the compound of the invention provides reduction in a human subject's baseline plasma or blood serum LDL-C by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% when administered to a human subject in an amount that is molar equivalent to about 50 mg to about 900 mg gemcabene per day.

In some embodiments, the compound of the invention provides reduction in a human subject's baseline plasma or blood serum LDL-C by at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, or at least about 80%, when administered to a human subject in an amount that is molar equivalent to about 50 mg to about 900 mg gemcabene per day.

In some embodiments, the compound of the invention provides reduction in a human subject's baseline plasma or blood serum total cholesterol by about 1% to about 80%, all subranges therein, when administered to a human subject in an amount that is molar equivalent to about 50 mg to about 900 mg gemcabene per day.

In some embodiments, the compound of the invention provides reduction in a human subject's baseline plasma or blood serum LDL-C by about 1% to about 80% or by about 1% to about 75% when administered to a human subject in an amount that is molar equivalent to about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, 300 mg, about 310 mg, about 320 mg, about 330 mg, about 340 mg, about 350 mg, about 360 mg, about 370 mg, about 380 mg, about 390 mg, 400 mg, about 410 mg, about 420 mg, about 430 mg, about 440 mg, about 450 mg, about 460 mg, about 470 mg, about 480 mg, about 490 mg, 500 mg, about 510 mg, about 520 mg, about 530 mg, about 540 mg, about 550 mg, about 560 mg, about 570 mg, about 580 mg, about 590 mg, 600 mg, about 610 mg, about 620 mg, about 630 mg, about 640 mg, about 650 mg, about 660 mg, about 670 mg, about 680 mg, about 690 mg, 700 mg, about 710 mg, about 720 mg, about 730 mg, about 740 mg, about 750 mg, about 760 mg, about 770 mg, about 780 mg, about 790 mg, 800 mg, about 810 mg, about 820 mg, about 830 mg, about 840 mg, about 850 mg, about 860 mg, about 870 mg, about 880 mg, about 890 mg, 900 mg, about 910 mg, about 920 mg, about 930 mg, about 940 mg, about 950 mg, about 960 mg, about 970 mg, about 980 mg, about 990 mg, or about 1000 mg of gemcabene per day.

In some embodiments, the compound of the invention provides reduction in a human subject's baseline plasma or blood serum apolipoprotein B (Apo B) by about 1% to about 50% when administered to a human subject at a dose of about 50 mg/day to about 900 mg/day. In some embodiments, the compound of the invention provides reduction in a human subject's baseline plasma or blood serum Apo B by about 1% to about 40% when administered to a human subject at a dose of about 50 mg/day to about 900 mg/day. In some embodiments, the compound of the invention provides reduction in a human subject's baseline plasma or blood serum Apo B by about 1% to about 30% when administered to a human subject at a dose of about 50 mg/day to about 900 mg/day. In some embodiments, the compound of the invention provides reduction in a human subject's baseline plasma or blood serum Apo B by about 5% to about 30% when administered to a human subject at a dose of about 50 mg/day to about 900 mg/day. In some embodiments, the compound of the invention provides reduction in a human subject's baseline plasma or blood serum Apo B by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%, when administered to a human subject at a dose of about 50 mg/day to about 900 mg/day. In some embodiments, the compound of the invention provides reduction in a human subject's baseline plasma or blood serum Apo B by at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, or at least about 60%, when administered to a human subject at a dose of about 50 mg/day to about 900 mg/day.

In some embodiments, the compound of the invention provides reduction in a human subject's baseline plasma or blood serum Apo B by about 1% to about 50% when administered to a human subject in an amount that is molar equivalent to about 50 mg to about 900 mg gemcabene per day. In some embodiments, the compound of the invention provides reduction in a human subject's baseline plasma or blood serum Apo B by about 1% to about 40%, about 1% to about 30%, or about 5% to about 30%, when administered to a human subject in an amount that is molar equivalent to about 50 mg to about 900 mg gemcabene per day. In some embodiments, the compound of the invention provides reduction in a human subject's baseline plasma or blood serum Apo B by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%, when administered to a human subject in an amount that is molar equivalent to about 50 mg to about 900 mg gemcabene per day. In some embodiments, the compound of the invention provides reduction in a human subject's baseline plasma or blood serum Apo B by at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, or at least about 60%, when administered to a human subject in an amount that is molar equivalent to about 50 mg to about 900 mg gemcabene per day.

In some embodiments, the compound of the invention provides reduction in a human subject's baseline plasma or blood serum Apo B by about 1% to about 50% when administered to a human subject in an amount that is molar equivalent to about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, 300 mg, about 310 mg, about 320 mg, about 330 mg, about 340 mg, about 350 mg, about 360 mg, about 370 mg, about 380 mg, about 390 mg, 400 mg, about 410 mg, about 420 mg, about 430 mg, about 440 mg, about 450 mg, about 460 mg, about 470 mg, about 480 mg, about 490 mg, 500 mg, about 510 mg, about 520 mg, about 530 mg, about 540 mg, about 550 mg, about 560 mg, about 570 mg, about 580 mg, about 590 mg, 600 mg, about 610 mg, about 620 mg, about 630 mg, about 640 mg, about 650 mg, about 660 mg, about 670 mg, about 680 mg, about 690 mg, 700 mg, about 710 mg, about 720 mg, about 730 mg, about 740 mg, about 750 mg, about 760 mg, about 770 mg, about 780 mg, about 790 mg, 800 mg, about 810 mg, about 820 mg, about 830 mg, about 840 mg, about 850 mg, about 860 mg, about 870 mg, about 880 mg, about 890 mg, or about 900 mg of gemcabene per day.

In some embodiments, the present invention provides compounds of the invention having (a) an amorphous form or a crystalline form and (b) a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and providing a plasma gemcabene $AUC_{(0-24)}$ ranging from about 250 μg·hr/mL at steady state to about 6000 μg·hr/mL at steady state when administered to a human subject at a dose of about 50 mg/day to about 900 mg/day.

In some embodiments, the present invention provides pharmaceutical compositions comprising an amorphous form or a crystalline form of the compounds of the invention having a dissolution profile value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and providing a plasma gemcabene $AUC_{(0-24)}$ ranging from about 250 μg·hr/mL at steady state to about 6000 μg·hr/mL at steady state when administered to a human subject at a dose of about 50 mg/day to about 900 mg/day.

In some embodiments, the present invention provides compounds of the invention having (a) an amorphous form or a crystalline form and (b) a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and providing a plasma gemcabene $AUC_{(0-24)}$ ranging from 250 μg·hr/mL at steady state to 6000 μg·hr/mL at steady state when administered to a human subject at a dose of about 50 mg/day to about 900 mg/day.

In some embodiments, the present invention provides pharmaceutical compositions comprising an amorphous form or a crystalline form of the compounds of the invention having a dissolution profile value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C. f 5° C. in no more than 30 minutes as measured by high-performance liquid chromatography using a detection wavelength of 210 nm and providing a plasma gemcabene $AUC_{(0-24)}$ ranging from 250 µg·hr/mL at steady state to 6000 µg·hr/mL at steady state when administered to a human subject at a dose of about 50 mg/day to about 900 mg/day.

In some embodiments, the present invention provides compounds of the invention having an amorphous form or a crystalline form and providing a plasma gemcabene $AUC_{(0-24)}$ ranging from about 200 µg·hr/mL at steady state to about 6000 µg·hr/mL at steady state when administered to a human subject at a dose of about 50 mg/day to about 900 mg/day. In some embodiments, the present invention provides compounds of the invention having an amorphous form or a crystalline form and providing a plasma gemcabene $AUC_{(0-24)}$ ranging from 200 µg·hr/mL at steady state to 6000 µg·hr/mL at steady state when administered to a human subject at a dose of about 50 mg/day to about 900 mg/day.

In some embodiments, the present invention provides pharmaceutical compositions comprising an amorphous form or a crystalline form of the compounds of the invention providing a plasma gemcabene $AUC_{(0-24)}$ ranging from about 200 µg·hr/mL at steady state to about 6000 µg·hr/mL at steady state when administered to a human subject at a dose of about 50 mg/day to about 900 mg/day. In some embodiments, the present invention provides pharmaceutical compositions comprising an amorphous form or a crystalline form of the compounds of the invention providing a plasma gemcabene $AUC_{(0-24)}$ ranging from 200 µg·hr/mL at steady state to 6000 µg·hr/mL at steady state when administered to a human subject at a dose of about 50 mg/day to about 900 mg/day.

In some embodiments, the present invention provides compounds of the invention having an amorphous form or a crystalline form and providing a plasma gemcabene $AUC_{(0-24)}$ ranging from 250 µg·hr/mL at steady state to 6000 µg·hr/mL at steady state when administered to a human subject at a dose of about 50 mg/day to about 900 mg/day.

In some embodiments, the present invention provides pharmaceutical compositions comprising an amorphous form or a crystalline form of the compounds of the invention providing a plasma gemcabene $AUC_{(0-24)}$ ranging from 250 µg·hr/mL at steady state to 6000 µg·hr/mL at steady state when administered to a human subject at a dose of about 50 mg/day to about 900 mg/day.

In some embodiments, the present invention provides compounds of the invention having an amorphous form or a crystalline form and providing a plasma gemcabene $AUC_{(0-24)}$ ranging from about 250 µg·hr/mL at steady state to about 6000 µg·hr/mL at steady state when administered to a human subject at a dose of about 50 mg/day to about 900 mg/day.

In some embodiments, the present invention provides pharmaceutical compositions comprising an amorphous form or a crystalline form of the compounds of the invention providing a plasma gemcabene $AUC_{(0-24)}$ ranging from about 250 µg·hr/mL at steady state to about 6000 µg·hr/mL at steady state when administered to a human subject at a dose of about 50 mg/day to about 900 mg/day.

In some embodiments, the present invention provides amorphous or crystalline compounds of the invention having a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and providing a plasma gemcabene $AUC_{(0-24)}$ ranging from about 200 µg·hr/mL at steady state to about 6000 µg·hr/mL at steady state when administered to a human subject at a dose of about 50 mg/day to about 900 mg/day.

In some embodiments, the present invention provides pharmaceutical compositions comprising an amorphous form or a crystalline form of the compounds of the invention having a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and providing a plasma gemcabene $AUC_{(0-24)}$ ranging from about 200 µg·hr/mL at steady state to about 6000 µg·hr/mL at steady state when administered to a human subject at a dose of about 50 mg/day to about 900 mg/day.

In some embodiments, the present invention provides amorphous or crystalline compounds of the invention having a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and providing a plasma gemcabene $AUC_{(0-24)}$ ranging from 200 µg·hr/mL at steady state to 6000 µg·hr/mL at steady state when administered to a human subject at a dose of about 50 mg/day to about 900 mg/day.

In some embodiments, the present invention provides pharmaceutical compositions comprising an amorphous form or a crystalline form of the compounds of the invention having a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and providing a plasma gemcabene $AUC_{(0-24)}$ ranging from 200 µg·hr/mL at steady state to 6000 µg·hr/mL at steady state when administered to a human subject at a dose of about 50 mg/day to about 900 mg/day.

In some embodiments, the present invention provides amorphous or crystalline compounds of the invention having a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and providing a plasma gemcabene $AUC_{(0-24)}$ ranging from 250 µg·hr/mL at steady state to 6000

μg·hr/mL at steady state when administered to a human subject at a dose of about 50 mg/day to about 900 mg/day.

In some embodiments, the present invention provides pharmaceutical compositions comprising an amorphous form or a crystalline form of the compounds of the invention having a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and providing a plasma gemcabene $AUC_{(0-24)}$ ranging from 250 μg·hr/mL at steady state to 6000 μg·hr/mL at steady state when administered to a human subject at a dose of about 50 mg/day to about 900 mg/day.

In some embodiments, the present invention provides amorphous or crystalline compounds of the invention having a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and providing a plasma gemcabene $AUC_{(0-24)}$ ranging from about 250 μg·hr/mL at steady state to about 6000 μg·hr/mL at steady state when administered to a human subject at a dose of about 50 mg/day to about 900 mg/day.

In some embodiments, the present invention provides pharmaceutical compositions comprising an amorphous form or a crystalline form of the compounds of the invention having a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and providing a plasma gemcabene $AUC_{(0-24)}$ ranging from about 250 μg·hr/mL at steady state to about 6000 μg·hr/mL at steady state when administered to a human subject at a dose of about 50 mg/day to about 900 mg/day.

In some embodiments, the present invention provides compounds of the invention having (a) an amorphous form or a crystalline form and (b) a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and proving a plasma gemcabene $AUC_{last}$ ranging from about 50 μg·hr/mL to about 7500 μg·hr/mL after a single dose administration of about 50 mg to about 900 mg to a human subject.

In some embodiments, the present invention provides pharmaceutical compositions comprising an amorphous form or a crystalline form of the compounds of the invention having a dissolution profile having a value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm and proving a plasma gemcabene $AUC_{last}$ ranging from about 50 μg·hr/mL to about 7500 μg·hr/mL after a single dose administration of about 50 mg to about 900 mg to a human subject.

In some embodiments, the present invention provides compounds of the invention having an amorphous form or a crystalline form and providing a plasma gemcabene $AUC_{last}$ ranging from about 50 μg·hr/mL to about 7500 μg·hr/mL after a single dose administration of about 50 mg to about 900 mg to a human subject.

the present invention provides pharmaceutical compositions comprising an amorphous form or a crystalline form of the compounds of the invention providing a plasma gemcabene $AUC_{last}$ ranging from about 50 μg·hr/mL to about 7500 μg·hr/mL after a single dose administration of about 50 mg to about 900 mg to a human subject.

In some embodiments, an effective dose of the compound of the invention can be a dose that achieves ≥10% mean reduction in low-density lipoprotein cholesterol (LDL-C) after 4 weeks of treatment. In some embodiments, an effective dose of the compound of the invention can be a dose that achieves ≥15% mean reduction in LDL-C after 4 weeks of treatment. In some embodiments, an effective dose of the compound of the invention can be a dose that achieves ≥5%, ≥6%, ≥7%, ≥8%, ≥9%, ≥10%, ≥11%, ≥12%, ≥13%, ≥14%, or 15% mean reduction in LDL-C after 4 weeks of treatment. In some embodiments, an effective dose of the compound of the invention can be a dose that achieves ≥5%, ≥6%, ≥7%, ≥8%, ≥9%, ≥10%, ≥11%, ≥12%, ≥13%, ≥14%, or 15% mean reduction in LDL-C after 4 weeks of daily administration of the compound of the invention in about 50 mg to about 900 mg per day.

In some embodiments, the pharmacokinetic values and properties of a compound of the invention is measured with a composition of the invention that is in the form of a tablet. In some embodiments, the tablet is a compressed tablet. In some embodiment, the compressed tablet is a film-coated compressed tablet.

In some embodiments, the pharmacokinetic values and properties of a compound of the invention is measured using a composition of the invention that is in the form of a capsule.

In some embodiments, $AUC_{(0-24)}$ or $AUC_{last}$ of a compound of the invention is measured with a composition of the invention that is in the form of a tablet. In some embodiments, the tablet is a compressed tablet. In some embodiment, the compressed tablet is a film-coated compressed tablet.

In some embodiments, $AUC_{(0-24)}$ or $AUC_{last}$ of a compound of the invention is measured using a composition of the invention that is in the form of a capsule.

In some embodiments, the pharmacokinetic values and properties disclosed herein are in connection with a human subject.

Methods for Making Gemcabene

The present invention further provides methods for making gemcabene. Gemcabene is useful for making the compounds of the invention. Gemcabene or gemcabene calcium can be prepared by a synthetic process as shown in Scheme 1.

Scheme 1. Synthesis of Gemcabene or Gemcabene Calcium

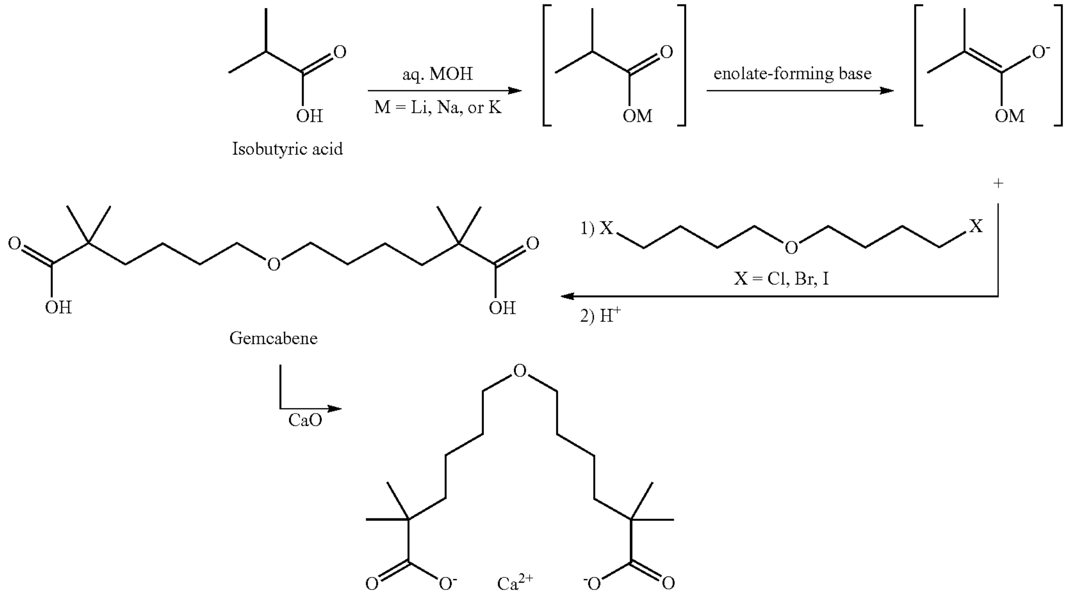

Isobutyric acid

Gemcabene

Gemcabene Calcium

Isobutyric acid is converted to an alkali metal salt. In some embodiments, isobutyric acid is converted to an alkali metal salt using an alkali metal hydroxide. In some embodiments, the alkali metal hydroxide is lithium hydroxide, sodium hydroxide or potassium hydroxide. In some embodiments, the alkali metal hydroxide is sodium hydroxide.

In some embodiments, the alkali metal hydroxide is lithium hydroxide, which converts isobutyric acid to lithium isobutyrate. In some embodiments, the alkali metal hydroxide is sodium hydroxide, which converts isobutyric acid to sodium isobutyrate. In some embodiments, the alkali metal hydroxide is potassium hydroxide, which converts isobutyric acid to potassium isobutyrate.

In some embodiments, the alkali metal hydroxide is present in an aqueous solution or suspension. In some embodiments, the alkali metal hydroxide is present in an about 30% (w/w) in aqueous solution.

In some embodiments, the alkali metal salt is sodium hydroxide. In some embodiments, the sodium hydroxide is present in an aqueous solution. In some embodiments, the aqueous solution of sodium hydroxide is 30% (w/w).

In some embodiments, isobutyric acid is converted to an alkali metal salt in the presence of an organic solvent. In some embodiments, the organic solvent is a hydrocarbon solvent. In some embodiments, the hydrocarbon solvent is benzene, toluene, xylene or an alkane. In some embodiments, the alkane is a $C_5$-$C_{12}$ alkane. In some embodiments, the alkane is pentane, hexane or heptane. In some embodiments, the alkane is n-pentane, n-hexane or n-heptane. In some embodiments, the alkane is n-heptane.

It is important to eliminate substantially all water from the reaction mixture comprising the isobutyrate alkali metal salt prior to proceeding to adding the enolate-forming base because the enolate-forming base can react with residual water. In some embodiments, water is removed by heterogeneous azeotropic distillation (composition in azeotrope: 12.9% water and 87.1% heptane; b.p. 79.2° C.) prior to adding the enolate-forming base. In some embodiments, heterogeneous azeotropic distillation of water is performed at about 100 to about 110° C. In some embodiments, heterogeneous azeotropic distillation of water is performed at about 105° C. In some embodiments, heterogeneous azeotropic distillation of water is performed at about 900 mbar to about 1100 mbar. In some embodiments, heterogeneous azeotropic distillation of water is performed at about 1000 mbar.

Prior to adding the enolate-forming base, to effectively remove substantially all water from the reaction mixture, the removal of water, for example, by heterogeneous azeotropic distillation, can be measured by volume. In other embodiments, Karl-Fisher analysis can be performed. In some embodiments, water, if any, present in the reaction mixture prior to the addition of the enolate-forming base is ≤0.05% w/w of the reaction mixture as determined by Karl-Fisher analysis. In some embodiments, water, if any, present in the reaction mixture prior to the addition of the enolate-forming base is 0.05% w/w or less, 0.04% w/w or less, 0.03% w/w or less, 0.02% w/w or less, 0.015% w/w or less, 0.0125% w/w or less, or 0.01% w/w or less of the reaction mixture as determined by Karl-Fisher analysis. In some embodiments, water, if any, present in the reaction mixture prior to the addition of the enolate-forming base is less than 0.05% w/w, less than 0.04% w/w, less than 0.03% w/w, less than 0.02% w/w, less than 0.015% w/w, less than 0.0125% w/w, or less than 0.01% w/w of the reaction mixture as determined by Karl-Fisher analysis.

In some embodiments, the alkali metal salt of isobutyric acid is converted to an enolate using an enolate-forming base. In some embodiments, the enolate-forming base is lithium hexamethyldisilazide, lithium diisopropylamide (LDA), lithium tetramethylpiperidide (LiTMP), or lithium diethylamide ($LiNEt_2$). In some embodiments, the enolate-forming base is LDA and is prepared in situ using diisopropylamine and an organolithium reagent, such as n-butyllithium, n-hexyllithium or n-heptyllithium. In some embodiments, the enolate-forming base is generated in an aprotic solvent. In some embodiments, the enolate-forming base is obtained commercially and is present in an aprotic solvent. In some embodiments, the enolate-forming base is generated in THF or solvent mixture comprising THF. In some embodiments, the enolate-forming base is in THF or solvent mixture comprising THF.

In some embodiments, the LDA is pre-made and obtained commercially, particularly in view of organolithium reagents' highly pyrogenic properties. In some embodiments, the LDA is pre-made. In some embodiments, the pre-made LDA is present in solution. In some embodiments, the pre-made LDA solution is about 25% w/w to about 30% w/w LDA. In some embodiments, the LDA is 28% w/w in heptane/THF/ethylbenzene. In some embodiments, the pre-made LDA is present in solution. In some embodiments, the pre-made LDA solution is about 1.5M to about 2.5M. In some embodiments, the LDA is 2.0 M to 2.2M in heptane/THF/ethylbenzene. In some embodiments, the addition of the enolate-forming base is performed under anhydrous conditions. In some embodiments, the addition of the enolate-forming base is performed under substantially anhydrous conditions. In some embodiments, the addition of the enolate-forming base is performed under conditions where the water content is ≤0.05% w/w of the reaction mixture as determined by Karl-Fisher analysis.

In some embodiments, the enolate-forming base is admixed with the alkali metal salt of isobutyric acid to provide an enolate of the alkali metal salt of isobutyric acid. The enolate-forming base can be added to the alkali metal salt of isobutyric acid, or vice versa. In some embodiments, the enolate-forming base is LDA, the alkali metal salt of isobutyric acid is sodium isobutyrate and the LDA is added to the sodium isobutyrate. In some embodiments, the enolate-forming base and the alkali metal salt of isobutyric acid are admixed at a temperature ranging from about 10° C. to about 15° C. In some embodiments, after the enolate-forming base and the alkali metal salt of isobutyric acid are admixed, the reaction mixture is heated at 42° C.±2° C. In some embodiments, the reaction mixture is heated at 42° C.±2° C. for about 30 minutes to 2 hours. In some embodiments, the reaction mixture is heated at 42° C.±2° C. for about 1 hour. In some embodiments, the enolate-forming base and the alkali metal salt of isobutyric acid are admixed in the presence of heptane, tetrahydrofuran (THF), or combination thereof. In some embodiments, the enolate-forming base and the alkali metal salt of isobutyric acid are admixed in the presence of n-heptane, tetrahydrofuran (THF), or combination thereof.

The enolate of the alkali metal salt of isobutyric acid is admixed with a bis-(4-halobutyl)ether. The enolate can be added to the bis-(4-halobutyl)ether, or vice versa. In some embodiments, the bis-(4-halobutyl)ether is bis-(4-chlorobutyl)ether; in some embodiments, the bis-(4-halobutyl) ether is bis-(4-bromobutyl)ether; and in some embodiments, the bis-(4-halobutyl)ether is bis-(4-iodobutyl)ether.

In some embodiments, about two equivalents of the enolate of the alkali metal salt of isobutyric acid are admixed with a bis-(4-halobutyl)ether. In some embodiments, about two to about three equivalents of the enolate of the alkali metal salt of isobutyric acid are admixed with a bis-(4-halobutyl)ether. In some embodiments, 2.2 to 2.5 equivalents of the enolate of the alkali metal salt of isobutyric acid are admixed with a bis-(4-halobutyl)ether.

In some embodiments, the bis-(4-halobutyl)ether is added to the enolate dropwise. In some embodiments, the bis-(4-halobutyl)ether is added to the enolate dropwise over about 1 hour to about 5 hours. In some embodiments, the bis-(4-halobutyl)ether is added to the enolate dropwise over about 1 hour to about 4 hours. In some embodiments, the bis-(4-halobutyl)ether is added to the enolate at a temperature ranging from about 40° C. to about 45° C. In some embodiments, the bis-(4-halobutyl)ether is added to the enolate at a temperature ranging from 40° C. to 44° C. In some embodiments, the bis-(4-halobutyl)ether is added to the enolate as a solution in THF. In some embodiments, the bis-(4-halobutyl)ether is bis-(4-chlorobutyl)ether, the enolate is a lithium enolate of sodium isobutyrate, the bis-(4-chlorobutyl)ether is added as a solution in THF to the lithium enolate of sodium isobutyrate at a temperature ranging from 40° C. to 44° C.

In some embodiments, after the addition of the bis-(4-halobutyl)ether, the reaction mixture is allowed to stir a temperature ranging from about 40° C. to about 45° C. In some embodiments, after the addition of the bis-(4-halobutyl)ether, the reaction mixture is allowed to stir at a temperature ranging from 40° C. to 44° C. In some embodiments, after the addition of the bis-(4-halobutyl)ether, the reaction mixture is allowed to stir for about 8 hours to about 30 hours. In some embodiments, after the addition of the bis-(4-halobutyl)ether, the reaction mixture is allowed to stir for at least 10 hours. In some embodiments, after the addition of the bis-(4-halobutyl)ether, the reaction mixture is allowed to stir for about 10 hours to about 24 hours. In some embodiments, after the addition of the bis-(4-halobutyl) ether, the reaction mixture is allowed to stir for about 14 hours to about 24 hours.

In some embodiments, after the addition of the bis-(4-halobutyl)ether, the reaction mixture is allowed to stir at a temperature ranging from 40° C. to 44° C. and until quantitative $^{1}H$ NMR analysis indicates ≤5% bis-(4-halobutyl) ether in the reaction mixture (e.g., ≥95% conversion of bis-(4-halobutyl)ether). In some embodiments, after the addition of bis-(4-halobutyl)ether, the reaction mixture is allowed to stir at a temperature ranging from 40° C. to 44° C. and until $^{1}H$ NMR analysis indicates 5% or less, 4% or less, 3% or less, 2% or less, or 1.5% or less bis-(4-halobutyl) ether in the reaction mixture. In some embodiments, after the addition of bis-(4-halobutyl)ether, the reaction mixture is allowed to stir at a temperature ranging from 40° C. to 44° C. and until $^{1}H$ NMR analysis indicates less than 5%, less than 4%, less than 3%, less than 2%, or less than 1.5% bis-(4-halobutyl)ether in the reaction mixture.

Once bis-(4-halobutyl)ether reaction is substantially complete (e.g., quantitative $^{1}H$ NMR analysis indicates ≤5% bis-(4-halobutyl)ether), an aqueous work-up can be performed to extract the gemcabene salt product into an aqueous phase. Once the gemcabene salt is contained in the aqueous phase, the aqueous phase can be acidified, for example, with a mineral acid, such as hydrochloric acid. Once the aqueous phase is acidified, and the gemcabene salt converted to gemcabene, the gemcabene can be extracted with an organic solvent. Useful organic solvents include heptane, hexane, methyl tetrahydrofuran, toluene, ethyl acetate, butyl acetate, cyclohexane, 2-butanone, and diisopropyl ether. In some embodiments, the organic solvent is heptane. In some embodiments, the organic solvent is n-heptane. In some embodiments, the aqueous phase is extracted multiple times with the organic solvent. In some embodiments, the organic solvent used in the extractions after the bis-(4-halobutyl)ether reaction is complete or substantially complete has a temperature ranging from about 40° C. to about 60° C. In some embodiments, the organic solvent used in the extractions after the bis-(4-halobutyl)ether reaction is complete or substantially complete has a temperature ranging from about 48° C. to about 54° C. In some embodiments, the extractions are performed at a temperature ranging from about 40° C. to about 60° C. (temperature indicates the temperature of the solvents used in extractions).

The organic layer containing gemcabene can be evaporated to substantial dryness. The resultant crude gemcabene can be admixed with water, which can be subsequently evaporated. In some embodiments, the water is evaporated at ≤60° C. The further resultant crude gemcabene can be dissolved in an organic solvent, such as heptane, and the organic solution can be washed with water and evaporated to substantial dryness. This process can be repeated one or more times. In some embodiments, the process is performed twice. In some embodiments, the process is performed at least twice.

In some embodiments, isobutyric acid impurity, resulting from, for example, use of more than two equivalents of the enolate of the alkali metal salt of isobutyric acid per equivalent of bis-(4-halobutyl)ether, can be removed by co-distillation with water. Without being bound by theory, it is believed that the isobutyric acid is removed as an azeotrope with water. The presence of isobutyric acid impurity in the crude gemcabene can adversely affect its crystallization and the purity of crystallized gemcabene.

In some embodiments, co-distillation of water is performed at a temperature ranging from about 100° C. to about 110° C. In some embodiments, co-distillation of water is performed at a temperature ranging from about 100° C. to about 105° C. In some embodiments, co-distillation of water is performed at ambient pressure. In some embodiments, co-distillation of water is performed at reduced pressure. In some embodiments, co-distillation of water is performed at reduced pressure such that co-distillation of water is performed at a temperature in ranging from about 35° C. to about 70° C. In some embodiments, co-distillation of water is performed at reduced pressure such that co-distillation of water is performed at a temperature ranging from about 40° C. to about 60° C. In some embodiments, co-distillation of water is performed at about 10 mbar to about 100 mbar.

In some embodiments, a first co-distillation with water provides crude gemcabene comprising isobutyric acid impurity in 5% w/w or less of the crude gemcabene as determined by ion chromatography. In some embodiments, a first co-distillation with water provides the crude gemcabene comprising isobutyric acid impurity in 5% w/w or less, 4% w/w or less, 3% w/w or less, 2% w/w or less, or 1% w/w or less of the crude gemcabene as determined by ion chromatography. In some embodiments, a first co-distillation with water provides the crude gemcabene comprising isobutyric acid impurity in less than 5% w/w, less than 4% w/w, less than 3% w/w, less than 2% w/w, or less than 1% w/w of the crude gemcabene as determined by ion chromatography. In some embodiments, a first co-distillation with water provides the crude gemcabene comprising isobutyric acid impurity in 0.9% w/w or less, 0.8% w/w or less, 0.7% w/w or less, 0.6% w/w or less, or 0.5% w/w or less of the crude gemcabene as determined by ion chromatography. In some embodiments, a first co-distillation with water provides the crude gemcabene comprising isobutyric acid impurity in less than 0.9% w/w, less than 0.8% w/w, less than 0.7% w/w, less than 0.6% w/w, or less than 0.5% w/w of the crude gemcabene as determined by ion chromatography. In some embodiments, a first co-distillation with water provides the crude gemcabene comprising isobutyric acid impurity in 0.8% w/w or less of the crude gemcabene as determined by ion chromatography.

In some embodiments, a second co-distillation with water provides the crude gemcabene comprising isobutyric acid impurity in 1% w/w or less of the crude gemcabene as determined by ion chromatography. In some embodiments, a second co-distillation with water provides the crude gemcabene comprising isobutyric acid impurity in 1.0% w/w or less, 0.9% w/w or less, 0.8% w/w or less, 0.7% w/w or less, 0.6% w/w or less, 0.5% w/w or less, 0.4% w/w or less, 0.3% w/w or less, or 0.2% w/w or less of the crude gemcabene as determined by ion chromatography. In some embodiments, a second co-distillation with water provides the crude gemcabene comprising isobutyric acid impurity in less than 1.0% w/w, less than 0.9% w/w, less than 0.8% w/w, less than 0.7% w/w, less than 0.6% w/w, less than 0.5% w/w, less than 0.4% w/w, less than 0.3% w/w, or less than 0.2% w/w of the crude gemcabene as determined by ion chromatography. In some embodiments, a second co-distillation with water provides the crude gemcabene comprising isobutyric acid impurity in 0.5% w/w or less, 0.4% w/w or less, 0.3% w/w or less, or 0.2% w/w or less of the crude gemcabene as determined by ion chromatography. In some embodiments, a second co-distillation with water provides the crude gemcabene comprising isobutyric acid impurity in 0.3% w/w or less of the crude gemcabene as determined by ion chromatography.

After distillation and/or evaporation of water and removal of isobutyric acid impurity, a water/heptane heterogeneous azeotropic distillation can be performed in order to remove substantially all water content as determined by Karl-Fisher analysis. In some embodiments, the water content, if any, is ≤0.05% w/w of the reaction mixture as determined by Karl-Fisher analysis. In some embodiments, the water content, if any, is 0.05% w/w or less, or 0.04% w/w or less of the reaction mixture as determined by Karl-Fisher analysis. In some embodiments, the water content, if any, is less than 0.05% w/w, or less than 0.04% w/w of the reaction mixture as determined by Karl-Fisher analysis.

In some embodiments, before crystallization of gemcabene, the crude gemcabene is passed through silica gel to remove impurities, such as any colored or polar impurities. In some embodiments, silica gel filtration is performed using 5% (v/v) THF in heptane as an eluent. In some embodiments, subsequent to the silica gel filtration, the silica gel is washed with only heptane. In some embodiments, heptane is n-heptane.

The gemcabene-containing fractions from silica gel filtration can be evaporated to substantial dryness and the resultant residue can be crystallized from an organic solvent or mixture of organic solvents. In some embodiments, the organic solvent is heptane or a mixture of heptane and THF. In some embodiments, the organic solvent is heptane in the absence of THF. In some embodiments, heptane is n-heptane.

In some embodiments, crude gemcabene is dissolved in the organic solvent at a temperature ranging from about 20° C. to about 50° C. In some embodiments, the crude gemcabene is dissolved in the organic solvent at a temperature ranging from 35° C. to 50° C.

In some embodiments, once the crude gemcabene is dissolved in the organic solvent, the organic solution is cooled to 15° C.±2° C. In some embodiments, the organic solution is cooled to 15° C.±2° C. and subsequently seeded with one or more gemcabene crystals. In some embodiments, the organic solvent is heptane. In some embodiments, the organic solvent is n-heptane.

In some embodiments, the gemcabene is allowed to crystallize at a temperature ranging from 9° C. to 16° C. In some embodiments, the gemcabene is allowed to crystallize at a temperature ranging from 10° C. to 15° C. In some embodiments, the gemcabene is allowed to crystallize at a temperature ranging from 10° C. to 14° C. In some embodiments, the gemcabene is allowed to crystallize at a temperature of 10° C., 11° C., 12° C., 13° C., 14° C., or 15° C. In some embodiments, the gemcabene is allowed to crystallize at a temperature of 12° C.

In some embodiments, the crude gemcabene before recrystallization comprises 2,2,7,7-tetramethyl-octane-1,8-dioic acid impurity. Allowing gemcabene to crystallize from heptane at a temperature ranging from 10° C. to 15° C. yields gemcabene containing substantially less 2,2,7,7-tetramethyl-octane-1,8-dioic acid impurity than gemcabene that is allowed to crystallize from heptane at a temperature below 10° C. Moreover, as shown in Table C, the gemcabene of Entry 4, which was allowed to crystallize from heptane maintained at 12-14° C. without further cooling contained significantly less 2,2,7,7-tetramethyl-octane-1,8-dioic acid than that contained in the gemcabene of the other Entries. In some embodiments, heptane is n-heptane.

ture of 12° C. yields gemcabene comprising 2,2,7,7-tetramethyl-octane-1,8-dioic acid impurity in less than 0.2% w/w, less than 0.15% w/w, less than 0.1% w/w, or less than 0.05% w/w of the crystallized gemcabene as determined by HPLC. In some embodiments, HPLC is equipped with charged aerosol detector (CAD). In some embodiments, HPLC is equipped with ultraviolet detector (UV). In some embodiments, heptane is n-heptane.

In some embodiments, a first gemcabene crystallization from heptane at a temperature ranging between 10° C. to 14° C. yields gemcabene containing 2,2,7,7-tetramethyl-octane-1,8-dioic acid in a range of 0.5% w/w to 0.1% w/w, 0.4% w/w to 0.1% w/w, 0.3% w/w to 0.1% w/w, or 0.2% w/w to 0.1% w/w of the crystallized gemcabene as determined by HPLC. In some embodiments, a first gemcabene crystallization from heptane at a temperature ranging between 10° C. to 14° C. yields gemcabene comprising 2,2,7,7-tetramethyl-octane-1,8-dioic acid in a range of 0.5% w/w to 0.01% w/w, 0.4% w/w to 0.01% w/w, 0.3% w/w to 0.01% w/w, or 0.2% w/w to 0.01% w/w of the crystallized gemcabene as determined by HPLC. In some embodiments, a first gemcabene

TABLE C

Summary of crystallization experiment with varying temperature and time

| Entry | $1^{st}$ Temp.<br>Time | Ramp time from $1^{st}$ Temp. to $2^{nd}$ Temp. | $2^{nd}$ Temp.<br>Time | Total stirring time (≤15° C.) | Yield of Gemcabene | Amount of TMODA by HPLC-CAD |
|---|---|---|---|---|---|---|
| 1 | 15° C.<br>4 h | 2.5 h<br>5° C./h | 5-6° C.<br>20.5 h | 27 h | 85% | 0.41% w/w |
| 2 | 15° C.<br>2.8 h | 1.2 h<br>~10.7° C./h | 5-8° C.<br>2.8 h | 6.5 h | 76% | 0.10% w/w |
| 3 | 15° C.<br>18.5 h | 2.4 h<br>5° C./h | 5-6° C.<br>4 h | 26 h | 85% | 0.32% w/w |
| 4 | 12-14° C.<br>20.5 h | — | — | 21.5 h | 83% | 0.03% w/w |
| 5 | 15-16° C.<br>1.8 h | 1.2 h<br>10° C./h | 5-8° C.<br>2.2 h | 5.3 h | 85% | 0.13% w/w |

TMODA = 2,2,7,7-Tetramethyl-octane-1,8-dioic acid;
HPLC-CAD = high-performance liquid chromatography equipped with a charged aerosol detector;
% w/w of the crystalized gemcabene In some embodiments, a first gemcabene crystallization from heptane at a temperature ranging from 9° C. to 16° C. yields gemcabene comprising 2,2,7,7-tetramethyl-octane-1,8-dioic acid impurity in ≤0.5% w/w of the crystallized gemcabene as determined by high-performance liquid chromatography (HPLC). In some embodiments, a second gemcabene crystallization from heptane at a temperature ranging from 10° C. to 15° C. once yields gemcabene comprising 2,2,7,7-tetramethyl-octane-1,8-dioic acid impurity in 50.5% w/w of the crystallized gemcabene as determined by high-performance liquid chromatography (HPLC). In some embodiments, a first gemcabene crystallization from n-heptane at a temperature ranging from 10° C. to 15° C. yields gemcabene comprising 2,2,7,7-tetramethyl-octane-1,8-dioic acid impurity, if any, in 0.5% w/w or less, 0.4% w/w or less, 0.3% w/w or less, 0.2% w/w or less, 0.15% w/w or less, 0.1% w/w or less, or 0.05% w/w or less of the crystallized gemcabene as determined by HPLC. In some embodiments, a first gemcabene crystallization from heptane at a temperature ranging from 10° C. to 15° C. yields gemcabene comprising 2,2,7,7-tetramethyl-octane-1,8-dioic acid impurity in less than 0.5% w/w, less than 0.4% w/w, less than 0.3% w/w, less than 0.2% w/w, less than 0.15% w/w, less than 0.1% w/w, or less than 0.05% w/w of the crystallized gemcabene as determined by HPLC. In some embodiments, a first gemcabene crystallization from heptane at a temperature ranging from 10° C. to 14° C. yields gemcabene comprising 2,2,7,7-tetramethyl-octane-1,8-dioic acid in a range of 0.5% w/w to 0.001% w/w, 0.4% w/w to 0.001% w/w, 0.3% w/w to 0.001% w/w, or 0.2% w/w to 0.001% w/w of the crystallized gemcabene as determined by HPLC. In some embodiments, heptane is n-heptane.

In some embodiments, the concentration of the crystallization solution affects the recovery of gemcabene. In some embodiments, the crystallization solution has a concentration greater than 0.3 g/mL crude gemcabene in the organic solvent or mixtures of organic solvent. In some embodiments, the crystallization solution has a concentration of ≥0.4 g/mL, ≥0.5 g/mL, or ≥0.6 g/mL crude gemcabene in the organic solvent or mixtures of organic solvent. In some embodiments, the crystallization solution has a concentration ranging from 0.3 g of crude gemcabene/mL of heptane to 0.9 g of crude gemcabene/mL of heptane. In some embodiments, crystallization solution has a concentration ranging from 0.5 g of crude gemcabene/mL of heptane to 0.8 g of crude gemcabene/mL of heptane. In some embodiments, the crystallization solution has a concentration ranging from 0.5 g of crude gemcabene/mL of heptane to 0.7 g of crude gemcabene/mL of heptane. In some embodiments, crystallization solution has a concentration of 0.6 g crude gemcabene/mL of heptane. In some embodiments, heptane is n-heptane.

The yield of gemcabene can be affected by the number of equivalents of isobutyric acid, alkali metal hydroxide or enolate-forming base in relation to bis-(4-halobutyl)ether. In some embodiments, molar equivalents ranging from 2.05 to 3.00 of each of isobutyric acid, alkali metal hydroxide, and enolate-forming base are used compared to 1.00 molar equivalent of bis-(4-halobutyl)ether. In some embodiments, molar equivalents ranging from 2.15 to 2.50 of each of isobutyric acid, alkali metal hydroxide, and enolate-forming base are used compared to 1.0 molar equivalent of bis-(4-halobutyl)ether. In some embodiments, molar equivalents ranging from 2.20 to 2.40 of each of isobutyric acid, alkali metal hydroxide, and enolate-forming base are used compared to 1.0 molar equivalent of bis-(4-halobutyl)ether. In some embodiments, 2.20 equivalents of each of isobutyric acid, alkali metal hydroxide, and enolate-forming are used compared to 1.0 molar equivalent of bis-(4-chlorobutyl) ether. In some embodiments, the alkali metal hydroxide is sodium hydroxide and the enolate-forming base is LDA. In some embodiments, the alkali metal hydroxide is sodium hydroxide, the enolate-forming base is LDA and the bis-(4-halobutyl)ether is bis-(4-iodobutyl)ether.

In some embodiments, gemcabene made according to any one of the methods disclosed herein has a purity ranging from about 85% w/w to 100% w/w as determined by high-performance liquid chromatography (HPLC). In some embodiments, gemcabene has a purity ranging from about 90% w/w to 100% w/w as determined by HPLC. In some embodiments, gemcabene has a purity ranging from about 95% w/w to 100% w/w as determined by HPLC. In some embodiments, gemcabene has a purity ranging from about 98% w/w to 100% w/w as determined by HPLC. In some embodiments, gemcabene has a purity ranging from about 99% w/w to 100% w/w as determined by HPLC. In some embodiments, gemcabene has a purity ranging from 99.0% to 100% as determined by HPLC. In some embodiments, gemcabene has a purity ranging from about 99.5% w/w to 100% w/w as determined by HPLC. In some embodiments, HPLC is equipped with a charged aerosol detector (CAD) or with an ultraviolet detector (UV).

In some embodiments, gemcabene made according to any one of the methods disclosed herein comprises isobutyric acid impurity in ≤0.5% w/w of the gemcabene as determined by ion chromatography (IC). In some embodiments, gemcabene comprises isobutyric acid impurity, if any, in 0.5% w/w or less, 0.4% w/w or less, 0.3% w/w or less, 0.2% w/w or less, 0.15% w/w or less, 0.1% w/w or less, or 0.05% w/w or less of the gemcabene as determined by IC. In some embodiments, gemcabene comprises isobutyric acid impurity in less than 0.5%, less than 0.4% w/w, less than 0.3% w/w, less than 0.2% w/w, less than 0.15% w/w, less than 0.1% w/w, or less than 0.05% w/w of the gemcabene as determined by IC. In some embodiments, gemcabene comprises isobutyric acid impurity in 0.05% w/w or less of the gemcabene as determined by IC. In some embodiments, gemcabene is substantially free of isobutyric acid impurity. In some embodiments, isobutyric acid impurity in gemcabene is below the quantification limit of the IC. In some embodiments, the quantification limit of isobutyric acid using an IC is 0.05% w/w.

In some embodiments, gemcabene made according to any one of the methods disclosed herein comprises 6-(4-hydroxybutoxy)-2,2-dimethylhexanoic acid impurity in ≤0.5% w/w of the gemcabene as determined by high-performance liquid chromatography (HPLC). In some embodiments, gemcabene comprises 6-(4-hydroxybutoxy)-2,2-dimethylhexanoic acid impurity in 0.5% w/w or less, 0.4% w/w or less, 0.3% w/w or less, 0.2% w/w or less, 0.15% w/w or less, 0.1% w/w or less, or 0.05% w/w or less of the gemcabene as determined by HPLC. In some embodiments, gemcabene comprises 6-(4-hydroxybutoxy)-2,2-dimethylhexanoic acid impurity, if any, in less than 0.5% w/w, less than 0.4% w/w, less than 0.3% w/w, less than 0.2% w/w, less than 0.15% w/w, less than 0.1% w/w, or less than 0.05% w/w of the gemcabene as determined by HPLC. In some embodiments, HPLC is equipped with a charged aerosol detector (CAD) or with an ultraviolet detector (UV).

In some embodiments, gemcabene made according to any one of the methods disclosed herein comprises (Z)-2,2-dimethyl-hex-4-enoic acid impurity in 50.5% w/w of the gemcabene as determined by high-performance liquid chromatography (HPLC). In some embodiments, gemcabene comprises (Z)-2,2-dimethyl-hex-4-enoic acid impurity in less than 0.5% w/w, less than 0.4% w/w, less than 0.3% w/w, less than 0.2% w/w, less than 0.15% w/w, less than 0.1% w/w, or less than 0.05% w/w of the gemcabene as determined by HPLC. In some embodiments, gemcabene comprises (Z)-2,2-dimethyl-hex-4-enoic acid impurity, if any, in 0.5% w/w or less, 0.4% w/w or less, 0.3% w/w or less, 0.2% w/w or less, 0.15% w/w or less, 0.1% w/w or less, or 0.05% w/w or less of the gemcabene as determined by HPLC. In some embodiments, HPLC is equipped with a charged aerosol detector (CAD) or with an ultraviolet detector (UV).

In some embodiments, gemcabene made according to any one of the methods disclosed herein comprises (E)-2,2-dimethyl-hex-4-enoic acid impurity in ≤1.0% w/w of the gemcabene as determined by high-performance liquid chromatography (HPLC). In some embodiments, gemcabene comprises (E)-2,2-dimethyl-hex-4-enoic acid impurity in ≤0.5% of the gemcabene as determined by HPLC. In some embodiments, gemcabene comprises (E)-2,2-dimethyl-hex-4-enoic acid impurity in less than 1.0% w/w, less than 0.9% w/w, less than 0.8% w/w, less than 0.7% w/w, less than 0.6% w/w, less than 0.5% w/w, less than 0.4% w/w, less than 0.3% w/w, less than 0.2% w/w, less than 0.15% w/w, less than 0.1% w/w, or less than 0.05% w/w of the gemcabene as determined by HPLC. In some embodiments, gemcabene comprises (E)-2,2-dimethyl-hex-4-enoic acid impurity, if any, in 1.0% w/w or less, 0.9% w/w or less, 0.8% w/w or less, 0.7% w/w or less, 0.6% w/w or less, 0.5% w/w or less, 0.4% w/w or less, 0.3% w/w or less, 0.2% w/w or less, 0.15% w/w or less, 0.1% w/w or less, or 0.05% w/w or less as determined by HPLC. In some embodiments, HPLC is equipped with a charged aerosol detector (CAD) or with an ultraviolet detector (UV).

The present invention further provides gemcabene made according to any one of the methods disclosed herein. The present invention further provides gemcabene purified according to any one of the methods disclosed herein. The present invention further provides gemcabene purified by dissolving the crude gemcabene in heptane and cooling the heptane solution to a temperature ranging from 10° C. to 15° C. to precipitate gemcabene. In some embodiments, heptane is n-heptane.

The present invention further provides a pharmaceutically acceptable salt of gemcabene, wherein gemcabene is synthesized according to any one of the methods disclosed herein. The present invention further provides a pharmaceutically acceptable salt of gemcabene, wherein gemcabene is purified according to any one of the methods disclosed herein. The present invention further provides a pharmaceutically acceptable salt of gemcabene, wherein gemcabene is purified by dissolving the crude gemcabene in heptane and cooling the heptane solution to a temperature ranging from 10° C. to 15° C. to precipitate gemcabene. In some embodiments, heptane is n-heptane.

In some embodiments, gemcabene synthesized according to any one of the methods disclosed herein can be converted into gemcabene calcium. In some embodiment, gemcabene is allowed to react with calcium oxide. In some embodiment, gemcabene is allowed to react with calcium oxide in ethanol. In some embodiment, gemcabene is allowed to react with calcium oxide in ethanol under refluxing conditions. After gemcabene was allowed to react with calcium oxide, the reaction mixture can be stirred at 22° C.±2° C. for about one hour and then can be filtered. The filtered product can then be dried under vacuum. In some embodiments, the drying is performed under stream of nitrogen under vacuum.

In some embodiments, purified water is added to the dried gemcabene calcium and heated. In some embodiments, purified water is added to the dried gemcabene calcium at atmospheric pressure and heated to a temperature range of about 80 to about 110° C. In some embodiments, purified water is added to the dried gemcabene calcium at atmospheric pressure and heated to a temperature range of about 85° C. to about 95° C. for about 5 hours to about 10 hours. In some embodiments, purified water is added to the dried gemcabene calcium at atmospheric pressure and heated to 90° C. for about 6 hours. Heating gemcabene calcium with purified water provides gemcabene calcium salt hydrate.

In some embodiments, gemcabene calcium salt hydrate is dried under vacuum. In some embodiments, gemcabene calcium salt hydrate is dried under vacuum at a temperature range of about 80° C. to about 110° C. In some embodiments, gemcabene calcium salt hydrate is dried under vacuum at a temperature range of about 85° C. to about 95° C. for at least 5 hours, at least 10 hours, or at least 15 hours. In some embodiments, gemcabene calcium salt hydrate is dried under vacuum at a temperature of 90° C. for at least 16 hours to yield gemcabene calcium salt hydrate Crystal Form 1. Similarly, gemcabene calcium salt solvate can be obtained with alcohol solvents, such as ethanol.

In some embodiments, gemcabene calcium salt hydrate or solvate prepared from gemcabene synthesized according to any one of the methods disclosed herein has a purity ranging from about 85% w/w to 100% w/w as determined by high-performance liquid chromatography (HPLC). In some embodiments, gemcabene calcium salt hydrate or solvate has a purity ranging from about 90% w/w to 100% w/w as determined by HPLC. In some embodiments, gemcabene calcium salt hydrate or solvate has a purity ranging from about 95% w/w to 100% w/w as determined by HPLC. In some embodiments, gemcabene calcium salt hydrate or solvate has a purity ranging from about 98% w/w to 100% w/w as determined by HPLC. In some embodiments, gemcabene calcium salt hydrate or solvate has a purity ranging from about 99% w/w to 100% w/w as determined by HPLC. In some embodiments, gemcabene calcium salt hydrate or solvate has a purity ranging from about 99.5% w/w to 100% w/w as determined by HPLC. In some embodiments, gemcabene calcium salt hydrate or solvate has a purity ranging from 99.5% w/w to 100% w/w as determined by HPLC. In some embodiments, gemcabene calcium salt hydrate or solvate has a purity ranging from 99.7% w/w to 100% w/w as determined by HPLC. In some embodiments, HPLC is equipped with a charged aerosol detector (CAD) or with an ultraviolet detector (UV).

In some embodiments, gemcabene calcium salt hydrate or solvate prepared from gemcabene synthesized according to any one of the methods disclosed herein comprises 6-(4-hydroxybutoxy)-2,2-dimethylhexanoic acid impurity in ≤0.5% w/w of the gemcabene calcium salt hydrate or solvate as determined by high-performance liquid chromatography (HPLC). In some embodiments, gemcabene calcium salt hydrate or solvate comprises 6-(4-hydroxybutoxy)-2,2-dimethylhexanoic acid impurity, if any, in less than 0.5%, less than 0.4% w/w, less than 0.3% w/w, less than 0.2% w/w, less than 0.15% w/w, less than 0.1% w/w, or less than 0.05% w/w of the gemcabene calcium salt hydrate or solvate as determined by HPLC. In some embodiments, gemcabene calcium salt hydrate or solvate comprises 6-(4-hydroxybutoxy)-2,2-dimethylhexanoic acid impurity in 0.5% w/w or less, 0.4% w/w or less, 0.3% w/w or less, 0.2% w/w or less, 0.15% w/w or less, 0.1% w/w or less, or 0.05% w/w or less of the gemcabene calcium salt hydrate or solvate as determined by HPLC. In some embodiments, HPLC is equipped with a charged aerosol detector (CAD) or with an ultraviolet detector (UV).

In some embodiments, gemcabene calcium salt hydrate or solvate prepared from gemcabene synthesized according to any one of the methods disclosed herein comprises 2,2,7,7-tetramethyl-octane-1,8-dioic acid impurity in 50.5% w/w of the gemcabene calcium salt hydrate or solvate as determined by high-performance liquid chromatography (HPLC). In some embodiments, gemcabene calcium salt hydrate or solvate comprises 2,2,7,7-tetramethyl-octane-1,8-dioic acid impurity in less than 0.5% w/w, less than 0.4% w/w, less than 0.3% w/w, less than 0.2% w/w, less than 0.15% w/w, less than 0.1% w/w, or less than 0.05% w/w of the gemcabene calcium salt hydrate or solvate as determined by HPLC. In some embodiments, gemcabene calcium salt hydrate or solvate comprises 2,2,7,7-tetramethyl-octane-1,8-dioic acid impurity, if any, in 0.5% w/w or less, 0.4% w/w or less, 0.3% w/w or less, 0.2% w/w or less, 0.15% w/w or less, 0.1% w/w or less, or 0.05% w/w or less of the gemcabene calcium salt hydrate or solvate as determined by HPLC. In some embodiments, gemcabene calcium salt hydrate or solvate comprises 2,2,7,7-tetramethyl-octane-1,8-dioic acid impurity in less than 0.2% w/w, less than 0.15% w/w, less than 0.1% w/w, or less than 0.05% w/w of the gemcabene calcium salt hydrate or solvate as determined by HPLC. In some embodiments, HPLC is equipped with a charged aerosol detector (CAD) or with an ultraviolet detector (UV).

In some embodiments, gemcabene calcium salt hydrate or solvate prepared from gemcabene synthesized according to any one of the methods disclosed herein comprises isobutyric acid impurity in ≤0.5% w/w of the gemcabene calcium salt hydrate or solvate as determined by ion chromatography (IC). In some embodiments, gemcabene calcium salt hydrate or solvate comprises isobutyric acid impurity in less than 0.5% w/w, less than 0.4% w/w, less than 0.3% w/w, less than 0.2% w/w, less than 0.15% w/w, less than 0.1% w/w, or less than 0.05% w/w of the gemcabene calcium salt hydrate or solvate as determined by IC. In some embodiments, gemcabene calcium salt hydrate or solvate comprises isobutyric acid impurity, if any, in 0.5% w/w or less, 0.4% w/w or less, 0.3% w/w or less, 0.2% w/w or less, 0.15% w/w or less, 0.1% w/w or less, or 0.05% w/w or less of the gemcabene calcium salt hydrate or solvate as determined by IC. In some embodiments, gemcabene calcium salt hydrate or solvate comprises isobutyric acid impurity in 0.07% w/w or less of the gemcabene calcium salt hydrate or solvate as determined by IC. In some embodiments, gemcabene calcium salt hydrate or solvate comprises isobutyric acid impurity in 0.05% w/w or less of the gemcabene calcium salt hydrate or solvate as determined by IC. In some embodiments, gemcabene calcium salt hydrate or solvate is substantially free of isobutyric acid impurity. In some embodiments, isobutyric acid impurity in gemcabene calcium salt hydrate or solvate is below the quantification limit of the IC. In one embodiment, the quantification limit of isobutyric acid using an IC is 0.05% w/w.

In some embodiments, gemcabene calcium salt hydrate or solvate made from gemcabene synthesized according to any one of the methods disclosed herein comprises (Z)-2,2-dimethyl-hex-4-enoic acid impurity in ≤0.5% w/w of the gemcabene calcium salt hydrate or solvate as determined by high-performance liquid chromatography (HPLC). In some embodiments, gemcabene calcium salt hydrate or solvate comprises (Z)-2,2-dimethyl-hex-4-enoic acid impurity in less than 0.5% w/w, less than 0.4% w/w, less than 0.3% w/w, less than 0.2% w/w, less than 0.15% w/w, less than 0.1% w/w, or less than 0.05% w/w of the gemcabene calcium salt hydrate or solvate as determined by HPLC. In some embodiments, gemcabene calcium salt hydrate or solvate comprises (Z)-2,2-dimethyl-hex-4-enoic acid impurity, if any, in 0.5% w/w or less, 0.4% w/w or less, 0.3% w/w or less, 0.2% w/w or less, 0.15% w/w or less, 0.1% w/w or less, or 0.05% w/w or less of the gemcabene calcium salt hydrate or solvate as determined by HPLC. In some embodiments, HPLC is equipped with a charged aerosol detector (CAD) or with an ultraviolet detector (UV).

In some embodiments, gemcabene calcium salt hydrate or solvate made from gemcabene synthesized according to any one of the method disclosed herein comprises E)-2,2-dimethyl-hex-4-enoic acid impurity in ≤0.5% w/w (of the gemcabene calcium salt hydrate or solvate as determined by HPLC. In some embodiments, gemcabene calcium salt hydrate or solvate comprises (E)-2,2-dimethyl-hex-4-enoic acid impurity in less than 0.5% w/w, less than 0.4% w/w, less than 0.3% w/w, less than 0.2% w/w, less than 0.15% w/w, less than 0.1% w/w, or less than 0.05% w/w of the gemcabene calcium salt hydrate or solvate as determined by HPLC. In some embodiments, gemcabene calcium salt hydrate or solvate comprises (E)-2,2-dimethyl-hex-4-enoic acid impurity, if any, in 0.5% w/w or less, 0.4% w/w or less, 0.3% w/w or less, 0.2% w/w or less, 0.15% w/w or less, 0.1% w/w or less, or 0.05% w/w or less of the gemcabene calcium salt hydrate or solvate as determined by HPLC. In some embodiments, HPLC is equipped with a charged aerosol detector (CAD) or with an ultraviolet detector (UV).

In some embodiments, gemcabene calcium salt hydrate or solvate made from gemcabene synthesized according to any one of the methods disclosed herein comprises 52.5 ppm bis-(4-chlorobutyl)ether impurity as determined by gas chromatography (GC). In some embodiments, gemcabene calcium salt hydrate or solvate comprises less than 2.5 ppm, less than 2.0 ppm, less than 1.5 ppm or less than 1.0 ppm bis-(4-chlorobutyl)ether impurity as determined by GC. In some embodiments, gemcabene calcium salt hydrate or solvate comprises 2.5 ppm or less, 2.0 ppm or less, 1.5 ppm or less, or 1.0 ppm or less bis-(4-chlorobutyl)ether impurity as determined by GC.

In some embodiments, gemcabene calcium salt hydrate or solvate prepared from gemcabene synthesized according to any one of the method disclosed herein contains ≤2.5 ppm 6-(4-chlorobutoxy)-2,2-dimethyl-hexanoic acid impurity as determined by gas chromatography (GC). In some embodiments, gemcabene calcium salt hydrate or solvate contains less than 2.5 ppm, less than 2.0 ppm, less than 1.5 ppm or less than 1.0 ppm 6-(4-chlorobutoxy)-2,2-dimethyl-hexanoic acid impurity as determined by GC. In some embodiments, gemcabene calcium salt hydrate or solvate contains 2.5 ppm or less, 2.0 ppm or less, 1.5 ppm or less, or 1.0 ppm or less 6-(4-chlorobutoxy)-2,2-dimethyl-hexanoic acid impurity as determined by GC.

In some embodiments, gemcabene calcium salt hydrate or solvate prepared from gemcabene synthesized according to any one of the method disclosed herein contains ≤2.5 ppm 1-chloro-4-hydroxybutane impurity as determined by gas chromatography (GC). In some embodiments, gemcabene calcium salt hydrate or solvate contains less than 2.5 ppm, less than 2.0 ppm, less than 1.5 ppm or less than 1.0 ppm 1-chloro-4-hydroxybutane impurity as determined by GC. In some embodiments, gemcabene calcium salt hydrate or solvate contains 2.5 ppm or less, 2.0 ppm or less, 1.5 ppm or less, or 1.0 ppm or less 1-chloro-4-hydroxybutane impurity as determined by GC.

In some embodiments, gemcabene calcium salt hydrate or solvate prepared from gemcabene synthesized according to any one of the method disclosed herein contains ≤8 ppm collectively the sum of 1-chloro-4-hydroxybutane, 6-(4-chlorobutoxy)-2,2-dimethyl-hexanoic acid and (bis-(4-chlorobutyl)ether impurities as determined by gas chromatography (GC). In some embodiments, gemcabene calcium salt hydrate or solvate contains less than 8 ppm, less than 7.0 ppm, less than 6 ppm or less than 5.0 ppm collectively the sum of 1-chloro-4-hydroxybutane, 6-(4-chlorobutoxy)-2,2-dimethyl-hexanoic acid and (bis-(4-chlorobutyl)ether impurities as determined by GC. In some embodiments, gemcabene calcium salt hydrate or solvate contains 8 ppm or less, 7.5 ppm or less, 7.0 ppm or less, or 6.5 ppm or less 1-chloro-4-hydroxybutane impurity as determined by GC.

In some embodiments, gemcabene calcium salt hydrate made from gemcabene synthesized according to any one of the methods disclosed herein comprises water in the range of about 2.0% w/w to about 5.0% w/w of the gemcabene calcium salt hydrate as determined by Karl-Fisher analysis. In some embodiments, gemcabene calcium salt hydrate prepared from gemcabene synthesized according to any one of the methods disclosed herein comprises water in the range of 2.0% w/w to 5.0% w/w of the gemcabene calcium salt hydrate as determined by Karl-Fisher analysis.

In some embodiments, gemcabene calcium salt hydrate or solvate made from gemcabene synthesized according to any one of the methods disclosed herein comprises calcium in a range from about 10% m/m to about 15% m/m of the gemcabene calcium salt hydrate or solvate as determined by inductively coupled plasma optical emission spectrometry (ICP-OES). In some embodiments, gemcabene calcium salt hydrate or solvate prepared from gemcabene synthesized according to any one of the methods disclosed herein comprises calcium in a range from about 10% m/m to about 14% m/m of the gemcabene calcium salt hydrate or solvate as determined by ICP-OES. In some embodiments, gemcabene calcium salt hydrate or solvate prepared from gemcabene synthesized according to any one of the methods disclosed herein comprises calcium in a range from 9.8% m/m to 13.8% m/m of the gemcabene calcium salt hydrate or solvate as determined by ICP-OES. In some embodiments, gemcabene calcium salt hydrate or solvate prepared from gemcabene synthesized according to any one of the methods disclosed herein comprises calcium in a range from 11.5% m/m to 12.5% m/m of the gemcabene calcium salt hydrate or solvate as determined by ICP-OES. In some embodiments, gemcabene calcium salt hydrate or solvate prepared from gemcabene synthesized according to any one of the methods disclosed herein comprises calcium in about 11.77% m/m of the gemcabene calcium salt hydrate or solvate as determined by ICP-OES.

In some embodiments, gemcabene calcium salt hydrate or solvate made from gemcabene synthesized according to any one of the methods disclosed herein comprises a gemcabene conjugate base component ranging from about 82% w/w to about 92% w/w of the gemcabene calcium salt hydrate or solvate as determined by high-performance liquid chromatography (HPLC), wherein the gemcabene conjugate base has the structure:

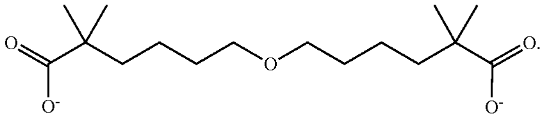 [SMILES: CC(C)(CCCCOCCCCC(C)(C)C(=O)[O-])C(=O)[O-]]

In some embodiments, gemcabene calcium salt hydrate or solvate made from gemcabene made according to any one of the methods disclosed herein comprises a gemcabene conjugate base component ranging from 82% w/w to 92% w/w of the gemcabene calcium salt hydrate or solvate as determined by high-performance liquid chromatography (HPLC). The gemcabene conjugate base component is percentage of the gemcabene calcium salt hydrate or solvate without accounting for water, solvent, and calcium content. In some embodiments, HPLC is equipped with an ultraviolet detector (UV).

In some embodiments, gemcabene calcium salt hydrate or solvate made from gemcabene made according to any one of the methods disclosed herein has an anhydrous gemcabene calcium content from about 98% w/w to about 105% w/w of the gemcabene calcium salt hydrate or solvate as determined by high-performance liquid chromatography (HPLC). In some embodiments, gemcabene calcium salt hydrate or solvate made from gemcabene made according to any one of the methods disclosed herein has an anhydrous gemcabene calcium content from 98% w/w to 105% w/w of the gemcabene calcium salt hydrate or solvate as determined by high-performance liquid chromatography (HPLC).

anhydrous gemcabene calcium content=(% gemcabene calcium as-is)/(100%−% water by Karl-Fisher analysis)

gemcabene calcium as-is =(% gemcabene)*[(molecular weight of gemcabene calcium)/(molecular weight of gemcabene)]

In some embodiments, gemcabene calcium salt hydrate or solvate made from gemcabene made according to any one of the methods disclosed herein comprises 2.0% or less of total impurities as determined by high-performance liquid chromatography. In some embodiments, gemcabene calcium salt hydrate or solvate prepared from gemcabene synthesized according to any one of the methods disclosed herein comprises total impurities in less than 2.0% w/w of the gemcabene calcium salt hydrate or solvate as determined by high-performance liquid chromatography (HPLC). In some embodiments, HPLC is equipped with a charged aerosol detector (CAD) or with an ultraviolet detector (UV). Different HPLC instrument's impurity analyses can be added to provide the sum of impurities. As used herein, an "impurities" refers to any organic compounds that are not gemcabene or a pharmaceutically acceptable salt of gemcabene that is detectable by HPLC. For example, isobutyric acid and bis-(4-halobutyl)ether are examples of impurities. Other examples of related substances are presented in Table D.

TABLE D

| Examples of Related Substances | |
|---|---|
| Impurity | Chemical structure |
| Isobutyric acid<br>$C_4H_8O_2$<br>MW 88.11 | 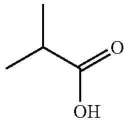 |
| Bis-(4-chlorobutyl)ether<br>$C_4H_{16}C_{12}O$<br>MW 199.12 | 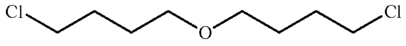 [SMILES: ClCCCCOCCCCCl] |
| 2,2,7,7-Tetramethyl-octane-1,8-dioic acid<br>$C_{12}H_{22}O_4$<br>MW 230.30 | 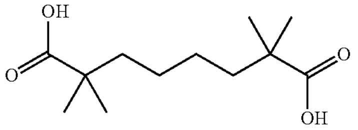 [SMILES: CC(C)(CCCCC(C)(C)C(=O)O)C(=O)O] |
| 6-(4-Hydroxybutoxy)-2,2-dimethylhexanoic acid<br>$C_{12}H_{24}O_4$<br>MW 232.32 | 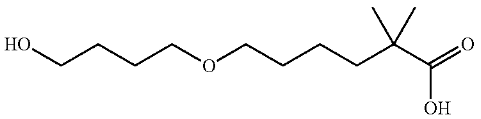 [SMILES: CC(C)(CCCCOCCCCO)C(=O)O] |
| (E)-2,2-Dimethyl-hex-4-enoic acid<br>$C_8H_{14}O_2$<br>MW 142.20 | 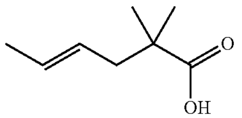 |

TABLE D-continued

| Examples of Related Substances | |
|---|---|
| Impurity | Chemical structure |
| (Z)-2,2-Dimethyl-hex-4-enoic acid<br>$C_8H_{14}O_2$<br>MW 142.20 | 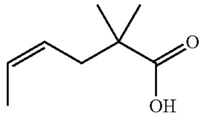 |
| 2,2-Dimethyl-hex-5-enoic acid<br>$C_8H_{14}O_2$<br>MW 142.20 | 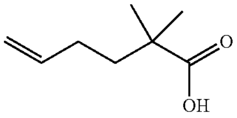 |
| 6-((5-Carboxyheptyl)oxy)-2,2-dimethylhexanoic acid<br>$C_{16}H_{30}O$<br>MW 302.41 | 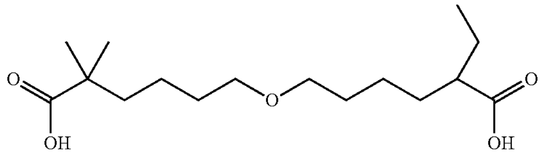 [SMILES: CCC(CCCCOCCCCC(C)(C)C(=O)O)C(=O)O] |
| 6-(7-Carboxy-7-methyl-5-ethenyl-octyloxy)-2,2-dimethyl-hexanoic acid<br>$C_{20}H_{36}O_5$<br>MW 356.50 | 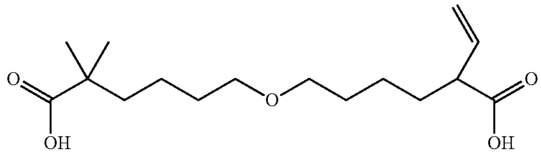 [SMILES: C=CC(CCCCOCCCCC(C)(C)C(=O)O)C(=O)O] |
| (Z)-6-(9-Carboxy-9-methyl-dec-6-enyloxy)-2,2-dimethyl-hexanoic acid<br>$C_{20}H_{36}O_5$<br>MW 356.50 | 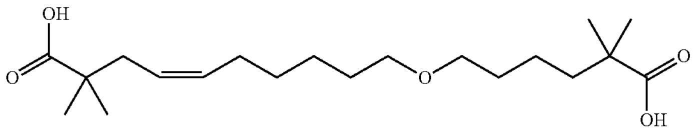 [SMILES: CC(C)(C/C=C\CCCCCOCCCCC(C)(C)C(=O)O)C(=O)O] |
| (E)-6-(9-Carboxy-9-methyl-dec-6-enyloxy)-2,2-dimethyl-hexanoic acid<br>$C_{20}H_{36}O_5$<br>MW 356.50 | 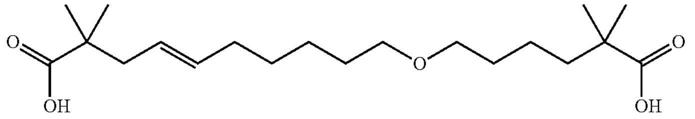 [SMILES: CC(C)(C/C=C/CCCCCOCCCCC(C)(C)C(=O)O)C(=O)O] |

The present invention further provides methods for purifying crude gemcabene, wherein the crude gemcabene comprises 2,2,7,7-tetramethyl-octane-1,8-dioic acid in no more than 5% w/w of the crude gemcabene as determined by high-performance liquid chromatography (HPLC), comprising: dissolving the crude gemcabene in heptane to provide a heptane solution of the crude gemcabene; and cooling the heptane solution to a temperature ranging from 10° C. to 15° C. to precipitate gemcabene, wherein the gemcabene comprises 2,2,7,7-tetramethyl-octane-1,8-dioic acid in 0.5% w/w or less of the gemcabene of as determined by high-performance liquid chromatography.

The present invention further provides methods for purifying crude gemcabene, wherein the crude gemcabene comprises 2,2,7,7-tetramethyl-octane-1,8-dioic acid in no more than 3% w/w of the crude gemcabene as determined by high-performance liquid chromatography (HPLC), comprising: dissolving the crude gemcabene in heptane to provide a heptane solution of the crude gemcabene; and cooling the heptane solution to a temperature ranging from 10° C. to 15° C. to precipitate gemcabene, wherein the gemcabene comprises 2,2,7,7-tetramethyl-octane-1,8-dioic acid in 0.5% w/w or less of the gemcabene of as determined by high-performance liquid chromatography. In some embodiments, the crude gemcabene comprises 2,2,7,7-tetramethyl-octane-1,8-dioic acid in no more than 2.5% w/w of the crude gemcabene as determined by HPLC. In some embodiments, the crude gemcabene comprises 2,2,7,7-tetramethyl-octane-1,8-dioic acid in no more than 2% w/w of the crude gemcabene as determined by HPLC. In some embodiments, the crude gemcabene comprises 2,2,7,7-tetramethyl-octane-1,8-dioic acid in no more than 1.5% w/w of the crude gemcabene as determined by HPLC. In some embodiments, the crude gemcabene comprises 2,2,7,7-tetramethyl-octane-1,8-dioic acid in no more than 1% w/w of the crude gemcabene as determined by HPLC.

The present invention further provides methods for purifying crude gemcabene, wherein the crude gemcabene comprises 2,2,7,7-tetramethyl-octane-1,8-dioic acid in no more than 1% w/w of the crude gemcabene as determined by high-performance liquid chromatography, comprising: dissolving the crude gemcabene in heptane to provide a heptane solution of the crude gemcabene; and cooling the heptane solution to a temperature ranging from 10° C. to 15° C. to precipitate gemcabene, wherein the gemcabene comprises 2,2,7,7-tetramethyl-octane-1,8-dioic acid in 0.5% w/w or less of the gemcabene of as determined by high-performance liquid chromatography.

In some embodiments, the crude gemcabene prior to purification comprises 2,2,7,7-tetramethyl-octane-1,8-dioic acid impurity in greater than 0.7% w/w and no more than 1% w/w of the crude gemcabene as determined by high-performance liquid chromatography (HPLC). In some embodiments, the crude gemcabene prior to purification comprises 2,2,7,7-tetramethyl-octane-1,8-dioic acid impurity in greater than 0.5% w/w and no more than 1% w/w of the crude gemcabene as determined by HPLC. In some embodiments, the crude gemcabene prior to purification comprises 2,2,7,7-tetramethyl-octane-1,8-dioic acid impurity in a range of 1.0% w/w to 0.5% w/w of the crude gemcabene as determined by HPLC.

In some embodiments, the gemcabene after purification comprises 2,2,7,7-tetramethyl-octane-1,8-dioic acid from 0.01% w/w to 0.5% w/w of the gemcabene as determined by high-performance liquid chromatography.

In some embodiments, the temperature of the heptane solution for purification ranges from 10° C. to 14° C. In some embodiments, the temperature of the heptane solution for purification is 12° C. In some embodiments, the temperature of the heptane solution during crystallization ranges from 10° C. to 14° C. In some embodiments, the temperature of the heptane solution during crystallization is 12° C.

In some embodiments, the crude gemcabene further comprises isobutyric acid in 0.5% w/w or less of the crude gemcabene as determined by ion chromatography. In some embodiments, the crude gemcabene comprises isobutyric acid in 0.3% or less of the crude gemcabene as determined by ion chromatography.

In some embodiments, the concentration of crude gemcabene in the heptane solution ranges from 0.3 g of crude gemcabene/mL of heptane to 0.8 g of crude gemcabene/mL of heptane. In some embodiments, the concentration of crude gemcabene in the heptane solution ranges from 0.5 g of crude gemcabene/mL of heptane to 0.7 g of crude gemcabene/mL of heptane. In some embodiments, the concentration of crude gemcabene in the heptane solution is 0.6 g of crude gemcabene/mL of heptane.

In some embodiments, the method of purifying crude gemcabene further comprises: dissolving the gemcabene in heptane to provide a heptane solution of the gemcabene; and cooling the heptane solution to a temperature ranging from 10° C. to 15° C. to precipitate recrystallized gemcabene.

In some embodiments of the method of purification of the crude gemcabene, heptane is n-heptane.

In some embodiments, the method of purifying crude gemcabene further comprises: allowing an enolate of an alkali metal salt of isobutyric acid to react with a bis-(4-halobutyl)ether to provide crude gemcabene salt and acidifying the crude gemcabene salt to provide the crude gemcabene. In some embodiments, the enolate of an alkali metal salt of isobutyric acid to react is allowed to react with the bis-(4-halobutyl)ether under conditions essentially free of water. In some embodiments, the method further comprising allowing sodium isobutyrate to react with an enolate-forming base to provide the enolate of sodium isobutyrate. In some embodiments, the method further comprising allowing isobutyric acid to react with sodium hydroxide to provide the sodium isobutyrate.

In some embodiments, the bis-(4-halobutyl)ether is bis-(4-chlorobutyl)ether.

In some embodiments, the enolate of the alkali metal salt of isobutyric acid is an enolate of sodium isobutyrate.

In some embodiments, the enolate-forming base is lithium hexamethyldisilazide, lithium diisopropylamide, lithium tetramethylpiperidide, or lithium diethylamide.

In some embodiments, the sodium hydroxide is in a water solution, and further comprising removing the water via evaporation after allowing the isobutyric acid to react with sodium hydroxide and before allowing the sodium isobutyrate to react with the enolate-forming base. In some embodiments, the sodium isobutyrate has a water content of 0.05% w/w or less of the reaction mixture comprising sodium isobutyrate as determined by Karl-Fisher analysis. In some embodiments, the sodium isobutyrate has a water content of about 0.05% w/w or less of the reaction mixture comprising sodium isobutyrate as determined by Karl-Fisher analysis.

In some embodiments, the enolate of the alkali metal salt of isobutyric acid is present in an amount of two or more molar equivalents and the bis-(4-halobutyl)ether present in an amount of one molar equivalent. In some embodiments, the enolate of an alkali metal salt of isobutyric acid is present in an amount of 2.1 to 2.4 molar equivalents and the bis-(4-halobutyl)ether present in an amount of one molar equivalent.

In some embodiments, the crude gemcabene further comprises isobutyric acid.

In some embodiments, at least some of the isobutyric acid is removed from the crude gemcabene via distillation after acidifying the crude gemcabene salt and before precipitating gemcabene from the heptane solution at a temperature ranging from 10° C. to 15° C. In some embodiments, the removal of isobutyric acid further comprising admixing the crude gemcabene and water prior to removing at least some of the isobutyric acid. In some embodiments, the distillation removes water and isobutyric acid. In some embodiments, the admixing the crude gemcabene and water and removing the water and at least some of the isobutyric acid is performed at least two times.

In some embodiments, the crude gemcabene after distillation comprises isobutyric acid in 0.5% w/w or less of the distilled crude gemcabene as determined by ion chromatography. In some embodiments, the crude gemcabene after distillation comprises isobutyric acid in 0.3% or less of the distilled crude gemcabene as determined by ion chromatography.

The present invention further provides gemcabene made by or purified by any one of the methods disclosed herein. In some embodiments, gemcabene comprises isobutyric acid in 0.10% w/w or less of the gemcabene as determined by ion chromatography. In some embodiments, gemcabene comprises isobutyric acid in 0.05% w/w or less of the gemcabene as determined by ion chromatography.

The present invention further provides a pharmaceutically acceptable salt of gemcabene made by or purified by any one of the methods disclosed herein. In some embodiments, the pharmaceutically acceptable salt is a calcium salt. In some embodiments, the calcium salt is a hydrate. In some embodiments, the calcium salt hydrate is Crystal Form 1. In some embodiments, the calcium salt hydrate is Crystal Form 2. In some embodiments, the calcium salt hydrate is Crystal Form C3. In some embodiments, the calcium salt is an ethanol solvate.

In some embodiments, the pharmaceutically acceptable salt of gemcabene comprises 2,2,7,7-tetramethyl-octane-1,8-dioic acid in 0.5% w/w or less of the pharmaceutically acceptable salt of gemcabene as determined by high-performance liquid chromatography. In some embodiments, the pharmaceutically acceptable salt gemcabene comprises water in 2% w/w to 5% w/w of the pharmaceutically acceptable salt of gemcabene as determined by Karl-Fisher analysis. In some embodiments, the pharmaceutically acceptable salt of gemcabene comprises isobutyric acid in 0.5% w/w or less of the pharmaceutically acceptable salt of gemcabene as determined by ion chromatography. In some embodiments, the pharmaceutically acceptable salt gemcabene comprises isobutyric acid in 0.10% w/w or less of the pharmaceutically acceptable salt of gemcabene as determined by ion chromatography. In some embodiments, the pharmaceutically acceptable salt gemcabene comprises isobutyric acid in 0.05% w/w or less of the pharmaceutically acceptable salt of gemcabene as determined by ion chromatography.

In some embodiments, the pharmaceutically acceptable salt gemcabene comprises 2.5 ppm or less of bis-(4-chlorobutyl)ether as determined by gas chromatography. In some embodiments, the pharmaceutically acceptable salt gemcabene comprises 2.5 ppm or less of. 6-(4-chlorobutoxy)-2,2-dimethyl-hexanoic acid as determined by gas chromatography. In some embodiments, the pharmaceutically acceptable salt gemcabene comprises 2.5 ppm or less of 1-chloro-4-hydroxybutane as determined by gas chromatography. In some embodiments, the pharmaceutically acceptable salt gemcabene comprises 8 ppm or less of sum of all genotoxic impurities, including but not limited to, bis-(4-chlorobutyl)ether, 1-chloro-4-hydroxybutane and 6-(4-chlorobutoxy)-2,2-dimethyl-hexanoic acid as determined by gas chromatography.

In some embodiments, the pharmaceutically acceptable salt gemcabene comprises total impurities in 2.0% w/w or less of the pharmaceutically acceptable salt of gemcabene as determined by high-performance liquid chromatography.

In some embodiments, the pharmaceutically acceptable salt gemcabene comprises a gemcabene conjugate base component in a range of 82% w/w to 92% w/w of the pharmaceutically acceptable salt of gemcabene as determined by high-performance liquid chromatography, wherein the gemcabene conjugate base component has the structure:

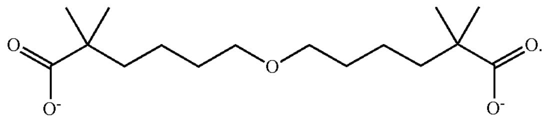 [SMILES: CC(CCC(C)(C)C(=O)[O-])COCCCCC(C)(C)C(=O)[O-]]

In some embodiments, the pharmaceutically acceptable salt gemcabene comprises calcium in about 10% m/m to about 14% m/m of the pharmaceutically acceptable salt of gemcabene as determined by inductively coupled plasma optical emission spectrometry. In some embodiments, the pharmaceutically acceptable salt gemcabene comprises calcium in about 9.8% m/m to 13.8% m/m of the pharmaceutically acceptable salt of gemcabene as determined by inductively coupled plasma optical emission spectrometry.

The present invention further provides pharmaceutical compositions comprising a pharmaceutically acceptable salt of gemcabene and a pharmaceutically acceptable carrier or vehicle, wherein gemcabene is synthesized according to any one of the methods disclosed herein. The present invention further provides pharmaceutical compositions comprising a pharmaceutically acceptable salt of gemcabene and a pharmaceutically acceptable carrier or vehicle, wherein gemcabene is purified according to any one of the methods disclosed herein. The present invention further provides pharmaceutical compositions comprising a pharmaceutically acceptable salt of gemcabene and a pharmaceutically acceptable carrier or vehicle, wherein gemcabene is purified according to any one of the methods disclosed by dissolving the crude gemcabene in heptane and cooling the heptane solution to a temperature ranging from 10° C. to 15° C. to precipitate gemcabene. In some embodiments, heptane is n-heptane.

Methods for Treatment or Prevention

The present invention provides methods for treating or preventing various diseases and conditions as disclosed herein, comprising administering to a subject in need thereof an effective amount of a compound of the invention. In some embodiments, the subject is human.

The present invention provides methods for treating or preventing liver disease or an abnormal liver condition, comprising administering to a subject in need thereof an effective amount of a compound of the invention.

Examples of liver disease or liver conditions include, but are not limited to, nonalcoholic fatty liver disease (NAFLD), nonalcoholic steatohepatitis (NASH), alcoholic steatohepatitis, cirrhosis, inflammation, liver fibrosis, partial fibrosis, primary biliary cirrhosis, primary sclerosing cholangitis, liver failure, hepatocellular carcinoma (HCC), liver cancer, hepatic steatosis, hepatocyte ballooning (also known as hepatocellular ballooning), hepatic lobular inflammation, and hepatic triglyceride accumulation. In some embodiments, the liver disease or the liver condition is NAFLD or NASH. In some embodiments, the liver disease or the liver condition is NAFLD. In other embodiments, the liver disease or the liver condition is NASH. In some embodiments, the liver disease or the liver condition is hepatic steatosis. In some embodiments, the liver disease or the liver condition is liver fibrosis.

In some embodiments, treating or preventing liver fibrosis, NAFLD, or NASH includes regressing, stabilizing, or inhibiting progression of liver fibrosis, NAFLD, or NASH.

The present invention further provides methods for reducing liver fat (fat content of the liver), stabilizing the amount of liver fat, or reducing the accumulation of liver fat, comprising administering to a subject in need thereof an effective amount of a compound of the invention. The present invention further provides methods for reducing liver steatosis (fat content of the liver), stabilizing the amount of liver triglycerides, or reducing the accumulation of liver triglycerides, comprising administering to a subject in need thereof an effective amount of a compound of the invention.

The present invention further provides methods for treating or preventing lobular inflammation or hepatocyte ballooning, comprising administering to a subject in need thereof an effective amount of a compound of the invention. In some embodiment, treating or preventing lobular inflammation or hepatocyte ballooning is slowing the progression of, stabilizing, or reducing the lobular inflammation or hepatocyte ballooning.

The present invention further provides methods for treating or preventing a disorder of lipoprotein metabolism, comprising administering to a subject in need thereof an effective amount of a compound of the invention.

Examples of disorders of lipoprotein metabolism include, but are not limited to, dyslipidemia, dyslipoproteinemia, mixed dyslipidemia, atherosclerotic cardiovascular disease (ASCVD), type IIb hyperlipidemia or familial combined hyperlipidemia, familial hypercholesterolemia, familial chylomicronemia syndrome, hypertriglyceridemia, dysbetalipoproteinemia, lipoprotein overproduction or deficiency, elevation of total cholesterol, elevation of low-density lipoprotein cholesterol concentration, elevation of very low-density lipoprotein cholesterol concentration, elevation of non-high-density lipoprotein (non-HDL) cholesterol concentration, elevation of apolipoprotein B concentration, elevation of apolipoprotein C-III concentration, elevation of C-reactive protein concentration, elevation of fibrinogen concentration, elevation of lipoprotein(a) concentration, elevation of interleukin-6 concentration, elevation of angiopoietin-like protein 3 concentration, elevation of angiopoietin-like protein 4 concentration, elevation of serum amyloid A concentration, elevation of PCSK9, increased risk of thrombosis, increased risk of a blood clot, low high-density lipoprotein (HDL)-cholesterol concentration, elevation of low-density lipoprotein concentration, elevation of very low-density lipoprotein concentration, elevation of triglyceride concentration, prolonged post-prandial lipemia, lipid elimination in bile, metabolic disorder, phospholipid elimination in bile, oxysterol elimination in bile, abnormal bile production, peroxisome proliferator activated receptor-associated disorder, hypercholesterolemia, hyperlipidemia and visceral obesity.

In some embodiments, the disorder of lipoprotein metabolism is dyslipidemia, dyslipoproteinemia, mixed dyslipidemia, atherosclerotic cardiovascular disease (ASCVD), type IIb hyperlipidemia, familial combined hyperlipidemia, familial hypercholesterolemia, familial chylomicronemia syndrome, hypertriglyceridemia, dysbetalipoproteinemia, metabolic syndrome, lipoprotein overproduction, lipoprotein deficiency, non-insulin dependent diabetes, abnormal lipid elimination in bile, a metabolic disorder, abnormal phospholipid elimination in bile, an abnormal oxysterol elimination in bile, an abnormal bile production, hypercholesterolemia, hyperlipidemia or visceral obesity. In other embodiments, the disorder of lipoprotein metabolism is mixed dyslipidemia, atherosclerotic cardiovascular disease (ASCVD), type IIb hyperlipidemia, familial combined hyperlipidemia, or familial hypercholesterolemia. In some embodiments, the disorder of lipoprotein metabolism is hypertriglyceridemia. In some embodiments, the disorder of lipoprotein metabolism is hypercholesterolemia. In other embodiments, the hypertriglyceridemia is a severe hypertriglyceridemia. "Severe hypertriglyceridemia" is where a subject has a baseline plasma triglyceride concentration of greater than or equal to 500 mg/dl. In some embodiments, familial hypercholesterolemia (FH) is homozygous FH (HoFH) or heterozygous FH (HeFH).

The present invention further provides methods for treating or preventing a peroxisome proliferator activated receptor-associated disorder.

The present invention further provides methods for reducing a subject's plasma or blood serum triglyceride concentration, comprising administering to a subject in need thereof an effective amount of a compound of the invention.

The present invention further provides methods for reducing in a subject's blood plasma or blood serum, the subject's total cholesterol concentration, low-density lipoprotein cholesterol concentration, low-density lipoprotein concentration, very low-density lipoprotein cholesterol concentration, very low-density lipoprotein concentration, non-HDL cholesterol concentration, non-HDL concentration, apolipoprotein B concentration, triglyceride concentration, apolipoprotein C-III concentration, C-reactive protein concentration, fibrinogen concentration, lipoprotein(a) concentration, interleukin-6 concentration, angiopoietin-like protein 3 concentration, angiopoietin-like protein 4 concentration, PCSK9 concentration, or serum amyloid A concentration, comprising administering to a subject in need thereof an effective amount of a compound of the invention. In some embodiments, a method for reducing a subject's blood plasma or blood serum total cholesterol concentration and reducing a subject's blood plasma or blood serum low-density lipoprotein cholesterol concentration, low-density lipoprotein concentration, very low-density lipoprotein cholesterol concentration, very low-density lipoprotein concentration, non-HDL cholesterol concentration, non-HDL concentration, apolipoprotein B concentration, triglyceride concentration, apolipoprotein C-III concentration, C-reactive protein concentration, fibrinogen concentration, lipoprotein(a) concentration, interleukin-6 concentration, angiopoietin-like protein 3 concentration, angiopoietin-like protein 4 concentration, PCSK9 concentration, or serum amyloid A concentration, comprising administering to a subject in need thereof an effective amount of a compound of the invention is provided. In some embodiments, the present invention provides methods for reducing in the subject's blood plasma or blood serum, the subject's triglyceride concentration or low-density lipoprotein cholesterol concentrations, comprising administering to a subject in need thereof an effective amount of a compound of the invention.

The present invention further provides methods for lowering in a subject's blood plasma or blood serum, the subject's low-density lipoprotein cholesterol (LDL-C) concentration, comprising administering to a subject in need thereof an effective amount of a compound of the invention, wherein the subject is on a stable dose of a statin.

The present invention provides methods for elevating in a subject's blood plasma or blood serum, the subject's high-density lipoprotein cholesterol concentration, high-density lipoprotein concentration, high-density cholesterol triglyceride concentration, adiponectin concentration or apolipoprotein A-I concentration, comprising administering to a subject in need thereof an effective amount of a compound of the invention.

The present invention provides methods for cholesterol or triglyceride mobilization from a subject's endothelial and epithelial cells to the subject's blood plasma or blood serum and transport for clearance and excretion, comprising administering to a subject in need thereof an effective amount of a compound of the invention.

The present invention provides methods for reducing a subject's risk of developing a thrombosis, a blood clot, a primary cardiovascular event, a secondary cardiovascular event, progression to nonalcoholic fatty liver disease, nonalcoholic steatohepatitis, liver cirrhosis, hepatocellular carcinoma, liver failure, pancreatitis, pulmonary fibrosis, or hyperlipoproteinemia type IIB, comprising administering to a subject in need thereof an effective amount of a compound of the invention. In some embodiments, the present invention provides methods for reducing a subject's risk of developing pancreatitis.

The present invention provides methods for reducing a subject's risk of developing an ApoC-II deficiency.

The present invention provides methods for treating or preventing fibrosis, steatosis, ballooning or inflammation in the liver of a subject, comprising administering to a subject in need thereof an effective amount of a compound of the invention. In some embodiments, treating or preventing ballooning or inflammation in the liver of a subject is reducing ballooning or inflammation in the liver of a subject. The present invention further provides reducing or inhibiting progression of fibrosis, steatosis, ballooning or inflammation in the liver of a subject, comprising administering to a subject in need thereof an effective amount of a compound of the invention.

The present invention provides methods for reducing post-prandial lipemia or preventing prolonged post-prandial lipemia, comprising administering to a subject in need thereof an effective amount of a compound of the invention. The present invention provides methods for decreasing the extent and duration of post-prandial lipemia, comprising administering to a subject in need thereof an effective amount of a compound of the invention. The present invention provides methods for decreasing the extent and duration of post-prandial lipemia, comprising administering to a subject in need thereof a composition of the invention.

The present invention provides methods for treating or preventing hypoalphalipoproteinemia.

The present invention provides methods for reducing a magnitude or duration of post-prandial lipemia, comprising administering to a subject in need thereof an effective amount of a compound of the invention.

The present invention provides methods for reducing a fat content of the liver of a subject, comprising administering to a subject in need thereof an effective amount of a compound of the invention. The present invention provides methods for reducing a steatosis of the liver of a subject, comprising administering to a subject in need thereof an effective amount of a compound of the invention.

The present invention further provides methods for reducing a subject's risk of thrombosis or blood clot, comprising administering to a subject in need thereof an effective amount of a compound of the invention.

In some embodiments, the therapeutic or prophylactic methods of the invention are effective to reduce a subject's plasma or blood serum triglyceride concentration to below about 200 mg/dl or to below about 150 mg/dl. In some embodiments, the therapeutic or prophylactic methods of the invention are effective to reduce a subject's plasma or blood serum triglyceride concentration to below about 200 mg/dl or to below about 150 mg/dl within about 8 to about 12 weeks after administering a compound of the invention.

In some embodiments, the therapeutic or prophylactic methods of the invention are effective to reduce the subject's plasma or blood serum triglyceride concentration by at least 10% in a subject whose baseline plasma or blood serum triglyceride concentration is 500 mg/dl or higher, comprising administering to a subject in need thereof an effective amount of a compound of the invention. In some embodiments, the therapeutic or prophylactic methods of the invention are effective to reduce the subject's plasma or blood serum triglyceride concentration by at least 10%, at least 15%, at least 20%, at least 25%, at least 30%, at least 35%, at least 40%, at least 45%, at least 50%, at least 55%, at least 60%, or any range between any of these values, of the baseline plasma or blood serum triglyceride concentration where the subject has a baseline plasma or blood serum triglyceride concentration of 500 mg/dl or higher. In some embodiments, the therapeutic or prophylactic methods of the invention are effective to reduce the subject's plasma or blood serum triglyceride concentration by up to about 60% of the baseline plasma or blood serum triglyceride concentration in a subject whose baseline plasma or blood serum triglyceride concentration is 500 mg/dl or higher, comprising administering to a subject in need thereof an effective amount of a compound of the invention.

In some embodiments, the therapeutic or prophylactic methods of the invention are effective to reduce the subject's plasma or blood serum triglyceride concentration by at least 10% in a subject whose baseline plasma or blood serum triglyceride concentration is 200 mg/dl or higher, comprising administering to a subject in need thereof an effective amount of a compound of the invention. In some embodiments, the therapeutic or prophylactic methods of the invention are effective to reduce the subject's plasma or blood serum triglyceride concentration by at least 10%, at least 15%, at least 20%, at least 25%, at least 30%, at least 35%, at least 40%, or any range between any of these values, of the baseline plasma or blood serum triglyceride concentration where the subject has a baseline plasma or blood serum triglyceride concentration is 200 mg/dl or higher. In some embodiments, the therapeutic or prophylactic methods of the invention are effective to reduce the subject's plasma or blood serum triglyceride concentration by up to about 35%, by up to about 36%, by up to about 37%, by up to about 38%, by up to about 39%, or by up to about 40% of the baseline plasma or blood serum triglyceride concentration in a subject whose baseline plasma or blood serum triglyceride concentration is 200 mg/dl or higher, comprising administering to a subject in need thereof an effective amount of a compound of the invention.

The present invention further provides methods for reducing a subject's plasma or blood serum LDL cholesterol concentration, comprising administering to a subject in need thereof an effective amount of a compound of the invention.

In some embodiments, the present methods are effective to reduce the subject's plasma or blood serum LDL cholesterol concentration to below about 130 mg/dl. In some embodiments, the present methods are effective to reduce the subject's plasma or blood serum LDL cholesterol concentration to below about 130 mg/dl within about 8 to about 12 weeks of administering a compound of the invention.

The present invention further provides methods for reducing a subject's ApoB concentration, comprising administering to a subject in need thereof an effective amount a compound of the invention. In some embodiments, the methods are effective to reduce the subject's ApoB concentration to below about 120 mg/dl. In some embodiments, the methods are effective to reduce the subject's ApoB concentration to below about 120 mg/dl within about 8 to about 12 weeks following administering a compound of the invention.

In some embodiments, the subject has atherometabolic syndrome, metabolic syndrome, type-2 diabetes, impaired glucose tolerance, obesity, dyslipidemia, hepatitis B, hepatitis C, a human immunodeficiency virus (HIV) infection, or a metabolic disorder such as Wilson's disease, a glycogen storage disorder, galactosemia, an inflammatory condition or an elevated body mass index above what is normal for the subject's gender, age or height. Without being bound by theory, metabolic syndrome, type-2 diabetes, impaired glucose tolerance, obesity, dyslipidemia, hepatitis B, hepatitis C, an HIV infection, or a metabolic disorder such as Wilson's disease, a glycogen storage disorder or galactosemia is believed to be a risk factor for developing fatty liver (steatosis).

In some embodiments, the subject has an HIV infection. In some embodiments, the subject has an HIV infection and the subject is being administered with a highly active antiretroviral therapy (HAART) agent such as an antiretroviral inhibitor. Without being bound by theory, a compound of the invention is believed to be catabolized to a much lesser extent by the same P450 enzymes that metabolize antiretroviral inhibitors when treating an HIV subject undergoing an antiretroviral inhibitor treatment.

In some embodiments, the present invention further provides methods for treating or preventing an HIV-associated the liver disease or the liver condition. In some embodiments, the present invention further provides methods for treating or preventing an HIV-associated NAFLD. In some embodiments, the present invention further provides methods for treating or preventing an HIV-associated lipodystrophy. In some embodiments, the present invention further provides methods for treating or preventing a liver disease or the liver condition, comprising administering an effective amount of a compound of the invention to a subject who has an HIV infection. In some embodiments, the present invention further provides methods for treating or preventing NAFLD, comprising administering an effective amount of a compound of the invention to a subject who has an HIV infection.

The present invention further provides methods for treating or preventing a disorder of glucose metabolism, comprising administering to a subject in need thereof an effective amount of a compound of the invention.

Examples of disorders of glucose metabolism include, but are not limited to, is insulin resistance, impaired glucose tolerance, impaired fasting glucose (concentrations in blood), diabetes mellitus, lipodystrophy, familial partial lipodystrophy, obesity, peripheral lipoatrophy, diabetic nephropathy, diabetic retinopathy, renal disease, and septicemia. In some embodiments, obesity is central obesity.

In some embodiments, the present invention further provides methods for treating or preventing a disorder of glucose metabolism, comprising administering an effective amount of a compound of the invention to a subject who has an HIV infection, In some embodiments, the present invention further provides methods for treating or preventing lipodystrophy, comprising administering an effective amount of a compound of the invention to a subject who has an HIV infection.

The present invention further provides methods for treating or preventing a cardiovascular disorder or a related vascular disorder, comprising administering to a subject in need thereof an effective amount of a compound of the invention.

Examples of cardiovascular disorders and related vascular disorders include, but are not limited to, arteriosclerosis, atherosclerosis, hypertension, coronary artery disease, myocardial infarction, arrhythmia, atrial fibrillation, heart valve disease, heart failure, cardiomyopathy, myopathy, pericarditis, impotence, and a thrombotic disorder.

The present invention further provides methods for reducing a subject's risk of having a cardiovascular or vascular event, comprising administering to a subject in need thereof an effective amount of a compound of the invention.

In some embodiments, the cardiovascular or vascular event is primary cardiovascular event. In other embodiments, the cardiovascular event is secondary cardiovascular event. Examples of cardiovascular events include, but are not limited to, myocardial infarction, stroke, angina, acute coronary syndrome, coronary artery bypass graft surgery and cardiovascular death. A primary cardiovascular event is the first cardiovascular event that a subject experiences. If the same subject experiences a second cardiovascular event, then the second cardiovascular event is a secondary cardiovascular event.

The present invention further provides methods for treating or preventing a disease caused by an increased level of fibrosis, comprising administering to a subject in need thereof an effective amount of a compound of the invention. In some embodiments, the disease caused by an increased level of fibrosis is a lung disease. In some embodiments, the disease caused by an increased level of fibrosis is a heart disease. In some embodiments, the disease caused by an increased level of fibrosis is a skin disease. Examples of diseases caused by an increased level of fibrosis include, but are not limited to, chronic obstructive pulmonary disease, cystic fibrosis, idiopathic pulmonary fibrosis, emphysema, nephrogenic fibrosis, endometrial fibrosis, perineural fibrosis, hepatic fibrosis, myocardial fibrosis, acute lung injury, radiation-induced lung injury following treatment for cancer, progressive massive fibrosis, a complication of coal workers' pneumoconiosis (lungs), cirrhosis (liver), atrial fibrosis, endomyocardial fibrosis, old myocardial infarction, arterial stiffness (heart), glial scar (brain), arthrofibrosis (knee, shoulder, other joints), Crohn's Disease (intestine), Dupuytren's contracture (hands, fingers), keloid (skin), mediastinal fibrosis (soft tissue of the mediastinum), myelofibrosis (bone marrow), Peyronie's disease (penis), nephrogenic systemic fibrosis (skin), retroperitoneal fibrosis (soft tissue of the retroperitoneum), scleroderma/systemic sclerosis (skin, lungs), and some forms of adhesive capsulitis (shoulder). In some embodiments, the disease caused by increased levels of fibrosis is a chronic obstructive pulmonary disease or an idiopathic pulmonary fibrosis.

The present invention further provides methods for treating or preventing a disease associated with increased inflammation, comprising administering to a subject in need thereof an effective amount of a compound of the invention. In some embodiments, the disease associated with increased inflammation is an autoimmune disease.

Examples of diseases associated with increased inflammation include, but are not limited to, multiple sclerosis, inflammatory bowel disease, celiac disease, Crohn's disease, antiphospholipid syndrome, atherosclerosis, autoimmune encephalomyelitis, autoimmune hepatitis, Graves' disease, ulcerative colitis, multiple sclerosis, myasthenia gravis, myositis, polymyositis, Raynaud's phenomenon, rheumatoid arthritis, scleroderma, Sjogren's syndrome, systemic lupus, type 1 diabetes and uveitis. In some embodiments, the disease associated with increased inflammation is multiple sclerosis, inflammatory bowel disease, celiac disease, or Crohn's disease.

The present invention further provides methods for preventing death from or increasing survival from a disease associated with increased inflammation, comprising administering to a subject in need thereof an effective amount of a compound of the invention. In some embodiments, the disease associated with increased inflammation is influenza, sepsis, or a viral disease.

Examples of viral diseases include, but are not limited to, influenza, human immunodeficiency virus infection, hepatitis B, and hepatitis C.

The present invention further provides methods for treating or preventing an inflammation, comprising administering to a subject in need thereof an effective amount of a compound of the invention. In some embodiments, the inflammation is indicated by an increased concentration of C-reactive protein in a patient's plasma or serum.

Examples of C-reactive protein related disorders include, but are not limited to, inflammation, ischemic necrosis, and a thrombotic disorder.

The present invention further provides methods for treating or preventing a sulfatase-2-related disorder, comprising administering to a subject in need thereof an effective amount of a compound of the invention. Examples of sulfatase-2-related disorders include, but are not limited to, disorders of lipogenesis or lipid modulation, elevated plasma or blood serum triglycerides or hyperlipidemia, hypercholesterolemia, diabetes, fatty liver disease, obesity, atherosclerosis, and/or cardiovascular diseases.

The present invention further provides methods for treating or preventing an apolipoprotein C-III-related disorder, comprising administering to a subject in need thereof an effective amount of a compound of the invention. Examples of apolipoprotein C-III-related disorders include, but are not limited to, disorders of lipogenesis or lipid modulation, elevated plasma or blood serum triglycerides or hyperlipidemia, hypercholesterolemia, diabetes, fatty liver disease, obesity, atherosclerosis, and/or cardiovascular diseases.

The present invention further provides methods for treating or preventing Alzheimer's disease, comprising administering to a subject in need thereof an effective amount of a compound of the invention.

The present invention further provides methods for treating or preventing Parkinson's disease, comprising administering to a subject in need thereof an effective amount of a compound of the invention.

The present invention further provides methods for treating or preventing pancreatitis, comprising administering to a subject in need thereof an effective amount of a compound of the invention.

The present invention further provides methods for treating or preventing the risk of developing pancreatitis, comprising administering to a subject in need thereof an effective amount of a compound of the invention.

The present invention further provides methods for treating or preventing a pulmonary disorder, comprising administering to a subject in need thereof an effective amount of a compound of the invention. In some embodiments, the pulmonary disorder is a chronic obstructive pulmonary disease or an idiopathic pulmonary fibrosis.

The present invention further provides methods for treating or preventing musculoskeletal discomfort, comprising administering to a subject in need thereof an effective amount of a compound of the invention.

The present invention further provides methods for reducing a subject's plasma or blood serum fibrinogen concentration, comprising administering to a subject in need thereof an effective amount of a compound of the invention.

In some embodiments, the subject's plasma or blood serum fibrinogen concentration is greater than 300 mg/dl. In some embodiments, the subject's plasma or blood serum fibrinogen concentration is greater than 400 mg/dl.

The present invention further provides methods for reducing a fibrosis score or a nonalcoholic fatty liver disease activity score in a subject, comprising administering to a subject in need thereof an effective amount of a compound of the invention. The nonalcoholic fatty liver disease activity score (NAS or NAFLD score) is a composite score that measures changes in NAFLD during therapeutic trials. NAS is a composite score comprised of three components that includes scores for steatosis, lobular inflammation and hepatocyte ballooning (Table 15). NAS is the unweighted sum of the scores for steatosis, lobular inflammation and hepatocyte ballooning. Steatosis grade is quantified as the percentage of hepatocytes that contain fat droplets. The fibrosis stage of the liver is evaluated separately from NAS by histological evaluation of the intensity of Sirius red staining of collagen in the pericentral region of liver lobules.

The present invention provides methods for slowing the progression of a component of NAS, comprising administering to a subject in need thereof a compound of the invention. The present invention provides methods for slowing the progression of a component of NAS, comprising administering to a subject in need thereof a composition of the invention.

The present invention provides methods for slowing the progression of steatosis, lobular inflammation, or hepatocyte ballooning, comprising administering to a subject in need thereof a compound of the invention. The present invention provides methods for slowing the progression of steatosis, lobular inflammation, or hepatocyte ballooning, comprising administering to a subject in need thereof a composition of the invention.

The present invention provides methods for slowing the progression of steatosis, comprising administering to a subject in need thereof a compound of the invention or a composition of the invention. The present invention provides methods for slowing the progression of lobular inflammation, comprising administering to a subject in need thereof a compound of the invention or a composition of the invention. The present invention provides methods for slowing the progression of hepatocyte ballooning, comprising administering to a subject in need thereof a compound of the invention or a composition of the invention.

The present invention further provides methods for reducing elevated total cholesterol, low-density lipoprotein cholesterol (LDL-C), apolipoprotein B (Apo B), triglyceride or non-high-density lipoprotein cholesterol in a subject, comprising administering to a subject in need thereof an effective amount of a compound of the invention. The present invention further provides methods for increasing high-density lipoprotein cholesterol in a subject, comprising administering to a subject in need thereof an effective amount of a compound of the invention. In some embodiments, the subject has primary hyperlipidemia. In some embodiments, the primary hyperlipidemia is heterozygous familial. In some embodiments, the primary hyperlipidemia is homozygous familial. In some embodiments, the primary hyperlipidemia is non-familial. In some embodiments, the subject has mixed hyperlipidemia.

The present invention further provides methods for treating or preventing a condition or disease associated with hepatic overexpression of sulfatase-2 (Sulf-2) mRNA, comprising administering to a subject in need thereof an effect amount of a compound of the invention. Without bound to any theory, it is believed that Sulf-2 inhibits hepatic disposal of C-TRLs, thereby increasing plasma or blood serum triglyceride concentration in a subject. Conditions or diseases associated with hepatic overexpression of Sulf-2 include but are not limited to, elevated plasma or blood serum triglycerides or hyperlipidemia, hypercholesterolemia, diabetes, fatty liver disease, obesity, atherosclerosis, and/or cardiovascular diseases.

The present invention further provides methods for treating or preventing a condition or disease associated with hepatic overexpression of ApoC-III mRNA, comprising administering to a subject in need thereof an effect amount of a compound of the invention. Without bound to any theory, it is believed that overexpression of ApoC-III mRNA leads to increased plasma or blood serum triglyceride concentration in a subject. Conditions or diseases associated with hepatic overexpression of ApoC-III include, but are not limited to, elevated blood serum triglycerides or hyperlipidemia, hypercholesterolemia, diabetes, fatty liver disease, obesity, atherosclerosis, and/or cardiovascular diseases.

The present invention further provides methods for treating or preventing a condition or disease associated with hepatic overexpression of ANGPTL3 mRNA, comprising administering to a subject in need thereof an effect amount of a compound of the invention. Without bound to any theory, it is believed that overexpression of ANGPTL3 mRNA leads to blockage of lipoprotein lipase activity and elevated plasma or blood serum triglyceride concentration in a subject. Conditions or diseases associated with hepatic overexpression of ANGPTL3 include, but are not limited to, elevated blood serum triglycerides or hyperlipidemia, hypercholesterolemia, diabetes, fatty liver disease, obesity, atherosclerosis, and/or cardiovascular diseases.

The present invention further provides methods for treating or preventing a condition or disease associated with hepatic overexpression of ANGPTL4 mRNA, comprising administering to a subject in need thereof an effect amount of a compound of the invention. Without bound to any theory, it is believed that overexpression of ANGPTL4 mRNA leads to blockage of lipoprotein lipase activity and elevated plasma or blood serum triglyceride concentration in a subject. Conditions or diseases associated with hepatic overexpression of ANGPTL4 include, but are not limited to, elevated blood serum triglycerides or hyperlipidemia, hypercholesterolemia, diabetes, fatty liver disease, obesity, atherosclerosis, and/or cardiovascular diseases.

The present invention further provides methods for treating or preventing a condition or disease associated with hepatic overexpression of ANGPTL8 mRNA, comprising administering to a subject in need thereof an effect amount of a compound of the invention. Without bound to any theory, it is believed that overexpression of ANGPTL8 mRNA leads to blockage of lipoprotein lipase activity and elevated plasma or blood serum triglyceride concentration in a subject. Conditions or diseases associated with hepatic overexpression of ANGPTL8 include, but are not limited to, elevated blood serum triglycerides or hyperlipidemia, hypercholesterolemia, diabetes, fatty liver disease, obesity, atherosclerosis, and/or cardiovascular diseases.

The present invention provides methods for lowering a subject's blood plasma or blood serum LDL-C concentration, comprising administering to a subject in need thereof an effective amount of a compound of the invention or a composition of the invention. The present invention further provides methods for reducing a subject's blood plasma or blood serum elevated total cholesterol or elevated LDL-C, comprising administering to a subject in need thereof an effective amount of a compound of the invention. In some embodiments, the subject has homozygous familial hypercholesterolemia (HoFH). In some embodiment, the subject is known to have HoFH. In some embodiments, the subject has heterozygous familial hypercholesterolemia (HeFH). In some embodiments, the subject is known to have HeFH. The therapeutic or prophylactic methods of the invention can further comprise administering an additional pharmaceutically active agent to a subject. The therapeutic or prophylactic methods of the invention can further comprise administering two or more additional pharmaceutically active agents to a subject. In some embodiments, the subject is on a stable dose of statin.

The present invention provides methods for lowering a subject's LDL-C concentration, comprising administering to a subject in need thereof an effective amount of a compound of the invention, wherein the subject is on a stable dose of a statin.

In some embodiments, the additional pharmaceutically active agent is a statin, lipid lowering agent, a PCSK9 inhibitor, Vitamin E, an ANGPTL3 inhibitor, an ANGPTL4 inhibitor, an ANGPTL8 inhibitor, a cholesterol absorption inhibitor, a ACC inhibitor, an ApoC-III inhibitor, an ACL inhibitor, a fish oil, a fibrate, a thyroid hormone beta receptor agonist, a farnesoid X receptor (FXR), a CCR2/CCR5 (C—C chemokine receptor types 2 (CCR2) and 5 (CCR5)) inhibitor or antagonist, a caspase protease inhibitor, an ASK-1 (Apoptosis signal-regulating kinase 1) inhibitor, a galectin-3 protein, a NOX (Nicotinamide adenine dinucleotide phosphate oxidase) inhibitor, an ileal bile acid transporter, a PPAR (peroxisome proliferator-activated receptor) agonist, a PPAR dual agonist, a pan-PPAR agonist, a sodium-glucose co-transporter 1 or 2 (SGLT1 or SGLT2) inhibitor, a dipeptidyl peptidase 4 (DPP4) inhibitor, a fatty acid synthase (FAS) inhibitor, a toll-like receptor antagonist, a thyroid hormone receptor-beta (THR-β) agonist, a liver-directed, selective THR-β agonist, an ACO1 modulator, a 1-mieloperoxidase inhibitor, a 1-ketohexokinase (1-KHK) inhibitor, an oxidative stress inhibitor, a fibroblast growth factor 21 (FGF21) or 19 (FGF19) inhibitor, a transforming growth factor beta-1 (TGF-β1) agonist, a hepatic de novo lipogenesis (DNL) inhibitor, an enoyl CoA hydratase inhibitor, a cholesterol 7-alpha hydroxylase (Cyp7A1) agonist, a Collagen Type 3 inhibitor, or a CETP inhibitor. The additional therapeutic agent can be a lipid-lowering treatment or agent. The lipid-lowering treatment or agent can be ezetimibe.

The therapeutic or prophylactic methods of the invention can further comprise administering a statin and ezetimibe.

In some embodiments, the subject is undergoing gastric bypass surgery.

The present invention further provides methods for treating or preventing heterozygous familial hypercholesterolemia (HeFH), comprising administering to a subject in need thereof an effective amount of a compound of the invention. The present invention further provides methods for treating or preventing atherosclerotic cardiovascular disease (ASCVD), comprising administering to a subject in need thereof an effective amount of a compound of the invention. In further embodiments, the atherosclerotic cardiovascular disease is a clinical atherosclerotic cardiovascular disease. In some embodiments, the subject is an adult. In some embodiments, the subject is on statin therapy. In some embodiments, the statin therapy is maximally tolerated statin therapy. In some embodiments, the methods further comprise administering a statin to the subject. In some embodiments, the subject has abnormally high plasma or blood serum LDL-C. In some embodiments, the maximally tolerated statin therapy is insufficient to lower the subject's plasma or blood serum LDL-C. In some embodiment, the maximally tolerated statin therapy is insufficient to lower the subject's plasma or blood serum LDL-C to the subject's goal plasma or blood serum LDL-C concentration.

A subject's goal plasma or blood serum LDL-C concentration varies with the subject's risk factor or factors, preexisting conditions, and/or health status. For example, LDL-C goal concentration for all human subjects, including human subjects with CHD (coronary heart disease) and other clinical forms of atherosclerotic disease should be less than 100 mg/dL. In addition, a reasonable or a desirable LDL-C goal concentration for all human subject with CHD and other clinical forms of atherosclerotic disease can be less than 70 mg/dL (Smith et al. *Circulation.* 2006; 113: 2363-2372).

The present invention further provides methods for treating or preventing HoFH, comprising administering to a subject in need thereof an effective amount of a compound of the invention. In some embodiments, the subject is on one or more other low-density lipoprotein (LDL) lowering therapies. In some embodiments, the methods further comprise administering an LDL-lowering therapy to the subject. Non-limiting examples of LDL-lowering therapies include statins, ezetimibe and LDL apheresis. In some embodiments, the subject has abnormally high LDL-C. In some embodiments, the other LDL-lowering therapy is insufficient to lower the subject's LDL-C. In some embodiments, the other LDL-lowering therapy is insufficient to lower the subject's LDL-C to the subject's goal concentration. In some embodiments, the methods further comprise administering one or more additional pharmaceutically active agents, as disclosed herein.

The present invention further provides methods for reducing risk of a cardiovascular event, comprising administering to a subject in need thereof an effective amount of a compound of the invention. In some embodiments, the subject has coronary heart disease (CHD). In some embodiments, the subject has a history of acute coronary syndrome (ACS). In some embodiments, the subject has been previously treated with a statin. In other embodiments, the subject has not been previously treated with a statin.

The present invention further provides methods for treating or preventing primary hypercholesterolemia, comprising administering to a subject in need thereof an effective amount of a compound of the invention. The primary hypercholesterolemia can be HeFH or non-familial hypercholesterolemia. In some embodiments, the present invention further provides methods for treating or preventing mixed hyperlipidemia in a subject, comprising administering to a subject in need thereof an effective amount of a compound of the invention. In some embodiments, the subject or the subject's symptoms are not effectively treated with statin therapy alone. As used herein, "not effectively treated with statin therapy alone" means that the subject's plasma or blood serum LDL-C is not lowered to the subject's goal concentration with a given treatment. In some embodiments, the subject had been administered with a statin and/or ezetimibe prior to administration of a compound of the invention. In some embodiments, the subject was treated with a statin and/or ezetimibe previously, prior to administration of a compound of the invention. In some embodiments, the methods further comprise administering a one or both of a statin and ezetimibe to the subject.

The present invention further provides methods for treating or preventing HoFH, comprising administering to a subject in need thereof an effective amount of a compound of the invention. In some embodiments, the method further comprises administering an adjunctive treatment. The adjunctive treatment can be one or more of a statin, ezetimibe and LDL apheresis. In some embodiments, the adjunctive treatment is LDL-lowering therapy. In some embodiments, the adjunctive treatment can be one or more of a statin, ezetimibe, LDL apheresis, PCSK9 inhibitor, and bile acid sequestrant. In some embodiments, the adjunctive treatment can be one or more of a statin, ezetimibe, LDL apheresis, PCSK9 inhibitor, bile acid sequestrant, lomitapide (Juxtapid®) and mipomersen (Kynamro®). In some embodiments, the adjunctive treatment can be one or more additional pharmaceutically active agents, as disclosed herein.

The present invention further provides methods for reducing risk of having myocardial infarction, having a stroke, needing a revascularization procedure or having angina, comprising administering to a subject in need thereof an effective amount of a compound of the invention. In some embodiments, the subject does not have coronary heart disease (CHD). In some embodiments, the subject has one or more risk factors for CHD. Examples of risk factors for CHD include, but are not limited to, high plasma or blood serum cholesterol, high plasma or blood serum triglyceride, high blood pressure, diabetes, prediabetes, overweight or obesity, smoking, lack of physical activity, unhealthy diets, stress. In addition, age, gender, and family history of early CHD can be a risk factor for CHD.

The present invention further provides methods for reducing a subject's risk of myocardial infarction or stroke, comprising administering to a subject in need thereof an effective amount of a compound of the invention. In some embodiments, the subject has type 2 diabetes. In some embodiments, the subject has type 2 diabetes and does not have CHD. In some embodiments, the subject has one or more risk factors for CHD.

The present invention further provides methods for reducing a subject's risk of non-fatal myocardial infarction, risk of fatal stroke or non-fatal stroke, need for a revascularization procedure, risk of congestive heart failure (CHF) or risk of angina, comprising administering to a subject in need thereof an effective amount of a compound of the invention. In some embodiments, the subject has CHD.

The present invention further provides methods for reducing in a subject's blood plasma or blood serum elevated total cholesterol, LDL-C, Apo B or triglyceride concentration, comprising administering to a subject in need thereof an effective amount of a compound of the invention. The present invention further provides methods for increasing high-density lipoprotein cholesterol in a subject, comprising administering to a subject in need thereof an effective amount of a compound of the invention. In some embodiments, the subject is an adult. In some embodiments, the subject has primary hyperlipidemia. Primary hyperlipidemia can be heterozygous familial or non-familial. In some embodiments, the subject has mixed dyslipidemia.

The present invention further provides methods for reducing in a subject's blood plasma or blood serum elevated triglyceride concentration, comprising administering to a subject in need thereof an effective amount of a compound of the invention. In some embodiments, the subject has hypertriglyceridemia. In some embodiments, the subject has primary dysbetalipoproteinemia. In yet some other embodiment, the subject has hypoalphalipoproteinemia.

The present invention further provides methods for reducing in a subject's blood plasma or blood serum total cholesterol or LDL-C concentration, comprising administering to a subject in need thereof an effective amount of a compound of the invention. In some embodiments, the subject has HoFH.

The present invention further provides methods for reducing in a subject's blood plasma or blood serum elevated total cholesterol, LDL-C or Apo B concentration, comprising administering to a subject in need thereof an effective amount of a compound of the invention. In some embodiments, the subject is a human male or a human female (e.g., postmenarcheal female) who is 10-17 years of age. In some embodiments, the subject has HeFH. In some embodiments, the subject's diet is insufficient to reduce the subject's elevated total cholesterol, LDL-C or Apo B. In some embodiments, the subject's life-style or diet and life-style is insufficient to reduce the subject's elevated total cholesterol, LDL-C or Apo B.

The present invention further provides methods for reducing a subject's risk of mortality, CHD death, non-fatal myocardial infarction, stroke or need for a revascularization procedure, comprising administering to a subject in need thereof an effective amount of a compound of the invention. In some embodiments, the subject is at high risk of a coronary event.

The present invention further provides methods for reducing in a subject's blood plasma or blood serum elevated total cholesterol, LDL-C, Apo B or triglyceride concentration, comprising administering to a subject in need thereof an effective amount of a compound of the invention. The present invention further provides methods for increasing in a subject's blood plasma or blood serum high-density lipoprotein cholesterol, comprising administering to a subject in need thereof an effective amount of a compound of the invention. In some embodiments, the subject has primary hyperlipidemia. In some embodiments, the primary hyperlipidemia is HeFH. In some embodiments, the primary hyperlipidemia is non-familial hyperlipidemia. In some embodiments, the subject has mixed dyslipidemia.

The present invention further provides methods for reducing in a subject's blood plasma or blood serum elevated triglyceride concentration, comprising administering to a subject in need thereof an effective amount of a compound of the invention. In some embodiments, the subject has hypertriglyceridemia. The present invention further provides methods for reducing in a subject's blood plasma or blood serum triglyceride or very-low-density lipoprotein cholesterol (VLDL-C), comprising administering to a subject in need thereof an effective amount of a compound of the invention. In some embodiments, the subject has primary dysbetalipoproteinemia.

The present invention further provides methods for reducing in a subject's blood plasma or blood serum elevated total cholesterol or LDL-C concentration, comprising administering to a subject in need thereof an effective amount of a compound of the invention. In some embodiments, the subject is an adult. In some embodiments, the subject has HoFH.

The present invention further provides methods for treating or preventing hypertriglyceridemia, comprising administering to a subject in need thereof an effective amount of a compound of the invention. In some embodiments, the method further comprises adjusting the subject's diet. In some embodiments, the method further comprises placing the subject on a low-fat diet.

The present invention further provides methods for treating or preventing primary dysbetalipoproteinemia, comprising administering to a subject in need thereof an effective amount of a compound of the invention. In some embodiments, the primary dysbetalipoproteinemia is Type III hyperlipoproteinemia. In some embodiments, the method further comprises adjusting the subject's diet. In some embodiments, the method further comprises placing the subject on a low-fat diet.

The present invention further provides methods for reducing in a subject's blood plasma or blood serum total cholesterol, LDL-C or Apo B concentration, comprising administering to a subject in need thereof an effective amount of a compound of the invention. In some embodiments, the subject has HoFH.

The present invention further provides methods for reducing in a subject's blood plasma or blood serum elevated LDL-C, total cholesterol, Apo B or triglyceride concentration, comprising administering to a subject in need thereof an effective amount of a compound of the invention. The present invention further provides methods for increasing in a subject's blood plasma or blood serum high-density lipoprotein cholesterol concentration, comprising administering to a subject in need thereof an effective amount of a compound of the invention. In some embodiments, the subject is an adult. In some embodiments, the subject has primary hypercholesterolemia. In some embodiments, the subject has mixed dyslipidemia.

The present invention further provides methods for treating or preventing severe hypertriglyceridemia, comprising administering to a subject in need thereof an effective amount of a compound of the invention. In some embodiments, the subject is an adult.

The present invention further provides methods for reducing the rate or incidence of myocardial infarction or stroke, comprising administering to a subject in need thereof an effective amount of a compound of the invention. In some embodiments, the subject has acute coronary syndrome (ACS). In some embodiments, the subject has non-ST-segment elevation ACS (unstable angina (UA)/non-ST-elevation myocardial infarction (NSTEMI)). In some embodiments, the subject has ST-elevation myocardial infarction (STEMI). In electrocardiography, the ST segment connects the QRS complex and the T wave. In some embodiments, the subject has had a previous myocardial infarction, previous stroke or established peripheral arterial disease. In some embodiments, the subject has had a recent myocardial infarction or recent stroke. In some embodiments, recent myocardial infarction or a recent stroke took event within one year. In some embodiments, ecent myocardial infarction or a recent stroke took event within three months.

The present invention further provides methods for reducing in a subject's blood plasma or blood serum total cholesterol, LDL-C or Apo B concentration, comprising administering to a subject in need thereof an effective amount of a compound of the invention. In some embodiments, the subject has primary hypercholesterolemia. Primary hypercholesterolemia can be heterozygous familial or non-familial. In some embodiments, the method further comprises administering an HMG-CoA reductase inhibitor to the subject.

The present invention further provides methods for reducing in a subject's blood plasma or blood serum total cholesterol or LDL-C concentration, comprising administering to a subject in need thereof an effective amount of a compound of the invention. In some embodiments, the subject has HoFH. In some embodiments, the method further comprises administering an additional lipid-lowering treatment to the subject. In some embodiments, the additional lipid-lowering treatment may be a statin (e.g., atorvastatin or simvastatin) or LDL apheresis.

The present invention further provides methods for reducing in a subject's blood plasma or blood serum elevated sitosterol or campesterol concentration, comprising administering to a subject in need thereof an effective amount of a compound of the invention. In some embodiments, the subject has homozygous familial sitosterolemia.

The present invention further provides methods for treating or preventing Type IV or Type V hyperlipidemia, comprising administering to a subject in need thereof an effective amount of a compound of the invention. In some embodiments, the subject has a risk of pancreatitis. In some embodiments, a change in the subject's diet does not adequately lower the subject's plasma or blood serum triglyceride concentrations. In some embodiments, a normal blood serum triglyceride concentration is less than 150 mg/dL according to ATP III Classification of serum triglycerides (National Institute of Health Publication No. 01-3305; May 2001; Cholesterol Guidelines). In some embodiments, the subject has an abnormally high serum triglyceride concentration. In some embodiments, the subject has a blood serum triglyceride concentration of over 2000 mg/dL and optionally has an elevation of VLDL-cholesterol or has fasting chylomicronemia. In some embodiments, the subject has a triglyceride of from 1000 to 2000 mg/dL and optionally has a history of pancreatitis or of recurrent abdominal pain typical of pancreatitis.

The present invention further provides methods for reducing risk of developing coronary heart disease, comprising administering to a subject in need thereof an effective amount of a compound of the invention. In some embodiments, the subject has Type IIb hyperlipidemia. In some embodiments, the subject does not have history of or symptoms of existing coronary heart disease. In some embodiments, the subject has had weight loss, dietary therapy, exercise, or was administered another pharmacologic agent (e.g., a bile acid sequestrant or nicotinic acid) that was ineffective to treat the subject's hyperlipidemia. In some embodiments, the subject has in a subject's blood plasma or blood serum, one or more of an abnormally low HDL-cholesterol concentration, an abnormally high LDL-cholesterol concentration and an abnormally high triglyceride concentration.

In some embodiments, the therapeutic or prophylactic methods of the invention further comprise administering an effective amount of an additional pharmaceutically active agent. In some embodiments, the therapeutic or prophylactic methods of the invention further comprise administering an effective amount of two or more additional pharmaceutically active agent.

In some embodiments, the additional pharmaceutically active agent is a statin. In some embodiments, statin is atorvastatin, simvastatin, pravastatin, rosuvastatin, fluvastatin, lovastatin, pitavastatin, mevastatin, dalvastatin, dihydrocompactin, or cerivastatin, or a pharmaceutically acceptable salt thereof. In some embodiments, the statin is atorvastatin calcium.

In some embodiments, the additional pharmaceutically active agent is a statin. In some embodiments, the additional pharmaceutically active agent is an HMG-CoA (3-hydroxy-3-methyl-glutaryl-coenzyme A) reductase inhibitor.

In some embodiments, the additional pharmaceutically active agent is a lipid modifying agent, lipid lowering agent, anti-fibrolytic agent, or an anti-inflammatory agent. In some embodiments, the additional pharmaceutically active agent is a cholesterol lowering agent. In other embodiments, the additional pharmaceutically active agent is a cholesterol absorption inhibitor. In other embodiments, the cholesterol absorption inhibitor is ezetimibe.

In some embodiments, the additional pharmaceutically active agent is a PCSK9 (proprotein convertase subtilisin/kexin type 9) inhibitor, Vitamin E, an ANGPTL3 inhibitor, an ANGPTL4 inhibitor, an ANGPTL8 inhibitor, a cholesterol absorption inhibitor, an ACC (acetyl-CoA carboxylase) inhibitor, an ApoC-III (apolipoprotein C-III) inhibitor, an ApoB (apolipoprotein B) synthesis inhibitor, an ACL (adenosine triphosphate citrate lyase) inhibitor, a microsomal transfer protein inhibitor, a fenofibric acid, a fish oil, a fibrate, a thyroid hormone beta receptor agonist, a farnesoid X receptor (FXR), a CCR2/CCR5 (C—C chemokine receptor types 2 (CCR2) and 5 (CCR5)) inhibitor or antagonist, a caspase protease inhibitor, an ASK-1 (Apoptosis signal-regulating kinase 1) inhibitor, a galectin-3 protein, a NOX (Nicotinamide adenine dinucleotide phosphate oxidase) inhibitor, an ileal bile acid transporter, a PPAR (peroxisome proliferator-activated receptor) agonist, a PPAR dual agonist, a pan-PPAR agonist, a sodium-glucose co-transporter 1 or 2 (SGLT1 or SGLT2) inhibitor, a dipeptidyl peptidase 4 (DPP4) inhibitor, a fatty acid synthase (FAS) inhibitor, a toll-like receptor antagonist, a thyroid hormone receptor-beta (THR-0) agonist, a liver-directed, selective THR-β agonist, an ACO1 modulator, a 1-mieloperoxidase inhibitor, a 1-ketohexokinase (1-KHK) inhibitor, an oxidative stress inhibitor, a fibroblast growth factor 21 (FGF21) or 19 (FGF19) inhibitor, a transforming growth factor beta-1 (TGF-β1) agonist, a hepatic de novo lipogenesis (DNL) inhibitor, an enoyl CoA hydratase inhibitor, a cholesterol 7-alpha hydroxylase (Cyp7A1) agonist, a Collagen Type 3 inhibitor, or a CETP (cholesterylester transfer protein) inhibitor. In other embodiments, the additional lipid lowering agent is PCSK9 inhibitor. In some embodiments, the additional lipid lowering agent is bempedoic acid, nicotinic acid, gemfibrozil, niacin, a bile-acid resin, a fibric acid derivative, or a cholesterol absorption inhibitor. In some embodiments, the additional lipid lowering agent is bempedoic acid, nicotinic acid, or gemfibrozil. In some embodiments the lipid-reducing agent is gemfibrozil. In some embodiments, the one or more pharmaceutically active agent is bempedoic acid.

Examples of fish oils include, but are not limited to, salmon oil, sardine oil, cod liver oil, tuna oil, herring oil, menhaden oil, mackerel oil, refined fish oils, and mixtures thereof. Fish oils comprise omega-3 fatty acids: eicosapentaenoic acid and docosahexaenoic acid. In some embodiments, the fish oil is prescription fish oil. In some embodiments, the eicosapentaenoic acid is enriched or esterified, such as, but not limited to an ethyl ester. In some embodiments, the eicosapentaenoic acid is enriched and esterified.

In some embodiments, the CETP inhibitor is dalcetrapib (CAS 211513-37-0), torcetrapib (CAS 262352-17-0), anacetrapib (CAS 875446-37-0), evacetrapib (CAS 1186486-62-3), BAY 60-5521 (CAS 893409-49-9), obicetrapib (866399-87-3), ATH-03 (Affris), DRL-17822 (Dr. Reddy's), DLBS-1449 (Dexa *Medica*), S-[2-[1-(2-ethylbutyl) cyclohexylcarbonylamino]phenyl]-2-methylthiopropionate, l-(2-ethyl-butyl)-cyclohexanecarboxylic acid (2-mercapto-phenyl)-amide or bis[2-[1-(2-ethylbutyl) cyclohexylcarbonylamino]phenyl] disulfide, or pharmaceutically acceptable salt thereof.

In some embodiments, the additional pharmaceutically active agent is an antibody to CETP. In some embodiments, the antibody to CETP is a monoclonal antibody. In other embodiments, the antibody to CETP is a monoclonal antibody (Mab, TP1) to CETP.

In some embodiments, the additional pharmaceutically active agent is an antibody against CETP. In some embodiments, the additional pharmaceutically active agent induces antibodies against CETP and is a vaccine. In some embodiments, the vaccine is TT/CETP (Rittershaus, C. W. et al., Arteriosclerosis, Thrombosis, and Vascular Biology. 2000; 20:2106-2112). In other embodiments, the additional pharmaceutically active agent induces antibodies against CETP and is CETi-1 (Celldex Therapeutics).

In some embodiments, the additional pharmaceutically active agent immunizes a subject with CETP or CETP protein fragment.

In some embodiments, the additional pharmaceutically active agent reduces CETP by inhibition with an SiRNA to CETP mRNA.

In some embodiments, the additional pharmaceutically active agent targets CETP transcription by administration of DNAi to the CETP gene. In other embodiments, the additional pharmaceutically active agent targets CETP transcription by administration of DNAi in an appropriate deliver vehicle such as a Smarticle™.

In some embodiments, the additional pharmaceutically active agent is an anti-coagulation agent or a lipid regulating agent. In some embodiments the anti-coagulation agent is aspirin, dabigatran, rivaroxaban, apixaban clopidogrel, clopNPT (conjugate of clopidogrel with 3-nitropyridine-2-thiol), prasugrel, ticagrelor, cangrelor, a platelet $P2Y_{12}$ receptor inhibitor, thienopyridine, warfarin (Coumadin) acenocoumarol, phenprocoumon, atromentin, phenindione, edoxaban betrixaban, letaxaban eribaxaban hirudin, lepirudin, bivalirudin, argatroban, dabigatran. ximelagatran, batroxobin, hementin, a heparin or vitamin E.

In some embodiments, the additional pharmaceutically active agent is simtuzumab (CAS 1318075-13-6), selonsertib (CAS 1448428-04-3), GS-9674 (Gilead Sciences), GS-0976 (Gliead Sciences), obeticholic acid (CAS 459789-99-2; Intercept), or cenicriviroc (CAS 497223-25-3; Allergan-Takeda), or pharmaceutically acceptable salt thereof. In some embodiments, the additional pharmaceutically active agent is, but is not limited to, elafibranor (Genfit), seladelpar (Cymabay), or EDP-305 (Enanta Pharmaceuticals).

In some embodiments, the additional pharmaceutically active agent is an anti-inflammatory agent, an anti-hypertensive agent, an anti-diabetic agent, an anti-obesity, an anti-fibrotic or an anti-coagulation agent. In some embodiments, the additional pharmaceutically active agent disclosed herein can be a pharmaceutically acceptable salt thereof. The pharmaceutically acceptable salt can be an acid addition salt where the pharmaceutically active agent is basic, e.g., includes a basic nitrogen atom, and can be a cationic salt. The pharmaceutically acceptable salt can be a base addition salt where the pharmaceutically active agent is acidic.

In some embodiments, the therapeutic or prophylactic methods of the invention do not induce hepatotoxicity or a musculoskeletal disorder.

In some embodiments, a subject to which a compound of the invention or composition of the invention is administered is on statin therapy. In some embodiments, the statin is atorvastatin, simvastatin, pravastatin, rosuvastatin, fluvastatin, lovastatin, pitavastatin, mevastatin, dalvastatin, dihydrocompactin, or cerivastatin, or a pharmaceutically acceptable salt thereof. In some embodiments, the statin is atorvastatin calcium.

In some embodiments, the therapeutic or prophylactic methods of the invention comprises administering to a subject in need thereof an effective amount of a compound of the invention. In some embodiments, any one of the therapeutic or prophylactic methods as disclosed herein can comprise administering to a subject in need thereof an effective amount of a composition of the invention in place of an effective amount of a compound of the invention. In some embodiments, any one of the therapeutic or prophylactic methods as disclosed herein can comprise administering to a subject in need thereof an effective amount of a composition of the invention.

Compositions of the Invention

The compositions of the invention comprise (i) an effective amount of a compound of the invention and (ii) a pharmaceutically acceptable carrier or vehicle.

In some embodiments, the compositions of the invention further comprise an effective amount of an additional pharmaceutically active agent, such as disclosed herein. In other embodiments, the compositions of the invention further comprise an effective amount of two or more additional pharmaceutically active agent as disclosed herein.

In some embodiments, the pharmaceutically acceptable carrier or vehicle, includes, but is not limited to, a binder, filler, diluent, disintegrant, wetting agent, lubricant, glidant, coloring agent, dye-migration inhibitor, sweetening agent or flavoring agent.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, PA); and mixtures thereof.

Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. In some embodiments, the binder is hydroxypropylcellulose.

The binder or filler can be present from about 2% to about 49% by weight of the compositions of the invention provided herein or any range within these values. In some embodiments, the binder or filler is present in the composition of the invention from about 5% to about 15% by weight. In some embodiments, the binder or filler is present in the composition of the invention at about 5%, 6%, 7%, 8%, 9%, 8%, 10%, 11%, 12%, 13%, 14%, or 15% by weight or any range within any of these values.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. In some embodiments, the diluent is lactose monohydrate. In another embodiment, the diluent is lactose monohydrate Fast-Flo 316 NF.

The compositions of the invention can comprise from about 5% to about 49% of a diluent by weight of composition or any range between any of these values. In some embodiments, the diluent is present in the compositions of the invention from about 15% to about 30% by weight. In some embodiments, the diluent is present in the composition of the invention at about 15%, 16%, 17%, 18%, 19%, 18%, 20%, 21%, 22%, 23%, 24%, 25%, 26%, 27%, 28%, 29%, or 30% by weight or any range within any of these values.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the compositions of the invention can vary. In some embodiments, the disintegrant is croscarmellose sodium. In some embodiments, the disintegrant is croscarmellose sodium NF (Ac-Di-Sol).

The compositions of the invention can comprise from about 0.5% to about 15% or from about 1% to about 10% by weight of a disintegrant. In some embodiments, the compositions of the invention comprise a disintegrant in an amount of about 5%, 6%, 7%, 8%, 9%, 8%, 10%, 11%, 12%, 13%, 14%, or 15% by weight of the composition or in any range within any of these values.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, MD) and CAB-O-SIL® (Cabot Co. of Boston, MA); and mixtures thereof. In some embodiments, the lubricant is magnesium stearate.

The compositions can of the invention can comprise about 0.1 to about 5% by weight of a lubricant. In some embodiments, the compositions of the invention comprise a lubricant in an amount of about 0.5%, 0.6%, 0.7%, 0.8%, 0.9%, 0.8%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, or 3.0%, by weight of the composition or in any range within any of these values.

Suitable glidants include colloidal silicon dioxide, CAB-O-SIL@ (Cabot Co. of Boston, MA), and talc, including asbestos-free talc.

Coloring agents include any of the approved, certified, water soluble FD&C dyes, and water insoluble FD&C dyes suspended on alumina hydrate, and color lakes and mixtures thereof.

Flavoring agents include natural flavors extracted from plants, such as fruits, and synthetic blends of compounds that provide a pleasant taste sensation, such as peppermint and methyl salicylate.

Sweetening agents include sucrose, lactose, mannitol, syrups, glycerin, sucralose, and artificial sweeteners, such as saccharin and aspartame.

Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether.

Solvents include glycerin, sorbitol, ethyl alcohol, and syrup.

Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients can serve several functions, even within the same formulation.

The compounds of the invention and the compositions of the invention can be formulated for administration by a variety of means including orally, parenterally, by inhalation spray, topically, or rectally in formulations containing pharmaceutically acceptable carriers, adjuvants and vehicles. The term "parenteral" as used here includes subcutaneous, intravenous, intramuscular, and intraarterial injections with a variety of infusion techniques. Intraarterial and intravenous injection as used herein includes administration through catheters.

The compounds of the invention and the compositions of the invention can be formulated in accordance with the routine procedures adapted for desired administration route. Accordingly, the compositions of the invention can take such forms as suspensions, solutions or emulsions in oily or aqueous vehicles, and can contain formulatory agents such as suspending, stabilizing and/or dispersing agents. The compounds of the invention and the compositions of the invention can be formulated as a preparation suitable for implantation or injection. Thus, for example, pharmaceutically acceptable salt of gemcabene and the compositions of the invention can be formulated with suitable polymeric or hydrophobic materials (e.g., as an emulsion in an acceptable oil) or ion exchange resins, or as sparingly soluble derivatives (e.g., as a sparingly soluble salt). The compounds of the invention and the compositions of the invention can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, PA.

In some embodiments, the compositions of the invention are suitable for oral administration. These compositions can comprise solid, semisolid, gelmatrix or liquid dosage forms suitable for oral administration. As used herein, oral administration includes buccal, lingual, and sublingual administration. Suitable oral dosage forms include, without limitation, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, syrups or any combination thereof. In some embodiments, compositions of the invention suitable for oral administration are in the form of a tablet or a capsule. In some embodiments, the composition of the invention is in a form of a tablet. In some embodiments, the composition of the invention is in a form of a capsule. In some embodiments, the compound of the invention is contained in a capsule.

In some embodiments, capsules are immediate release capsules. Non-limiting example of a capsule is a coni-snap@ hard gelatin capsule.

The compositions of the invention can be in the form of compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which can be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. A film coating can impart the same general characteristics as a sugar coating. Multiple compressed tablets are compressed tablets made by more than one compression cycle, including layered tablets, and press-coated or dry-coated tablets.

In some embodiments, the coating is a film coating. In some embodiments, the film coating comprises Opadry White and simethicone emulsion 30% USP.

In some embodiments, the compound of the invention is contained in a tablet. In some embodiments, the compound of the invention is contained in a compressed tablet. In some embodiments, the compound of the invention is contained in a film-coated compressed tablet. In some embodiments, the compositions of the invention are in the form of film-coated compressed tablets.

In some embodiments, the compositions of the invention is prepared by fluid bed granulation of the compound of the invention with one or more pharmaceutically acceptable carrier, vehicle, or excipients. In some embodiments, the compositions of the invention prepared by fluid bed granulation process can provide tablet formulation with good flowability, good compressibility, fast dissolution, good stability, and/or minimal to no cracking. In some embodiments, the fluid bed granulation process allows preparation of formulations having high drug loading, such as over 70% or over 75% of a compound of the invention.

The compositions of the invention can be in the form of soft or hard capsules, which can be made from gelatin, methylcellulose, starch, or calcium alginate. The hard gelatin capsule, also known as the dry-filled capsule (DFC), can comprise of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells can contain a preservative to prevent the growth of microorganisms. Suitable preservatives are those as described herein, including methyl- and propyl-parabens, and sorbic acid. The liquid, semisolid, and solid dosage forms provided herein can be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules can also be coated as known by those of skill in the art in order to modify or sustain dissolution of the active ingredient.

The compositions of the invention can be in liquid or semisolid dosage forms, including emulsions, solutions, suspensions, elixirs, and syrups. An emulsion can be a two-phase system, in which one liquid is dispersed in the form of small globules throughout another liquid, which can be oil-in-water or water-in-oil. Emulsions can include a pharmaceutically acceptable non-aqueous liquids or solvent, emulsifying agent, and preservative. Suspensions can include a pharmaceutically acceptable suspending agent and preservative. Aqueous alcoholic solutions can include a pharmaceutically acceptable acetal, such as a di-(lower alkyl)acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs can be clear, sweetened, and hydroalcoholic solutions. Syrups can be concentrated aqueous solutions of a sugar, for example, sucrose, and can comprise a preservative. For a liquid dosage form, for example, a solution in a polyethylene glycol can be diluted with a sufficient quantity of a pharmaceutically acceptable liquid carrier, e.g., water, to be measured conveniently for administration.

The compositions of the invention for oral administration can be also provided in the forms of liposomes, micelles, microspheres, or nanosystems. Miccellar dosage forms can be prepared as described in U.S. Pat. No. 6,350,458.

The compositions of the invention can be provided as non-effervescent or effervescent, granules and powders, to be reconstituted into a liquid dosage form. Pharmaceutically acceptable carriers and excipients used in the non-effervescent granules or powders can include diluents, sweeteners, and wetting agents. Pharmaceutically acceptable carriers and excipients used in the effervescent granules or powders can include organic acids and a source of carbon dioxide.

Coloring and flavoring agents can be used in all of the above dosage forms. And, flavoring and sweetening agents are especially useful in the formation of chewable tablets and lozenges.

The compositions of the invention can be formulated as immediate or modified release dosage forms, including delayed-, extended, pulsed-, controlled, targeted-, and programmed-release forms.

In some embodiments, the compositions of the invention comprise a film-coating.

The compositions of the invention can comprise another active ingredient that does not impair the composition's therapeutic or prophylactic efficacy or can comprise a substance that augments or supplements the composition's efficacy.

The tablet dosage forms can comprise a pharmaceutically acceptable salt of gemcabene in powdered, crystalline, or granular form, and can further comprise a carrier or vehicle described herein, including binder, disintegrant, controlled-release polymer, lubricant, diluent, or colorant.

In some embodiments, the compositions of the invention comprise from about 50 mg to about 900 mg, about 150 mg to about 600 mg, or about 150 mg to about 300 mg of a compound of the invention. In some embodiments, the compositions of the invention comprise a compound of the invention in an amount of about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, or an amount ranging from and to any of these values. In some embodiments, the compositions of the invention comprise about 50 mg of a compound of the invention. In some embodiments, the compositions of the invention comprise about 150 mg of a compound of the invention. In some embodiments, the compositions of the invention comprise about 300 mg of a compound of the invention. In some embodiments, the compositions of the invention comprise about 600 mg of a compound of the invention.

In some embodiments, the compositions of the invention comprise a compound of the invention in an amount that is a molar equivalent to 50 mg to about 900 mg, about 150 mg to about 600 mg, or about 150 mg to about 300 mg of gemcabene. In some embodiments, the compositions of the invention comprise a compound of the invention in an amount that is a molar equivalent to about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, or about 900 mg gemcabene or an amount ranging from and to any of these values. In some embodiments, the compositions of the invention comprise a pharmaceutically acceptable salt of gemcabene in an amount that is a molar equivalent to about 50 mg. In some embodiments, the compositions of the invention comprise a compound of the invention in an amount that is a molar equivalent to about 150 mg of gemcabene. In some embodiments, the compositions of the invention comprise a compound of the invention in an amount that is a molar equivalent to about 300 mg. In some embodiments, the compositions of the invention comprise a compound of the invention in an amount that is a molar equivalent to about 600 mg.

In other embodiments, the compositions of the invention comprise a compound of the invention in an amount of about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, or any amount ranging from and to these values. In some embodiments, the compound of the invention is gemcabene calcium salt hydrate Crystal Form 1. In some embodiments, the compound of the invention is gemcabene calcium salt hydrate Crystal Form 2. In other embodiments, the compound of the invention is gemcabene calcium salt hydrate Crystal Form C1. In other embodiments, the compound of the invention is gemcabene calcium salt hydrate Crystal Form C2. In other embodiments, the compound of the invention is gemcabene calcium salt hydrate Crystal Form C3. In some embodiments, the compound of the invention is an amorphous gemcabene calcium salt hydrate.

In other embodiments, the compositions of the invention comprise a compound of the invention in an amount that is a molar equivalent to about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, or about 900 mg gemcabene, or any amount ranging from and to these values. In some embodiments, the compound of the invention is gemcabene calcium salt hydrate Crystal Form 1. In some embodiments, the compound of the invention is gemcabene calcium salt hydrate Crystal Form 2. In other embodiments, the compound of the invention is gemcabene calcium salt hydrate Crystal Form C1. In other embodiments, the compound of the invention is gemcabene calcium salt hydrate Crystal Form C2. In other embodiments, the compound of the invention is gemcabene calcium salt hydrate Crystal Form C3. In some embodiments, the compound of the invention is an amorphous gemcabene calcium salt hydrate.

In some embodiments, the compositions of the invention are in the form of a tablet or a capsule. In some embodiments, the compositions of the invention comprise a compound of the invention having a PSD90 ranging from 45 μm to about 75 μm and are in the form of a tablet or a capsule. In some embodiments, the compositions of the invention comprise a compound of the invention having a PSD90 ranging from 50 μm to about 75 μm and are in the form of a tablet or a capsule.

In one aspect, the tablet or the capsule comprises about 50 mg of a compound of the invention having a PSD90 ranging from 40 μm to about 75 μm. In one aspect, the tablet or the capsule comprises about 50 mg of a compound of the invention having a PSD90 ranging from 45 μm to about 75 μm. In one aspect, the tablet or the capsule comprises about 50 mg of a compound of the invention having a PSD90 ranging from 50 μm to about 75 μm.

In some embodiments, the tablet or the capsule comprises a compound of the invention having a PSD90 ranging from 40 μm to about 75 μm in an amount that is a molar equivalent to about 50 mg of gemcabene. In some embodiments, the tablet or the capsule comprises a compound of the invention having a PSD90 ranging from 45 μm to about 75 μm in an amount that is a molar equivalent to about 50 mg of gemcabene. In some embodiments, the tablet or the capsule comprises a compound of the invention having a PSD90 ranging from 50 μm to about 75 μm in an amount that is a molar equivalent to about 50 mg of gemcabene.

In one aspect, the tablet or the capsule comprises about 150 mg of a compound of the invention having a PSD90 ranging from 40 μm to about 75 μm. In one aspect, the tablet or the capsule comprises about 150 mg of a compound of the invention having a PSD90 ranging from 45 μm to about 75 μm. In one aspect, the tablet or the capsule comprises about 150 mg of a compound of the invention having a PSD90 ranging from 50 μm to about 75 μm.

In some embodiments, the tablet or the capsule comprises a compound of the invention having a PSD90 ranging from 40 μm to about 75 μm in an amount that is a molar equivalent to about 150 mg of gemcabene. In some embodiments, the tablet or the capsule comprises a compound of the invention having a PSD90 ranging from 45 μm to about 75 μm in an amount that is a molar equivalent to about 150 mg of gemcabene. In some embodiments, the tablet or the capsule comprises a compound of the invention having a PSD90 ranging from 50 μm to about 75 μm in an amount that is a molar equivalent to about 150 mg of gemcabene.

In some embodiments, the tablet or the capsule comprises about 300 mg of a compound of the invention having a PSD90 ranging from 40 μm to about 75 μm In some embodiments, the tablet or the capsule comprises about 300 mg of a compound of the invention having a PSD90 ranging from 45 μm to about 75 μm In some embodiments, the tablet or the capsule comprises about 300 mg of a compound of the invention having a PSD90 ranging from 50 μm to about 75 μm.

In some embodiments, the tablet or the capsule comprises a compound of the invention having a PSD90 ranging from 40 μm to about 75 μm in an amount that is a molar equivalent to about 300 mg of gemcabene. In some embodiments, the tablet or the capsule comprises a compound of the invention having a PSD90 ranging from 45 μm to about 75 μm in an amount that is a molar equivalent to about 300 mg of gemcabene. In some embodiments, the tablet or the capsule comprises a compound of the invention having a PSD90 ranging from 50 μm to about 75 μm in an amount that is a molar equivalent to about 300 mg of gemcabene.

In some embodiments, the tablet or the capsule comprises about 600 mg of a compound of the invention having a PSD90 ranging from 40 μm to about 75 μm. In some embodiments, the tablet or the capsule comprises about 600 mg of a compound of the invention having a PSD90 ranging from 45 μm to about 75 μm. In some embodiments, the tablet or the capsule comprises about 600 mg of a compound of the invention having a PSD90 ranging from 50 μm to about 75 μm.

In some embodiments, the tablet or the capsule comprises a compound of the invention having a PSD90 ranging from 40 μm to about 75 μm in an amount that is a molar equivalent to about 600 mg of gemcabene. In some embodiments, the tablet or the capsule comprises a compound of the invention having a PSD90 ranging from 45 μm to about 75 μm in an amount that is a molar equivalent to about 600 mg of gemcabene. In some embodiments, the tablet or the capsule comprises a compound of the invention having a PSD90 ranging from 50 μm to about 75 μm in an amount that is a molar equivalent to about 600 mg of gemcabene.

In some embodiments, the compositions of the invention comprise gemcabene calcium salt hydrate Crystal Form 1 having a PSD90 ranging from 40 μm to about 75 μm and are in the form of a tablet or a capsule. In some embodiments, the compositions of the invention comprise gemcabene calcium salt hydrate Crystal Form 1 having a PSD90 ranging from 45 μm to about 75 μm and are in the form of a tablet or a capsule. In some embodiments, the compositions of the invention comprise gemcabene calcium salt hydrate Crystal Form 1 having a PSD90 ranging from 50 μm to about 75 μm and are in the form of a tablet or a capsule.

In some embodiments, the tablet or the capsule comprises about 150 mg of gemcabene calcium salt hydrate Crystal Form 1 having a PSD90 ranging from 40 μm to about 75 μm. In some embodiments, the tablet or the capsule comprises about 150 mg of gemcabene calcium salt hydrate Crystal Form 1 having a PSD90 ranging from 45 μm to about 75 μm. In some embodiments, the tablet or the capsule comprises about 150 mg of gemcabene calcium salt hydrate Crystal Form 1 having a PSD90 ranging from 50 μm to about 75 μm. In some embodiments, the tablet or the capsule comprises gemcabene calcium salt hydrate Crystal Form 1 having a PSD90 ranging from 40 μm to about 75 μm, from 45 μm to about 75 μm, or from 50 μm to about 75 μm, in an amount that is molar equivalent to about 150 mg of gemcabene.

In some embodiments, the tablet or the capsule comprises about 300 mg of gemcabene calcium salt hydrate Crystal Form 1 having a PSD90 ranging from 40 μm to about 75 μm. In some embodiments, the tablet or the capsule comprises about 300 mg of gemcabene calcium salt hydrate Crystal Form 1 having a PSD90 ranging from 45 μm to about 75 μm. In some embodiments, the tablet or the capsule comprises about 300 mg of gemcabene calcium salt hydrate Crystal Form 1 having a PSD90 ranging from 50 μm to about 75 μm. In some embodiments, the tablet or the capsule comprises gemcabene calcium salt hydrate Crystal Form 1 having a PSD90 ranging from 40 μm to about 75 μm, from 45 μm to about 75 μm, or from 50 μm to about 75 μm, in an amount that is molar equivalent to about 300 mg of gemcabene.

In some embodiments, the tablet or the capsule comprises about 600 mg of gemcabene calcium salt hydrate Crystal Form 1 having a PSD90 ranging from 40 μm to about 75 μm. In some embodiments, the tablet or the capsule comprises about 600 mg of gemcabene calcium salt hydrate Crystal Form 1 having a PSD90 ranging from 45 μm to about 75 μm. In some embodiments, the tablet or the capsule comprises about 600 mg of gemcabene calcium salt hydrate Crystal Form 1 having a PSD90 ranging from 50 μm to about 75 μm. In some embodiments, the tablet or the capsule comprises gemcabene calcium salt hydrate Crystal Form 1 having a PSD90 ranging from 40 μm to about 75 μm, from 45 μm to about 75 μm, or from 50 μm to about 75 μm, in an amount that is molar equivalent to about 600 mg of gemcabene.

In other embodiments, the tablet or the capsule comprises about 900 mg of gemcabene calcium salt hydrate Crystal Form 1 having a PSD90 ranging from 40 μm to about 75 μm. In other embodiments, the tablet or the capsule comprises about 900 mg of gemcabene calcium salt hydrate Crystal Form 1 having a PSD90 ranging from 45 μm to about 75 μm. In other embodiments, the tablet or the capsule comprises about 900 mg of gemcabene calcium salt hydrate Crystal Form 1 having a PSD90 ranging from 50 μm to about 75 μm. In some embodiments, the tablet or the capsule comprises gemcabene calcium salt hydrate Crystal Form 1 having a PSD90 ranging from 40 μm to about 75 μm, from 45 μm to about 75 μm, or from 50 μm to about 75 μm, in an amount that is molar equivalent to about 900 mg of gemcabene.

In some embodiments, the compositions of the invention comprise gemcabene calcium salt hydrate Crystal Form 2 having a PSD90 ranging from 40 μm to about 75 μm and are in the form of a tablet or a capsule. In some embodiments, the compositions of the invention comprise gemcabene calcium salt hydrate Crystal Form 2 having a PSD90 ranging from 45 μm to about 75 μm and are in the form of a tablet or a capsule. In some embodiments, the compositions of the invention comprise gemcabene calcium salt hydrate Crystal Form 2 having a PSD90 ranging from 50 μm to about 75 μm and are in the form of a tablet or a capsule.

In some embodiments, the tablet or the capsule comprises about 150 mg of gemcabene calcium salt hydrate Crystal Form 2 having a PSD90 ranging from 40 μm to about 75 μm. In some embodiments, the tablet or the capsule comprises about 150 mg of gemcabene calcium salt hydrate Crystal Form 2 having a PSD90 ranging from 45 μm to about 75 μm or from 50 μm to about 75 μm. In some embodiments, the tablet or the capsule comprises gemcabene calcium salt hydrate Crystal Form 2 having a PSD90 ranging from 40 μm to about 75 μm, from 45 μm to about 75 μm, or from 50 μm to about 75 μm, in an amount that is molar equivalent to about 150 mg of gemcabene.

In some embodiments, the tablet or the capsule comprises about 300 mg of gemcabene calcium salt hydrate Crystal Form 2 having a PSD90 ranging from 40 μm to about 75 μm. In some embodiments, the tablet or the capsule comprises about 300 mg of gemcabene calcium salt hydrate Crystal Form 2 having a PSD90 ranging from 45 μm to about 75 μm or from 50 μm to about 75 μm. In some embodiments, the tablet or the capsule comprises gemcabene calcium salt hydrate Crystal Form 2 having a PSD90 ranging from 40 μm to about 75 μm, from 45 μm to about 75 μm, or from 50 μm to about 75 μm, in an amount that is molar equivalent to about 300 mg of gemcabene.

In some embodiments, the tablet or the capsule comprises about 600 mg of gemcabene calcium salt hydrate Crystal Form 2 having a PSD90 ranging from 40 μm to about 75 μm. In some embodiments, the tablet or the capsule comprises about 600 mg of gemcabene calcium salt hydrate Crystal Form 2 having a PSD90 ranging from 45 μm to about 75 μm or from 50 μm to about 75 μm. In some embodiments, the tablet or the capsule comprises gemcabene calcium salt hydrate Crystal Form 2 having a PSD90 ranging from 40 μm to about 75 μm, from 45 μm to about 75 μm, or from 50 μm to about 75 μm, in an amount that is molar equivalent to about 600 mg of gemcabene.

In some embodiments, the tablet or the capsule comprises about 900 mg of gemcabene calcium salt hydrate Crystal Form 2 having a PSD90 ranging from 40 μm to about 75 μm.

In some embodiments, the tablet or the capsule comprises about 900 mg of gemcabene calcium salt hydrate Crystal Form 2 having a PSD90 ranging from 45 μm to about 75 μm or from 50 μm to about 75 μm. In some embodiments, the tablet or the capsule comprises gemcabene calcium salt hydrate Crystal Form 2 having a PSD90 ranging from 40 μm to about 75 μm, from 45 μm to about 75 μm, or from 50 μm to about 75 μm, in an amount that is molar equivalent to about 900 mg of gemcabene.

In some embodiments, the compositions of the invention comprise gemcabene calcium salt hydrate Crystal Form C3 having a PSD90 ranging from 40 μm to about 75 μm and are in the form of a tablet or a capsule. In some embodiments, the compositions of the invention comprise gemcabene calcium salt hydrate Crystal Form C3 having a PSD90 ranging from 45 μm to about 75 μm and are in the form of a tablet or a capsule. In some embodiments, the compositions of the invention comprise gemcabene calcium salt hydrate Crystal Form C3 having a PSD90 ranging from 50 μm to about 75 μm and are in the form of a tablet or a capsule.

In some embodiments, the tablet or the capsule comprises about 150 mg of gemcabene calcium salt hydrate Crystal Form C3 having a PSD90 ranging from 40 μm to about 75 μm. In some embodiments, the tablet or the capsule comprises about 150 mg of gemcabene calcium salt hydrate Crystal Form C3 having a PSD90 ranging from 45 μm to about 75 μm or from 50 μm to about 75 μm. In some embodiments, the tablet or the capsule comprises gemcabene calcium salt hydrate Crystal Form C3 having a PSD90 ranging from 40 μm to about 75 μm, from 45 μm to about 75 μm, or from 50 μm to about 75 μm, in an amount that is molar equivalent to about 150 mg of gemcabene.

In some embodiments, the tablet or the capsule comprises about 300 mg of gemcabene calcium salt hydrate Crystal Form C3 having a PSD90 ranging from 40 μm to about 75 μm. In some embodiments, the tablet or the capsule comprises about 300 mg of gemcabene calcium salt hydrate Crystal Form C3 having a PSD90 ranging from 45 μm to about 75 μm or from 50 μm to about 75 μm. In some embodiments, the tablet or the capsule comprises gemcabene calcium salt hydrate Crystal Form C3 having a PSD90 ranging from 40 μm to about 75 μm, from 45 μm to about 75 μm, or from 50 μm to about 75 μm, in an amount that is molar equivalent to about 300 mg of gemcabene.

In some embodiments, the tablet or the capsule comprises about 600 mg of gemcabene calcium salt hydrate Crystal Form C3 having a PSD90 ranging from 40 μm to about 75 μm. In some embodiments, the tablet or the capsule comprises about 600 mg of gemcabene calcium salt hydrate Crystal Form C3 having a PSD90 ranging from 45 μm to about 75 μm or from 50 μm to about 75 μm. In some embodiments, the tablet or the capsule comprises gemcabene calcium salt hydrate Crystal Form C3 having a PSD90 ranging from 40 μm to about 75 μm, from 45 μm to about 75 μm, or from 50 μm to about 75 μm, in an amount that is molar equivalent to about 600 mg of gemcabene.

In some embodiments, the tablet or the capsule comprises about 900 mg of gemcabene calcium salt hydrate Crystal Form C3 having a PSD90 ranging from 40 μm to about 75 μm. In some embodiments, the tablet or the capsule comprises about 900 mg of gemcabene calcium salt hydrate Crystal Form C3 having a PSD90 ranging from 45 μm to about 75 μm or from 50 μm to about 75 μm In some embodiments, the tablet or the capsule comprises gemcabene calcium salt hydrate Crystal Form C3 having a PSD90 ranging from 40 μm to about 75 μm, from 45 μm to about 75 μm, or from 50 μm to about 75 μm, in an amount that is molar equivalent to about 900 mg of gemcabene.

In some embodiments, the compositions of the invention comprise a compound of the invention in an amount of about 38.5 wt % to about 99.9 wt %, about 79 wt % to about 98 wt %, about 65% to about 98 wt %, or about 50 wt % to about 70 wt % of the total weight of the pharmaceutical composition. In some embodiments, the compositions of the invention comprise a compound of the invention in an amount of about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.5%, or about 99.9% by weight of the composition, or an amount ranging from and to any of these values.

In some embodiments, the compositions of the invention comprise gemcabene calcium salt hydrate Crystal Form 1 in an amount of about 38.5 wt % to about 99.9 wt %, about 79 wt % to about 98 wt %, about 65% to about 98 wt %, or about 50 wt % to about 70 wt % of the total weight of the pharmaceutical composition. In some embodiments, the compositions of the invention comprise gemcabene calcium salt hydrate Crystal Form 2 in an amount of about 38.5 wt % to about 99.9 wt %, about 79 wt % to about 98 wt %, about 65% to about 98 wt %, or about 50 wt % to about 70 wt % of the total weight of the pharmaceutical composition. In some embodiments, the compositions of the invention comprise gemcabene calcium salt hydrate Crystal Form C3 in an amount of about 38.5 wt % to about 99.9 wt %, about 79 wt % to about 98 wt %, about 65% to about 98 wt %, or about 50 wt % to about 70 wt % of the total weight of the pharmaceutical composition. In some embodiments, the compositions of the invention comprise amorphous gemcabene calcium salt hydrate in an amount of about 38.5 wt % to about 99.9 wt %, about 79 wt % to about 98 wt %, about 65% to about 98 wt %, or about 50 wt % to about 70 wt % of the total weight of the pharmaceutical composition.

In some embodiments, the compositions of the invention further comprise another pharmaceutically active agent. In some embodiments, the compositions of the invention further comprise about 0.1 mg to about 100 mg, about 5 mg to about 80 mg, about 10 mg to about 60 mg or about 10 mg to about 40 mg of a statin or a pharmaceutically acceptable salt thereof. In other embodiments, the compositions of the invention comprise a statin or a pharmaceutically acceptable salt thereof in an amount of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, 11 mg, about 12 mg, about 13 mg, about 14 mg, about 15 mg, about 16 mg, about 17 mg, about 18 mg, about 19 mg, about 20 mg, 21 mg, about 22 mg, about 23 mg, about 24 mg, about 25 mg, about 26 mg, about 27 mg, about 28 mg, about 29 mg, about 30 mg, 31 mg, about 32 mg, about 33 mg, about 34 mg, about 35 mg, about 36 mg, about 37 mg, about 38 mg, about 39 mg, about 40 mg, 41 mg, about 42 mg, about 43 mg, about 44 mg, about 45 mg, about 46 mg, about 47 mg, about 48 mg, about 49 mg, about 50 mg, 51 mg, about 52 mg, about 53 mg, about 54 mg, about 55 mg, about 56 mg, about 57 mg, about 58 mg, about 59 mg, about 60 mg, 61 mg, about 62 mg, about 63 mg, about 64 mg, about 65 mg, about 66 mg, about 67 mg, about 68 mg, about 69 mg, about 70 mg, 71 mg, about 72 mg, about 73 mg, about 74 mg, about 75 mg, about 76 mg, about 77 mg, about 78 mg, about 79 mg, about 80 mg, 81 mg, about 82 mg, about 83 mg, about 84 mg, about 85 mg, about 86 mg, about 87 mg, about 88 mg, about 89 mg, about 90 mg, 91 mg, about 92 mg, about 93 mg, about 94 mg, about 95 mg, about 96 mg, about 97 mg, about 98 mg, about 99 mg, about 100 mg, or an amount ranging from and to these values. In some embodiments, the statin is an atorvastatin calcium.

In some embodiments, a composition of the invention comprising a compound of the invention further comprises a statin or a pharmaceutically acceptable salt thereof in an amount of about 0.001 wt % to about 75 wt %, about 0.005 wt % to about 61.5 wt %, about 2 wt % to about 35 wt %, or about 2 wt % to about 21 wt % of the composition. In some embodiments of the present disclosure, the compositions of the invention comprise a statin or a pharmaceutically acceptable salt thereof in an amount of about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, or about 75%, by weight of the composition, or an amount ranging from and to these values. In some embodiments of the present disclosure, the compositions of the invention comprise a statin or a pharmaceutically acceptable salt thereof in an amount of about 61%, about 61.1%, about 61.2%, about 61.3%, about 61.4%, about 61.5%, about 61.6%, about 61.7%, about 61.8%, about 61.9%, or about 62.0%, by weight of the composition, or an amount ranging from and to these values.

In some embodiments, the compositions of the invention further comprise about 0.1 mg to about 50 mg, about 1 mg to about 30 mg, about 5 mg to about 20 mg or about 10 mg of ezetimibe or a pharmaceutically acceptable salt thereof. In other embodiments, the compositions of the invention comprise ezetimibe or a pharmaceutically acceptable salt thereof in an amount of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, 11 mg, about 12 mg, about 13 mg, about 14 mg, about 15 mg, about 16 mg, about 17 mg, about 18 mg, about 19 mg, about 20 mg, 21 mg, about 22 mg, about 23 mg, about 24 mg, about 25 mg, about 26 mg, about 27 mg, about 28 mg, about 29 mg, about 30 mg, 31 mg, about 32 mg, about 33 mg, about 34 mg, about 35 mg, about 36 mg, about 37 mg, about 38 mg, about 39 mg, about 40 mg, 41 mg, about 42 mg, about 43 mg, about 44 mg, about 45 mg, about 46 mg, about 47 mg, about 48 mg, about 49 mg, or about 50 mg, or an amount ranging from and to these values. In some embodiments, the compositions of the invention further comprise two pharmaceutically active agents. In some embodiments, the compositions of the invention further comprise a) about 0.1 mg to about 50 mg, about 1 mg to about 30 mg, about 5 mg to about 20 mg or about 10 mg of ezetimibe or a pharmaceutically acceptable salt thereof and b) about 0.1 mg to about 100 mg, about 5 mg to about 80 mg, about 10 mg to about 60 mg or about 10 mg to about 40 mg of a statin or a pharmaceutically acceptable salt thereof. In other embodiments, the compositions of the invention comprise a) ezetimibe or a pharmaceutically acceptable salt thereof in an amount of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, 11 mg, about 12 mg, about 13 mg, about 14 mg, about 15 mg, about 16 mg, about 17 mg, about 18 mg, about 19 mg, about 20 mg, 21 mg, about 22 mg, about 23 mg, about 24 mg, about 25 mg, about 26 mg, about 27 mg, about 28 mg, about 29 mg, about 30 mg, 31 mg, about 32 mg, about 33 mg, about 34 mg, about 35 mg, about 36 mg, about 37 mg, about 38 mg, about 39 mg, about 40 mg, 41 mg, about 42 mg, about 43 mg, about 44 mg, about 45 mg, about 46 mg, about 47 mg, about 48 mg, about 49 mg, or about 50 mg, or an amount ranging from and to these values, and b) a statin or a pharmaceutically acceptable salt thereof in an amount of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, 11 mg, about 12 mg, about 13 mg, about 14 mg, about 15 mg, about 16 mg, about 17 mg, about 18 mg, about 19 mg, about 20 mg, 21 mg, about 22 mg, about 23 mg, about 24 mg, about 25 mg, about 26 mg, about 27 mg, about 28 mg, about 29 mg, about 30 mg, 31 mg, about 32 mg, about 33 mg, about 34 mg, about 35 mg, about 36 mg, about 37 mg, about 38 mg, about 39 mg, about 40 mg, 41 mg, about 42 mg, about 43 mg, about 44 mg, about 45 mg, about 46 mg, about 47 mg, about 48 mg, about 49 mg, about 50 mg, 51 mg, about 52 mg, about 53 mg, about 54 mg, about 55 mg, about 56 mg, about 57 mg, about 58 mg, about 59 mg, about 60 mg, 61 mg, about 62 mg, about 63 mg, about 64 mg, about 65 mg, about 66 mg, about 67 mg, about 68 mg, about 69 mg, about 70 mg, 71 mg, about 72 mg, about 73 mg, about 74 mg, about 75 mg, about 76 mg, about 77 mg, about 78 mg, about 79 mg, about 80 mg, 81 mg, about 82 mg, about 83 mg, about 84 mg, about 85 mg, about 86 mg, about 87 mg, about 88 mg, about 89 mg, about 90 mg, 91 mg, about 92 mg, about 93 mg, about 94 mg, about 95 mg, about 96 mg, about 97 mg, about 98 mg, about 99 mg, about 100 mg, or an amount ranging from and to these values. In some embodiments, the statin is an atorvastatin calcium.

In some embodiments, a composition of the invention comprising gemcabene calcium salt hydrate Crystal Form 1, gemcabene calcium salt hydrate Crystal Form 2 or gemcabene calcium salt hydrate Crystal Form C3 further comprises a statin or a pharmaceutically acceptable salt thereof in an amount of about 0.001 wt % to about 75 wt %, about 0.005 wt % to about 61.5 wt %, about 2 wt % to about 35 wt %, or about 2 wt % to about 21 wt % of the composition.

In some embodiments, the compositions of the invention comprise a compound of the invention in an amount of about 50 mg to about 900 mg and statin or a pharmaceutically acceptable salt thereof in an amount of about 1 mg to about 80 mg. In some embodiments, the compositions of the invention comprise a compound of the invention in an amount of about 150 mg to about 600 mg and statin or a pharmaceutically acceptable salt thereof in an amount of about 10 mg to about 40 mg. In some embodiments, the compositions of the invention a compound of the invention in an amount of about 150 mg to about 300 mg and statin or a pharmaceutically acceptable salt thereof in an amount of about 10 mg to about 40 mg. In some embodiments, the compositions of the invention a compound of the invention in an amount of about 150 mg to about 900 mg and statin or a pharmaceutically acceptable salt thereof in an amount of about 10 mg to about 60 mg.

In some embodiments, the compositions of the invention comprise gemcabene calcium salt hydrate Crystal Form 1 in an amount of about 50 mg to about 900 mg and statin or a pharmaceutically acceptable salt thereof in an amount of about 1 mg to about 80 mg. In some embodiments, the compositions of the invention comprise gemcabene calcium salt hydrate Crystal Form 1 in an amount of about 150 mg to about 600 mg and statin or a pharmaceutically acceptable salt thereof in an amount of about 10 mg to about 40 mg. In some embodiments, the compositions of the invention comprise gemcabene calcium salt hydrate Crystal Form 1 in an amount of about 150 mg to about 300 mg and statin or a pharmaceutically acceptable salt thereof in an amount of about 10 mg to about 40 mg. In some embodiments, the compositions of the invention comprise gemcabene calcium salt hydrate Crystal Form 1 in an amount of about 150 mg to about 900 mg and statin or a pharmaceutically acceptable salt thereof in an amount of about 10 mg to about 60 mg.

In some embodiments, the compositions of the invention comprise a compound of the invention in an amount of about 38.5 wt % to about 99.9 wt % and a statin or a pharmaceutically acceptable salt thereof in an amount of about 0.1 wt % to about 61.5 wt % of the composition. In other embodiments, the compositions of the invention comprise a compound of the invention in an amount of about 65 wt % to about 98 wt % and a statin or a pharmaceutically acceptable salt thereof in an amount of about 2 wt % to about 35 wt % of the composition. In some embodiments, the compositions of the invention comprise a compound of the invention in an amount of about 79 wt % to about 98 wt % and a statin or a pharmaceutically acceptable salt thereof in an amount of about 2 wt % to about 21 wt % of the composition. In some embodiments, the pharmaceutically acceptable salt is a calcium salt. In some embodiments, the calcium salt is a calcium salt hydrate. In some embodiments, the calcium salt hydrate is calcium salt hydrate Crystal Form 1.

In some embodiments, the additional pharmaceutically active agent is present in an amount of about 10 mg to 100 mg or about 5 mg to 50 mg in the compositions of the invention. In some embodiments, the additional pharmaceutically active agent is present in an amount of about 10 mg, about 20 mg, about 30 mg, about 40 mg, about 50 mg, about 60 mg, about 70 mg, about 80 mg, about 90 mg, about 100 mg, or any range between any of these values in the compositions of the invention.

In some embodiments, the compositions of the invention can further comprise an excipient such as a diluent, a disintegrant, a wetting agent, a binder, a glidant, a lubricant, or any combination thereof. In some embodiments, a tablet comprises a binder. And, in some embodiments, the binder comprises microcrystalline cellulose, dibasic calcium phosphate, sucrose, corn starch, polyvinylpyrridone, hydroxypropyl cellulose, hydroxymethyl cellulose, or any combination thereof. In other embodiments, the tablet comprises a disintegrant. In other embodiments, the disintegrant comprises sodium croscarmellose, sodium starch glycolate, or any combination thereof. In other embodiments, the tablet comprises a lubricant. And, in some embodiments, the lubricant comprises magnesium stearate stearic acid, hydrogenated oil, sodium stearyl fumarate, or any combination thereof.

In some embodiments, the compositions of the invention are in the form of a tablet that comprises a binder such as any of the binders described herein.

In some embodiments, the compositions of the invention are in the form of a tablet that comprises a disintegrant such as any of the disintegrants described herein.

In some embodiments, the compositions of the invention are in the form of a tablet that comprises a lubricant such as any of the lubricants described herein.

In some embodiments, the compositions of the invention can be in a modified release or a controlled release dosage form. In some embodiments, the compositions of the invention can comprise particles exhibiting a particular release profile. For example, the composition of the invention can comprise a compound of the invention in an immediate release form while also comprising a statin or a pharmaceutically acceptable salt thereof in a modified release form, both compressed into a single tablet. Other combination and modification of release profile can be achieved as understood by one skilled in the art. Examples of modified release dosage forms suited for pharmaceutical compositions of the instant invention are described, without limitation, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

In some embodiments, the compositions of the invention are a matrix-controlled release dosage form. For example, the compositions of the invention can comprise about 300 mg to about 600 mg of a compound of the invention provided as a matrix-controlled release form. In some embodiments, a matrix-controlled release form can further comprise an additional pharmaceutically active agent. In some embodiments, the release profile of the compound of the invention and of the additional pharmaceutically active agent is the same or different. Suitable matrix-controlled release dosage forms are described, for example, in Takada et al in "Encyclopedia of Controlled Drug Delivery," Vol. 2, Mathiowitz ed., Wiley, 1999.

In some embodiments, the compositions of the invention comprise from about 10 mg to about 40 mg of the statin and from about 300 mg to about 600 mg of a compound of the invention, wherein the composition is in a matrix-controlled modified release dosage form.

In some embodiments, the matrix-controlled release form comprises an erodible matrix comprising water-swellable, erodible, or soluble polymers, including synthetic polymers, and naturally occurring polymers and derivatives, such as polysaccharides and proteins.

In some embodiments, the erodible matrix of the matrix-controlled release form comprises chitin, chitosan, dextran, or pullulan; gum agar, gum arabic, gum karaya, locust bean gum, gum tragacanth, carrageenans, gum ghatti, guar gum, xanthan gum, or scleroglucan; starches, such as dextrin or maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), carrrboxymethyl ethyl cellulose (CMEC) hydroxyethyl cellulose (HEC), hydroxypropyl cellulose (HPC), cellulose acetate (CA), cellulose propionate (CP), cellulose butyrate (CB), cellulose acetate butyrate (CAB), cellulose acetate phthalate (CAP), cellulose acetate trimellitate (CAT), hydroxypropyl methyl cellulose (HPMC), HPMCP, HPMCAS, hydroxypropyl methyl cellulose acetate trimellitate (HPMCAT), or ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, NJ); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; or other acrylic acid derivatives, such as homopolymers and copolymers of butylmethacrylate, methylmethacrylate, ethylmethacrylate, ethylacrylate, (2-dimethylaminoethyl)methacrylate, or (trimethylaminoethyl)methacrylate chloride; or any combination thereof.

In other embodiments, the compositions of the invention are in a matrix-controlled modified release form comprising a non-erodible matrix. In some embodiments, the statin, the compound of the invention is dissolved or dispersed in an inert matrix and is released primarily by diffusion through the inert matrix once administered. In some embodiments, the non-erodible matrix of the matrix-controlled release form comprises an insoluble polymer, such as polyethylene, polypropylene, polyisoprene, polyisobutylene, polybutadiene, polymethylmethacrylate, polybutylmethacrylate, chlorinated polyethylene, polyvinylchloride, a methyl acrylate-methyl methacrylate copolymer, an ethylene-vinylacetate copolymer, an ethylene/propylene copolymer, an ethylene/ethyl acrylate copolymer, a vinylchloride copolymer with vinyl acetate, a vinylidene chloride, an ethylene or a propylene, an ionomer polyethylene terephthalate, a butyl rubber epichlorohydrin rubber, an ethylene/vinyl alcohol copolymer, an ethylene/vinyl acetate/vinyl alcohol terpolymer, an ethylene/vinyloxyethanol copolymer, a polyvinyl chloride, a plasticized nylon, a plasticized polyethyleneterephthalate, a natural rubber, a silicone rubber, a polydimethylsiloxane, a silicone carbonate copolymer, or a hydrophilic polymer, such as an ethyl cellulose, a cellulose acetate, a crospovidone, or a cross-linked partially hydrolyzed polyvinyl acetate; a fatty compound, such as a carnauba wax, a microcrystalline wax, or a triglyceride; or any combination thereof.

The compositions of the invention that are in a modified release dosage form can be prepared by methods known to those skilled in the art, including direct compression, dry or wet granulation followed by compression, melt-granulation followed by compression.

In some embodiments, the compositions of the invention comprise a tablets-in-capsule system, which can be a multifunctional and multiple unit system comprising versatile mini-tablets in a hard gelatin capsule. The mini-tablets can be rapid-release, extended-release, pulsatile, delayed-onset extended-release minitablets, or any combination thereof. In some embodiments, combinations of mini-tablets or combinations of mini-tablets and minibeads comprising multiple active pharmaceutical agents can each have specific lag times, of release multiplied pulsatile drug delivery system (DDS), site-specific DDS, slow-quick DDS, quick/slow DDS and zero-order DDS.

In some embodiments, the compositions of the invention are in an osmotic-controlled release dosage form.

In some embodiments, the osmotic-controlled release device comprises a one-chamber system, a two-chamber system, asymmetric membrane technology (AMT), an extruding core system (ECS), or any combination thereof. In some embodiments, such devices comprise at least two components: (a) the core which contains the active pharmaceutical agent(s); and (b) a semipermeable membrane with at least one delivery port, which encapsulates the core. The semipermeable membrane controls the influx of water to the core from an aqueous environment of use so as to cause drug release by extrusion through the delivery port(s).

In some embodiments, the core of the osmotic device optionally comprises an osmotic agent, which creates a driving force for transport of water from the environment of use into the core of the device. One class of osmotic agents useful in the present invention comprises water-swellable hydrophilic polymers, which are also referred to as "osmopolymers" or "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly(acrylic) acid, poly (methacrylic) acid, polyvinylpyrrolidone (PVP), cross-linked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

Another class of osmotic agents comprises osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the compound of the invention dissolves following administration. For example, an amorphous sugar, such as Mannogeme EZ (SPI Pharma, Lewes, DE) can be included to provide faster delivery during the first couple of hours (e.g., about 1 to about 5 hrs) to promptly produce prophylactic or therapeutic efficacy, and gradually and continually release of the remaining amount to maintain the desired level of therapeutic or prophylactic effect over an extended period of time. In some embodiments, the gemcabene or pharmaceutically acceptable salt thereof is released from the compositions of the invention at such a rate to replace the amount of the compound of the invention metabolized or excreted by the subject.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

The semipermeable membranes can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the compound of the invention released and the release rate can substantially be modulated via the thickness and porosity of the semipermeable membrane, the composition of the core, and the number, size, and position of the delivery ports.

In some embodiments, the pharmaceutical composition in an osmotic controlled-release dosage form can further comprise additional conventional excipients as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In some embodiments, the pharmaceutical composition provided herein is formulated as asymmetric membrane technology (AMT) controlled-release dosage form that comprises an asymmetric osmotic membrane that coats a core comprising the active ingredient(s) and other pharmaceutically acceptable excipients. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In some embodiments, the pharmaceutical composition provided herein is formulated as ESC controlled-release dosage form that comprises an osmotic membrane that coats a core comprising the compound of the invention, hydroxylethyl cellulose, and other pharmaceutically acceptable excipients.

In some embodiments, the compositions of the invention are a modified release dosage form that is fabricated as a multiparticulate-controlled release dosage form that comprises a plurality of particles, granules, or pellets, microparticulates, beads, microcapsules and microtablets, ranging from about 10 μm to about 3 mm, about 50 μm to about 2.5 mm, or from about 100 μm to 1 mm in diameter.

The multiparticulate-controlled release dosage forms can provide a prolonged release dosage form with an improved bioavailability. Suitable carriers to sustain the release rate of the compound of the invention include, without limitation, ethyl cellulose, HPMC, HPMC-phtalate, colloidal silicondioxide and Eudragit-RSPM.

Pellets suitable to be used in the compositions and therapeutic or prophylactic methods of the invention comprise 50-80% (w/w) of a drug and 20-50% (w/w) of microcrystalline cellulose or other polymers. Suitable polymers include, but are not limited to, microcrystalline wax, pregelatinized starch and maltose dextrin.

Beads can be prepared in capsule and tablet dosage forms. Beads in tablet dosage form can demonstrate a slower dissolution profile than microparticles in capsule form. Microparticle fillers suitable for compositions and therapeutic or prophylactic methods of the invention include, without limitation, sorbitan monooleate (Span 80), HPMC, or any combination thereof. Suitable dispersions for controlled release latex include, for example, ethyl-acrylate and methyl-acrylate.

In some embodiments, the compositions of the invention are in the form or microcapsules and/or microtablets. In some embodiments, microcapsules comprise extended release polymer microcapsules containing a statin and a compound of the invention with various solubility characteristics. Extended release polymer microcapsules can be prepared with colloidal polymer dispersion in an aqueous environment. In other embodiments, microcapsules suitable for the compositions and methods provided herein can be prepared using conventional microencapsulating techniques (Bodmeier & Wang, 1993).

Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989. Excipients for such technologies are commercially available and described in US Pharmacopeia, and gemcabene salts are prepared as described in U.S. Pat. No. 6,861,555 or in International Application Publication WO 2016/077832 as, for example, gemcabene calcium salt single polymorph.

Other excipients as described herein can be blended with the compositions of the invention to aid in processing and forming the multiparticulates. The resulting particles can themselves constitute the multiparticulate dosage form or can be coated by various film-forming materials, such as enteric polymers, water-swellable, or water-soluble polymers. The multiparticulates can be further processed as a capsule or a tablet.

In other embodiments, the compositions of the invention are in a dosage form that has an instant releasing component and at least one delayed releasing component, and is capable of giving a discontinuous release of the compound in the form of at least two consecutive pulses separated in time from 0.1 hrs to 24 hrs.

The invention further provides a kit comprising a composition of the invention and instructions for its use. The kit can further comprise a composition comprising an additional pharmaceutically active agent. In some embodiments the kit comprises a composition of the invention comprising from about 50 mg to about 900 mg of a compound of the invention and another composition comprising from about 0.1 mg to about 80 mg of a statin; and instructions for the use thereof. In some embodiments the kit comprises a composition of the invention comprising from about 50 mg to about 900 mg of a compound of the invention and another composition comprising from about 10 mg to about 80 mg of a statin; and instructions for the use thereof. In some embodiments, the kit comprises a composition of the invention comprising from about 150 mg to about 600 mg of a compound of the invention and from about 10 mg to about 40 mg of a statin; and instructions for the use thereof.

In some embodiments the kit comprises a composition of the invention comprising from about 50 mg to about 900 mg of a compound of the invention and another composition comprising from about 5 mg to about 80 mg of an atorvastatin or a pharmaceutically acceptable salt thereof; and instructions for the use thereof. In some embodiments the kit comprises a composition of the invention comprising from about 50 mg to about 900 mg of a compound of the invention and another composition comprising from about 10 mg to about 80 mg of an atorvastatin or a pharmaceutically acceptable salt thereof; and instructions for the use thereof. In some embodiments, the kit comprises a composition of the invention comprising from about 150 mg to about 600 mg of a compound of the invention and from about 10 mg to about 40 mg of an atorvastatin or a pharmaceutically acceptable salt thereof; and instructions for the use thereof.

In some embodiments, the kit comprises a composition of the invention comprising from about 50 mg to about 900 mg of a compound of the invention and another composition comprising from about 5 mg to about 20 mg of ezetimibe or a pharmaceutically acceptable salt thereof; and instructions for the use thereof. In some embodiments, the kit comprises a composition of the invention comprising from about 50 mg to about 900 mg of a compound of the invention and another composition comprising from about 10 mg of ezetimibe or a pharmaceutically acceptable salt thereof; and instructions for the use thereof. In some embodiments, the kit comprises a composition of the invention comprising from about 150 mg to about 600 mg of a compound of the invention and another composition comprising from about 10 mg of ezetimibe or a pharmaceutically acceptable salt thereof; and instructions for the use thereof.

In some embodiments the kit comprises a) a composition of the invention comprising from about 50 mg to about 900 mg of a compound of the invention, b) a composition comprising from about 5 mg to about 80 mg of a statin or a pharmaceutically acceptable salt thereof, c) a composition comprising from about 5 mg to about 20 mg of ezetimibe or a pharmaceutically acceptable salt thereof, and d) instructions for the use thereof. In some embodiments the kit comprises a) a composition of the invention comprising from about 50 mg to about 900 mg of a compound of the invention, b) a composition comprising from about 10 mg to about 80 mg of a statin or a pharmaceutically acceptable salt thereof, c) a composition comprising about 10 mg of ezetimibe or a pharmaceutically acceptable salt thereof, and d) instructions for the use thereof. In some embodiments the kit comprises a) a composition of the invention comprising from about 150 mg to about 600 mg of a compound of the invention, b) a composition comprising from about 10 mg to about 40 mg of a statin or a pharmaceutically acceptable salt thereof, c) a composition comprising about 10 mg of ezetimibe or a pharmaceutically acceptable salt thereof, and d) instructions for the use thereof.

In some embodiments the kit comprises a) a composition of the invention comprising from about 50 mg to about 900 mg of a compound of the invention, b) a composition comprising from about 5 mg to about 80 mg of an atorvastatin or a pharmaceutically acceptable salt thereof, c) a composition comprising from about 5 mg to about 20 mg of ezetimibe or a pharmaceutically acceptable salt thereof, and d) instructions for the use thereof. In some embodiments the kit comprises a) a composition of the invention comprising from about 50 mg to about 900 mg of a compound of the invention, b) a composition comprising from about 10 mg to about 80 mg of an atorvastatin or a pharmaceutically acceptable salt thereof, c) a composition comprising about 10 mg of ezetimibe or a pharmaceutically acceptable salt thereof, and d) instructions for the use thereof. In some embodiments the kit comprises a) a composition of the invention comprising from about 150 mg to about 600 mg of a compound of the invention, b) a composition comprising from about 10 mg to about 40 mg of an atorvastatin or a pharmaceutically acceptable salt thereof, c) a composition comprising about 10 mg of ezetimibe or a pharmaceutically acceptable salt thereof, and d) instructions for the use thereof.

In some embodiments, the composition of the invention and the other composition are contained in separate containers. In some embodiments, the composition of the invention and the other composition are contained in the same container.

In some embodiments, the container is a bottle, vial, blister pack, or any combination thereof. In some embodiments, the container is a bottle, vial, blister pack, or any combination thereof with a closure (e.g., a cap, a top, or a sealed package to provide the composition of the invention in a closed system).

In some embodiments, the statin is atorvastatin, simvastatin, pravastatin, rosuvastatin, fluvastatin, lovastatin, pitavastatin, mevastatin, dalvastatin, dihydrocompactin, or cerivastatin, or any pharmaceutically acceptable salt thereof. In some embodiments, the statin is atorvastatin or a pharmaceutically acceptable salt thereof.

In some embodiments, the composition of the invention or the other composition is in the form of a tablet.

In some embodiments, the tablet comprises one or more excipients selected from a diluent, a disintegrant, a wetting agent, a binder, a glidant, a lubricant, or any combination thereof.

In some embodiments, the compositions of the invention are administered to a subject in need thereof. In some embodiments, the composition of the invention is in a unit dose form. In some embodiments as used herein, "unit dose" or "unit-dose" refers to a specific formulation containing a specific amount of a compound of the invention. In a non-limiting example, a unit dose of can be a tablet comprising about 300 mg of a compound of the invention. In some embodiments, a unit dose comprises about 50 mg, about 150 mg, about 300 mg, or about 600 mg of a compound of the invention. In another embodiment, a unit dose comprises a compound of the invention in an amount that is molar equivalent to about 150 mg, about 300 mg, or about 600 mg gemcabene.

In some embodiments, the compositions of the invention are administered to a subject in need thereof, once, twice, three times, or four times a day. In some embodiments, the compositions of the invention are administered to a subject in need thereof in ways that allows a daily dose of about 600 mg to about 900 mg of a compound of the invention. In some embodiments, the compositions of the invention are administered to a subject in need thereof in ways that allows a daily dose in an amount that is molar equivalent to about 600 mg to about 900 mg of gemcabene. In some embodiments, the daily dose is about 600 mg of a compound of the invention. In another embodiment, the daily dose is an amount that is molar equivalent to 600 mg of gemcabene.

In some embodiments, the compositions of the invention comprise about 300 mg of a compound of the invention and are administered to a subject in need thereof once a day. In some embodiments, the compositions of the invention comprise about 300 mg of a compound of the invention and are administered to a subject in need thereof twice a day. In some embodiments, the compositions of the invention comprise about 300 mg of a compound of the invention and are administered to a subject in need thereof three times a day.

In some embodiments, the compositions of the invention comprise a compound of the invention in an amount that is molar equivalent to about 300 mg of gemcabene and are administered to a subject in need thereof once a day. In some embodiments, the compositions of the invention comprise a compound of the invention in an amount that is molar equivalent to about 300 mg of gemcabene and are administered to a subject in need thereof twice a day. In some embodiments, the compositions of the invention comprise a compound of the invention in an amount that is molar equivalent to about 300 mg of gemcabene and are administered to a subject in need thereof three times a day.

In some embodiments, the compositions of the invention comprise about 600 mg of a compound of the invention and are administered to a subject in need thereof once a day. In some embodiments, the compositions of the invention comprise a compound of the invention in an amount that is molar equivalent to about 600 mg of gemcabene and are administered to a subject in need thereof once a day.

In some embodiments, the compositions of the invention comprise about 150 mg of a compound of the invention and are administered to a subject in need thereof once a day. In some embodiments, the compositions of the invention comprise about 150 mg of a compound of the invention and are administered to a subject in need thereof twice a day. In some embodiments, the compositions of the invention comprise about 150 mg of a compound of the invention and are administered to a subject in need thereof three times a day. In some embodiments, the compositions of the invention comprise about 150 mg of a compound of the invention and are administered to a subject in need thereof four times a day.

In some embodiments, two separate unit doses, each comprising about 150 mg of a compound of the invention, are administered to a subject in need thereof once a day. In some embodiments, two separate unit doses, each comprising about 150 mg of a compound of the invention, are administered to a subject in need thereof twice a day (total 600 mg/day). In some embodiments, two separate unit doses, each comprising about 150 mg of a compound of the invention, are administered to a subject in need thereof three times a day (total 900 mg/day).

In some embodiments, the compositions of the invention comprising a compound of the invention in an amount that is molar equivalent to about 150 mg of gemcabene is administered to a subject in need thereof once a day. In some embodiments, the compositions of the invention comprising a compound of the invention in an amount that is molar equivalent to about 150 mg of gemcabene is administered to a subject in need thereof twice a day. In some embodiments, the compositions of the invention comprising a compound of the invention in an amount that is molar equivalent to about 150 mg of gemcabene is administered to a subject in need thereof three times a day. In some embodiments, the compositions of the invention comprising a compound of the invention in an amount that is molar equivalent to about 150 mg of gemcabene is administered to a subject in need thereof four times a day.

In some embodiments, two separate unit doses, each comprising a compound of the invention in an amount that is molar equivalent to about 150 mg of gemcabene, are administered to a subject in need thereof once a day. In some embodiments, two separate unit doses, each comprising a compound of the invention in an amount that is molar equivalent to about 150 mg of gemcabene, are administered to a subject in need thereof twice a day (total 600 mg/day=two separate unit doses (150 mg×2)×2 (twice a day)). In some embodiments, two separate unit doses, each comprising a compound of the invention in an amount that is molar equivalent to about 150 mg of gemcabene, are administered to a subject in need thereof three times a day (total 900 mg/day).

EXAMPLES

Example 1: Chemical Synthesis of Gemcabene Calcium Salt Hydrate Crystal Form 1

Scheme 2: Synthesis of 6-(5-carboxy-5-methyl-hexyloxy)-2,2-dimethylhexanoic acid (Gemcabene)

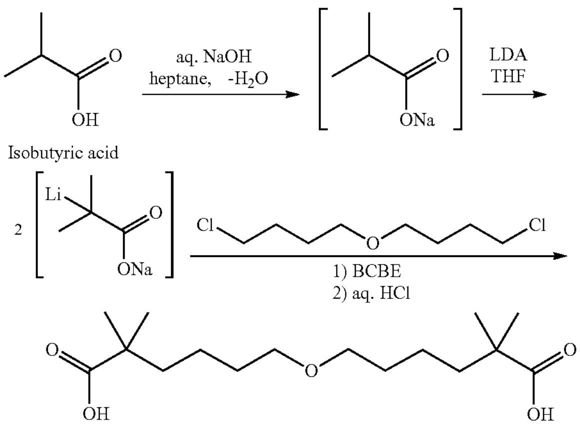

Isobutyric acid

Gemcabene

Step 1. 6-(5-carboxy-5-methyl-hexyloxy)-2,2-dimethylhexanoic acid (Gemcabene): In a reactor (ST-1005, glass-lined, 1600 l), isobutyric acid (41.0 kg, 466 mol, 2.2 equiv) and heptane (276 kg) were combined and a molar equivalent of 30% sodium hydroxide was charged (62.1 kg), followed by water (1.1 kg) and heptane (126 kg) under stirring. The mixture was refluxed with water removal until the rate of water removal effectively stopped. Then, a Karl-Fisher analysis of the water content was performed to confirm removal of water (water content measured 0.012%). Tetrahydrofuran (THF) (279 kg) was added followed by a lithium diisopropylamide solution (lithium diisopropylamide 28% w/w in heptane/THF/ethylbenzene, 174.6 kg, 2.2 equiv) at 10° C.-15° C. After flushing with THF (33.8 kg) the mixture was heated at 42° C.±2° C. for about 1 hour. Bis-(4-chlorobutyl)ether (42.0 kg, 211 mol, 1.0 equiv, BCBE) diluted with THF (11.6 kg) was added at 40° C.-45° C. in four hours. After flushing with THF (11.4 kg) the mixture was heated at 42° C.±2° C. for 14-24 hours. Water (159 kg) was added and the resultant precipitate was dissolved at 52° C.±2° C. The aqueous layer was then separated. Additional water was added (159 kg) to the upper organic layer at 50° C.±2° C. and the layers were separated. The aqueous layer was combined with the first aqueous layer and the organic layer was discarded. The aqueous layer was combined with heptane (177 kg) and an excess of concentrated hydrochloric acid was added (299 kg) at 25° C.-50° C. The product-containing organic layer was separated, and the aqueous layer was extracted with heptane (106 kg) at 50° C.±2° C. The aqueous layer was then discarded. The combined product-containing heptane layer was washed twice with water (64 kg) at 50° C.±2° C. and the aqueous layers were discarded. The heptane layer was evaporated to dryness at ≤60° C. The resultant residue was mixed twice with water (320 kg each wash) and evaporated to dryness at ≤60° C. The remaining material was dissolved in heptane (286 kg) at 22° C.±2° C. and washed with water (193 kg) and the aqueous layer was discarded. The heptane layer was evaporated to dryness at ≤60° C. and co-evaporated three-times with heptane (each 109 kg). Karl-Fisher analysis indicated water content was 0.04%. The resultant residue was dissolved in heptane (130 kg) and THF (1.4 kg) at 22° C. f 2° C., filtered through silica gel (64.0 kg) and the silica gel was washed first with heptane (246 kg)/THF (16.0 kg) mixture and then only with heptane (492 kg). The collected filtrate was concentrated to a volume of about 150 L at ≤60° C. The solution was transferred to a smaller vessel (ST-164, glass-lined, 160 1) with heptane (44 kg), followed by evaporation to dryness at ≤60° C. $^1$H NMR analysis of the crude indicated 96.7% purity. The crude gemcabene was dissolved in heptane (55.0 kg) at 40° C.±5° C. and the heptane solution was cooled to 15° C.±2° C. After seeding with gemcabene crystals (30 g), the solution was cooled to 12° C. After crystallization for 18 hours, the product was isolated on a filter drier (FT-1001, stainless steel, 1000 l), washed in three portions with cold heptane (3×9.6 kg) and dried in vacuum at 35° C.±2° C. for 15 hours, to give 50.7 kg (167 mol). The resulting yield was about 79%. The purified gemcabene contained 0.4% 2,2,7,7-Tetramethyl-octane-1,8-dioic acid.

Scheme 3: Synthesis of 6-(5-carboxy-5-methyl-hexyloxy)-2,2-dimethylhexanoic acid calcium (gemcabene calcium salt) hydrate Crystal Form 1

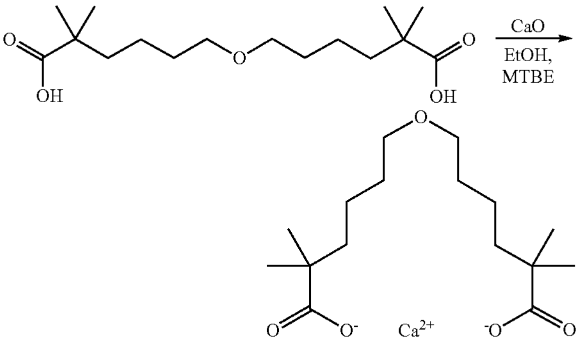

Step 2. 6-(5-Carboxy-5-methyl-hexyloxy)-2,2-dimethylhexanoic acid calcium (gemcabene calcium salt) hydrate Crystal Form 1: Gemcabene (50.5 kg; 167 mol, 1.00 equiv, from Step 1) was dissolved in ethanol (347 kg, denatured with 1% cyclohexane) and filtered through a 1.2 μm filter in the reaction vessel (ST-1005, glass-lined, 16001). The equipment was flushed with additional ethanol (38 kg). Calcium oxide (9.35 kg, 167 mol, 1.00 equiv) was added at 22° C. under stirring, and the mixture is heated at reflux for 20-25 hours. The resulting mixture was cooled to 52° C.±2° C. and tert-butyl methyl ether (125 kg, filtered through a 1.2 μm filter) was charged. After cooling to 22° C.±2° C., the mixture was stirred for an additional hour. The crystalline ethyl alcohol solvate was isolated by filtration in an agitated filter dryer (FT-1001, stainless steel, 1000 l) and washed with tert-butyl methyl ether in three portions (3×37 kg, filtered through a 1.2 μm filter). The crystalline ethyl alcohol solvate was dried with interval agitation (3 minutes stirring, 15 minutes not stirring) at a jacket temperature of 30° C. for 66 minutes, 50° C. for 30 minutes, 70° C. for 30 minutes, and 90° C. for at least 12 hours in vacuum with a stream of 20 L/h nitrogen. Vacuum was broken with nitrogen and purified water (6.29 kg, 349 mol, 2.09 equiv) was added with agitation and stirring was continued at atmospheric pressure at 90° C. for 6 hours. Vacuum was re-established, and the crystalline hydrate was dried at 90° C. for at least 16 hours to yield gemcabene calcium salt hydrate Crystal Form 1 (53.2 kg, 157 moles). The resulting amount was about 94% yield and this sample is referred to as "neat" or a sample "obtained as neat" (pre-milling).

Step 3. Milling of 6-(5-Carboxy-5-methyl-hexloxy)-2,2-dimethylhexanoic acid calcium (gemcabene calcium salt) hydrate Crystal Form 1: The gemcabene calcium salt hydrate Crystal Form 1 obtained in Step 2 (53.2 kg, 157 mol) was milled using a pinmill (MP160) with a dedicated rotor and stator equipped with 4 pin rows (n. 699), under nitrogen flow. An amount of 49.3 kg of gemcabene calcium Crystal Form 1 with a PSD90 ranging from 40 µm to 75 µm was obtained in 93% yield.

Methods

Unless otherwise noted, following methods were used to determine purities and impurities of gemcabene and pharmaceutically acceptable salt of gemcabene.

High-Performance Liquid Chromatography (HPLC)—Impurities

Operating Parameters:

| | |
|---|---|
| Instrument Type: | Agilent 1200 Series or ThermoScientific Ultimate 3000 UHPLC (QC-HPLC-26), or equivalent |
| Column: | Ace Excel 3 C4, 150 mm × 2.1 mm, 3 µm (CPS 164/x), or suitable equivalent |
| Flow Rate: | 0.4 mL/min |
| Run Time: | 60 minutes |
| Mobile Phase A: | Water + 0.1% v/v formic acid |
| Mobile Phase B: | Acetonitrile + 0.1% v/v formic acid |
| Column Temperature: | 40° C. |
| Injection Volume: | 5 µL (for sample and blank) |
| Detection: | UV at 205 nm |
| | Charged aerosol detector (CAD) (nebulizer: 30° C., gain range: 200 pA, filter: 4 or corona) |
| Acquisition Time | 43 min |
| Sample Concentration | 10 mg/mL |
| Sample Solvent, Blank, Flush solution | Acetonitrile/Water/Formic acid 430:570:1 v/v/v |

Gradient:

| Time (min) | Mobile Phase A (%) | Mobile Phase B (%) |
|---|---|---|
| 0.0 | 90 | 10 |
| 1.0 | 90 | 10 |
| 30.0 | 5 | 95 |
| 35.0 | 5 | 95 |
| 35.1 | 90 | 10 |
| 43.0 | 90 | 10 |

Sample Solution (10 mg/mL): 100 mg (±5 mg) sample was added to a 10 mL-flask and Sample Solvent was added to the mark.

Reference Mix Stock Solutions (0.5 mg/mL for gemcabene and 0.25 mg/L for other substances): 10 mg (±1 mg) gemcabene+5 mg (±1 mg) 2,2,7,7-tetramethyl-octane-1,8-dioic acid+5 mg (±1 mg) 6-(4-hydroxybutoxy)-2,2-dimethylhexanoic acid+5 mg (±1 mg) 2,2-dimethyl-hex-4-enoic acid (E/Z ratio approximately 5:1) were added in a 20 mL-flask and the Sample Solvent was added to the mark (Reference Mix Stock). 2.0 mL of Reference Mix Stock was added to a 20 mL-flask and the Sample Solvent was added to the mark (Diluted Reference Stock).

Illustrative Injection Sequence

| Injection No. | Injection Volume | Sample | Detection Method Relied On for References |
|---|---|---|---|
| 1 | 5.0 µL | Blank | |
| 2 | 5.0 µL | Blank | |
| 3 | 0.5 µL | Diluted Reference Stock | CAD |
| 4 | 1.0 µL | Diluted Reference Stock | CAD |
| 5 | 2.0 µL | Diluted Reference Stock | CAD + UV |
| 6 | 5.0 µL | Diluted Reference Stock | CAD + UV |
| 7 | 1.0 µL | Reference Mix Stock | CAD + UV |
| 8 | 2.0 µL | Reference Mix Stock | UV |
| 9 | 5.0 µL | Reference Mix Stock | UV |
| 10 | 10.0 µL | Reference Mix Stock | UV |
| 11 | 5.0 µL | Blank | |
| 12 | 5.0 µL | Sample 1 | |
| 13 | 5.0 µL | Sample 1 repeat | |
| 14 | 5.0 µL | Blank | |
| 15 | 5.0 µL | Sample 2 | |
| 16 | 5.0 µL | Sample 2 repeat | |
| 17 | 5.0 µL | Blank | |

System Suitability Test Criteria:

No interfering peaks in the Blank

Calibration criteria: $R^2 \geq 0.98$

Evaluation:

UV: Reporting threshold: 0.05% w/w

Impurity content of (E)-2,2-dimethyl-hex-4-enoic acid was evaluated against calibration of reference material.

Impurity content of (Z)-2,2-dimethyl-hex-4-enoic acid was evaluated against calibration of reference material.

All known impurities not detected with CAD are calibrated with the standard 2,2-dimethyl-hex-4-enoic acid (E/Z mixture).

CAD: Reporting threshold: 0.05% w/w

Impurity content of 6-(4-hydroxybutoxy)-2,2-dimethylhexanoic acid was evaluated against calibration of reference material.

Impurity content of 2,2,7,7-tetramethyl-octane-1,8-dioic acid was evaluated against calibration of reference material.

Any unknown impurities were evaluated against calibration of 2,2,7,7-tetramethyl-octane-1,8-dioic acid.

Total HPLC impurities (% w/w)=Sum of impurities by UV and sum of impurities by CAD.

High-Performance Liquid Chromatography (HPLC)—Gemcabene Calcium Purity and Conjugate Base of Gemcabene Component Analysis Operating Parameters:

| | |
|---|---|
| Instrument Type: | Agilent 1200 Series or ThermoScientific Ultimate 3000 UHPLC (QC-HPLC-26), or equivalent |
| Column: | Ace Excel 3 C4, 150 mm × 2.1 mm, 3 µm (CPS 164/x), or suitable equivalent |
| Flow Rate: | 0.4 mL/min |
| Run Time: | 60 minutes |
| Mobile Phase A: | Water + 0.1% v/v formic acid |
| Mobile Phase B: | Acetonitrile + 0.1% v/v formic acid |
| Column Temperature: | 40° C. |
| Injection Volume: | 2.0 µL (for sample and blank) |
| Detection: | UV at 210 nm |
| Acquisition Time | 43 min |
| Sample Concentration | 10 mg/mL |
| Sample Solvent, Blank, Rinsing solution | Acetonitrile/Water/Formic acid 430:570:1 v/v/v |

Gradient:

| Time (min) | Mobile Phase A (%) | Mobile Phase B (%) |
|---|---|---|
| 0.0 | 90 | 10 |
| 1.0 | 90 | 10 |
| 30.0 | 5 | 95 |
| 35.0 | 5 | 95 |
| 35.1 | 90 | 10 |
| 43.0 | 90 | 10 |

Sample Solution (10 mg/mL): 100 mg (±5 mg) sample was added to a 10 mL-flask and Sample Solvent was added to the mark.

Reference Gemcabene Solutions (10 mg/mL): 100 mg (±5 mg) gemcabene was added in a 10 mL-flask and the Sample Solvent was added to the mark (Reference).

Illustrative Injection Sequence

| Injection No. | Injection Volume | Sample |
|---|---|---|
| 1 | 2.0 μL | Blank |
| 2 | 2.0 μL | Blank |
| 3 | 2.0 μL | Reference 1 |
| 4 | 2.0 μL | Reference 2 |
| 5 | 2.0 μL | Reference 3 |
| 6 | 2.0 μL | Reference 4 |
| 7 | 2.0 μL | Reference 5 |
| 8 | 2.0 μL | Reference 6 |
| 9 | 2.0 μL | Reference Drift Check |
| 10 | 2.0 μL | Blank |
| 11 | 2.0 μL | Sample 1 |
| 12 | 2.0 μL | Sample 1 repeat |
| 13 | 2.0 μL | Blank |
| 14 | 2.0 μL | Sample 2 |
| 15 | 2.0 μL | Sample 2 repeat |
| 16 | 2.0 μL | Blank |
| 17 | 2.0 μL | Reference Drift Check |
| 18 | 2.0 μL | Blank |

System Suitability Test Criteria:

No interfering peaks in the Blank

Relative Standard Deviation (6 Reference injections) ≤2.0%

Recovery (of each Reference injection) 98.0-102.0% w/w

Evaluation:

UV: Gemcabene purity evaluated against calibration of Reference material.

Ion Chromatography (IC)

Operating Parameters:

| | |
|---|---|
| Instrument Type: | Dionex ICS-5000+ SP, ICS-5000+ EG, Dionex ICS-5000+DC, Autosampler AS, or equivalent |
| IC Column: | Dionex ion pac AS11-HC (147/xx) or equivalent |
| Flow Rate: | 0.4 mL/min |
| Run Time: | 60 minutes |
| Mobile Phase | Water (IC quality)<br>Eluent Generator KOH (e g., Dionex EGC III KOH Eluent Generator Cartridge - Product no. 074532) |
| Suppressor set | 112 mA |
| Cell Temperature: | 35° C. |
| Injection Volume: | 10 μL |
| Oven temperature | 30° C. |
| Flow rate | 1.5 mL/min |
| Sample Concentration | 5 mg/mL |
| Blank for Sample Solvent and Standard solutions | Standard solutions: Water (IC quality)<br>Sample solutions: Water/acetonitrile (IC quality) 1:1 + 0.05% trifluoroacetic acid (HPLC grade) |

Gradient:

| Time (min) | KOH Gradient (mM) | Flow Rate (mL/min) |
|---|---|---|
| 0.0 | 1 | 1.5 |
| 5.0 | 1 | 1.5 |
| 14.0 | 15 | 1.5 |
| 23.0 | 30 | 1.5 |
| 23.1 | 1 | 1.5 |
| 30.0 | 1 | 1.5 |

Sample Solution (5 mg/mL): 25 mg (±1.0 mg) sample was added to a 5 mL-flask and dissolved with water/acetonitrile 1:1+0.05% trifluoroacetic acid and filled to the mark. The flask was placed in an ultrasound bath for 10 min and then left to cool for approx. 1 hr. Then the solution was observed to make sure it was clear and had no particles (no deposit). If there were particles, sample was filtered into a vial via the syringe filter (e.g. filter 0.45 um—for organic PTFE solutions) (discarded 2-3 ml filtrate in advance to saturate the filter). If no particles were present, the sample can be analyzed without filtration.

Standard Stock Solutions (1000 μg/mL): 50 μL isobutyric acid was added to a 50 mL-flask and water was added to the mark (Reference Stock).

Standard Stock Solutions (100 μg/mL): 1.0 mL of Reference Stock was diluted to 10 mL with water. Other standard solutions were prepared as shown below.

| Concentration of Standard Solution (μg/mL) | Volume of 100 μg/mL Stock Solution | Volume of water added |
|---|---|---|
| 25 | 250 μL | 750 μL |
| 15 | 150 μL | 850 μL |
| 10 | 100 μL | 900 μL |
| 5 | 50 μL | 950 μL |
| 2.5 | 100 μL of 25 μL Stock Solution | 900 μL |

Illustrative Injection Sequence

| Injection No. | Sample |
|---|---|
| 1 | Blank - water (3 injections) |
| 2 | Standard 2.5 μg/mL |
| 3 | Standard 5.0 μg/mL |
| 4 | Standard 10.0 μg/mL |
| 5 | Standard 15.0 μg/mL |
| 6 | Standard 25.0 μg/mL |
| 7 | Standard 2.5 μg/mL |
| 8 | Blank - water |
| 9 | Blank - water/acetonitrile 1:1 + 0.05% trifluoroacetic acid |
| 10 | Sample 1 |
| 11 | Sample 2 |
| 12 | Blank - water (3 injections) |
| 13 | Check Standard 25.0 μg/mL |
| 14 | Blank - water (2 injections) |

System Suitability Test Criteria:

$R^2$≥0.99

% Drift agreement: 97%-103%

Bottom count Standard 25.0 μg/mL≥2500

Asymmetry (Target) Standard 25.0 μg/mL≤2.0

S/N (signal-to-noise ratio) Standard 25.0 μg/mL≥10

Evaluation: Limit of quantification was 2.50 μg/mL which corresponds to 0.05% w/w.

Gas Chromatography (GC)—Bis-(4-Chlorobutyl)Ether and Residual Solvents

Operating Parameters:

| | |
|---|---|
| Instrument Type: | Agilent 68900N or equivalent |
| Detector: | FID (flame ionization detector) |
| Data System: | Dionex-Chromeleon |
| Flow Split: | 16 mL/min |
| Split Ratio: | 1:10 |
| Column: | Capillary, fused silica, 30 m × 0.25 mm × 0.5 μm |
| Stationary Phase: | RTX-5 Amine |
| Carrier Gas (Flow) | He 4.6 (0.6 mL/min; constant flow) |
| Pressure | 117 Kpa |
| Make-up Gas (Flow) | $N_2$ (35 mL/min) |
| Synthetic Air | 450 mL/min |
| Hydrogen Gas | 35 mL/min |
| Injector Temp./ Detector Temp. | 220° C./220° C. |
| Injection volume | 100 μL |

Temperature Program:

| Temp. (° C.) | Time (min) | Rate (° C./min) |
|---|---|---|
| 45 | 9 | 20 |
| 205 | 3.1 | — |

Stock bis-(4-chlorobutyl)ether: Exactly 125 mg (5 ppm*) of bis-(4-chlorobutyl)ether was added to a 20 mL volumetric flask containing 10 ml of N-methyl-2-pyrrolidone (NMP). The volumetric flask was filled to the mark with NMP. *The value in ppm refers to 100 μl of stock uplift and 125 mg nominal weight.

Stock Solution: 125 mg (1000 ppm*) n-hexane, 250 mg (2000 ppm*) THF, 125 mg (1000 ppm*) diisopropylamine, 250 mg (2000 ppm*) ethylbenzene and 125 mg (1000 ppm*) of cyclohexane were accurately measured into a 20 mL volumetric flask containing approximately 10 mL of NMP. The volumetric flask was filled to the mark with NMP and solution was mixed until it became homogeneous. *The value in ppm refers to 100 μl of stock uplift and 125 mg nominal weight.

Spiking Solution: Exactly 250 mg (10000 ppm*) of each of n-heptane, t-butyl methyl ether, and ethanol were weighed into a 20 mL volumetric flask containing approximately 10 mL NMP. 20 μL of Stock bis-(4-chlorobutyl)ether and 4 mL of Stock Solution was added to the volumetric flask. Then, the volumetric flask was filled to the mark with NMP and solution was mixed until it became homogeneous. *The value in ppm refers to 100 μl of stock uplift and 125 mg nominal weight.

Sample Preparation: Approximately 110-140 mg of finely powdered gemcabene calcium was weighed into a GCHS vial and exact mass was recorded. 3 mL of water was added with a pipette and 100 μL NMP was added with a microliter syringe and the vial was closed immediately. The sample solution was mixed via ultrasonication for approximately 5 min.

Spiked Sample Preparation: Approximately 110-140 mg of finely powdered gemcabene calcium was weighed into a GCHS vial and exact mass was recorded. 3 mL of water was added with a pipette. Then, an appropriate amount of Spiking Solution (10 μL, 20 μL, 30 μL, 40 μL, 50 μL, etc.) and NMP (together with Spiking Solution should be 100 μL) were added. The vial was closed immediately. The sample solution was mixed via ultrasonication for approximately 5 min.

Inductively Coupled Plasma Optical Emission Spectrometry (ICP-OES)

Method is based on Ph. Eur., chapter 2.2.57 "Inductively Coupled Plasma-Atomic Emission Spectrometry" and USP-NF, chapter <730> "Plasma Spectrochemistry".

Operating Parameters and Reagents:

| | |
|---|---|
| Instrument: | ICP - Optical Emission spectrometer (Vista-PRO, Agilent or suitable equivalent) |
| Emission wavelength | 317.93 nm |
| Plasma observation | Axial |
| Plasma power | 1200 W |
| Plasma gas flow | 16.5 L/min Ar |
| Auxiliary gas flow | 1.5 L/min Ar |
| Nebulizer | Concentric |
| Spray chamber | Cyclon spray chamber |
| Nebulizer gas flow | 0.75 L/min |
| Pump rate | 20 rpm |
| Reagents: | |
| Water | Deionized or higher purity |
| Nitric Acid | Conc. (min 65% m/m), for analysis or higher purity, e.g., suprapur ® |
| Hydrochloric acid | 30%, for analysis or higher purity, e.g., suprapur ® |
| Ca Standard solution (1000 mg/L) | Single Element Standards for ICP (e.g., AccuTrace, ICP-09N-1) |
| Quality control material | A reference substance containing the analyte other than the one used for preparation of calibration solutions, e.g. Calcium D- Gluconate Monohydrate |

System Suitability Test:

| | |
|---|---|
| Quality Control: | Analyzed the quality control sample at least once. The relative deviation from the expected analyte concentration must not exceed ±10% for the analyte |
| Linearity Check: | Evaluated data from linear regression calculation. Correlation coefficients must be ≥0.999 |
| Blank Solutions: | The blank solutions were analyzed. For Bach determination, the Ca concentration of the blank solution must not be more than 1% of the lowest concentration of the test solutions |

Solutions:

| | |
|---|---|
| Calibration solutions | Laboratory prepared mixtures with known and suitable element concentrations. Prepared at least 4 calibration solutions (including zero solution) from the stock standard solution by appropriate dilution with water and addition of 2 mL of conc. $HNO_3$ per 100 mL; selected the calibration range according to the expected analyte concentration. E.g. for an element content of 11.8% m/m (8.0, 12.0 and 16.0) mg/L would be suitable concentrations. |
| Zero solution | Prepared as described for the calibration solutions, but without addition of any standard solution. |
| Test solutions | Test solutions were prepared in duplicate. Weighed approx. 25 mg of the test substance accurately (to within 0.01 mg) into a digestion vessel. Added 2.0 mL of nitric acid and 0.2 mL of |

-continued

| | |
|---|---|
| | hydrochloric acid to the test substance. Capped the digestion vessel. Allowed the mixture to react for approximately 15 minutes in an ultrasonic bath at room temperature. Placed the loosely capped vessel into the digestion autoclave. Operated the digestion autoclave according to the manufacturer's instructions. After completion of the digestion procedure and after cooling the digestion vessel down to ambient temperature added 3.0 mL of nitric acid and diluted to 250 mL with deionized water using volumetric flasks. Volumes may be adapted as long as the ratio remains the same. |
| Blank solutions | Prepared in duplicate analogously to the test solutions but without any test substance. |
| Quality control sample solution | The quality control solution was prepared from the quality control material after corresponding digestion (see test solution) by appropriate dilution with water. The analyte concentration must be within the calibrated range. |

Measurement: The emission of the zero solution and the calibration solutions were measured using suitable Instrument parameters (see above). The emission of blank solution, quality control solution and test solutions were measured. If necessary, the test solutions were diluted with zero solution (dilution factor f) to obtain a reading within the calibration range. Alternatively, new calibration solutions were prepared in order to adapt the calibration range.

Calculation: The calibration function was determined using the corresponding readings. The analyte element concentration was calculated in the test solutions from the measured emission with this calibration function subtracting the reading of the zero solution. The analyte element concentration was calculated in the test substance using the equation below. These calculations were done by the Instrument software.

$$c = \frac{a \times V \times f}{m \times 10000}$$

c=concentration of analyte element in the Lest substance (% m/m)

a=analyte concentration in the test solution (mg/L)

V=volume of the test solution (mL)

f=dilution factor, e.g. f=1.0 if the test solution is not diluted m=mass of test substance (g)

10000 is a conversion factor (mg/kg to % m/m).

Both, values of the duplicate determination (with 2 decimals) and the mean value (1 decimal) were reported.

Karl-Fisher Analysis

Karl-Fisher analysis was performed according to Ph. Eur. 2.5.32. For Karl-Fisher Analysis, limit of quantification was 0.05% w/w.

Example 2: Solubility Studies of Gemcabene Calcium Salt Crystal Form 1

Approximately 20 mg of gemcabene calcium Crystal Form 1 was added to 5×2 mL vials. The solubility in 5 solvents was tested using a solvent addition method. Solvents included acetone, ethanol, ethyl acetate, t-butyl methyl ether (t-BME) and water. Solvent was added in 5 volume (100 μL) aliquots until either dissolution or 2 mL in total had been added. Between each addition, samples were heated to 60° C. (40° C. for acetone and t-BME). Any solids remaining after 24 hours at ambient were analyzed by X-ray powder diffraction (XRPD). Water sample dissolved and did not precipitate even after 48 hours at <5° C. Table 1 shows the result of the solubility studies.

TABLE 1

Solubility of gemcabene calcium salt Crystal Form 1

| Solvent | Solubility (mg/mL) | Crystalline Form |
|---|---|---|
| Acetone | <10 | Form 1 |
| Ethanol | <10 | Form 1 |
| Ethyl Acetate | <10 | Form 1 |
| t-Butyl Methyl Ether (t-BME) | <10 | Form 1 |
| Water | 33 | N/A |

Example 3: Amorphous Gemcabene Calcium Salt

Figure 52A:
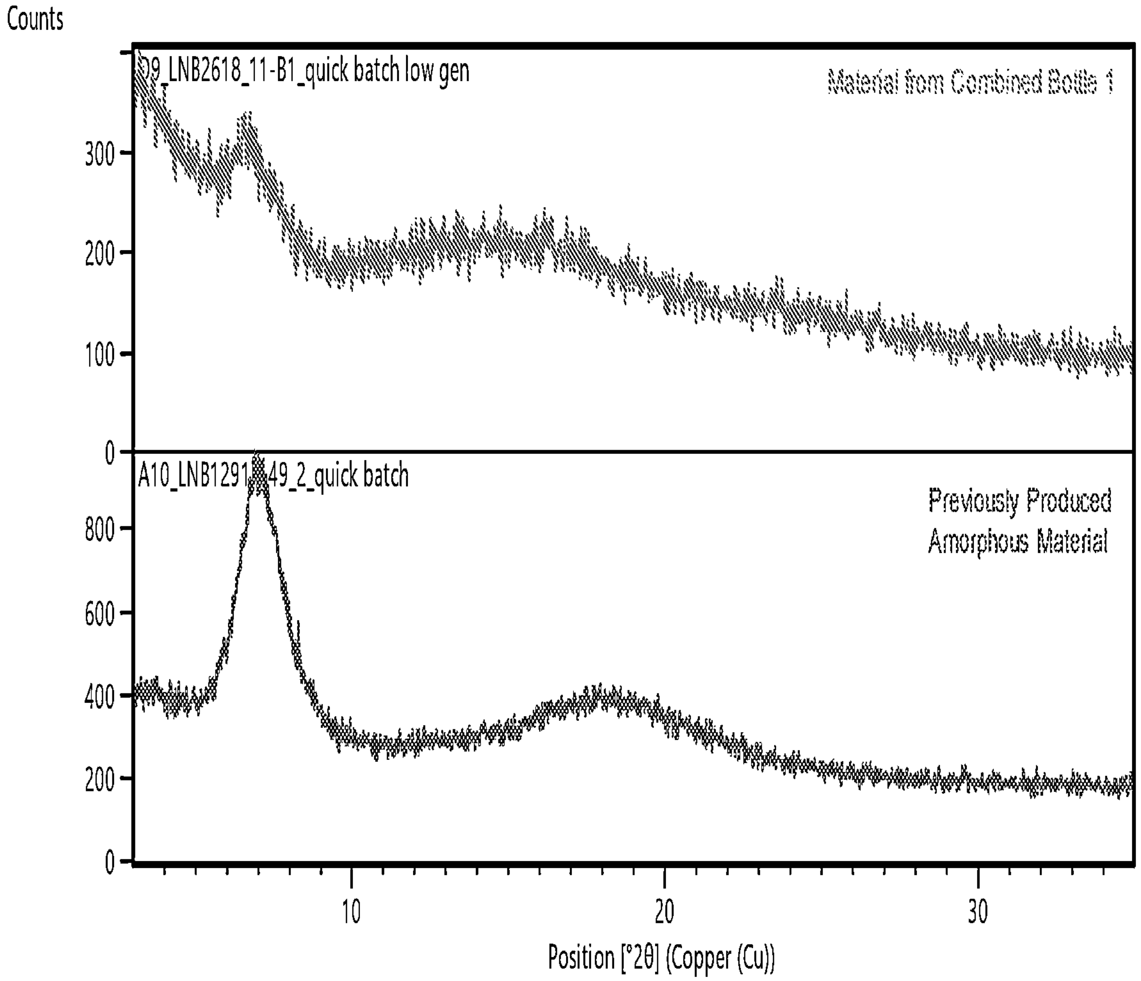
FIG. 52A is a X-ray powder diffractogram of amorphous gemcabene calcium salt.
Figure 52B:
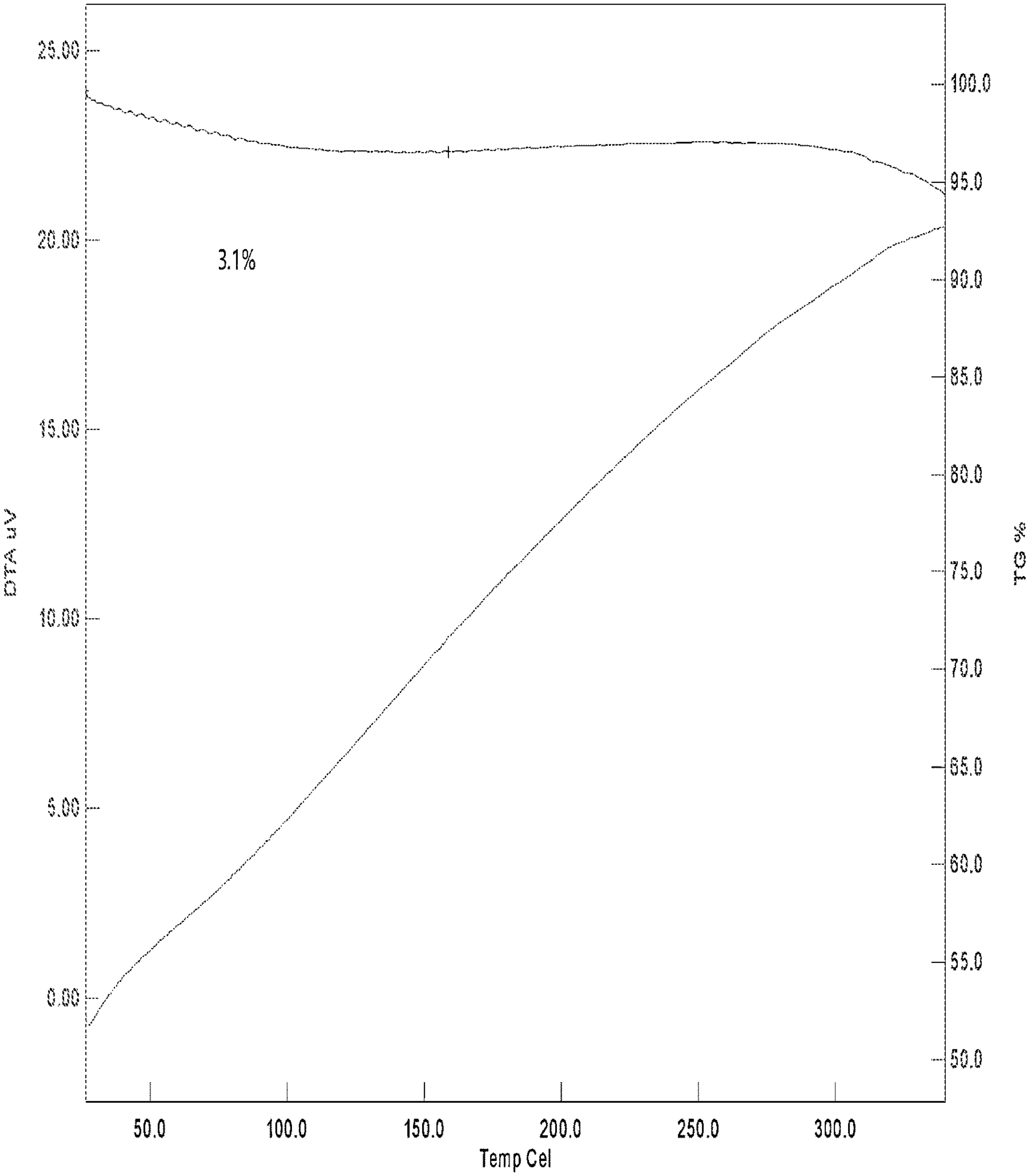
FIG. 52B is an overlay of a thermogravimetric analysis (TGA) thermogram and differential thermal analysis (DTA) thermogram of amorphous gemcabene calcium salt.
Figure 52C:
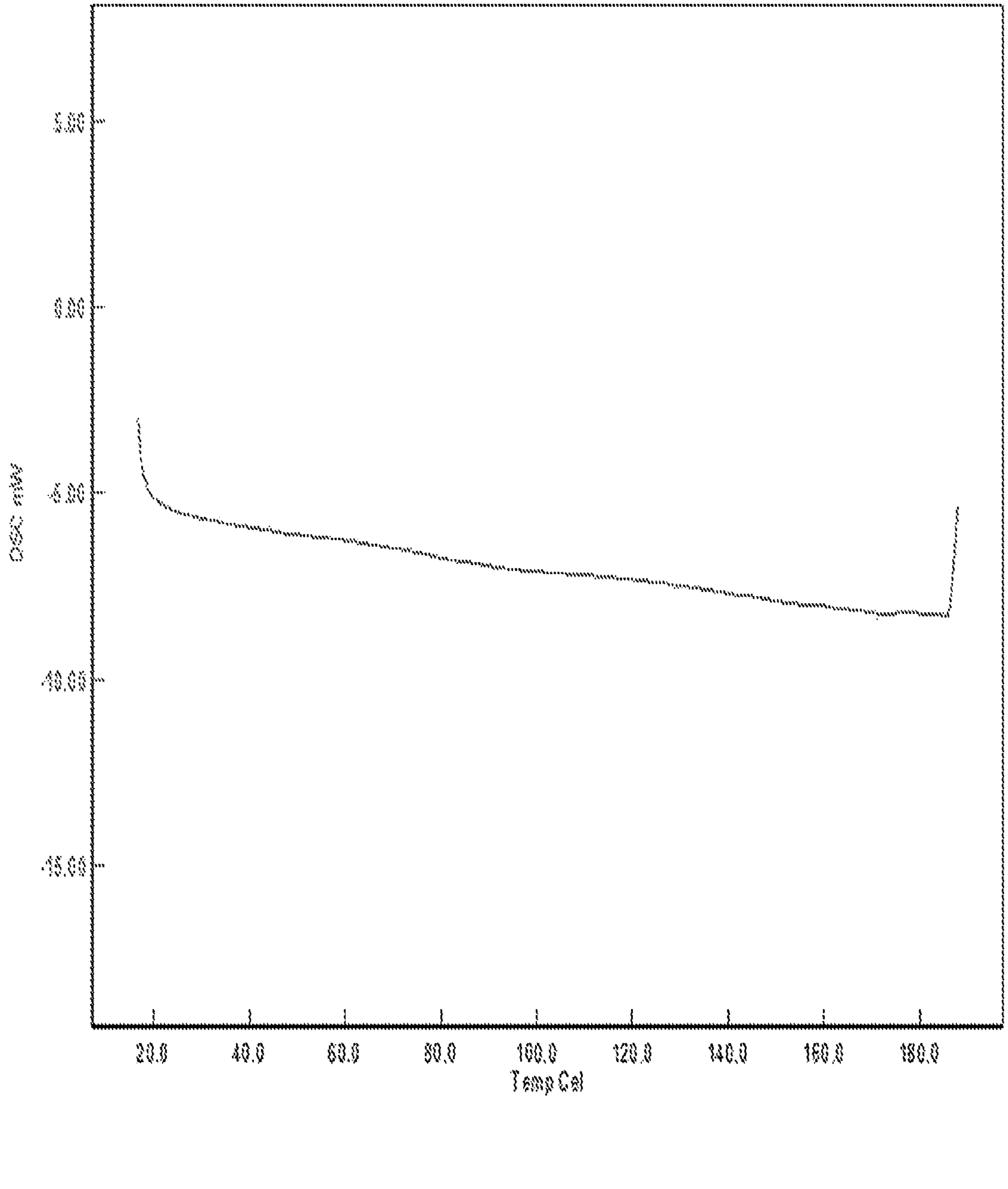
FIG. 52C is a differential scanning calorimetry (DSC) thermogram of amorphous gemcabene calcium salt.

Gemcabene calcium salt Crystal Form 1 was prepared as described in Example 1. Approximately 40 g of gemcabene calcium salt Crystal Form 1 was weighed. To this, approximately 800 mL of water was added and mixed at ambient temperature for dissolution. After approximately 4 hours, the solid was found to have dissolved and the solution was transferred to a 2 L round bottom flask. The solution was then frozen before being placed on a freeze dryer for approximately 72 hours. X-ray powder diffraction (XRPD) analysis of a combined lot of material showed that the diffractogram is consistent with reference amorphous data (FIG. 52A). Polarized light microscope (PLM) images showed glass-like particles with limited birefringence. Thermogravimetric analysis (TGA) showed a weight loss of 3.1% up to 150° C. (FIG. 52B). No thermal events were noted in the differential thermal analysis (DTA) or in the differential scanning calorimetry (DSC) (FIGS. 52B and 52C). The moisture content of the material was determined to be 2.62% by Karl-Fisher titration. The amorphous gemcabene calcium salt was determined to have a gemcabene content (% gemcabene) of 88.85% on a % w/w basis by high-performance liquid chromatography equipped with charged aerosol detector (HPLC-CAD). Particle size distribution (PSD) analysis returned a D10 value of 5.2 μm, a D50 value of 26.4 μm and a D90 value of 60.3 μm.

On large scale (greater than 1 kg scale), the amorphous form was obtained by drying gemcabene calcium ethanol solvate. The amorphous solid was difficult to handle due to electrostatic properties and a relatively low bulk density of <0.3 g/mL (tapped).

Example 4: Gemcabene Calcium Salt Crystal Form 2

Gemcabene calcium salt Crystal Form 1 was prepared as described in Example 1. To a 5 L glass reactor held at 70°

Figure 53A:
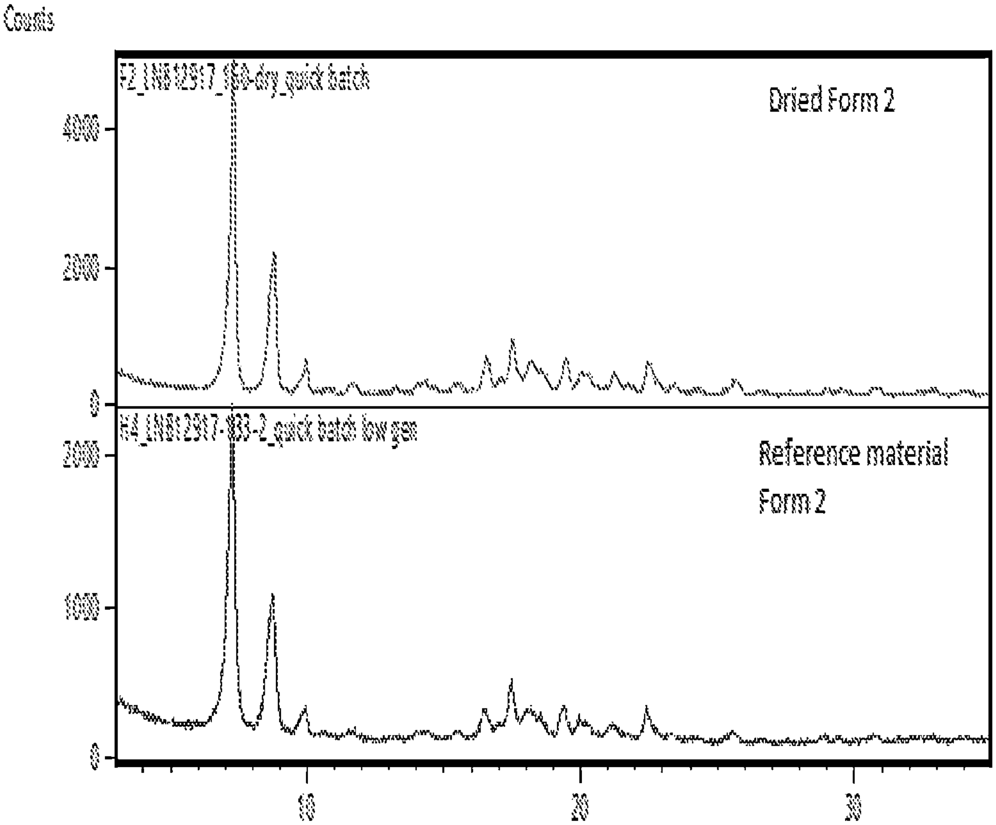
FIG. 53A is a X-ray powder diffractogram of gemcabene calcium salt Crystal Form 2.
Figure 53B:
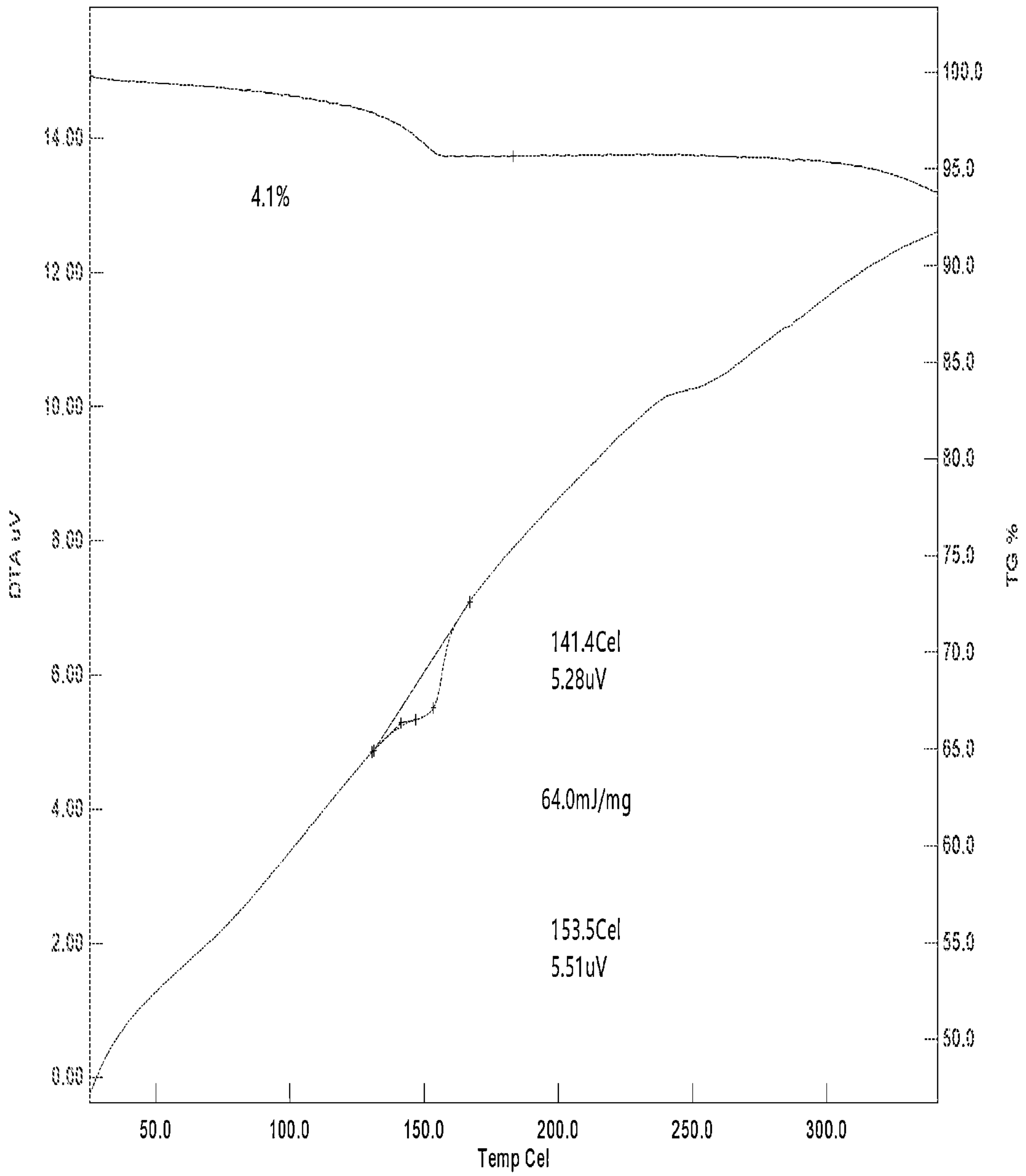
FIG. 53B is an overlay of a thermogravimetric analysis (TGA) thermogram and differential thermal analysis (DTA) thermogram of gemcabene calcium salt Crystal Form 2.

C., approximately 160 g of gemcabene calcium salt Crystal Form 1 was added, along with approximately 2.4 L of an ethanol:water (90:10 v/v %) solution. The slurry was then mixed at 120 RPM using a 4 pitch-blade PTFE impeller for approximately 2 hours. After 2 hours, a further 824 mL water was added to the slurry (new solvent ratio of ethanol: water (67:33 v/v %)) and the material was then left to slurry for approximately 18 hours. The crystallization was then cooled to 40° C. and the stirring rate decreased to 100 RPM. The crystallization was held for 2 hours then separated by filtration. The solid was then dried at 80° C. for 48 hours. An isolated yield of approximately 69% was recovered. Samples of the wet and dried material were analyzed by X-ray powder diffraction (XRPD) spectroscopy (FIG. 53A) and were confirmed to be gemcabene calcium salt Crystal Form 2. Polarized light microscope (PLM) images of the dried solid showed agglomerated particles with limited birefringence. Theremogravimetric analysis showed a weight loss of 4.1% up to 200° C., associated with solvent loss (FIG. 53B). A single endothermic event is noted in the differential thermal analysis (DTA) at onset 141° C. and a peak at 154° C., likely associated with solvent loss 9 FIG. 53B). The mother liquor was determined to have a concentration of 18.47 mg/mL by high-performance liquid chromatography (HPLC). The gemcabene calcium salt Crystal Form 2 was determined to have a gemcabene content (% gemcabene) of 86.91% w/w. Gas chromatography analysis of the material showed a residual ethanol content of 61 ppm. Particle size distribution (PSD) analysis was carried out and gave a D10 value of 5.0 μm, a D50 of 14.4 μm and a D90 of 38.2 μm.

Example 5: Gemcabene Calcium Salt Crystal Form C3

Figure 54A:
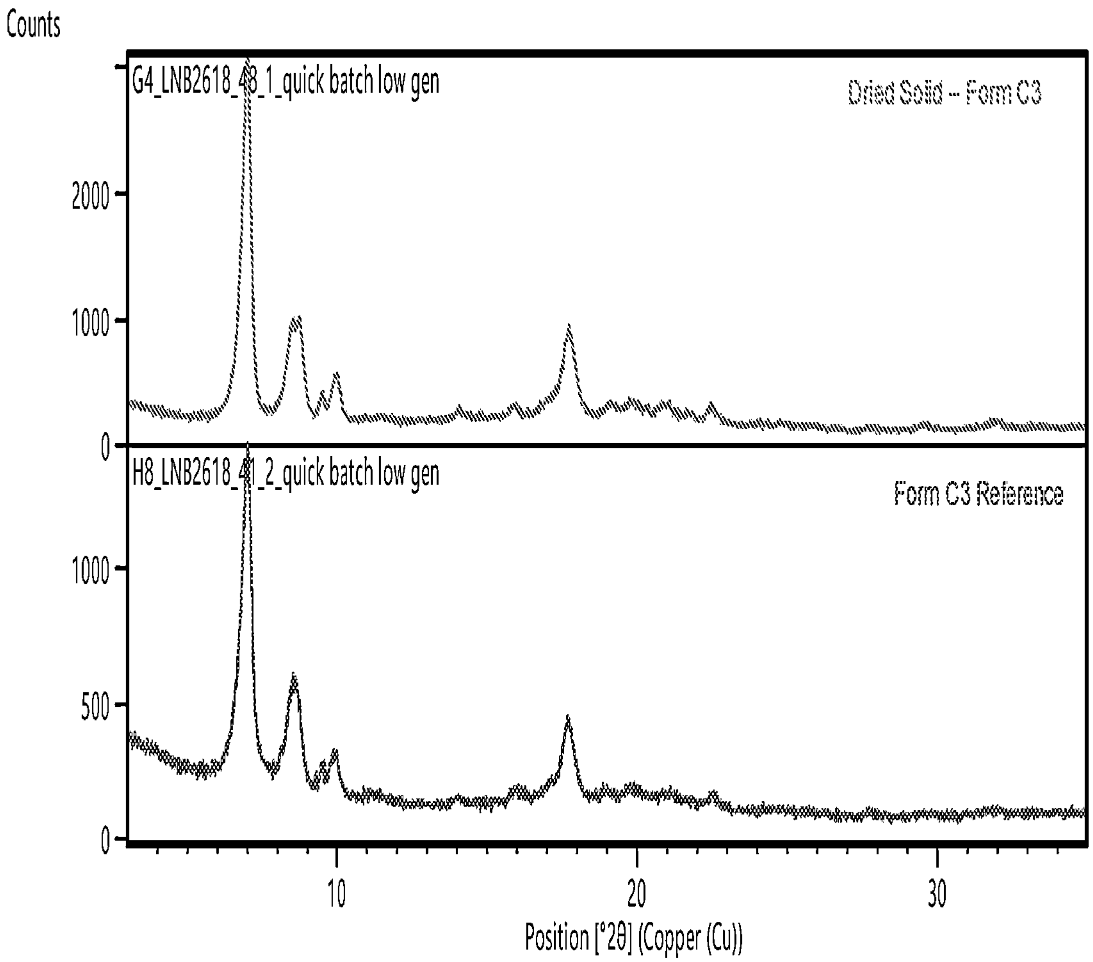
FIG. 54A is a X-ray powder diffractogram of gemcabene calcium salt Crystal Form C3.
Figure 54B:
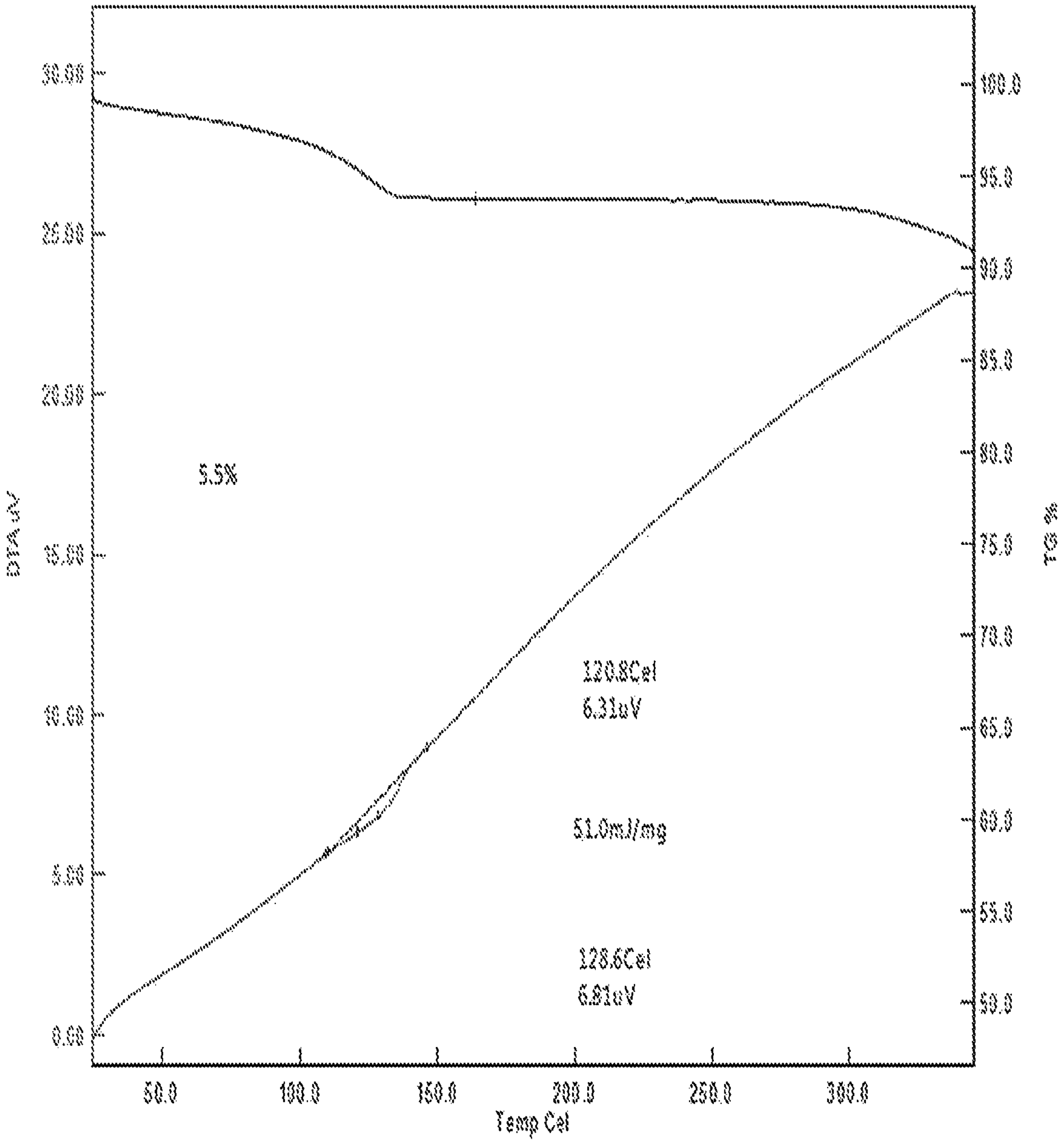
FIG. 54B is an overlay of a thermogravimetric analysis (TGA) thermogram and differential thermal analysis (DTA) thermogram of gemcabene calcium salt Crystal Form C3.
Figure 54C:
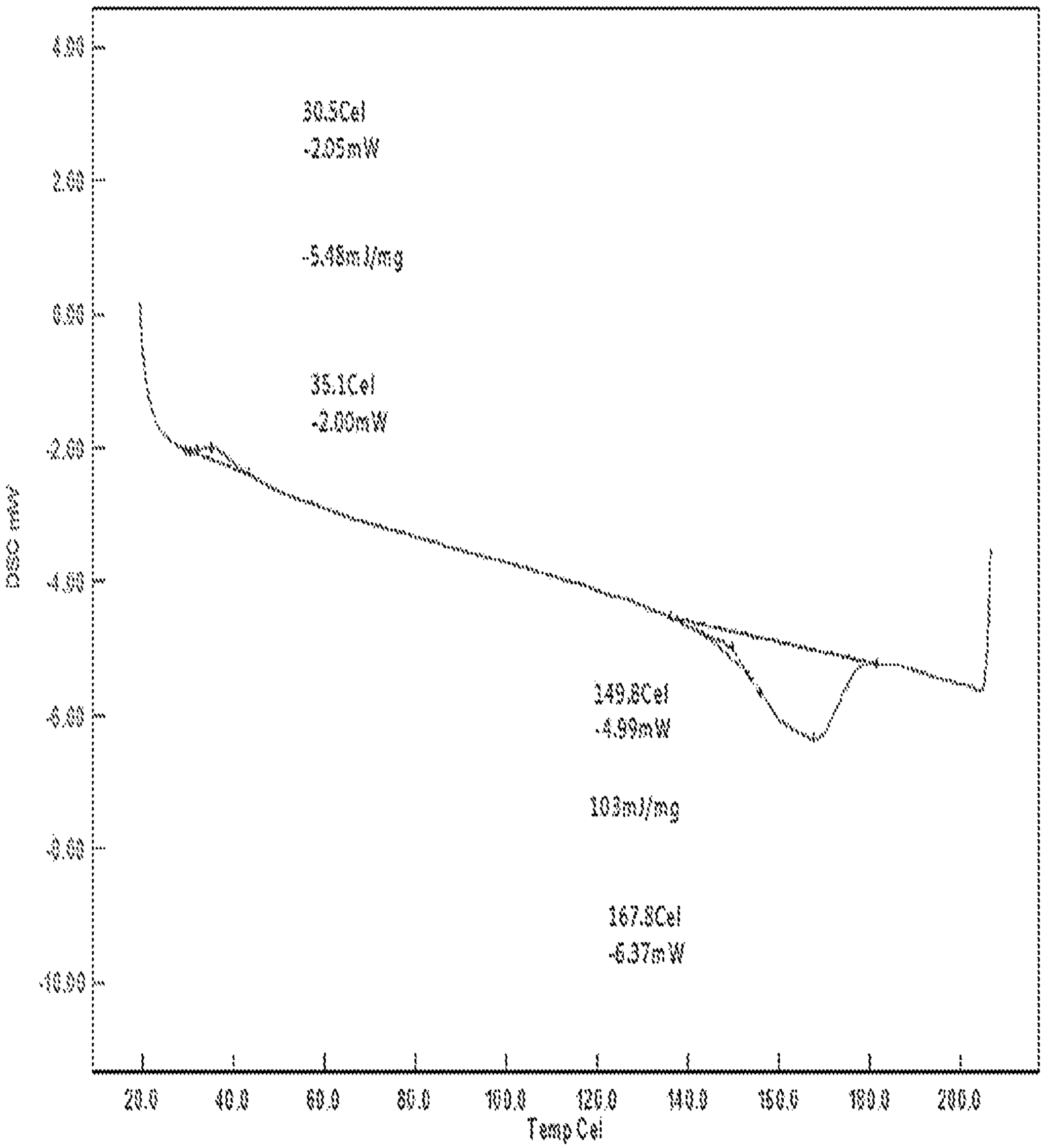
FIG. 54C is a differential scanning calorimetry (DSC) thermogram of gemcabene calcium salt Crystal Form C3.

Amorphous form of gemcabene calcium salt was prepared as described in Example 3. To a large crystallization dish, approximately 50 g of amorphous gemcabene calcium salt was added. To the crystallization dish, 250 mL ethanol was added in 50 mL aliquots, with the material mixed between additions to ensure even solvent distribution. The mixture was mixed several times during drying to minimize large aggregate formation. The material was then dried at ambient under vacuum for approximately 72 hours. X-ray powder diffraction (XRPD) spectroscopy analysis showed that the dried material was consistent with gemcabene calcium salt Crystal Form C3. Polarized light microscope (PLM) images showed agglomerated particles with limited birefringence. Thermogravimetric analysis showed a weight loss of 5.5% up to 160° C. (FIG. 54B). A single endothermic event was noted in the differential thermal analysis (DTA) at onset 121° C., with a peak at 129° C. (FIG. 54B). Differential scanning calorimetry (DSC) analysis showed an exothermic event at onset 31° C., with a peak 35° C., followed by a single endothermic event at onset 150° C., with a peak at 167° C. (FIG. 53C). The moisture content of the material was determined to be 2.1% by Karl-Fisher titration. The gemcabene calcium salt Crystal Form C3 was determined to have a gemcabene content (% gemcabene) of 83.98% on a % w/w basis was determined by high-performance liquid chromatography equipped with charged aerosol detector (HPLC-CAD). Gas chromatography analysis showed a residual ethanol content of 76070 ppm. Particle size distribution (PSD) analysis returned a D10 value of 8.8 μm, a D50 value of 20.4 μm and a D90 value of 44.3 μm.

Example 6: Gemcabene Calcium Salt Ethanol Solvate

Figure 55A:
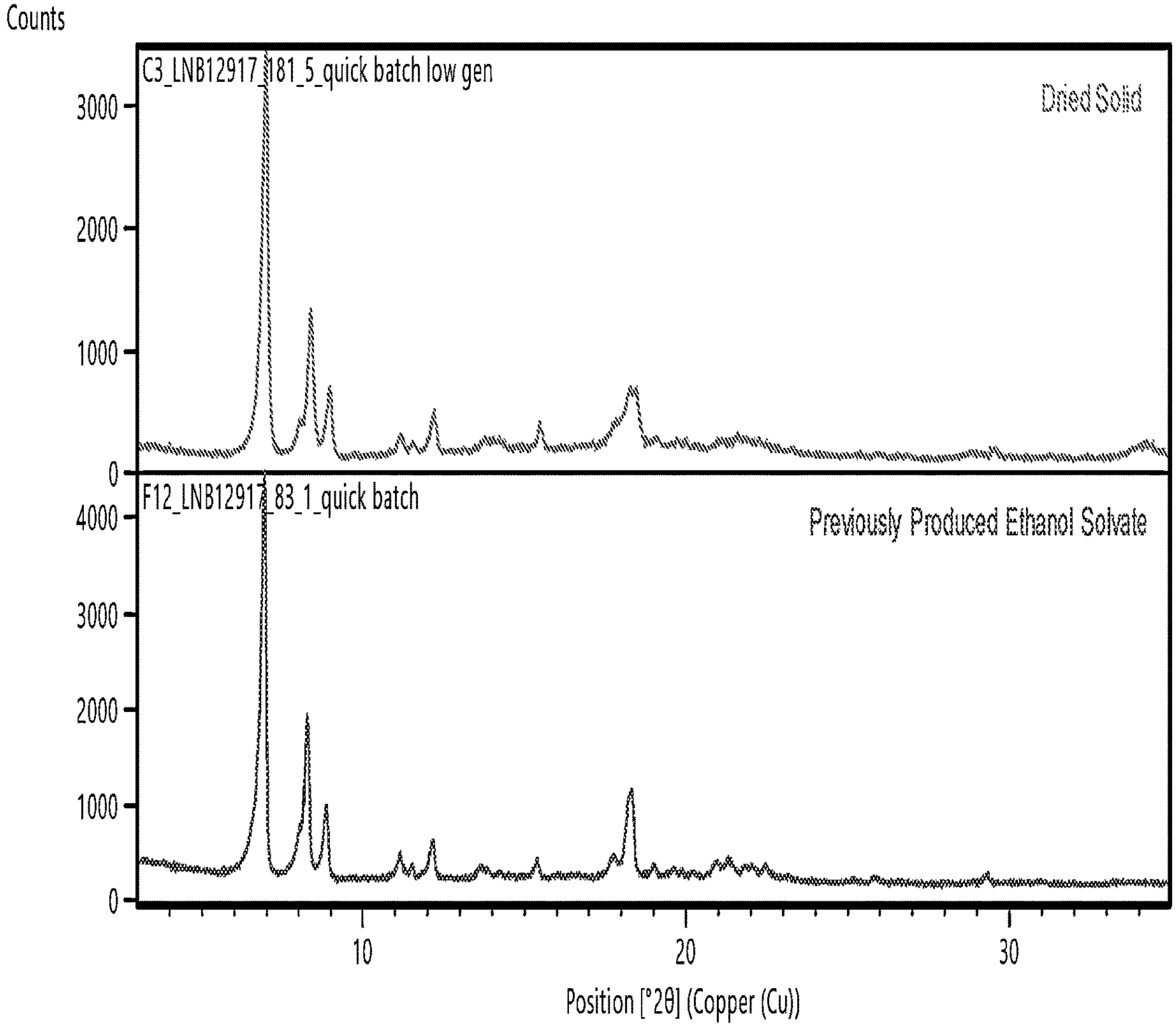
FIG. 55A is a X-ray powder diffractogram of crystalline gemcabene calcium salt ethanol solvate.
Figure 55B:
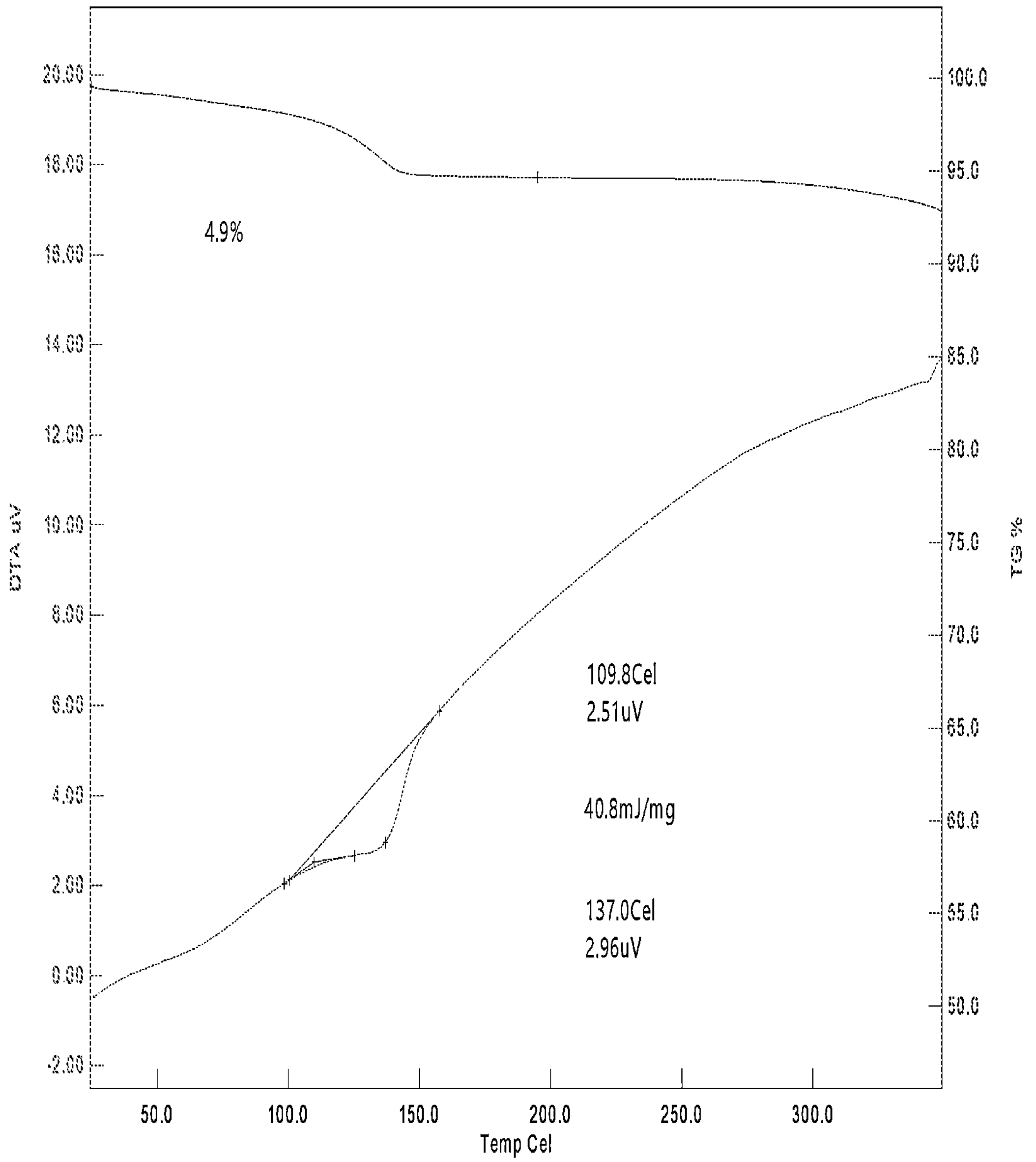
FIG. 55B is an overlay of a thermogravimetric analysis (TGA) thermogram and differential thermal analysis (DTA) thermogram of crystalline gemcabene calcium salt ethanol solvate.

To a 5 L glass reactor at 70° C., approximately 266 g of gemcabene was dissolved in 1 L of ethanol. To the solution, approximately 1 equivalent calcium oxide (approximately 49.3 g) and additional 1.5 L ethanol were added. The slurry was then mixed at 150 RPM, using a 4 pitch-blade PTFE impeller for approximately 18 hours. The solution was then cooled to 25° C. and held for 1 hour. A total of 840 mL t-butyl methyl ether (t-BME) was then added as anti-solvent. After addition, the mixing rate was lowered to 120 RPM and the vessel held at these conditions for 2 hours, then the precipitate was filtered. t-BME was used to rinse the vessel prior to washing the solid. The solid was then left to dry on the filter for approximately 10 minutes. The damp solid was then placed in a crystallization dish and dried at ambient temperature for 90 hours. An isolated yield of approximately 63% was recovered from the scale up. Samples of the wet and dried material were analyzed by -ray powder diffraction (XRPD) spectroscopy (FIG. 55A), and were confirmed to be crystalline gemcabene calcium salt ethanol solvate. Polarized light microscope (PLM) images of the dried solid show agglomerated particles with limited birefringence. Thermogravimetric analysis showed a weight loss of 4.9% up to 200° C., associated with solvent loss (FIG. 55B). A single endothermic event was noted in the differential thermal analysis (DTA) at onset 110° C. and a peak at 137° C., likely associated with solvent loss (FIG. 55B). The mother liquor was determined to have a concentration of 21.59 mg/mL by high-performance liquid chromatography (HPLC). The crystalline gemcabene calcium salt ethanol solvate was determined to have a gemcabene content (% gemcabene) of 90.51% w/w. Gas chromatography analysis of the material showed a residual ethanol content of 28628 ppm and a residual t-BME content of 511 ppm. Particle size distribution (PSD) analysis was performed and gave a D10 value of 3.3 μm, a D50 of 31.8 μm and a D90 of 85 μm.

Example 7: Gemcabene Calcium Salt Hydrate Crystal Forms C1, C2 and C3 (Collectively, Gemcabene Calcium Salt Hydrate Crystal Form C)

Gemcabene calcium salt hydrate Crystal Forms C1-C3 were obtained by way of prolonged drying by charging the wet amorphous form of gemcabene calcium salt hydrate product to an agitated pan dryer at temperatures of 80° C. for at least 24 hours then at higher temperature up to 100° C. for 24 hours or more. Depending on the temperature of drying and the duration of drying, various forms of Crystal Form C were obtained, including Crystal Form C1, Crystal Form C2, and Crystal Form C3.

Example 8: Determination of Particle Size Distribution by Laser Light Diffraction

Material and Methods

Particle Size Distribution by Laser Light Diffraction: The particle size distribution was determined in accordance with the Fraunhofer light diffraction method. A coherent laser beam was passed through the sample and the resulting diffraction pattern was focused on a multi-element detector. Because the diffraction pattern depends, among other parameters, on particle size, the particle size distribution (PSD) was calculated based on the measured diffraction patter of the sample.

Stock dispersion solution was prepared by adding a few drops of the dispersing aid (e.g., 1% w/w solution of a detergent in white spirit such as Span 80, Fluka (85548-250 ml)) to an appropriate amount of substance and mixed carefully. The dispersion was then slowly diluted to a final volume of about 10 ml while vortexing. The suspension cell of the instrument (Malvern Mastersizer 2000 equipped with Hydro 2000S sample dispersion unit) was filled with dispersion medium and a background measurement was taken. The stock dispersion was added to the suspension cell until an optical concentration of 5% to 15% was reached. Once the measurement was initialized, the final optical concentration increased following the internal ultrasonication step and did not exceed 25%. The cumulative volume distribution was determined in accordance with the instrument's instruction manual.

The PSD10, PSD50, and PSD90 values were determined from the cumulative volume distribution of each measurement. Values smaller than 10 μm were reported to one decimal place. Results larger than 10 μm were reported as single digit values. Sample parameters used in analysis are shown below:

| Analysis Model: | General Purpose | Sensitivity: | Normal |
|---|---|---|---|
| Dispersion accessory: | Hydro 2000S | Re-circulation Rate: | 1500 RPM |
| Particle RI: | 0 | Absorption | 0 |
| Dispersant RI: | 1.430 | Sample Mass: | Approx. 100 mg |
| Sonication Time: | 60 seconds | Internal Sonication Power: | 100% |
| Obscuration: | 5-20% | Pre-measurement Delay: | 300 seconds |
| Dispersant: | 0.2% Span-80 in Stoddard Solvent, with 5 minutes of equilibration prior to the background measurement | | |

Scanning Electron Microscopy: Scanning electron micrographs were obtained using a FEI Phenom SEM using 5 kV of accelerating voltage. The samples were prepared for imaging by mounting a small quantity (about 1 mg-10 mg) of sample to an aluminum sample stub using a piece of two-sided carbon tape. A conductive gold/palladium coating was applied to the sample to prevent charging effects from interfering with the imaging process. Electron micrographs were then collected. Magnification, image height, and a graduated micron bar can be found at the bottom of each micrograph.

Gemcabene calcium salt hydrate Crystal Form 1 having various particle sizes were prepared by use of different milling techniques. Total of nine Samples (Samples 1-9, Table 2) of gemcabene calcium salt hydrate Crystal Form 1 were subjected to the laser light diffraction particle size analysis. The PSD90 of each Sample determined by laser light diffraction is shown in Table 2.

Samples 1-3 (Table 2): These samples were prepared by milling Sample 5 (Table 2) under different conditions. Sample 1 was prepared by milling Sample 5 using Fitzpatrick Comminuting Machine model L1A at high speed (8946 RPM) through an 80-mesh screen. The resulting particle size after milling had PSD90 of about 150 μm. Sample 2 was prepared by further milling Sample 1 using a pinmill. The PSD90 of Sample 2 was about 75 μm. Sample 3 was prepared by further milling Sample 1 using a Fitzpatrick Comminuting Machine model L1A at high speed. The PSD90 of Sample 3 was about 110 μm.

Samples 4, 5, 6, and 9 (Table 2): These samples were prepared by direct recrystallization (neat). Samples 4 and 6 each had a PSD90 of 52 μm. Samples 5 and 9 were also prepared by direct recrystallization; however, these samples had a PSD90 of 431 μm and 996 μm, respectively. The unusually high PSD90 compared to the other two neat samples may be explained by their higher content of specific impurities (e.g., 2,2,7,7-tetramethyl-octane-1,8-dioic acid) and larger amounts of residual solvents (e.g., ethanol).

Samples 7 and 8: These samples were prepared from various batches of gemcabene calcium salt hydrate Crystal Form 1 crystallized by precipitating it neat, then milled with a pinmill.

TABLE 2

PSD90 of Batches of Gemcabene Calcium Salt Hydrate Crystal Form 1

| Sample | PSD90 (μm) |
|---|---|
| 1 | 151 |
| 2 | 76 |
| 3 | 110 |
| 4 | 52 |
| 5 | 431 |
| 6 | 52 |
| 7 | 62 |
| 8 | 48 |
| 9 | 996 |

Figure 2:
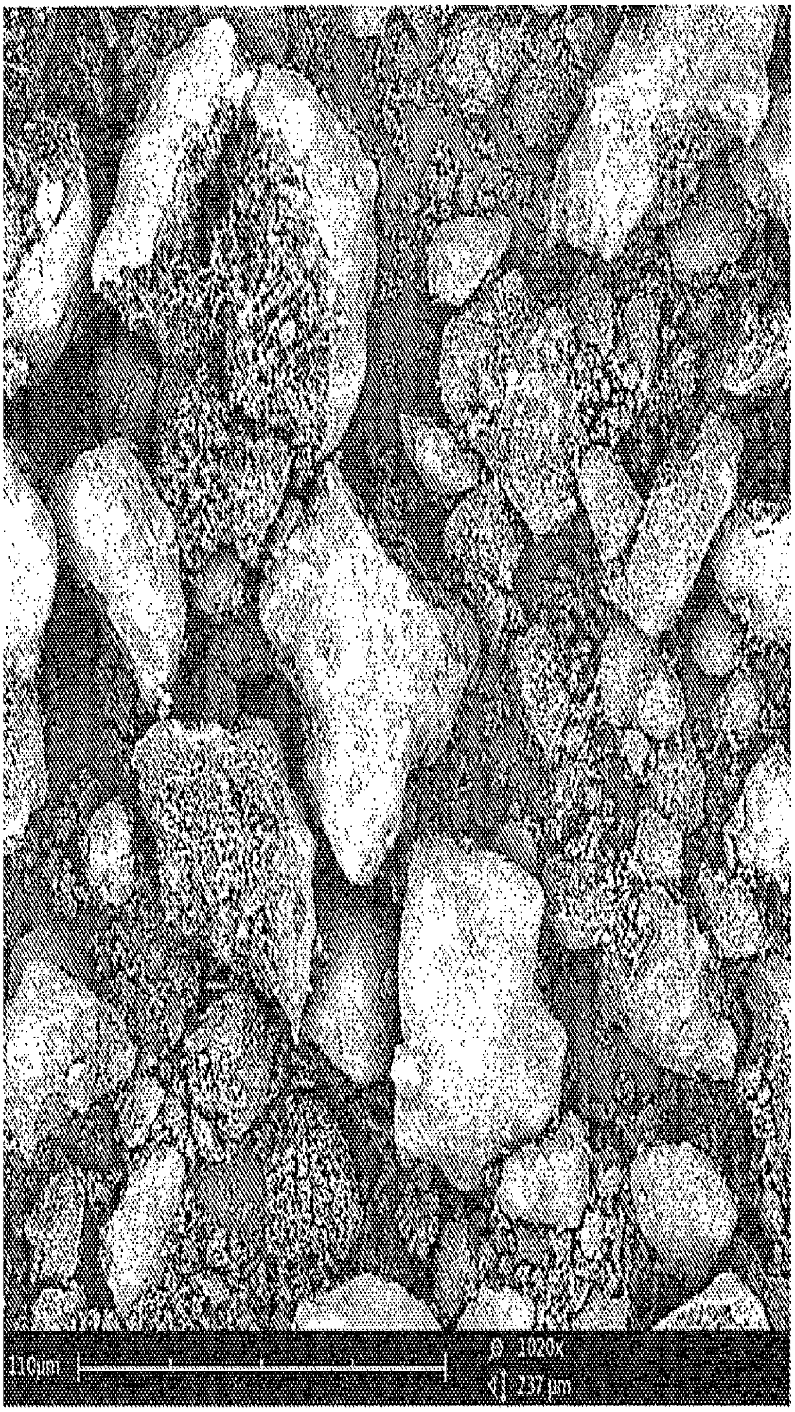
FIG. 2 is a scanning electron micrograph of gemcabene calcium salt hydrate Crystal Form 1 having a particle size distribution characterized by a PSD90 of about 58 μm as measured by laser light diffraction.

Scanning electron micrograph of Sample 4 (Table 2) is as shown in FIG. 2.

As described in Examples 6 and 7 below, Gemcabene calcium salt hydrate Crystal Form 1 of Samples 1-4 and 6-8 (Table 2) was used to produce drug product tablets by wet granulation in fluidized bed. Tablets could not be manufactured from Samples 5 and 9 (Table 2) because the particle size distribution was too large and the particles did not fluidize in the fluidized bed granulation. Further, gemcabene calcium salt hydrate Crystal Form 1 having a PSD90 less than about 30 μm showed difficulties in the formulation process due to electrostatic properties and low loose density.

Example 9: Powder Diffraction Study of Gemcabene Calcium Salt Hydrate Crystal Form 1 and Water and Ethanol Content Powder X-ray diffraction (PXRD) was performed using a Panalytical X'Pert Powder diffractometer using CuKα radiation (λ=1.54056 Å). Samples were mounted onto a flat sample support. Data were collected with a scan step size of 0.004178° and a time per step of 5.08 s in the 5-45° 2θ range under ambient conditions. A background was collected under the same conditions and subtracted, leaving primarily the diffraction of the sample.

Each PXRD pattern was analyzed using the GSAS II crystallography data analysis software program, utilizing the peak fit function. Peaks were selected and peak position, intensity, and full width at half maximum ("FWHM") were allowed to refine freely. The small residual background was fit using a 5-term polynomial function which was allowed to refine freely.

Figure 28:
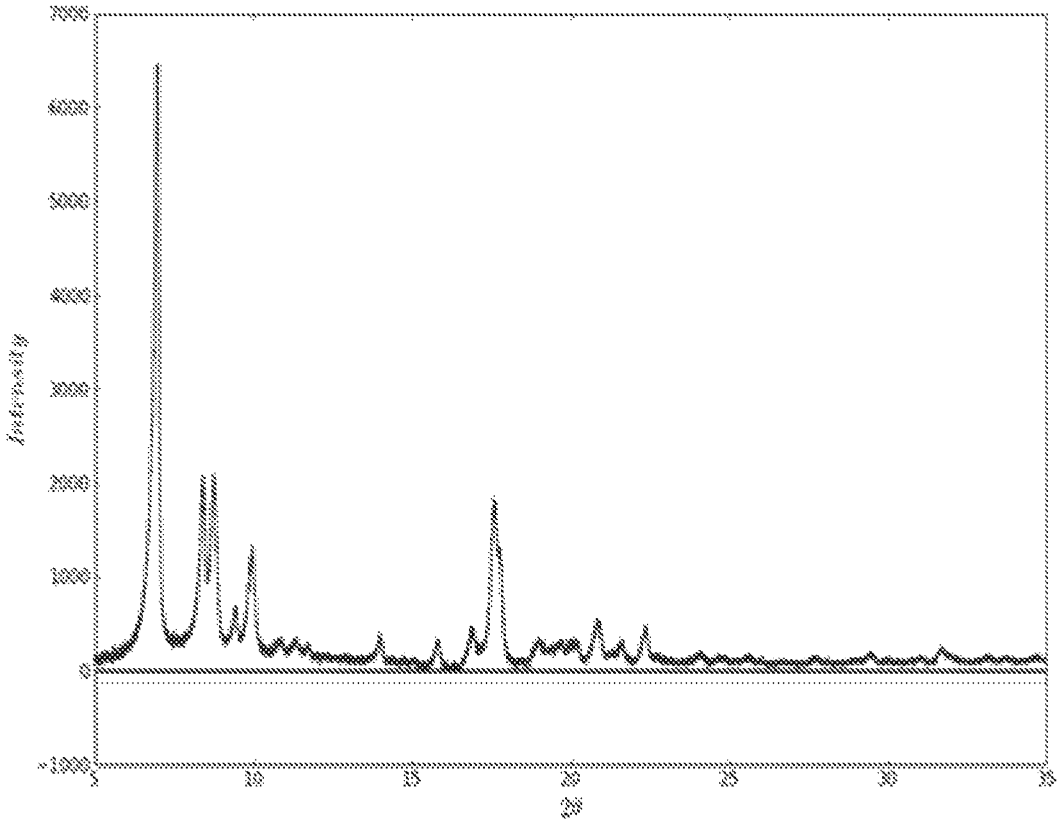
FIG. 28 is a powder X-ray diffractogram of gemcabene calcium salt hydrate Crystal Form 1 having a PSD90 of 52 μm as measured by laser light diffraction (Sample 4 in Table 2).
Figure 29:
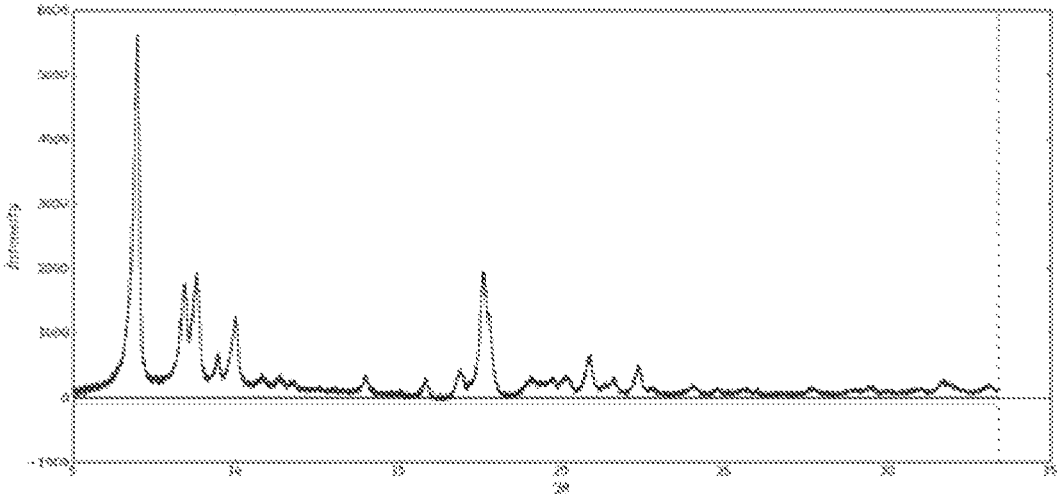
FIG. 29 is a powder X-ray diffractogram of gemcabene calcium salt hydrate Crystal Form 1 having a PSD90 of 62 μm as measured by laser light diffraction (Sample 7 in Table 2).

The PXRD results for Samples 4 and 7 (Table 2) demonstrated that both samples are gemcabene calcium salt hydrate Crystal Form 1 (FIGS. 28 and 29). Thus, the particle size minimally affects the diffraction pattern, and the Crystal Form 1 is preserved during the milling process. The water content indicates that Samples 4 and 6-8 (Table 2) are a monohydrate, with a water content of about 3.5% w/w, corresponding to about 0.78 equivalents of water per a mole of gemcabene calcium salt (Table 3). The water content specification is between 2% w/w to 5% w/w to correspond to a monohydrate. The water contents of two other gemcabene calcium salt hydrate Crystal Form 1 samples having PSD90 of 55 μm (Sample 10) and PSD90 of 47 μm (Sample 11) were determined to be about 3.7% w/w in each sample, which corresponds to about 0.82 equivalents of water per a mole of gemcabene calcium salt. Thus, the water content of gemcabene calcium salt hydrate Crystal Form 1 with PDS90 ranging from 47 μm to 62 μm had a water content of about 3.5% w/w to about 3.7% w/w, corresponding to about 0.78 to about 0.82 equivalents of water per a mole of gemcabene calcium salt.

The ethanol content specification is less than 5000 ppm. For example, the ethanol content in Samples 4 and 6-10 was determined to range from 710 ppm to 1840 ppm.

The loose bulk densities of Samples 4 and 6-10 ranged from 0.25 g/mL to 0.30 g/mL and the tapped bulk densities of Samples 4 and 6-10 ranged from 0.33 g/mL to 0.49 g/mL (Table 3).

The mixer speed was maintained to sufficiently mix the hydroxypropyl cellulose without generating foam. The mixing was continued until the hydroxypropyl cellulose was completely dissolved and a clear homogeneous solution was obtained.

The spray pump was verified to deliver a rate of 100 to 350 g/minute of the hydroxypropyl cellulose solution.

The Glatt 30 fluid bed granulator was set with a process air volume of 500 $m^3$ per hour, an inlet air temperature of 70° C., and exhaust temperature of 45° C.±10° C.

Gemcabene calcium salt hydrate Crystal Form 1 and lactose monohydrate were milled with a 45R mesh screen, for example with Quadro Comil 197 Ultra equipped with a Round Impeller (45R screen; 0.045" opening size; round), to de-lump and the material was captured in a container double lined with polyethylene bags.

After pre-heating, the fluid bed granulator was charged with de-lumped gemcabene calcium salt hydrate Crystal Form land lactose monohydrate. Once the powder fluidization began, the binding solution was sprayed over the powder. After the powder was wet, the spray rate was reduced and the air volume was adjusted until all binder solution was sprayed. The inlet air volume was adjusted to ensure fluidization of granules and the target temperature was kept at about 28° C. After all binder solution was applied, granulation was continued with water to achieve acceptable visual granulation endpoint. The granulation was dried to a loss on drying (LOD) value of not more than 2.0%.

The rate of spraying the binding solution can vary depending on the scale of the granulation, etc. For example, for 22 L granulator/drying bowl size scale, the spray rate of the binder can be at 75-90 g/min for first 30-45 minutes then 50-65 g/min for the remaining time until theoretical amount is sprayed on. Further, if required, purified water can be added to continue granulation until visually acceptable granulation is achieved before drying.

TABLE 3

Water and Ethanol Contents and Bulk Density

| | Sample 4 | Sample 6 | Sample 7 | Sample 8 | Sample 10 | Sample 11 |
|---|---|---|---|---|---|---|
| PSD90 | 52 μm | 52 μm | 62 μm | 48 μm | 55 μm | 47 μm |
| Water content | 3.5% w/w | 3.5% w/w | 3.5% w/w | 3.5% w/w | 3.7% w/w | 3.7% w/w |
| Ethanol content | 1100 ppm | 1480 ppm | 1620 ppm | 1781 ppm | 710 ppm | 1840 ppm |
| Loose Bulk Density | 0.25 g/mL | 0.25 g/mL | 0.30 g/mL | 0.26 g/mL | 0.27 g/mL | 0.26 g/mL |
| Tapped Bulk Density | 0.39 g/mL | 0.41 g/mL | 0.49 g/mL | 0.39 g/mL | 0.33 g/mL | 0.36 g/mL |

Example 10: Gemcabene Calcium Salt Hydrate Crystal Form 1 Granulation

Gemcabene calcium salt hydrate Crystal Form 1 from each of Samples 1-4 and 6-8 of Table 2 was granulated with excipients using a fluid bed granulation process. A sample batch formula for gemcabene calcium salt hydrate Crystal Form 1 granulation is shown in Table 4.

Blend Formulation-Intragranular

The binding solution was prepared by weighing 41.06 kg of purified water and adding to a stainless-steel mixer and mixed. The mixing took about 1.5-2.5 hours. Hydroxylpropyl cellulose was slowly added to the water while mixing.

The bulk dried granulated samples prepared from Samples 1-4 and 6-8 from Example 8, Table 2, are referred to as Samples 1G, 2G, 3G, 4G, 6G, 7G, and 8G, respectively.

Bulk-dried granulation Samples 1G, 2G, 3G, 4G, 6G, 7G and 8G were each milled through a 39R mesh screen and collected in a container double-lined with polyethylene bags (e.g., Quadro Comil 197 Ultra equipped with a round bar impeller) to provide Samples 1M, 2M, 3M, 4M, 6M, 7M, and 8M, respectively.

TABLE 4

| Gemcabene Calcium Salt Hydrate Crystal Form 1 Granulation Sample Formulation | |
|---|---|
| Components | % w/w |
| Intragranular | |
| Gemcabene Calcium Salt Hydrate Crystal Form 1 | 63.8 |
| Lactose Monohydrate Fast-Flo 316 NF | 23.4 |
| Hydroxypropyl Cellulose (Klucel EF) | 8.0 |
| Extragranular | |
| Croscarmellose Sodium NF | 4.0 |
| Magnesium Stearate NF | 0.8 |
| | Total: 100 |

Blend Formulation-Extragranular

A V-blender was charged with the milled Samples 1M-4M and 6M-8M. Croscarmellose Sodium was passed through a 20 mesh hand screen and charged into the V-blender with the granulation and blended for 10 minutes. A bag containing the magnesium stearate component was rinsed with the granulation blend. The mixture was filtered through a 20 mesh screen, added to the V-blender and blended for about 3 minutes. The final granulation blend was discharged into drums which are double lined with polyethylene bags and sealed.

The completed final blends were discharged and weighed prior to proceeding to the compression process. The discharged final blends based on Samples 1M-4M and 6M-8M are referred to as Samples 1FB, 2FB, 3FB, 4FB, 6FB, 7FB, and 8FB, respectively.

Example 11: Gemcabene Calcium Salt Hydrate Crystal Form 1 Film-Coated Tablet Formulation Samples 1FB-4FB and 6FB-8FB were compressed 300-mg film-coated tablets. A sample tablet formula is shown in Table 5.

TABLE 5

| Gemcabene Calcium Salt Hydrate Crystal Form 1 Film-Coated Tablet Formulation | |
|---|---|
| Components | % w/w |
| Core Ingredients | |
| Gemcabene Calcium Salt Hydrate Crystal Form 1 Samples 1FB-4FB and 6FB-8FB, Example 10 | 100.00 |
| Coating Ingredients | |
| Opadry White YS 1-7040 | 2.98 |
| Simethicone Emulsion 30% USP | 0.02 |
| | Total: 103.0 |

Each of Samples 1FB-4FB was added, separately, to a tablet press equipped with a force feeder. Samples 1FB-4FB were respectively compressed per specified parameters in Table 6. The tablet weight and hardness were adjusted to target tablet weight and hardness, and were passed through a metal detector and tablet de-duster and collected into double lined polyethylene bags.

Samples 1FB, 2FB, 3FB, 4FB, 6FB, 7FB, and 8FB were compressed on a rotary tablet press using 0.2759"×0.6285" oval tooling to a theoretical fill weight of 470 mg. See Table 6 below for compression parameters, batch weight variation and tablet properties. All tablets compressed well and had a low relative standard deviation (RSD) for tablet weight variation. Tablets prepared from Samples 1FB, 2FB, 3FB, 4FB, 6FB, 7FB, and 8FB are referred to as Tablets A, B, C, D, F, G, and H, respectively.

TABLE 6

Compression Parameters and Tablet Properties of Gemcabene Calcium Salt Hydrate Crystal Form 1 300 mg Film-Coated Tablets

| | Tablet A | Tablet B | Tablet C | Tablet D |
|---|---|---|---|---|
| Final Blend Sample | Sample 1FB | Sample 2FB | Sample 3FB | Sample 4FB |
| D90 of gemcabene calcium salt hydrate Crystal Form 1 in each Sample | 151 μm | 76 μm | 110 μm | 52 μm |
| Compression | | | | |
| Tablet Tooling Size | | 0.2759" × 0.6285" oval | | |
| Tablet Press | MiniPress | MiniPress | MiniPress | Stokes GEM |
| Pre-Compression Force (kN) | n/a | n/a | n/a | 8 |
| Compression Force (kN) | n/a | n/a | n/a | 7 |
| Turret Speed | 32 Dial Setting | 13 RPM | 17 RPM | 41.1 RPM |
| Hopper Type | Gravity Feeder | Gravity Feeder | Gravity Feeder | Force Feeder |
| Feeder Speed (RPM) | n/a | n/a | n/a | 39.9 |
| Tablet Weight Variation | | | | |
| Target Weight of 10 tablets (g) | | 4.700 | | |
| Target Weight Range of 10 tablets (±5%) (g) | | 4.465-4.935 | | |
| In-Process Average Weight (g) | 4.7809 | 4.6845 | 4.7293 | 4.715 |
| In-Process Weight Variance (% RSD) | 0.554 | 0.532 | 1.482 | 1.466 |
| In-Process Weight Variance Range (g) | ±0.053 | ±0.089 | ±0.137 | ±0.152 |
| Target Individual Tablet Weight (g) | | 0.470 | | |

TABLE 6-continued

Compression Parameters and Tablet Properties of Gemcabene Calcium Salt Hydrate Crystal Form 1 300 mg Film-Coated Tablets

| | Tablet A | Tablet B | Tablet C | Tablet D |
|---|---|---|---|---|
| Target Individual Tablet Weight Range (±10%) (g) | 0.423-0.517 | | | |
| End of Run Average Weight (g) | 0.4718 | 0.4696 | 0.4645 | 0.469 |
| End of Run Weight Variance (% RSD) | 1.312 | 1.036 | 3.275 | 2.586 |
| End of Run Weight Variance Range (g) | ±0.022 | ±0.014 | ±0.058 | ±0.045 |
| Tablet Properties | | | | |
| Average Tablet Hardness (kp) | 17.5 | 16.2 | 14.9 | 16.2 |
| Average Tablet Thickness (mm) | 6.08 | 6.02 | 5.74 | 6.21 |
| End of Run Friability (%) | 0.0 | 0.0 | 0.2 | 0.0 |

Each batch was film-coated in either the experimental Vector Coater LDCS instrument (Tablets A-C, Table 6) or the GMP Compu-Lab 24 (Tablet D, Table 6). The film-coating suspension consisted of Opadry White YS 1-7040 and Simethicone Emulsion 30% USP.

Purified water was weighed into a stainless-steel container and mixed to create a vortex. Simethicone emulsion and Opadry White YS 1-7040 were added to the purified water and mixed for a minimum of 50 minutes or until the suspension was visually uniform. Tablets A-D were, separately, divided into two batches and are weighed out for coating. The Tablets were charged into a coating pan heated to an outlet temperature of 42° C. (±2° C.). The Tablets were film-coated to a 3.0% weight gain (±1.0%). After 90% of theoretical amount of film-coating suspension for each batch were sprayed, the average weight was checked and spraying continued to achieve a weight gain of 2.0% to 4.0%. Tablets were allowed to dry and cool down. The Tablets were packaged in tared containers double lined with polyethylene bags.

Film-coated Tablets F-H were prepared by the same process used for making Tablet D.

Example 12: Granulation of Gemcabene Calcium Salt Amorphous Form

An amorphous form of the gemcabene calcium salt was utilized in the preparation of a laboratory scale granulation batch. The laboratory scale fluid-bed granulation equipment was a Freund-Vector MFL-01 laboratory fluid-bed processor configured for a top-spray process, which is a scaled-down Glatt equipment used for the granulation of the clinical batches. Table 7A gives the quantitative theoretical composition of the tablet formulation and the laboratory scale batch size.

TABLE 7A

Composition of Gemcabene Tablets (300 mg)

| Ingredient | Concentration % w/w | mg/ Tablet | Amount/ Batch (g) |
|---|---|---|---|
| Intra-Granular Materials | | | |
| Gemcabene Calcium, Amorphous | 63.83 | 300.0[1] | 75.0[1] |
| Lactose Monohydrate, NF (316 Fast-Flo) | 23.37 | 109.84[1] | 27.46[1] |
| Hydroxypropyl Cellulose, NF (Klucel EF) | 8.0 | 37.6 | 9.4 |
| Water, Purified[2] | N/A[2] | N/A[2] | 178.6[2] |
| Extra-Granular Materials | | | |
| Croscarmellose Sodium, NF (Ac-Di-Sol) | 4.0 | 18.8 | 4.7[3] |
| Magnesium stearate | 0.80 | 3.76 | 0.94[3] |
| Total | 100.0 | 470.0 | 117.5 |

[1]Gemcabene calcium and lactose were adjusted for each Tablet to provide the amorphous form of gemcabene calcium salt in an amount that is a molar equivalent to 300 mg gemcabene.

[2]Water is removed during processing and not accounted for in the batch weight or Tablet weight.

[3]Extra-granular component quantities are adjusted based on expected granulation yield.

Figure 30:
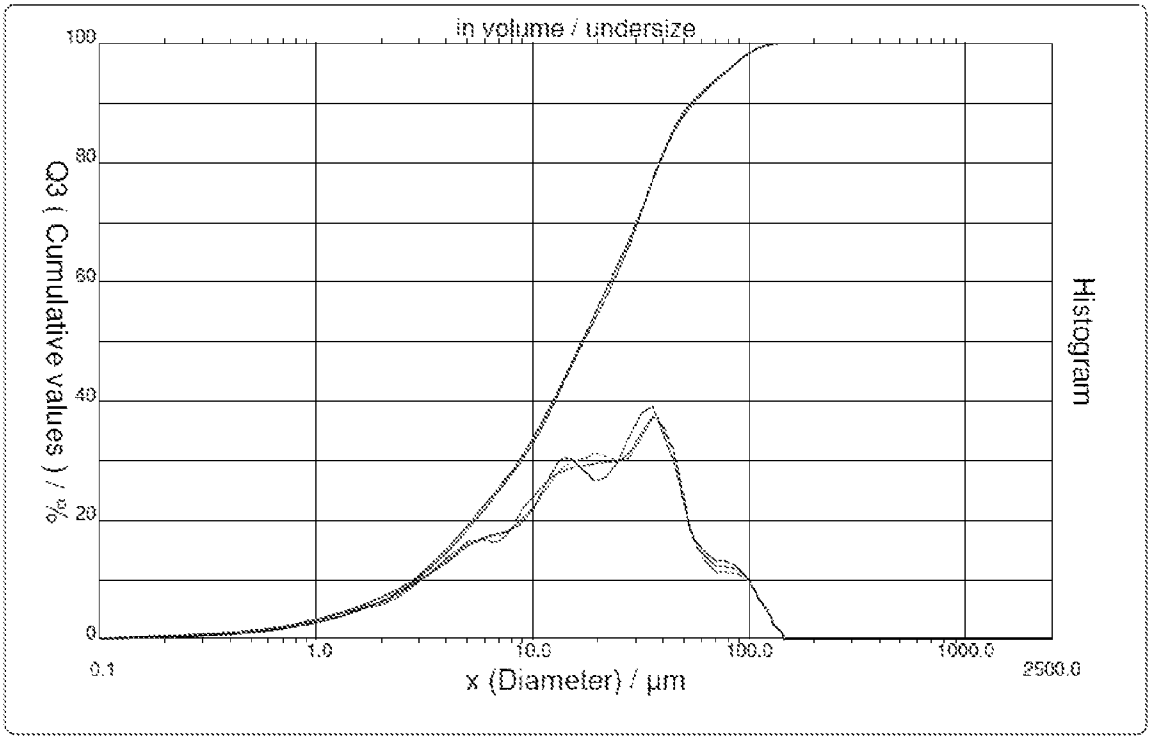
FIG. 30 shows measurements of amorphous gemcabene calcium particle size distribution.

High-performance liquid chromatography (HPLC) indicated that the amorphous gemcabene calcium contained 80.9% (w/w) molar equivalent of gemcabene. Thus, the amount of the amorphous gemcabene calcium charged to the batch was adjusted by this factor, resulting in 92.71 g of amorphous gemcabene calcium being dispensed with a commensurate decrease in the lactose monohydrate quantity to 9.75 g. The amorphous gemcabene calcium was screened to form a uniform powder for use in the granulation process using a #40 mesh (425 μm) sieve and 92.72 g of the screened material was dispensed into the granulator. Bulk and tapped density testing and particle size analysis by laser diffraction were performed using excess screened material. Bulk and tapped density testing was performed per USP <616> using a 100 mL graduated cylinder. Laser diffraction particle size analysis was performed using a Cilas 1180LD laser diffraction particle size analyzer with a dry powder dispersion method as described in Example 8 for gemcabene calcium salt Crystal Form 1 (see also Table 7B for laser diffraction particle size analysis conditions). Table 7C reports the physical testing results. Particle size results are reported as the average of three replicate measurements in terms of a volume distribution and FIG. 30 displays an overlay of the particle size distributions obtained from these three measurements.

TABLE 7B

| Particle size analysis conditions using Cilas 1180LD | |
|---|---|
| Analysis Parameter | Value |
| Analysis Mode | Dry Powder |
| Optical Model | Fraunhofer |
| Dispersion Media | Air |
| Dispersion Media RI | 1.000 |
| Powder Distributor Frequency (Hz) | 50 |
| Powder Distributor Power (%) | 90 |
| Hopper Gap Setting | 2 |
| Dispersion Air Pressure (mb) | 3000 |
| Background measurement (sec.) | 10 |
| Sample Measurement (sec.) | 10 |
| Sample Size (mg) | 500 |

TABLE 7C

| Particle size and density of amorphous gemcabene calcium | |
|---|---|
| Average Particle Size in μm (% RSD) | |
| $D_{10}$ | 2.833 (2.3) |
| $D_{50}$ | 17.006 (0.9) |
| $D_{90}$ | 54.580 (2.1) |
| Powder Density | |
| Bulk Density (g/mL) | 0.11 |
| Tapped Density (g/mL) | 0.25 |
| Carr's Index | 56.0% |

Amorphous gemcabene calcium and Lactose Monohydrate were charged into the fluid-bed's expansion chamber and were allowed to mix for 2 minutes using a process air flow of 50 L per minute (LPM). The fluid bed charge was then granulated by the addition of a granulation solution, consisting of water and Hydroxypropyl Cellulose (Klucel® EF). This solution was dispensed into the granulator as an atomized spray from the fluid-bed's air atomized spray nozzle. Target granulation process parameters were scaled for the MFL-01 fluid-bed from the large-scale granulation process. Table 7D reports the target processing parameters.

TABLE 7D

| Target Granulation Parameters for Freund-Vector MFL-01 Fluid-Bed | |
|---|---|
| Parameter | Target Value |
| Inlet Temperature | 70° C. |
| Product Temperature | <37° C. |
| Air Flow | 50 LPM |
| Solution Flow Rate | 5 g/min |
| Atomization pressure | 10 psi |

Addition of the granulating fluid to the amorphous gemcabene calcium resulted in heavy agglomeration of the amorphous gemcabene calcium particles. Granulating fluid addition rates of 50%, 37%, and 24% of the original 5 g/min target rate were evaluated in an attempt to prevent the agglomeration. However, the agglomeration continued and worsened with the addition of any amount of granulating fluid. As the amount of agglomeration increased, the process air volume was continually increased to maintain fluidization of the powder bed. Higher process air volume with a slower granulating fluid addition rate also did not seem to reduce the agglomeration issue. The continued agglomeration at higher air flow and lower spray rate could have resulted from the large amounts of large agglomerates which were already present in the powder bed or could be an indication that any amount of aqueous granulating fluid will cause excessive agglomeration, even if dried off of the powder bed rapidly. Typically, the combination of low spray rate and high air flow results in quick drying of the granulating fluid, decreasing the time the powder surface is exposed to the solvent and affecting rapid deposition of the polymer binder. These conditions reduce the potential for agglomeration, however, due to the very low density of the amorphous gemcabene calcium, it would not be possible to start the fluid-bed granulation process with a high process air volume without forcing all of the drug substance particles out of the spray zone and into the filters. It was concluded that the solubility and density characteristics of the amorphous gemcabene calcium evaluated in this study are not conducive to granulation using the current formulation and process

Figure 1B:
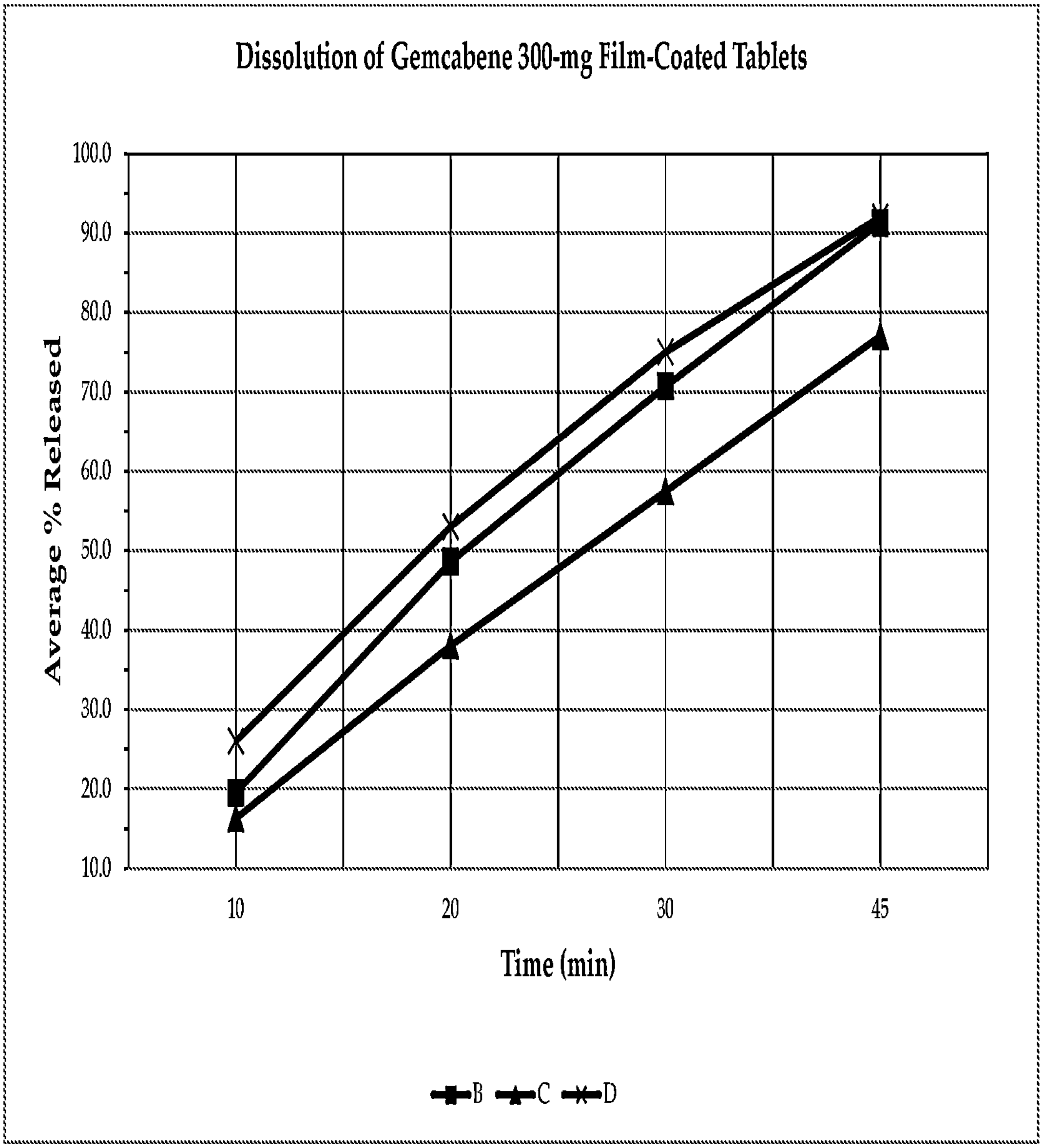
FIG. 1B is a line graph showing a dissolution profile of gemcabene from a composition of the invention in the form of a film-coated tablet.

Example 13: Dissolution Profiles of Gemcabene Film-Coated Tablets (300 mg) Prepared from Gemcabene Calcium Salt Crystal Form 1 Having Various PSD90 Values Dissolution: The dissolution profiles for 300-mg film-coated Tablets A-D and F-H of gemcabene Calcium Salt Hydrate Crystal Form 1 were measured in 900 mL pH 5.0 potassium acetate (50 mM) buffer using USP Apparatus 2 (paddles) set to 50 rpm. Each % dissolution time point was quantified by HPLC using a detection wavelength of 210 nm (FIG. 1A, FIG. 1B and Table 8). FIGS. 1A and 1B, showing mean dissolution, demonstrates that the particle size distribution of the gemcabene calcium salt hydrate Crystal Form 1 does influence the dissolution profiles of the immediate release tablets. The tablets made from gemcabene calcium salt hydrate Crystal Form 1 having a PSD90 of 151 μm and 110 μm, Tablets A and C, respectively, showed significantly lower release profiles than Tablets B and D, prepared with gemcabene calcium salt hydrate Crystal Form 1 having a PSD90 of 76 μm and 52 μm, respectively. Specifically, the average % release values at 20, 30 and 45 minutes are lower with Tablets A and C when compared with % dissolution of Tablets B and D. For example, the amount of gemcabene detected at 45 minutes was about 8% to 15% lower for Tablets A and C than that of the Tablets made from gemcabene calcium salt hydrate Crystal Form 1 having a smaller particle size (Tablets B and D). Tablets G and H, made from gemcabene calcium salt hydrate Crystal Form 1 having a PSD90 of 62 μm and 48 μm, respectively, show a more favorable dissolution profile with almost 40% average release at 10 min and essentially 100% average release at 30 min. Meanwhile, when drug substance gemcabene Calcium Salt Hydrate Crystal Form 1 is used neat (recrystallized only), the dissolution profiles show lower release profiles.

TABLE 8

PSD90 for Gemcabene Calcium Crystal Form 1 and Dissolution Profiles of Their Corresponding Immediate Release 300-mg Strength Tablets

| | Gemcabene Calcium Sample No. (Example 8, Table 2) | | | | | | | | |
|---|---|---|---|---|---|---|---|---|---|
| | 1 | 2 | 3 | 4 | 5 | 6 | 7 | 8 | 9 |
| Milling Condition | Milled - Fitzmill | Milled - Pinmill | Milled - Fitzmill | Neat | Neat | Neat | Milled - Pinmill | Milled - Pinmill | Neat - recrystallized |
| $D_{10}$ | 6.3 μm | 4.8 μm | 5.3 μm | 5.8 μm | 7.8 μm | 7.8 μm | 5.4 μm | 8.2 μm | 17 μm |
| $D_{50}$ | 50.4 μm | 22.9 μm | 32.2 μm | 22 μm | 101 μm | 25 μm | 20 μm | 24 μm | 386 μm |
| $D_{90}$ | 151 μm | 76 μm | 110 μm | 52 μm | 431 μm | 52 μm | 62 μm | 48 μm | 996 μm |

| | Tablet Dissolution (average % released) Tablet (Example 11) | | | | | | |
|---|---|---|---|---|---|---|---|
| | A | B | C | D | F | G | H |
| 10 min | 20 | 19 | 16 | 26 | 23 | 37 | 39 |
| 20 min | 45 | 49 | 38 | 53 | 53 | 78 | 77 |
| 30 min | 66 | 71 | 57 | 75 | 76 | 100 | 93 |
| 45 min | 86 | 91 | 77 | 92 | 93 | 103 | 98 |
| 60 min | N/A | 96 | 89 | 96 | 94 | 101 | 98 |
| 75 min | N/A | 97 | 92 | 97 | 94 | 101 | 99 |

Dissolution medium (50 mM potassium acetate): Prepared by dissolving 245 g of potassium acetate into an aliquot of deionized water. The aliquot was transferred to a 50 L carboy and diluted to volume. The pH was adjusted to 5.0±0.05 using glacial acetic acid. The dissolution medium was deaerated using helium sparge or other appropriate means.

Standard: In duplicate, 39 mg gemcabene was accurately weighed and transferred to a 100 mL volumetric flask, then dissolved in about 10 mL of acetonitrile (ACN). If necessary, sonication can be used to dissolve gemcabene. The gemcabene solution was diluted to volume with the dissolution medium.

Dissolution Parameters:

| | |
|---|---|
| Dissolution Medium: | 50 mM Potassium Acetate in water, adjusted to pH 5.0 with glacial acetic acid |
| Dissolution Apparatus: | USP Type 2, Paddles |
| Rotation Speed: | 50 rpm |
| Sample: | Gemcabene Calcium Salt Hydrate Crystal Form 1 300 mg; n = 6 tablets; 1 tablet per vessel in a basket sinker |
| Solution volume: | 900 mL |
| Solution temperature: | 37° C. ± 5° C. |
| Sampling times: | 10, 20, 30, 45, 60, and/or 75 minutes |
| Sampling technique: | Withdraw 2 mL sample with a syringe and stainless-steel cannula with a 45 μm filter tip into an HPLC vial |

Operating Parameters:

a) Die paddles were set to a rotation speed of 50 rpm.

b) Each vessel was filled with 900 mL of dissolution medium.

c) Randomly 6 tablets were selected and the weight of each was recorded.

d) Each tablet was placed inside a Japanese basket sinker.

e) The temperature was measured in one of the center vessels using a calibrated thermometer as the paddle is rotating midway between the top of the paddle and top of the fluid and midway between the shaft and the side of the vessel. The temperature should be 37° C.±5° C.

f) One tablet was placed within a sinker at precisely timed intervals to allow for adequate sampling time.

g) 2 mL sample aliquot was withdrawn using an appropriate syringe and stainless-steel cannula equipped with a 45 μm filter tip into an HPLC vial. Samples were withdrawn at a point halfway between the side of the vessel and the paddle and halfway between the top of the paddle and the surface of the fluid. Sampling times were 10, 20, 30, 45, 60 and/or 75 minutes.

Chromatographic Procedures:

a) Equilibrated the HPLC system until a steady baseline is achieved.

b) Injected the dissolution medium once.

c) Injected at least 5 replicates of the working standard.

d) Injected the check standard at least once.

e) Injected the sample solutions.

f) Interspersed injections of the working standard throughout the run, i.e., every 12 samples to bracket the samples.

g) Injected a final working standard.

HPLC Parameters for Dissolution:

Column: Agilent Zorbax SB-C18; 4.6 mm×150 mm. 3.5 micron particle size

| | |
|---|---|
| Flow Rate: | 1.1 mL/minute |
| Run Time: | 8 minutes |
| Autosampler Temperature: | Ambient |
| Column Temperature: | 30° C. |
| Injection Volume: | 100 μL |
| Detection | UV at 210 nm |
| Mobile Phase | 0.1% Trifluoroacetic acid in 55% water and 45% acetonitrile (To prepare 2 L, mix 1100 mL water with 900 mL ACN and 2 mL TFA) |

Calculation:

The concentration (mg/mL) of the sample solution was calculated for each time point as follows or by using validated software such as OpenLAB or equivalent.

$$\text{Sample concentration (mg/mL)} = \frac{\text{Sample area} \cdot \text{Sample area}}{\text{Mean standard area}}$$

Gemcabene detected (mg) in dissolution medium (pH 5.0 potassium acetate) as "gemcabene released" which is calculated for each vessel as follows or using a validated software such as DataCal, OpenLAB, or equivalent.

$$\text{mg released} = Un \times [Vdf - (n-1)Va] + Va \times (\text{sum of concentrations from previous time points})$$

where:

n=Sampling time point (pull number)

Un=Concentration of sample solution at time point n

Va=Aliquot in mL taken from the dissolution test at each time point Vdf=Initial dissolution fluid volume Calculation of Percent Released is Determined by:

$$\%\ \text{release} = \frac{\text{mg gemcabene released} \times 100}{300\ \text{mg}^{*}\ (\text{theoretical})}$$

*each gemcabene calcium salt hydrate Crystal Form 1 300-mg film-coated tablet comprises gemcabene calcium salt hydrate Crystal Form 1 in an amount that is a molar equivalent to 300 mg gemcabene.

Dissolution data for Tablets A-D and F-H are shown in the following Tables, respectively: Tables 8a and 8b; Table 9; Table 10; Table 11; Table 12; Table 13; and Table 14, where the release of gemcabene is determined by the amount of gemcabene measured by the above described HPLC method. Dissolution profiles of Tablets A-D and F-H are shown in FIG. 1A and dissolution profiles of Tablets B-D are separately shown in FIG. 1B.

The dissolution profile of Tablets B, D, and F-H was more favorable than the dissolution profile of Tablets A and C which comprise gemcabene calcium salt hydrate Crystal Form 1 having a higher PSD90, 151 μm and 110 μm, respectively. Without bound to any theory, it is believed that the more favorable (fast) dissolution profile is a useful indicator of the tablet having good bioavailability. Further, it was unexpected that Tablet C, comprising gemcabene calcium salt hydrate Crystal Form 1 having PSD90 of 110 μm, had a significantly slower dissolution profile.

TABLE 8a

| Dissolution of Tablet A Core (without coating) % Gemcabene Released | | | | |
|---|---|---|---|---|
| Vessel | 10 min | 20 min | 30 min | 45 min |
| 1 | 26.185 | 49.647 | 70.120 | 87.055 |
| 2 | 24.456 | 47.671 | 67.379 | 88.133 |
| 3 | 23.504 | 46.602 | 65.245 | 86.151 |
| 4 | 22.655 | 46.022 | 64.617 | 85.128 |
| 5 | 24.655 | 48.552 | 67.436 | 87.689 |
| 6 | 23.645 | 46.601 | 64.776 | 85.748 |
| Mean | 24.183 | 47.516 | 66.595 | 86.651 |
| Low | 22.655 | 46.022 | 64.617 | 85.128 |
| High | 26.185 | 49.647 | 70.120 | 88.133 |
| SD | 1.216 | 1.382 | 2.135 | 1.168 |
| RSD | 5.027 | 2.908 | 3.206 | 1.348 |

TABLE 8b

| Dissolution of Tablet A (with film-coating) % Gemcabene Released | | | | |
|---|---|---|---|---|
| Vessel | 10 min | 20 min | 30 min | 45 min |
| 1 | 19.421 | 43.714 | 64.599 | 84.468 |
| 2 | 15.499 | 39.490 | 59.544 | 83.413 |

TABLE 8b-continued

| Dissolution of Tablet A (with film-coating) % Gemcabene Released | | | | |
|---|---|---|---|---|
| Vessel | 10 min | 20 min | 30 min | 45 min |
| 3 | 23.398 | 49.853 | 69.968 | 89.379 |
| 4 | 20.957 | 45.741 | 66.079 | 86.129 |
| 5 | 25.111 | 50.627 | 69.757 | 89.009 |
| 6 | 16.243 | 41.722 | 63.072 | 84.596 |
| Mean | 20.105 | 45.191 | 65.503 | 86.166 |
| Low | 15.499 | 39.490 | 59.544 | 83.413 |
| High | 25.111 | 50.627 | 69.968 | 89.379 |
| SD | 3.827 | 4.434 | 4.015 | 2.503 |
| RSD | 19.034 | 9.812 | 6.129 | 2.905 |

TABLE 9

| Dissolution of Tablet B (with film-coating) % Gemcabene Released | | | | | | |
|---|---|---|---|---|---|---|
| Vessel | 10 min | 20 min | 30 min | 45 min | 60 min | 75 min |
| 1 | 18.531 | 47.224 | 71.161 | 92.173 | 96.435 | 97.046 |
| 2 | 15.373 | 43.974 | 65.189 | 86.578 | 96.564 | 97.946 |
| 3 | 20.488 | 53.624 | 75.229 | 94.020 | 95.657 | 96.345 |
| 4 | 19.044 | 46.574 | 66.740 | 86.923 | 95.778 | 96.698 |
| 5 | 18.372 | 49.163 | 72.574 | 93.673 | 95.258 | 95.428 |
| 6 | 18.301 | 45.257 | 66.152 | 86.938 | 96.151 | 97.477 |
| Mean | 18.352 | 47.636 | 69.507 | 90.051 | 95.974 | 96.824 |
| Low | 15.373 | 43.974 | 65.189 | 86.578 | 95.258 | 95.428 |
| High | 20.488 | 53.624 | 75.229 | 94.020 | 96.564 | 97.946 |
| SD | 1.671 | 3.422 | 4.061 | 3.603 | 0.499 | 0.887 |
| RSD | 9.104 | 7.184 | 5.842 | 4.001 | 0.519 | 0.916 |

TABLE 10

| Dissolution of Tablet C (with film-coating) % Gemcabene Released | | | | | | |
|---|---|---|---|---|---|---|
| Vessel | 10 min | 20 min | 30 min | 45 min | 60 min | 75 min |
| 1 | 17.741 | 41.468 | 60.825 | 80.464 | 89.915 | 92.809 |
| 2 | 12.074 | 32.037 | 50.139 | 69.983 | 82.200 | 88.409 |
| 3 | 14.699 | 41.048 | 63.126 | 83.968 | 92.724 | 93.998 |
| 4 | 18.698 | 42.520 | 61.312 | 79.153 | 87.457 | 89.530 |
| 5 | 20.750 | 46.465 | 67.330 | 87.000 | 95.459 | 97.243 |
| 6 | 14.373 | 35.472 | 52.447 | 73.099 | 85.753 | 89.800 |
| Mean | 16.389 | 39.835 | 59.196 | 78.944 | 88.918 | 91.965 |
| Low | 12.074 | 32.037 | 50.139 | 69.983 | 82.200 | 88.409 |
| High | 20.750 | 46.465 | 67.330 | 87.000 | 95.459 | 97.243 |
| SD | 3.216 | 5.199 | 6.577 | 6.434 | 4.807 | 3.346 |
| RSD | 19.623 | 13.052 | 11.111 | 8.149 | 5.406 | 3.638 |

TABLE 11

| Dissolution of Tablet D (with film-coating) % Gemcabene Released | | | | | | |
|---|---|---|---|---|---|---|
| Vessel | 10 min | 20 min | 30 min | 45 min | 60 min | 75 min |
| 1 | 25.770 | 50.495 | 72.020 | 92.076 | 94.268 | 94.986 |
| 2 | 29.914 | 60.458 | 80.483 | 95.123 | 95.552 | 95.794 |
| 3 | 32.129 | 58.965 | 77.012 | 92.797 | 98.039 | 97.950 |
| 4 | 28.373 | 55.191 | 73.012 | 89.905 | 95.555 | 96.125 |
| 5 | 26.092 | 53.150 | 76.424 | 94.140 | 95.621 | 95.250 |
| 6 | 31.105 | 58.851 | 78.952 | 93.448 | 94.130 | 93.925 |
| Mean | 28.897 | 56.185 | 76.317 | 92.915 | 95.528 | 95.672 |
| Low | 25.770 | 50.495 | 72.020 | 89.905 | 94.130 | 93.925 |
| High | 32.129 | 60.458 | 80.483 | 95.123 | 98.039 | 97.950 |
| SD | 2.618 | 3.890 | 3.292 | 1.813 | 1.404 | 1.350 |
| RSD | 9.060 | 6.924 | 4.313 | 1.951 | 1.470 | 1.411 |

TABLE 12

| Dissolution of Tablet F (with film-coating) % Gemcabene Released | | | | | | |
|---|---|---|---|---|---|---|
| Vessel | 10 min | 20 min | 30 min | 45 min | 60 min | 75 min |
| 1 | 37.879 | 77.964 | 97.609 | 102.938 | 103.238 | 103.353 |
| 2 | 36.379 | 75.350 | 99.708 | 103.297 | 104.917 | 105.165 |
| 3 | 40.569 | 82.713 | 98.911 | 100.091 | 100.608 | 100.575 |
| 4 | 45.200 | 90.337 | 98.665 | 98.762 | 98.921 | 98.885 |
| 5 | 42.600 | 86.051 | 97.941 | 98.373 | 98.474 | 98.453 |
| 6 | 38.683 | 81.721 | 100.230 | 100.309 | 100.774 | 100.766 |
| Mean | 40.219 | 82.356 | 98.844 | 100.628 | 101.155 | 101.200 |
| Low | 36.379 | 75.350 | 97.609 | 98.373 | 98.474 | 98.453 |
| High | 45.200 | 90.337 | 100.230 | 103.297 | 104.917 | 105.165 |
| SD | 3.261 | 5.408 | 1.004 | 2.069 | 2.495 | 2.602 |
| RSD | 8.109 | 6.567 | 1.016 | 2.056 | 2.466 | 2.571 |

TABLE 13

| Dissolution of Tablet G (with film-coating) % Gemcabene Released | | | | | | |
|---|---|---|---|---|---|---|
| Vessel | 10 min | 20 min | 30 min | 45 min | 60 min | 75 min |
| 1 | 37.879 | 77.964 | 97.609 | 102.938 | 103.238 | 103.353 |
| 2 | 36.379 | 75.350 | 99.708 | 103.297 | 104.917 | 105.165 |
| 3 | 40.569 | 82.713 | 98.911 | 100.091 | 100.608 | 100.575 |
| 4 | 45.200 | 90.337 | 98.665 | 98.762 | 98.921 | 98.885 |
| 5 | 42.600 | 86.051 | 97.941 | 98.373 | 98.474 | 98.453 |
| 6 | 38.683 | 81.721 | 100.230 | 100.309 | 100.774 | 100.766 |
| Mean | 40.219 | 82.356 | 98.844 | 100.628 | 101.155 | 101.200 |
| Low | 36.379 | 75.350 | 97.609 | 98.373 | 98.474 | 98.453 |
| High | 45.200 | 90.337 | 100.230 | 103.297 | 104.917 | 105.165 |
| SD | 3.261 | 5.408 | 1.004 | 2.069 | 2.495 | 2.602 |
| RSD | 8.109 | 6.567 | 1.016 | 2.056 | 2.466 | 2.571 |

TABLE 14

| Dissolution of Tablet H (with film-coating) % Gemcabene Released | | | | | | |
|---|---|---|---|---|---|---|
| Vessel | 10 min | 20 min | 30 min | 45 min | 60 min | 75 min |
| 1 | 29.083 | 59.044 | 86.406 | 98.545 | 95.413 | 98.720 |
| 2 | 41.482 | 83.201 | 96.143 | 97.923 | 97.529 | 98.017 |
| 3 | 32.032 | 64.900 | 87.653 | 100.838 | 101.299 | 101.551 |
| 4 | 47.784 | 90.267 | 95.939 | 97.080 | 97.218 | 97.222 |
| 5 | 41.097 | 82.074 | 96.770 | 98.167 | 98.308 | 98.577 |
| 6 | 41.810 | 83.249 | 97.292 | 98.101 | 98.131 | 98.173 |
| Mean | 38.881 | 77.122 | 93.367 | 98.442 | 97.983 | 98.710 |
| Low | 29.083 | 59.044 | 86.406 | 97.080 | 95.413 | 97.222 |
| High | 47.784 | 90.267 | 97.292 | 100.838 | 101.299 | 101.551 |
| SD | 6.963 | 12.231 | 4.948 | 1.270 | 1.925 | 1.488 |
| RSD | 17.908 | 15.859 | 5.299 | 1.290 | 1.964 | 1.507 |

Example 14: Content Uniformity of Gemcabene Calcium Salt Hydrate Crystal Form 1 Tablets Content Uniformity Assay: Tablets were tested for content uniformity using HPLC in accordance with USP <905>.

Content uniformity of the gemcabene calcium salt hydrate Crystal Form 1 300-mg film-coated tablets (see Example 13) were determined. Individually 10 tablets (e.g., from the group of Tablet A) were weighed and weights recorded. For each test, 1 tablet was placed in a 200 mL volumetric flask. The flask was filled about halfway with water:acetonitrile: formic acid (60:40:0.1; mobile phase A) solution, sonicated to dissolve and stirred occasionally. The solution was swirled and equilibrated to room temperature. The solution was diluted to volume with mobile phase A and mixed well. About 5 mL of solution was filtered through a 0.45 μm PTFE (polytetrafluoroethylene) 25 mm filter, discarding the first 5 mL and collecting the remainder in a HPLC vial.

The sample solutions were evaluated via HPLC against the sensitivity solution, working standard, check standards, marker solutions, and a mobile phase A blank. Data were collected using validated HPLC system software. Content uniformity results were consistent among all batches and did not appear to be affected by the particle size distribution of the gemcabene calcium salt hydrate Crystal Form 1.

| | |
|---|---|
| Flow Rate: | 1.0 mL/minute |
| Run Time: | 60 minutes |
| Autosampler Temperature: | Ambient |
| Column Temperature: | 40° C. |
| Injection Volume: | 50 μL |
| Detection: | UV at 214 nm |
| Mobile Phase A: | 60:40:0.1 Water:Acetonitrile:Formic Acid |
| Mobile Phase B: | 10:90:0.1 Water:Acetonitrile:Formic Acid |

HPLC System for Dissolution Study:

Column: Waters Symmetry C18 3.5 μm, 4.6 mm×150 mm, Part No. WAT 200632 or equivalent Gradient:

| Time (min) | Mobile Phase A (%) | Mobile Phase B (%) |
|---|---|---|
| 0.0 | 100 | 0 |
| 20.0 | 100 | 0 |
| 40.0 | 60 | 40 |
| 45.0 | 0 | 100 |
| 45.1 | 100 | 0 |
| 60.0 | 100 | 0 |

Gemcabene Working/Check Standard: In duplicate, about 60.0 mg of gemcabene reference standard was weighed into a 25 mL volumetric flask and diluted to volume with mobile phase A to yield a concentration of 2.4 mg/mL (expressed as free diacid).

Sensitivity Solution: 1.0 mL of the gemcabene working or check standard was transferred into a 100 mL volumetric flask, diluted to volume with mobile phase A and mixed well. 1.0 mL of this solution was transferred into a 20 mL volumetric flask. Diluted to volume with mobile phase A and mixed well for a nominal concentration of 1.2 μg/mL of gemcabene.

Calculation: The content uniformity was calculated based on the following formula.

$$\%\text{ Released} = \frac{PAsmp \times DF \times C \times P \times 100\%}{PAstd \times N \times 300\text{ mg}^{*}}$$

where: PAsmp=Peak area of gemcabene

DF=Dilution factor of samples

C=Working standard concentration mg/mL (expressed as gemcabene)

P=Purity factor of reference standard

PAstd=Average peak area of gemcabene in all working standard injections

N=Number of tablets added to the flask

* each gemcabene calcium salt hydrate Crystal Form 1 300-mg film-coated tablet comprises gemcabene calcium salt hydrate Crystal Form 1 in an amount that is a molar equivalent to 300 mg gemcabene theoretical gemcabene molar equivalent of gemcabene calcium salt in each tested 300 mg tablets.

TABLE 15

| Content uniformity analysis results | | | | |
|---|---|---|---|---|
| | Tablet Lot No. | | | |
| | Tablet A | Tablet B | Tablet C | Tablet D |
| | Gemcabene Calcium Salt Hydrate Crystal Form 1 PSD90 | | | |
| | 151 μm | 76 μm | 110 μm | 52 μm |
| Tablet Test No. | % released | % released | % released | % released |
| 1 | 96.7 | 94.9 | 92.0 | 94.7 |
| 2 | 95.6 | 94.7 | 93.1 | 96.2 |
| 3 | 96.0 | 97.7 | 88.8 | 94.1 |
| 4 | 93.5 | 96.6 | 89.5 | 97.1 |
| 5 | 96.2 | 96.0 | 92.2 | 95.5 |
| 6 | 92.9 | 94.4 | 93.3 | 96.0 |
| 7 | 92.5 | 96.9 | 89.9 | 100.6 |
| 8 | 92.8 | 97.6 | 94.7 | 98.9 |
| 9 | 93.0 | 95.1 | 94.4 | 97.0 |
| 10 | 93.0 | 96.0 | 95.7 | 96.0 |
| % RSD | 1.8 | 1.24 | 2.53 | 2.0 |
| Average % released | 94.2 | 96.0 | 92.4 | 96.6 |
| Acceptance Value | 8.3 | 5.4 | 11.7 | 6.5 |

Each granulation of Example 10 did not over wet or require additional water to complete. Each granulation produced a blend with exceptional flow properties and tablets of adequate hardness with low friability. Thus, further optimization can be necessary to perform at larger batch sizes.

Content uniformity testing showed low RSD and acceptable acceptance value (AV) values for tablets from all granulations (Table 15). The effect of particle size was reflected in the dissolution profiles of the tablets. For instance, the tablets prepared from gemcabene calcium salt hydrate Crystal Form 1 having a PSD90 of 110 μm (Tablet C) and a PSD90 of 151 μm (Tablet A), showed 8%-15% slower release at the 45-minute time point than the tablets prepared from gemcabene calcium salt hydrate Crystal Form 1 having a PSD90 value of 40 μm to about 75 μm. This is a significant decrease and provides a different profile than that of the other tablets.

Further, content uniformity and dissolution properties of three different lots of 300 mg tablet prepared with gemcabene calcium salt hydrate Crystal Form 1 having a PSD90 of 50-65 μm were measured as shown in Table 16.

TABLE 16

| Content uniformity and dissolution properties of 300-mg film-coated tablets prepared with gemcabene calcium salt hydrate Crystal Form 1 | | | | |
|---|---|---|---|---|
| | Tablet | | | |
| | Tablet D | Tablet F | Tablet G | |
| | PSD90 of gemcabene calcium salt hydrate Crystal Form 1 | | | |
| | 52 μm | 52 μm | 62 μm | Mean (n = 3 Lots) |
| Mean (N = 10) mg/tablet | 289.8 | 283.5 | 305.1 | 292.8 |
| Content Uniformity: | 96.6% | 94.5% | 101.70% | 97.6% |
| % CV | 2.0% | 1.8% | 1.4% | 1.7% |
| Dissolution: | | | | |
| Mean (N = 6) % | | | | |

TABLE 16-continued

| Content uniformity and dissolution properties of 300-mg film-coated tablets prepared with gemcabene calcium salt hydrate Crystal Form 1 | | | | |
|---|---|---|---|---|
| | Tablet | | | |
| | Tablet D | Tablet F | Tablet G | |
| | PSD90 of gemcabene calcium salt hydrate Crystal Form 1 | | | |
| | 52 μm | 52 μm | 62 μm | Mean (n = 3 Lots) |
| Dissolved in: | | | | |
| 10 minutes | 26 | 23 | 37 | 28.7 |
| 20 minutes | 53 | 53 | 78 | 61.3 |
| 30 minutes | 75 | 76 | 100 | 83.7 |
| 45 minutes | 92 | 93 | 103 | 96 |

Example 15: Effect of Gemcabene Calcium Salt Hydrate Crystal Form 1 in STAM™ Mice, a Murine Model of Non-Alcoholic Steatosis Hepatitis (NASH)-Hepatocellular Carcinoma (HCC) (Murine STAM™ Model of NASH-HCC)

A study was performed to evaluate the efficacy of gemcabene calcium salt hydrate Crystal Form 1 having a PSD90 of 52 μm as measured by laser light diffraction, in treating non-alcoholic steatosis hepatitis (NASH) in the murine STAM™ model of NASH-HCC. The murine STAM™ model of NASH-HCC is a high-fat caloric (HFC)-fed mouse model, in which pathological progression is very similar to that in humans as they develop liver steatosis, inflammation, and partial fibrosis (Kohli and Feldstein, *J Hepatol,* 155, 941-943, doi:10.1016/j.jhep.2011.04.010 (2011)).

Briefly, two-day old neonatal C57BL/6 male mice were administered low-dose streptozotocin (STZ), and were subsequently fed a HFC diet from 4 weeks of age. In this model, the mice typically develop liver steatosis and diabetes, reaching steatohepatitis within 3 weeks, followed by cirrhosis within 8 weeks, and carcinoma within 16 weeks. In the current study, mice were administered daily oral gemcabene calcium salt hydrate Crystal Form 1 starting at week 6 of age and were sacrificed at week 9. Telmisartan (with antisteatotic, anti-inflammatory and antifibrotic effects in STAM™ mice) was used as a positive comparator. A baseline reference group was administered vehicle at day 2 of age, and from week 6 of age was vehicle-treated and chow-fed. Five STAM™ groups were streptozocin-treated at day 2 of age and fed a HFC-diet beginning with week 4 of age. These STAM™ groups were orally administered from week 6 one of the following: water-vehicle, gemcabene calcium salt hydrate Crystal Form 1 at 30, 100 and 300 mg/kg daily, or telmisartan (MICARDIS®) 10 mg/kg daily. Telmisartan (MICARDIS®) was purchased from Boehringer Ingelheim GmibH (Germany) and dissolved in pure water. All groups were sacrificed at week 9. The treatment schedule is summarized in Table 17. Vehicle, gemcabene calcium salt hydrate Crystal Form 1, or telmisartan were administered by oral gavage once daily.

TABLE 17

| Treatment schedule | | | | | | | |
|---|---|---|---|---|---|---|---|
| Group | No. mice | Mice | Test substance | Dose (mg/kg) | Volume (mL/kg) | Regimen | Sacrifice (wks) |
| 1 | 8 | Normal | Vehicle | — | 10 | PO[1], QD[2], 6 wks-9 wks | 9 |
| 2 | 8 | STAM ™ | Vehicle | — | 10 | PO, QD, 6 wks-9 wks | 9 |
| 3 | 8 | STAM ™ | Gemcabene calcium salt hydrate Crystal Form 1 | 30 | 10 | PO, QD, 6 wks-9 wks | 9 |
| 4 | 8 | STAM ™ | Gemcabene calcium salt hydrate Crystal Form 1 | 100 | 10 | PO, QD, 6 wks-9 wks | 9 |
| 5 | 8 | STAM ™ | Gemcabene calcium salt hydrate Crystal Form 1 | 300 | 10 | PO, QD, 6 wks-9 wks | 9 |
| 6 | 8 | STAM ™ | Telmisartan | 10 | 10 | PO, QD, 6 wks-9 wks | 9 |

[1]PO: by mouth
[2]QD: once a day

Liver, whole blood and biochemistry parameters of mice tested in this study were analyzed. The biochemistry panel (hepatic lipids, fasting glucose, transaminases and other parameters) results are shown in Table 18.

TABLE 18

| Biochemistry Results | | | | | | |
|---|---|---|---|---|---|---|
| | Parameter (mean ± SD) | | | | | |
| | Vehicle in Normal Day 18: n = 8 Day 21: n = 8 | Vehicle in NASH Day 18: n = 8 Day 21: n = 8 | Gemcabene[1] 30 mg/kg Day 18: n = 8 Day 21: n = 8 | Gemcabene[1] 100 mg/kg Day 18: n = 8 Day 21: n = 8 | Gemcabene[1] 300 mg/kg Day 18: n = 8 Day 21: n = 8 | Telmisartan 10 mg/kg Day 18: n = 8 Day 21: n = 7 |
| At 3 days prior to termination after 8 hours of fasting (Day 18) | | | | | | |
| Fasting blood glucose (mg/dL) | 117 ± 27 | 440 ± 53 | 437 ± 42 | 441 ± 46 | 407 ± 15 | 742 ± 90 |
| Plasma insulin (ng/mL) | 0.89 ± 0.44 | 0.12 ± 0.04 | 0.13 ± 0.04 | 0.17 ± 0.06 | 0.13 ± 0.04 | 0.16 ± 0.04 |
| At termination (Day 21) | | | | | | |
| Non-fasting blood glucose (mg/dL) | 168 ± 11 | 584 ± 60 | 607 ± 48 | 653 ± 53 | 638 ± 63 | 856 ± 62 |
| Plasma alanine aminotransferase (U/L) | 18 ± 3 | 50 ± 23 | 41 ± 15 | 27 ± 7 | 32 ± 14 | 39 ± 15 |
| Plasma aspartate aminotransferase (U/L) | 61 ± 13 | 116 ± 48 | 100 ± 44 | 88 ± 32 | 147 ± 122 | 121 ± 38 |
| Plasma alkaline phosphatase (U/L) | 313 ± 35 | 394 ± 68 | 382 ± 78 | 642 ± 167 | 794 ± 57 | 567 ± 104 |
| Plasma gamma-glutamyl transferase (U/L) | 1 ± 0 | 1 ± 0 | 1 ± 0 | 1 ± 0 | 1 ± 0 | 1 ± 0 |
| Plasma blood urea nitrogen (mg/dL) | 30.2 ± 2.6 | 28.5 ± 5.7 | 25.0 ± 3.9 | 29.8 ± 4.3 | 30.1 ± 5.8 | 85.0 ± 17.4 |
| Plasma creatinine (mg/dL) | 0.2 ± 0.1 | 0.1 ± 0.0 | 0.1 ± 0.0 | 0.1 ± 0.1 | 0.2 ± 0.1 | 0.1 ± 0.0 |
| Plasma total bilirubin (mg/dL) | 0.3 ± 0.0 | 0.2 ± 0.1 | 0.2 ± 0.1 | 0.3 ± 0.2 | 0.3 ± 0.1 | 0.3 ± 0.1 |
| Plasma ketone body (mM) | 0.44 ± 0.21 | 9.28 ± 2.77 | 9.43 ± 2.35 | 5.75 ± 3.24 | 5.68 ± 3.08 | 8.11 ± 3.27 |
| Liver triglyceride (mg/g liver) | 5.1 ± 1.4 | 49.1 ± 9.8 | 49.2 ± 8.6 | 58.4 ± 14.5 | 56.0 ± 13.9 | 31.7 ± 6.4 |
| Liver hydroxyproline (μg/mg total protein) | 0.71 ± 0.11 | 0.74 ± 0.10 | 0.66 ± 0.12 | 0.74 ± 0.38 | 0.70 ± 0.10 | 0.91 ± 0.12 |
| Plasma triglyceride (mg/dL) | 184 ± 33 | 555 ± 262 | 319 ± 198 | 191 ± 57 | 149 ± 32 | 569 ± 256 |
| Plasma total cholesterol (mg/dL) | 96 ± 8 | 160 ± 22 | 194 ± 17 | 228 ± 37 | 234 ± 45 | 208 ± 19 |
| Plasma ApoC-III (gg/mL) | 6.6 ± 0.4 | 7.5 ± 1.4 | 6.6 ± 0.8 | 6.0 ± 2.5 | 6.2 ± 0.7 | 6.2 ± 0.7 |
| Plasma leptin (ng/mL) | 3.4 ± 1.5 | 4.6 ± 2.9 | 3.1 ± 1.2 | 4.3 ± 1.2 | 3.2 ± 1.1 | 2.9 ± 1.1 |
| Plasma CRP (gg/mL) | 2.0 ± 0.3 | 2.8 ± 0.4 | 2.5 ± 0.3 | 1.9 ± 0.3 | 1.9 ± 0.4 | 3.0 ± 0.4 |
| Plasma adiponectin (gg/mL) | 6.5 ± 1.1 | 4.1 ± 0.8 | 4.1 ± 0.9 | 4.1 ± 0.5 | 4.9 ± 0.5 | 6.8 ± 0.9 |
| Liver free fatty acid (pEq/g liver) | 16.2 ± 5.6 | 28.2 ± 6.4 | 35.1 ± 8.4 | 38.4 ± 8.5 | 46.0 ± 5.5 | 46.8 ± 10.7 |

[1]Gemcabene calcium salt hydrate Crystal Form 1 (PSD90 = 52 μm)

Measurement of Liver Biochemistry

Measurement of Liver Triglyceride and Free Fatty Acid Content

Liver total lipid-extracts were obtained according to the method of Folch J. et al., *J. Biol. Chem.* 1957; 226: 497. Liver samples were homogenized in 20 volumes of chloroform-methanol (2:1, v/v) and incubated overnight at room temperature. After washing with chloroform-methanol-water (8:4:3, v/v/v), the extracts in the lower chloroform phase were evaporated to dryness, and dissolved in isopropanol. Liver triglyceride and free fatty acid contents were measured with a Triglyceride E-test and NEFA C-test, respectively (Wako Pure Chemical Industries).

Measurement of Liver Hydroxyproline Content

To quantify liver hydroxyproline content, frozen liver samples were processed by an alkaline-acid hydrolysis method as follows. Liver samples were defatted with 100% acetone, dried in the air, dissolved in 2 N NaOH at 65° C., and autoclaved at 121° C. for 20 minutes. The lysed samples (400 μL) were acid-hydrolyzed with 400 μL of 6N HCl at 121° C. for 20 minutes, and neutralized with 400 μL of 4N NaOH containing 10 mg/mL activated carbon. AC buffer (2.2 M acetic acid/0.48 M citric acid, 400 μL) was added to the samples, followed by centrifugation to collect the supernatant. A standard curve of hydroxyproline was constructed with serial dilutions of trans-4-hydroxy-L-proline (Sigma-Aldrich) starting at 16 μg/mL. The prepared samples and standards (each 400 L) were mixed with 400 μL chloramine T solution (Wako Pure Chemical Industries, Osaka, Japan) and incubated for 25 minutes at room temperature. The samples were then mixed with Ehrlich's solution (400 μL) and heated at 65° C. for 20 minutes to develop the color. After samples were cooled on ice and centrifuged to remove precipitates, the optical density of each supernatant was measured at 560 nm. The concentrations of hydroxyproline were calculated from the hydroxyproline standard curve. Protein concentrations of liver samples were determined using a BCA protein assay kit (Thermo Fisher Scientific, USA) and used to normalize the calculated hydroxyproline values. Liver hydroxyproline levels were expressed as μg per mg protein.

Biochemistry

Biochemistry results are summarized in Table 18.

Blood Analysis 3 Days Prior to Termination after 8 Hours of Fasting

Fasting Whole Blood Glucose

The Vehicle-treated STAM™ mice showed a significant increase in fasting whole blood glucose concentrations compared with the vehicle-treated normal group. The telmisartan-treated mice showed a significant increase in fasting whole blood glucose concentrations compared with the vehicle-treated STAM™ mice. There were no significant differences in fasting whole blood glucose concentrations between the vehicle-treated STAM™ mice and the gemcabene calcium salt hydrate Crystal Form 1 (PSD90=52 μm)-treated mice.

Fasting Plasma Insulin

The vehicle-treated STAM™ mice showed a significant decrease in fasting plasma insulin concentrations compared with the vehicle-treated normal mice. There were no significant differences in fasting plasma insulin concentrations between the vehicle-treated STAM™ mice and any of the other treatment groups.

Blood Analysis at Termination (Table 18)

Whole Blood Glucose

The vehicle-treated STAM™ mice showed a significant increase in whole blood glucose levels compared with the vehicle-treated normal mice. The telmisartan-treated mice showed a significant increase in whole blood glucose levels compared with the vehicle-treated STAM™ mice. There were no significant differences in whole blood glucose levels between the vehicle-treated STAM™ mice and the gemcabene calcium salt hydrate Crystal Form 1 (PSD90=52 μm)-treated mice.

Plasma Alanine Aminotransferase (ALT)

The vehicle-treated STAM™ mice showed a significant increase in plasma ALT levels compared with the vehicle-treated normal mice. The gemcabene calcium salt hydrate Crystal Form 1 (PSD90=52 μm)-treated 100 mg/kg mice showed a significant decrease in plasma ALT levels compared with the vehicle-treated STAM™ mice. There were no significant differences in plasma ALT concentrations between the vehicle-treated STAM™ mice and any of the other treatment groups.

Plasma Aspartate Aminotransferase (AST)

There were no significant differences in plasma AST levels between the Vehicle-treated STAM™ mice and any of the treatment groups.

Plasma Alkaline Phosphatase (ALP)

The gemcabene calcium salt hydrate Crystal Form 1-treated 100 and 300 mg/kg mice and telmisartan-treated mice showed significant increases in plasma ALP levels compared with the vehicle-treated NASH group. There were no significant differences in plasma ALP levels between the vehicle-treated STAM™ mice and any of the other treatment groups.

Plasma Gamma-Glutamyl Transferase (GGT)

There were no significant differences in plasma GGT levels between the vehicle-treated STAM™ mice and any of the treatment groups.

Plasma Blood Urea Nitrogen (BUN)

The telmisartan-treated mice showed a significant increase in plasma BUN levels compared with the vehicle-treated STAM™ mice. There were no significant differences in plasma BUN levels between the vehicle-treated STAM™ mice and any of the other treatment groups.

Plasma Creatinine

The vehicle-treated STAM™ mice showed a significant decrease in plasma creatinine levels compared with the vehicle-treated normal mice. The gemcabene calcium salt hydrate Crystal Form 1 (PSD90=52 μm)-treated 300 mg/kg mice showed a significant increase in plasma creatinine levels compared with the vehicle-treated STAM™ group. There were no significant differences in plasma creatinine levels between the vehicle-treated STAM™ mice and any of the other treatment groups.

Plasma Total Bilirubin

There were no significant differences in plasma total bilirubin levels between the vehicle-treated STAM™ mice and any of the treatment groups.

Plasma Ketone Body

The vehicle-treated STAM™ mice showed a significant increase in plasma ketone body levels compared with the vehicle-treated normal mice. There were no significant differences in plasma ketone body levels between the Vehicle-treated STAM™ mice and any of the other treatment groups.

Liver Triglyceride

The vehicle-treated STAM™ mice showed a significant increase in liver triglyceride contents compared with the vehicle-treated normal mice. The telmisartan-treated mice showed a significant decrease in liver triglyceride content compared with the vehicle-treated STAM™ mice. There were no significant differences in liver triglyceride content between the vehicle-treated STAM™ mice and gemcabene calcium salt hydrate Crystal Form 1-treated groups.

Liver Hydroxyproline

There were no significant differences in liver hydroxyproline contents between the vehicle-treated STAM™ mice and any of the treatment groups.

Plasma Triglyceride

Figure 9:
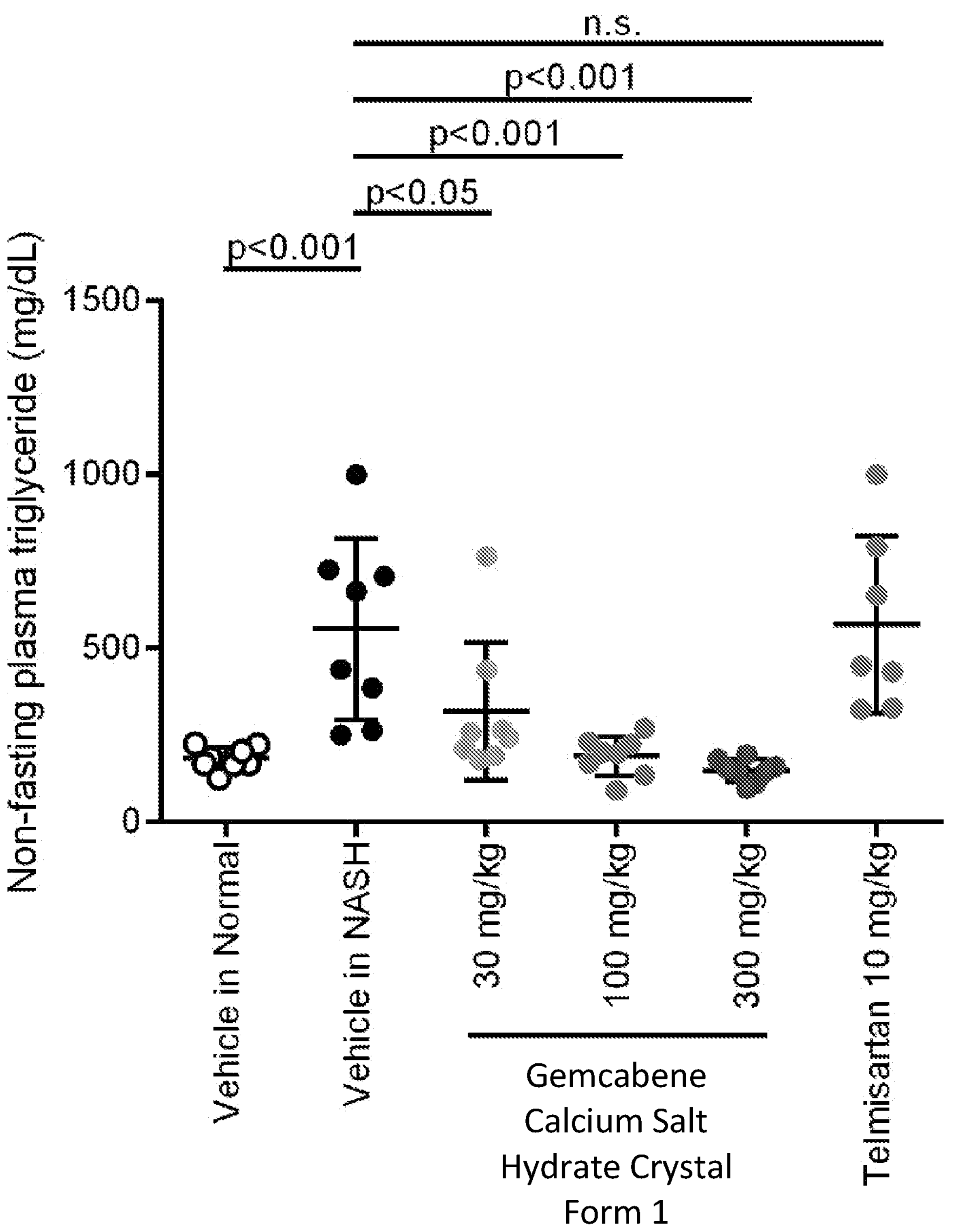
FIG. 9 is a graph showing non-fasting plasma triglyceride concentrations in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 10:
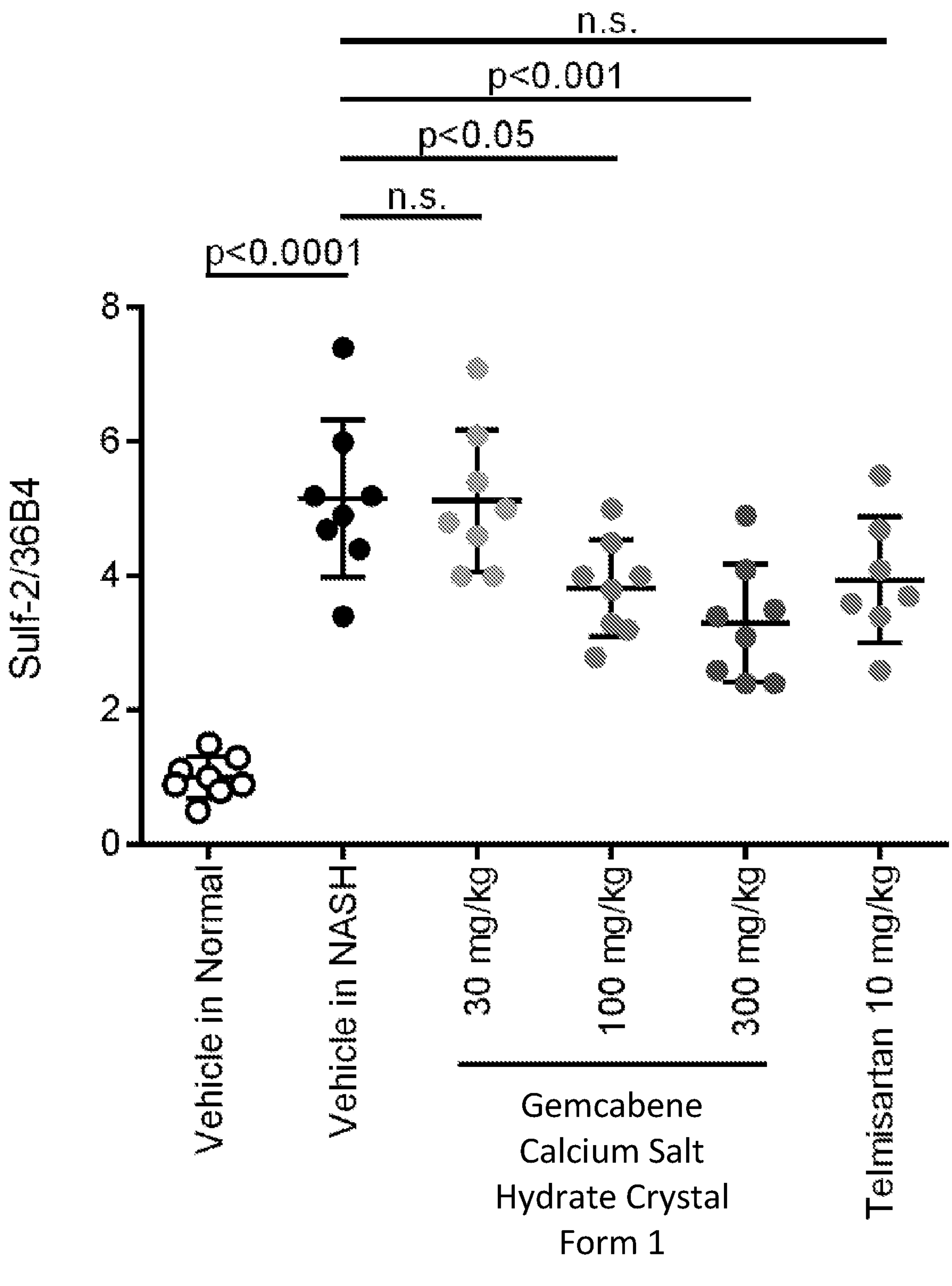
FIG. 10 is a graph showing gene expression levels of hepatic sulfatase 2 (Sulf-2) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 11:
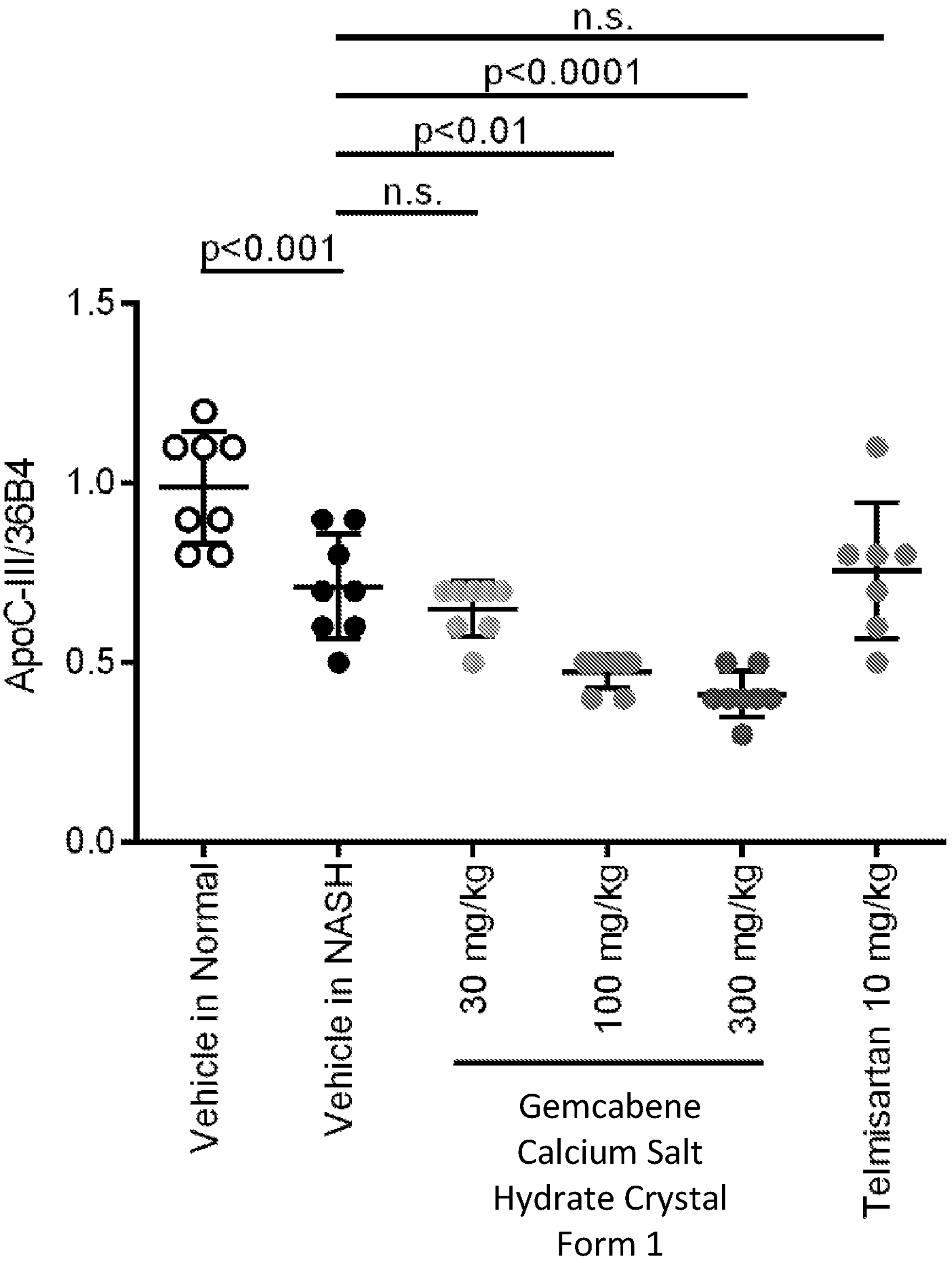
FIG. 11 is a graph showing gene expression levels for hepatic apolipoprotein C-III (ApoC-III) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 12:
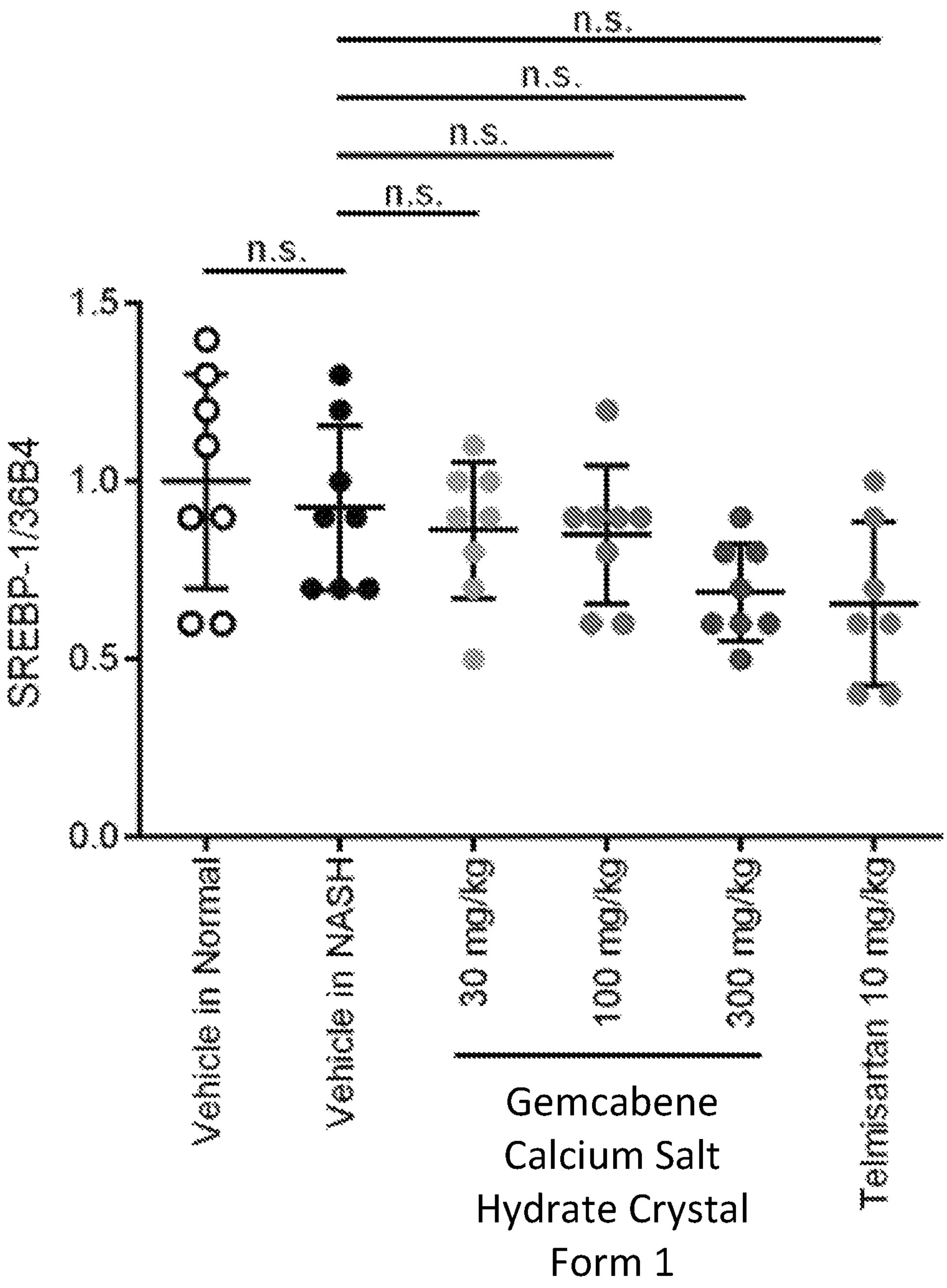
FIG. 12 is a graph showing gene expression levels for hepatic sterol regulatory element binding transcription factor 1 (SREBP-1) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 13:
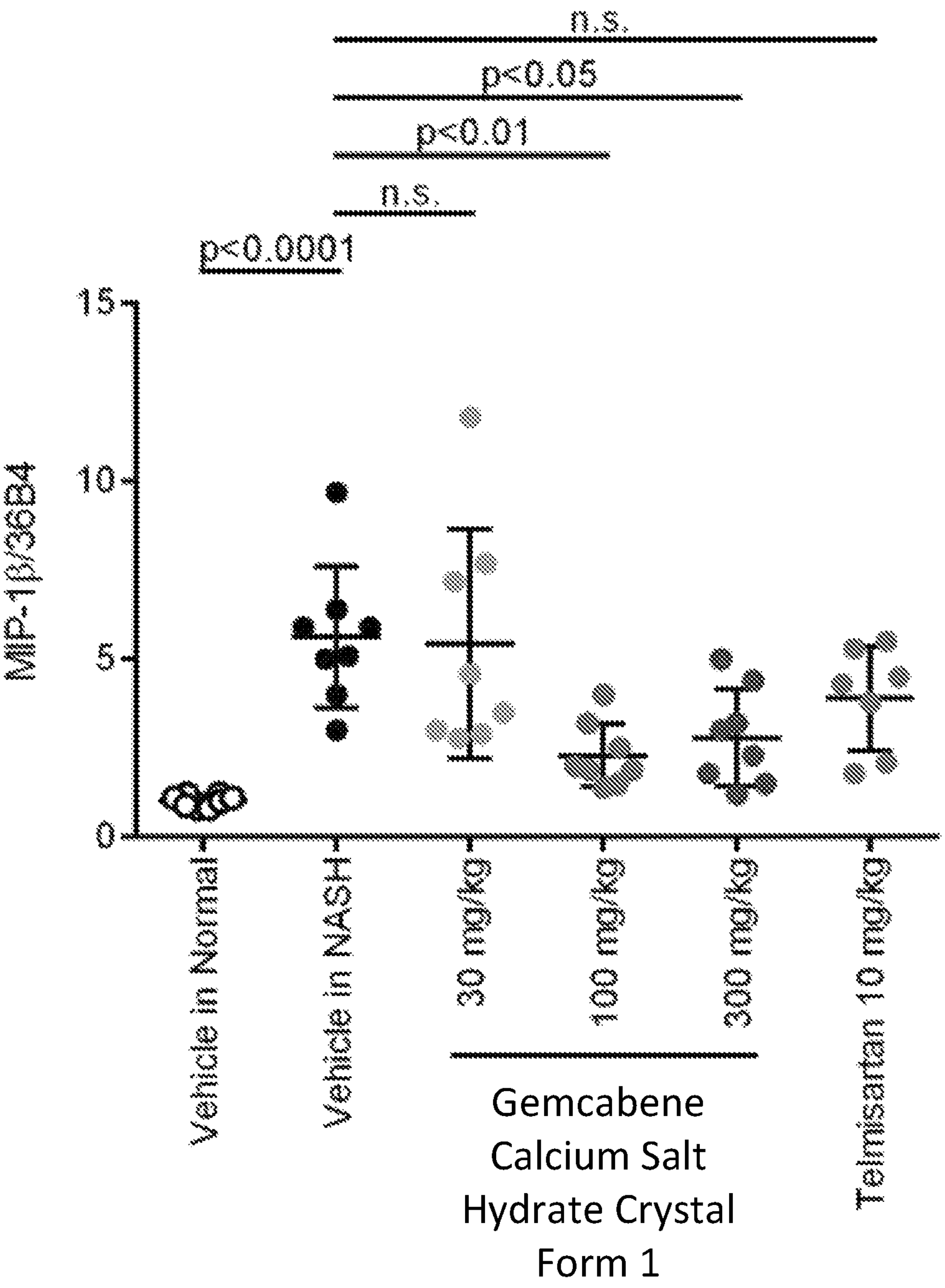
FIG. 13 is a graph showing gene expression levels for hepatic chemokine (C—C motif) ligand 4 (MIP-10) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 14:
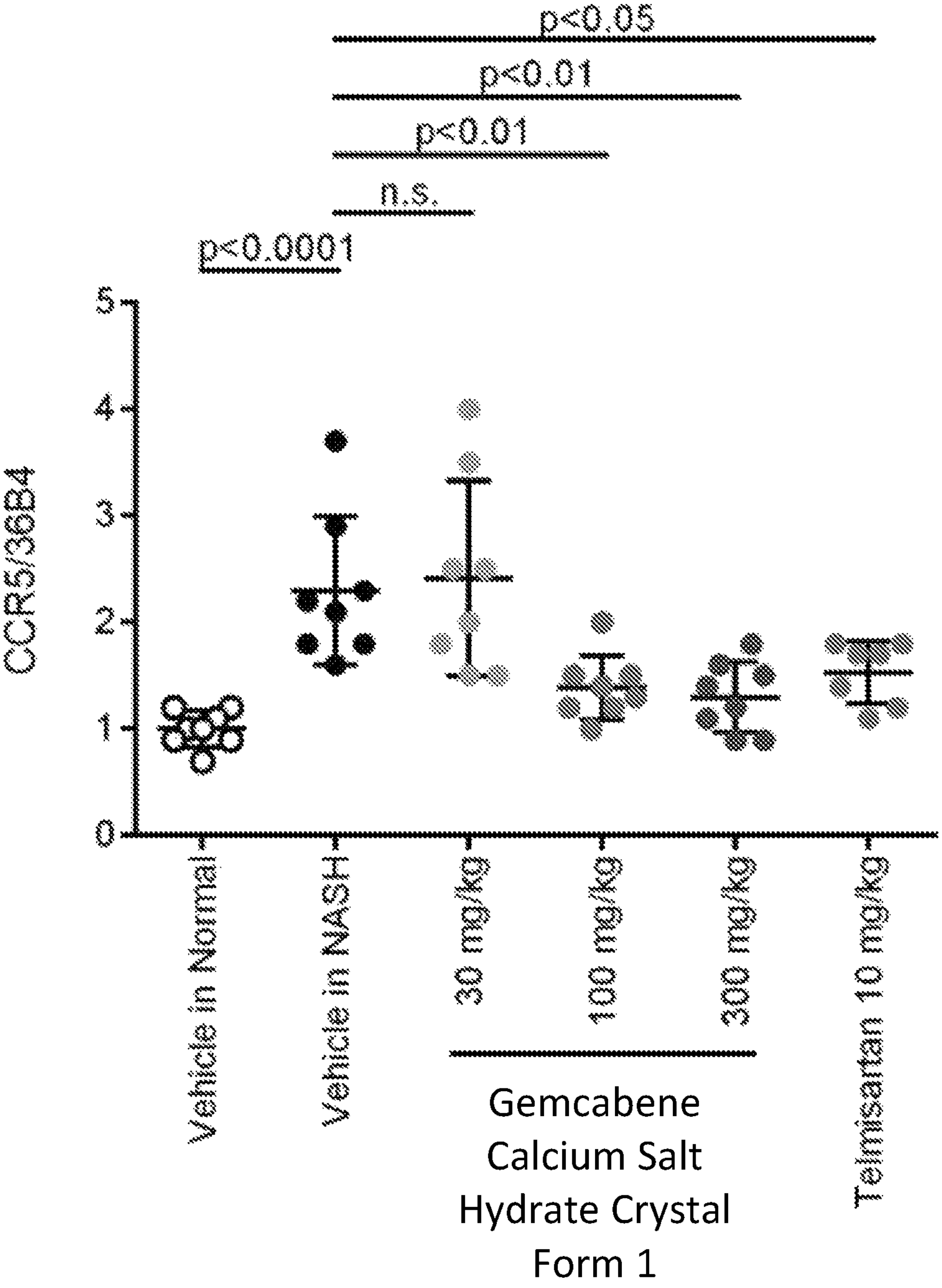
FIG. 14 is a graph showing gene expression levels for hepatic chemokine (C—C motif) receptor 5 (CCR5) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 15:
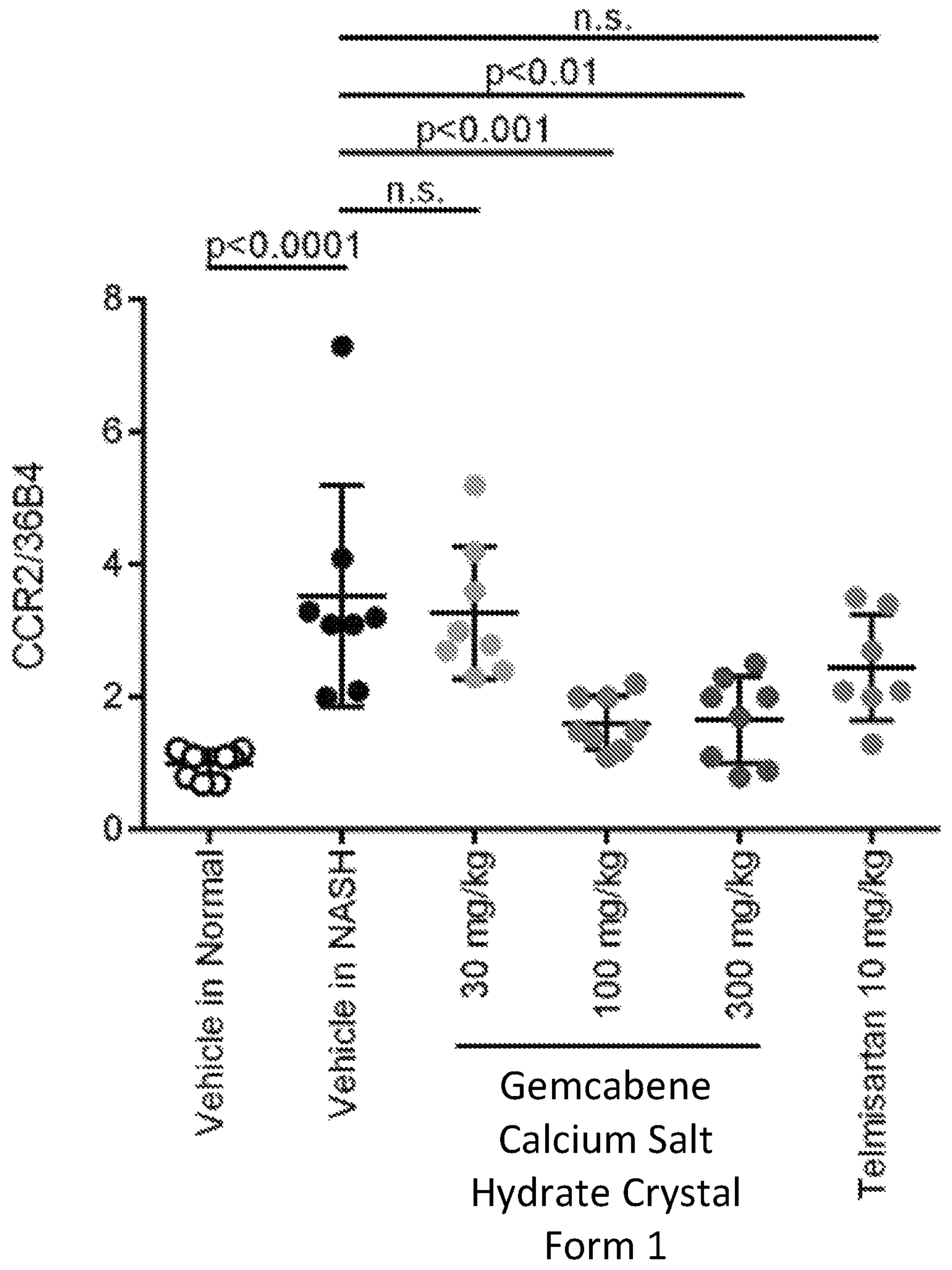
FIG. 15 is a graph showing gene expression levels for chemokine (C—C motif) receptor 2 (CCR2) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 16:
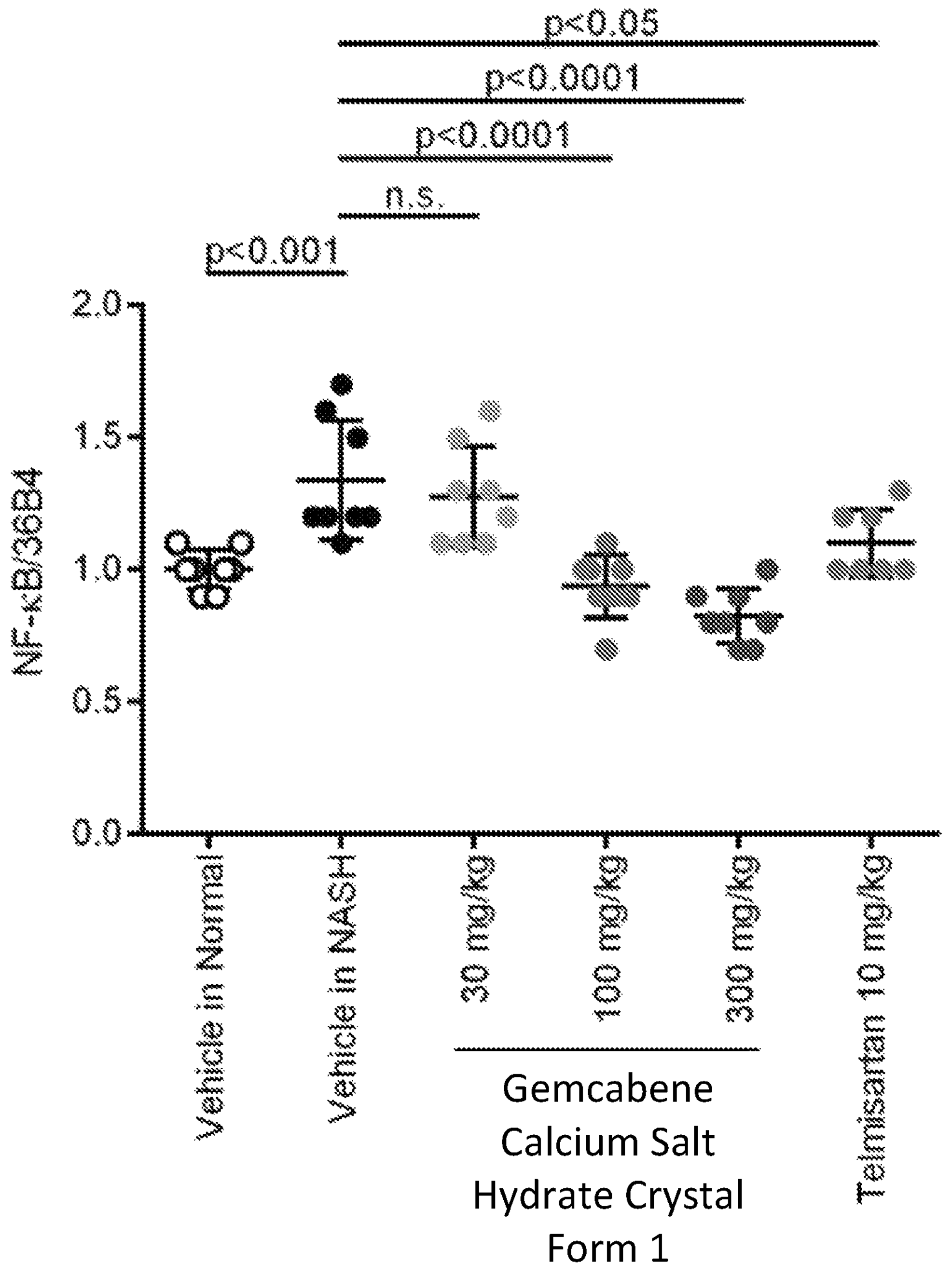
FIG. 16 is a graph showing gene expression levels for hepatic nuclear factor of kappa light polypeptide gene enhancer in B cells 1 (NF-κB) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 17:
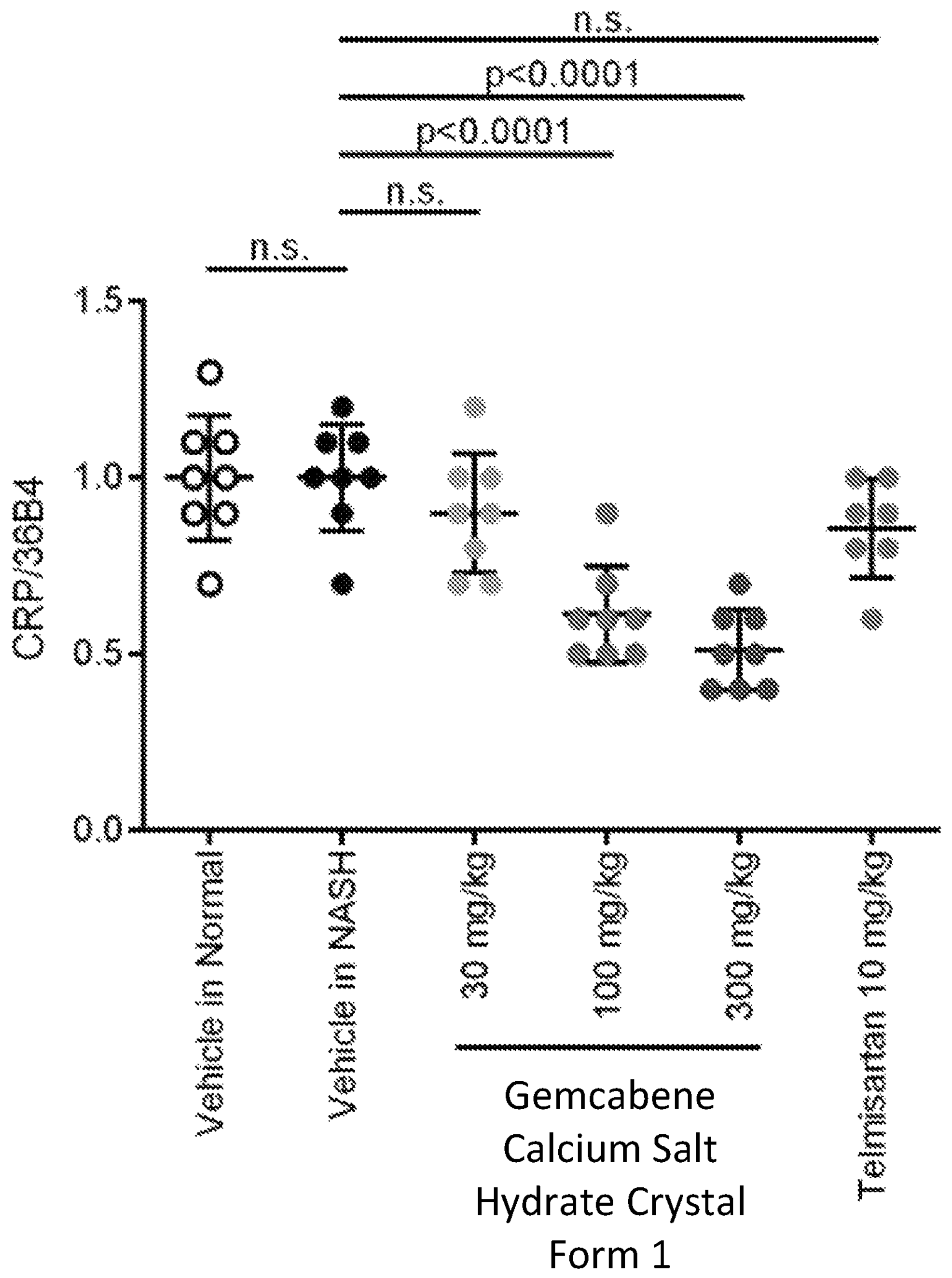
FIG. 17 is a graph showing gene expression levels for hepatic C-reactive protein, pentraxin-related (CRP) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 18:
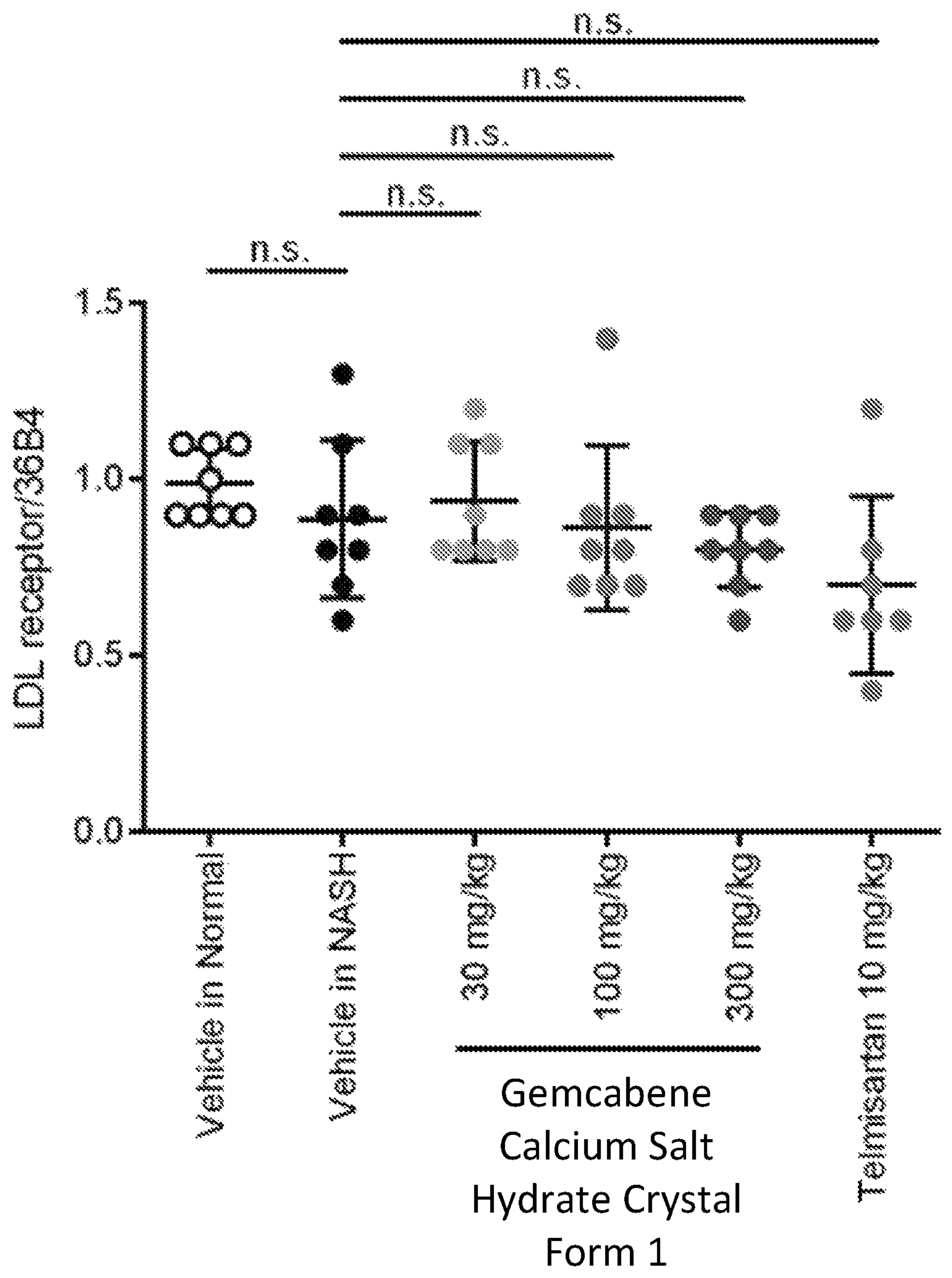
FIG. 18 is a graph showing gene expression levels for hepatic low-density lipoprotein receptor (LDL-receptor) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 19:
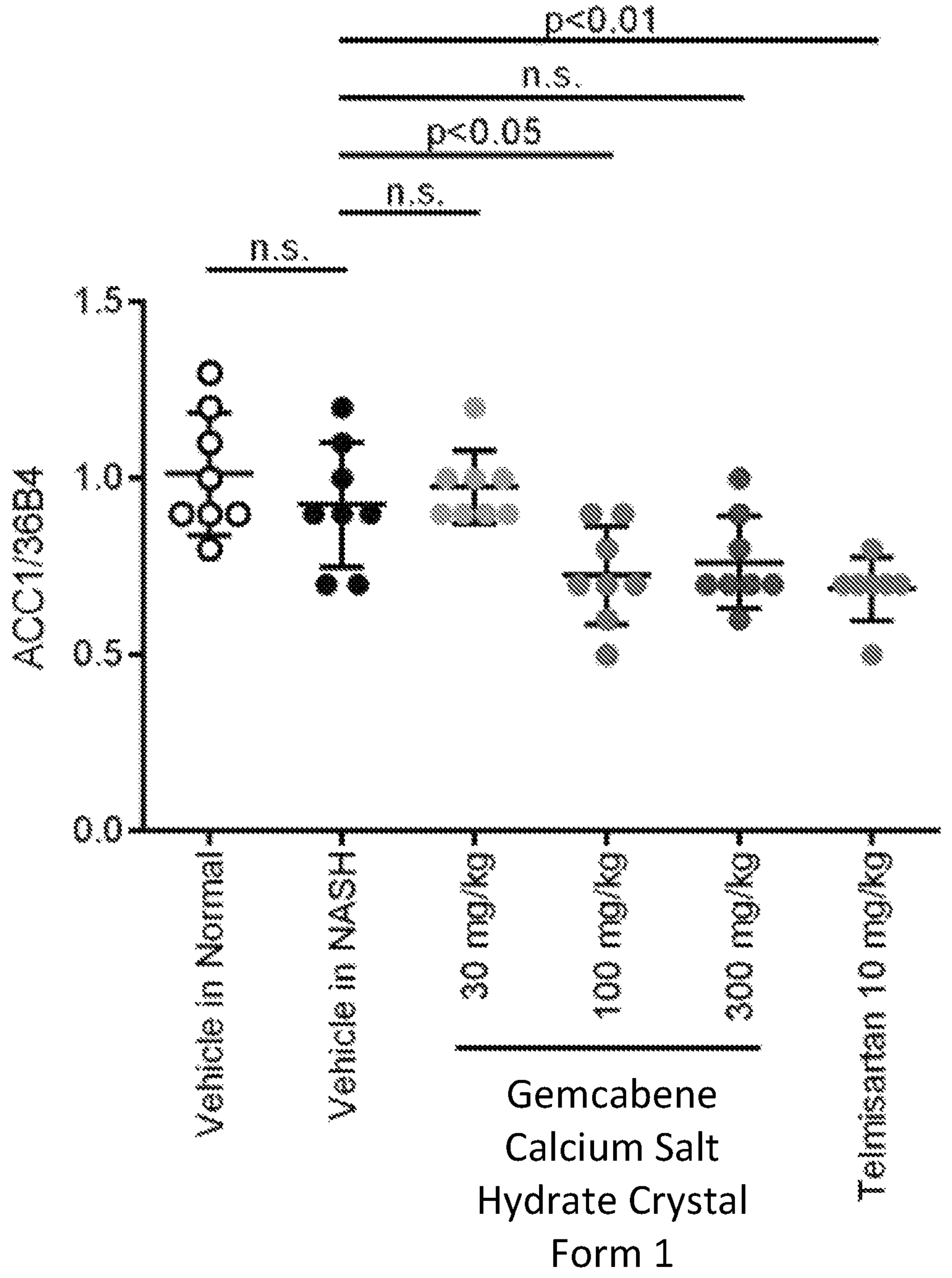
FIG. 19 is a graph showing gene expression levels for hepatic acetyl-coenzyme A carboxylase alpha (ACC1) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 20:
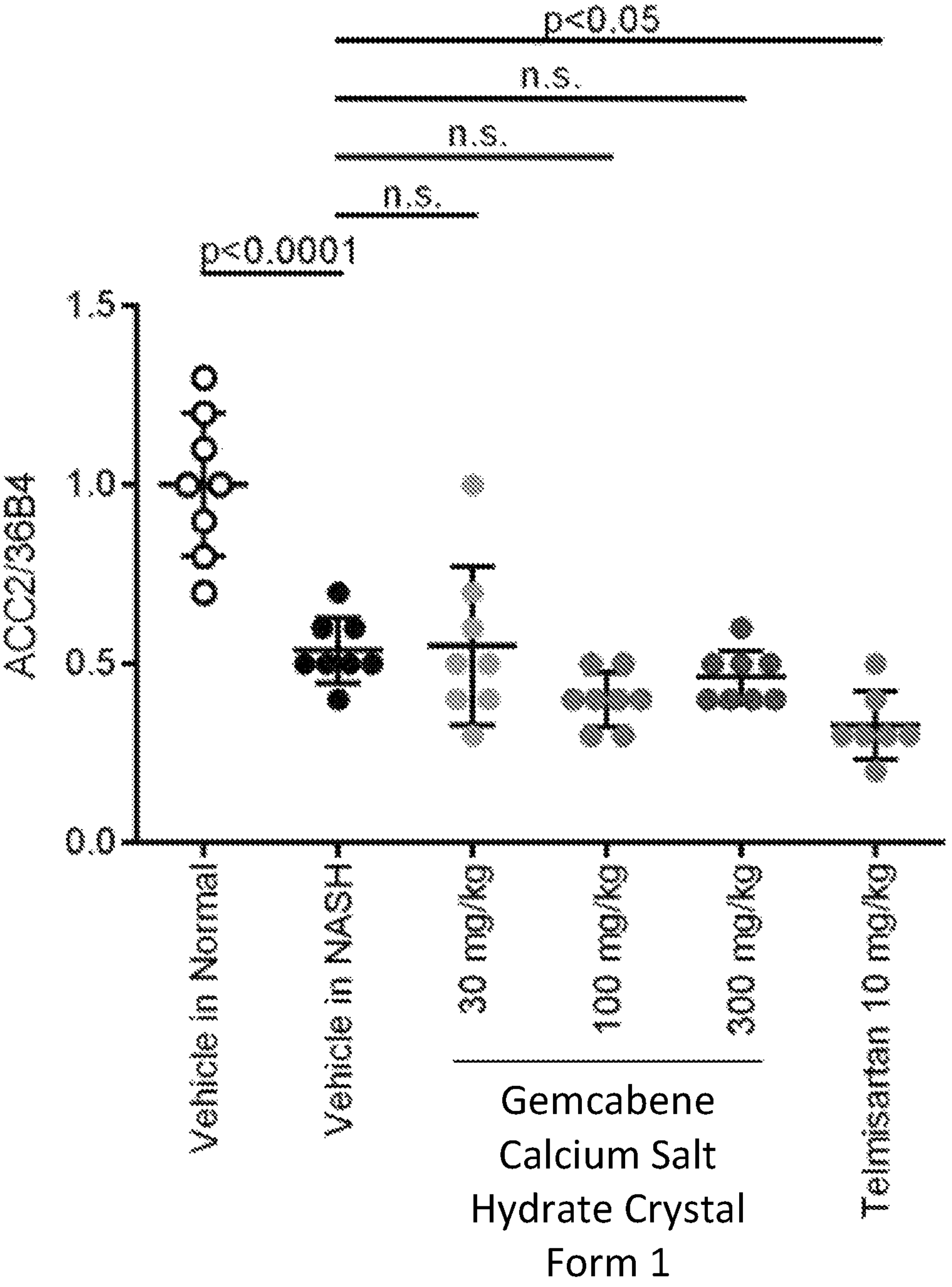
FIG. 20 is a graph showing gene expression levels for hepatic acetyl-coenzyme A carboxylase beta (ACC2) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 21:
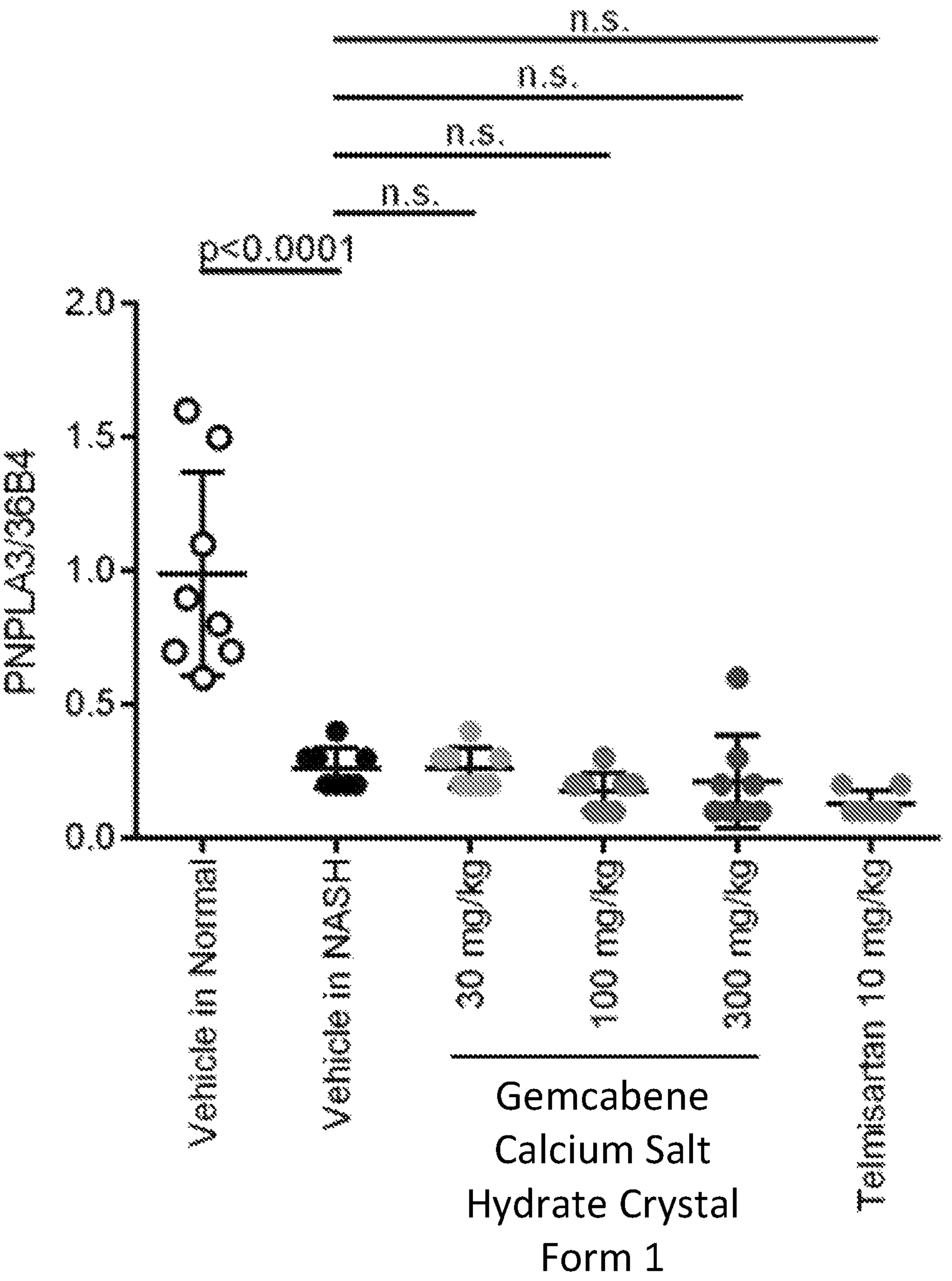
FIG. 21 is a graph showing gene expression levels for hepatic patatin-like phospholipase domain containing 3 (PNPLA3) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 22:
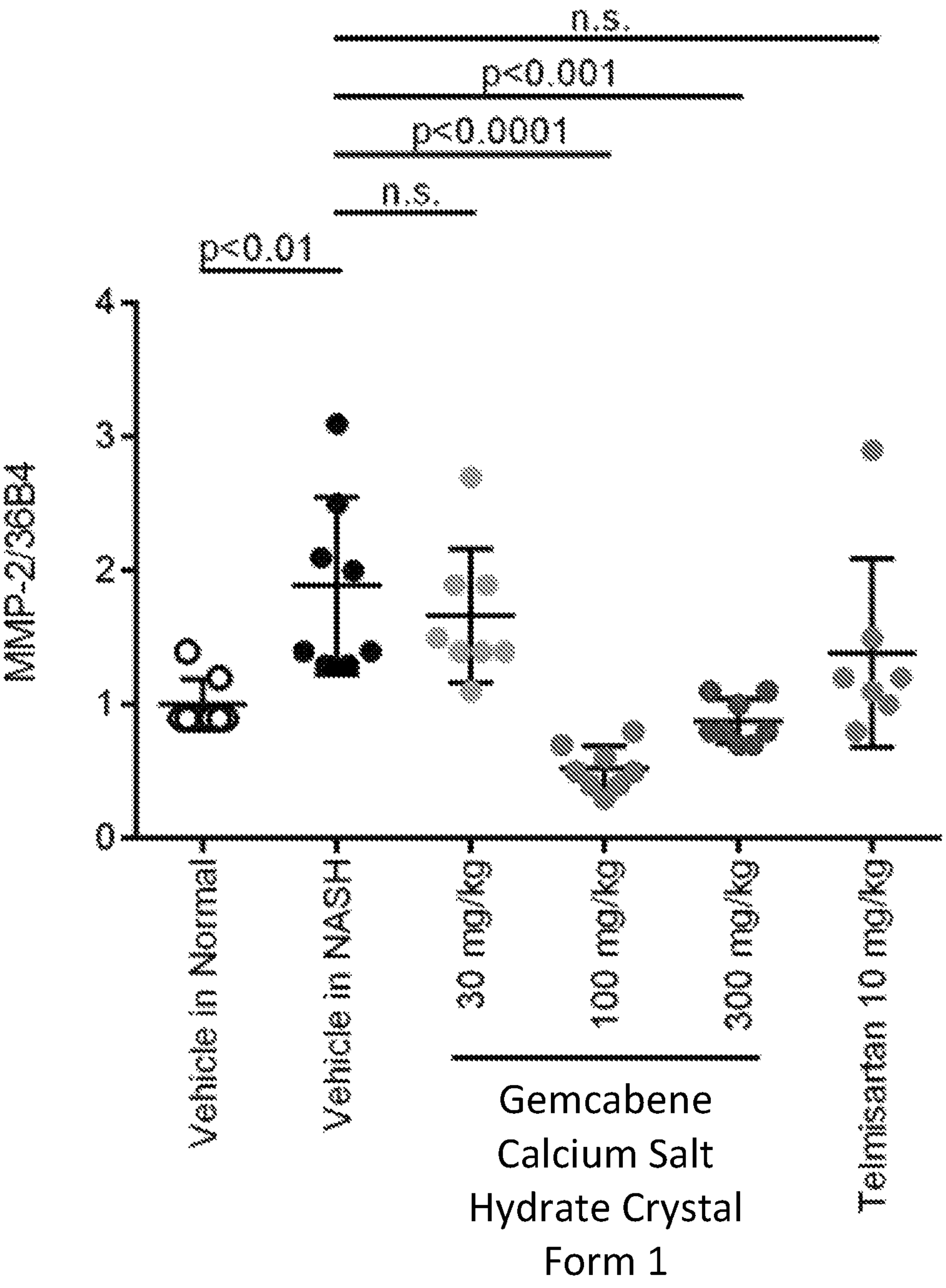
FIG. 22 is a graph showing gene expression levels for hepatic matrix metalloproteinase 2 (MMP-2) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 23:
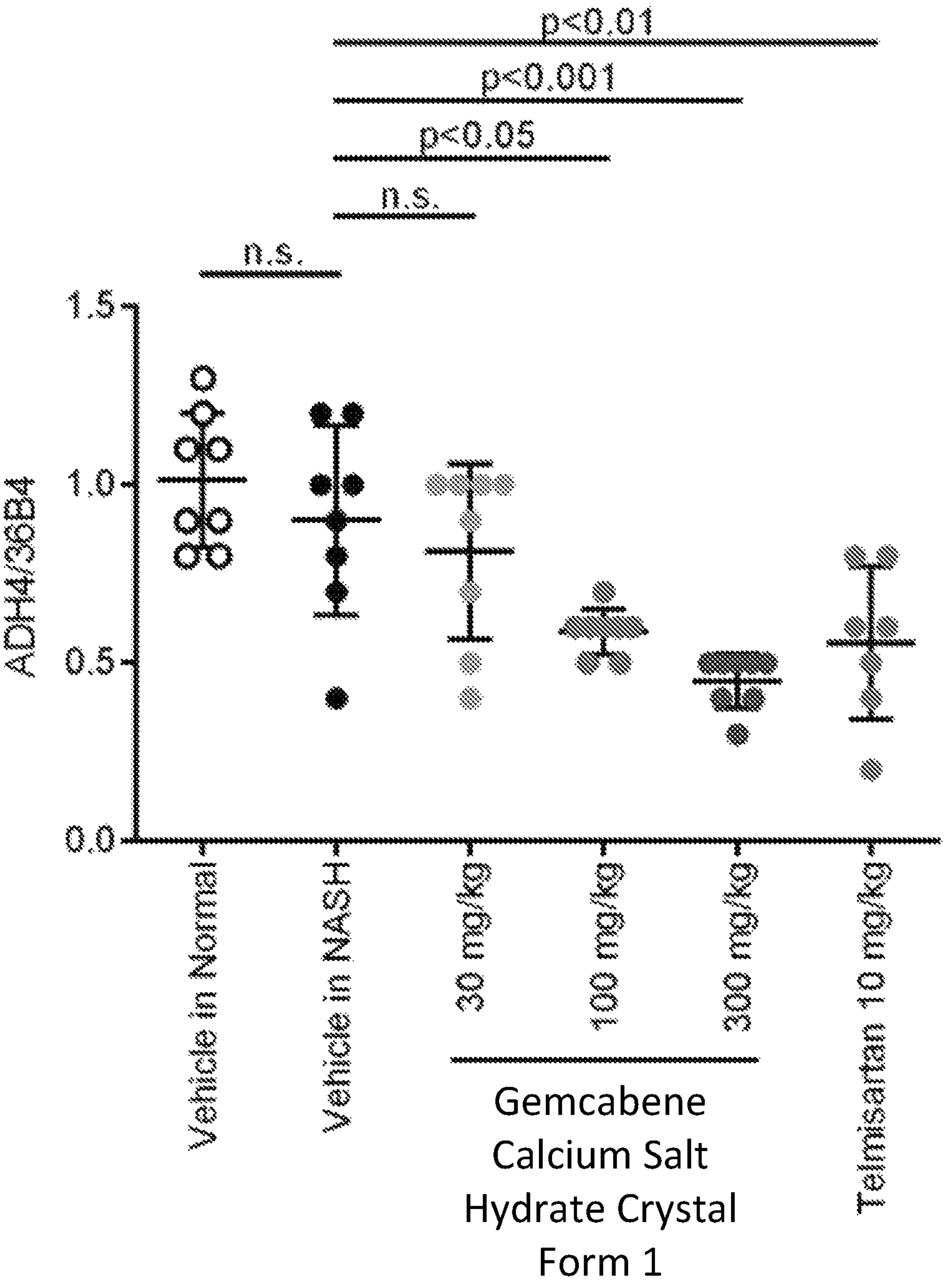
FIG. 23 is a graph showing gene expression levels for hepatic alcohol dehydrogenase 4 (class II), pi polypeptide (ADH4) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 24:
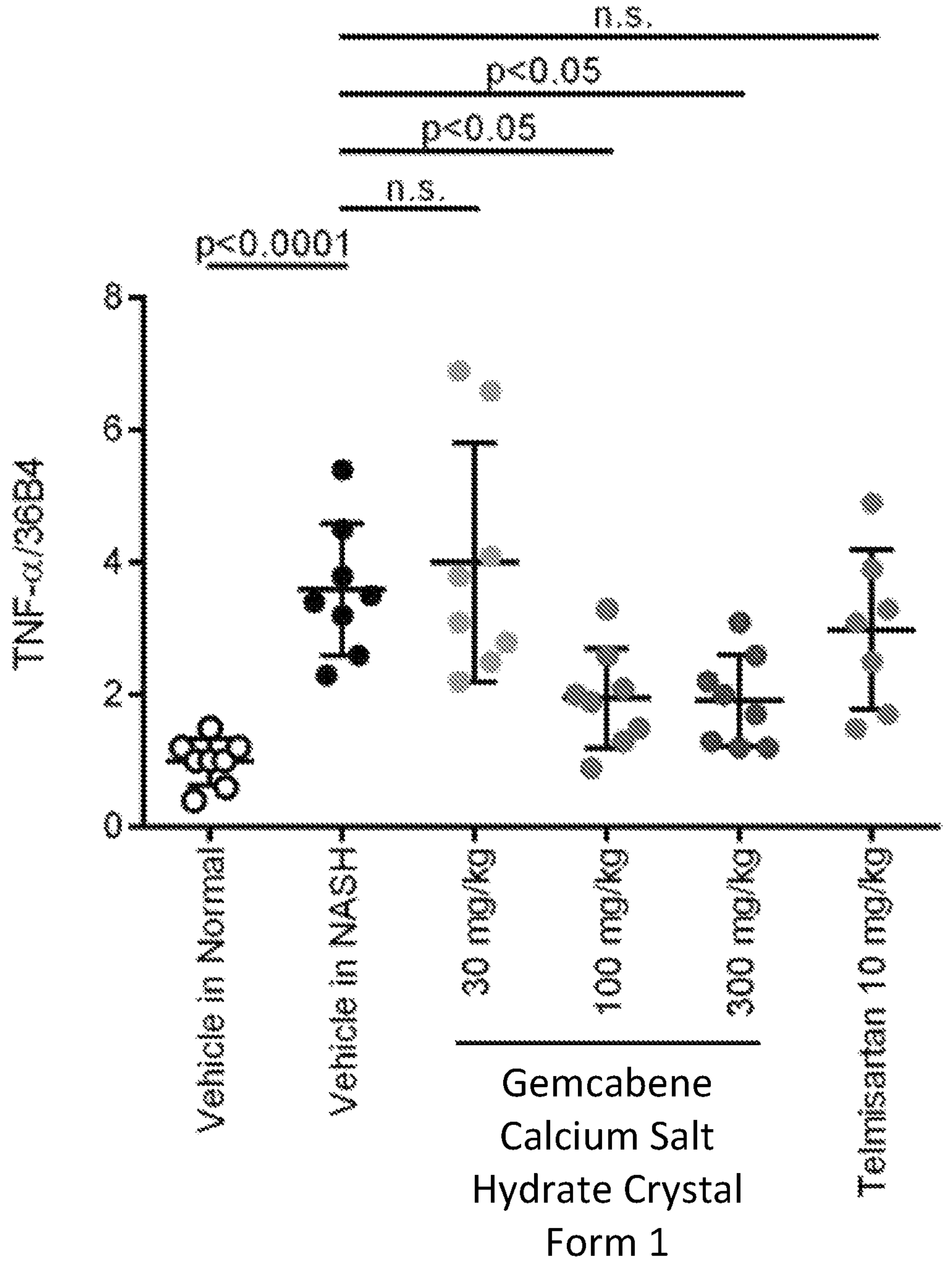
FIG. 24 is a graph showing hepatic gene expression levels for tumor necrosis factor alpha (TNF-α) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 25:
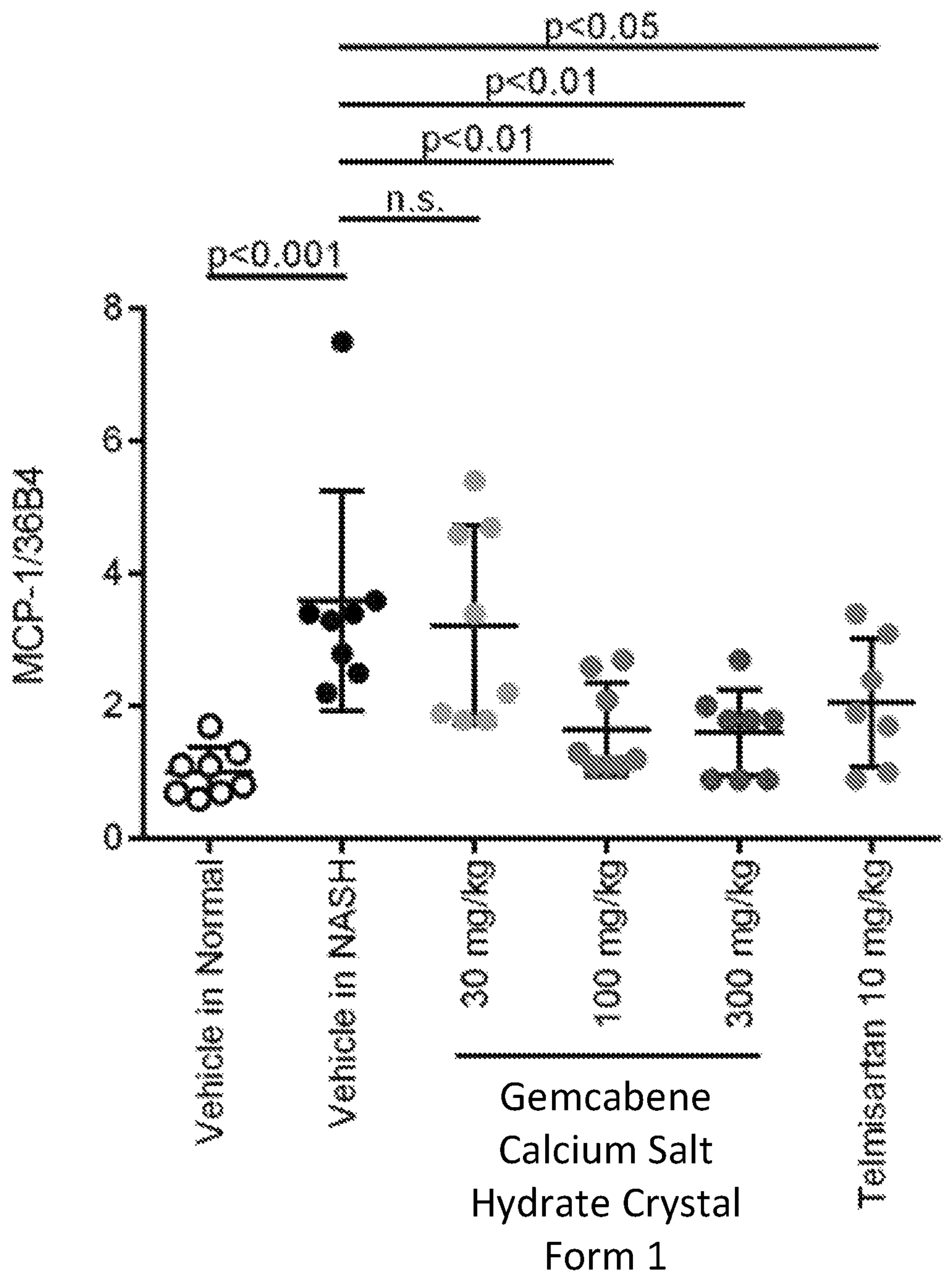
FIG. 25 is a graph showing gene expression levels for hepatic chemokine (C—C motif) ligand 2 (MCP-1) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 26:
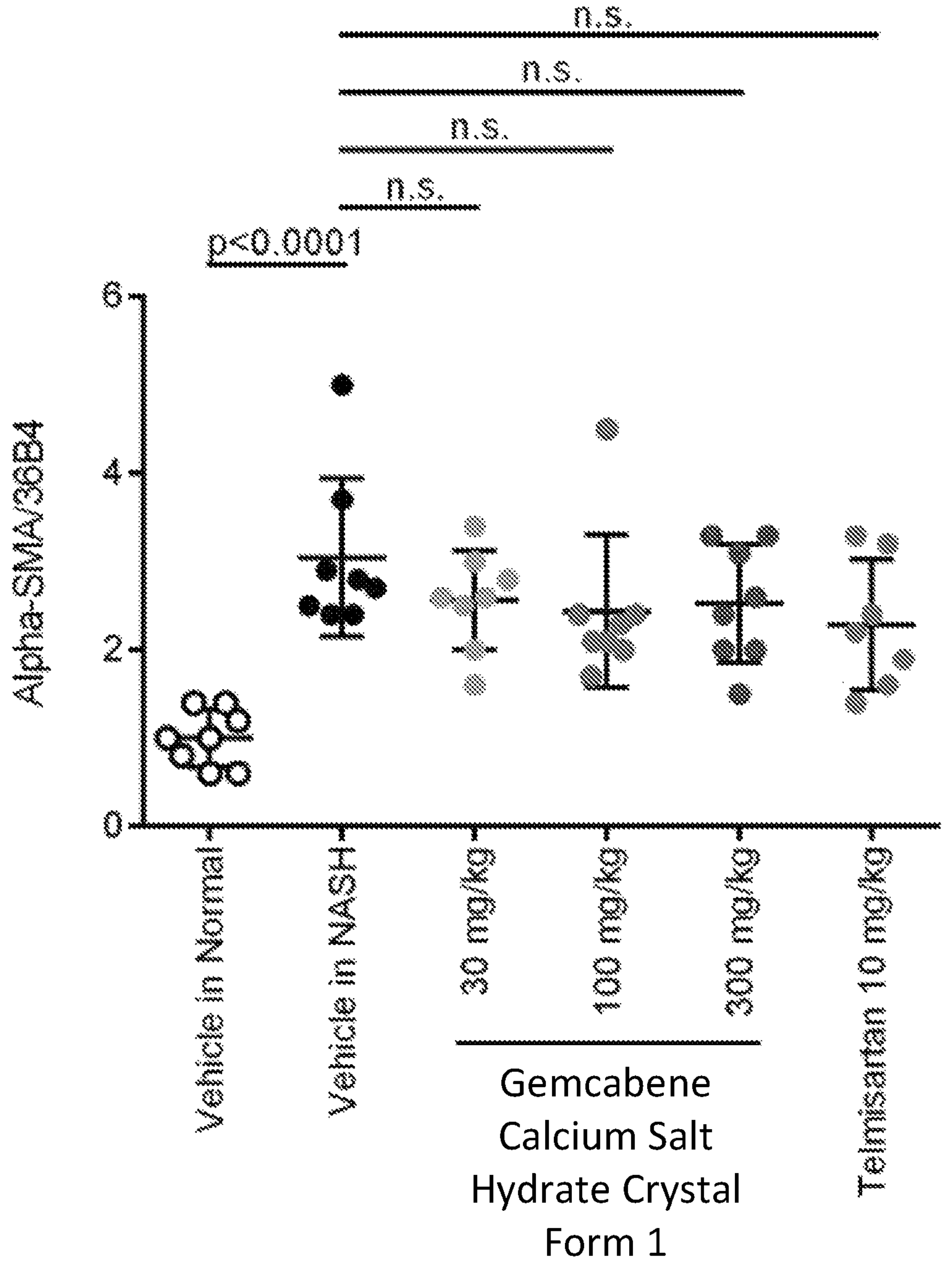
FIG. 26 is a graph showing hepatic gene expression levels for actin, alpha smooth muscle actin (α-SMA) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 27:
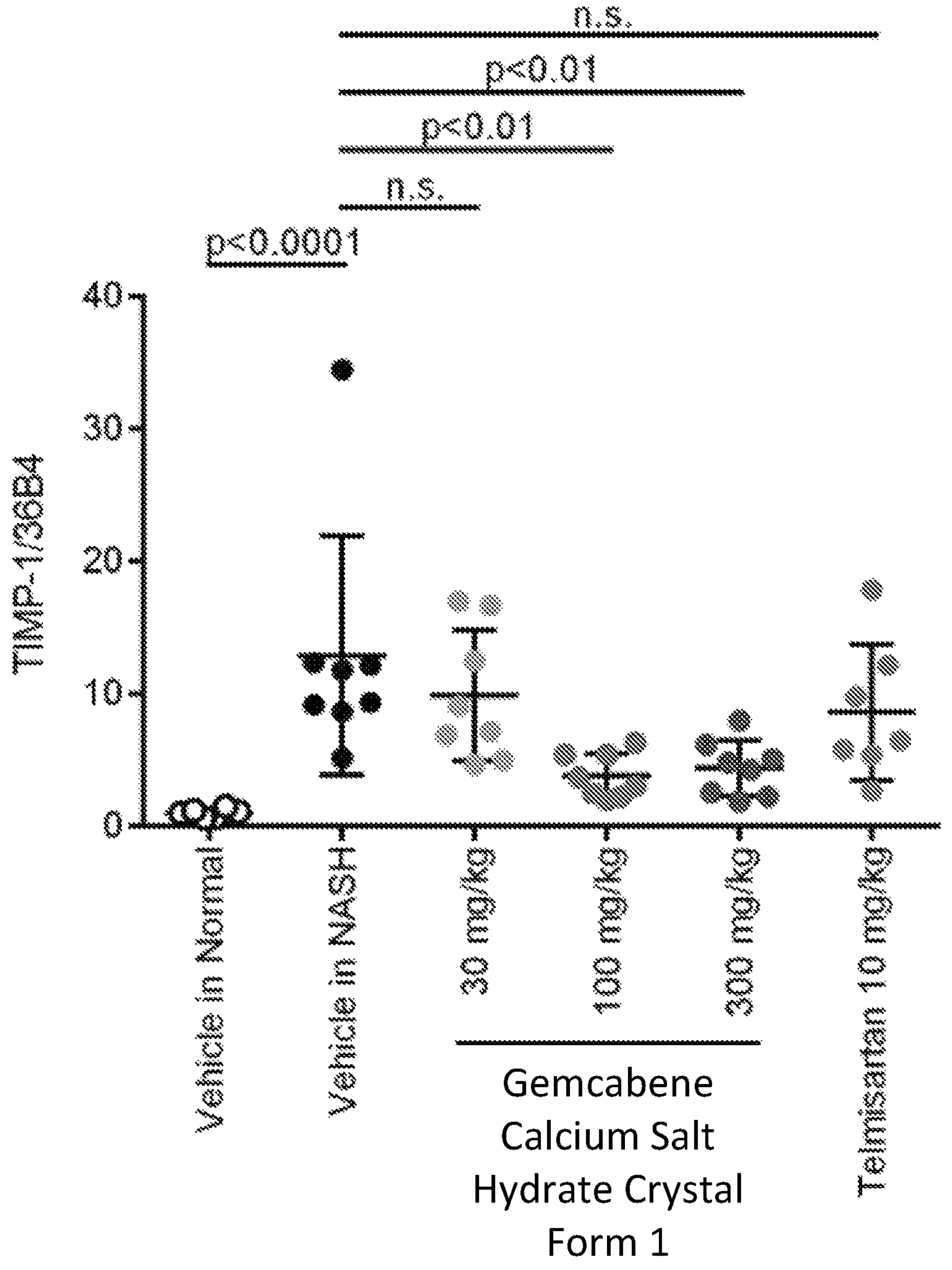
FIG. 27 is a graph showing gene expression levels for hepatic tissue inhibitor of metalloproteinase 1 (TIMP-1) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).

The vehicle-treated STAM™ mice showed a significant increase in plasma triglyceride concentrations compared with the vehicle-treated normal mice. The gemcabene calcium salt hydrate Crystal Form 1 (PSD90=52 μm)-treated mice showed significant decreases in plasma triglyceride concentrations compared with the vehicle-treated STAM™ mice in a dose-dependent manner (see FIG. 9). There was no significant difference in plasma triglyceride concentrations between the vehicle-treated STAM™ mice and the telmisartan-treated mice.

Plasma Total Cholesterol

The vehicle-treated STAM™ mice showed a significant increase in plasma total cholesterol concentrations compared with the vehicle-treated normal mice. The gemcabene calcium salt hydrate Crystal Form 1 (PSD90=52 μm)-treated 100 and 300 mg/kg mice and the telmisartan-treated mice showed significant increases in plasma total cholesterol concentrations compared with the Vehicle-treated STAM™ mice. There was no significant difference in plasma total cholesterol concentrations between the vehicle-treated STAM™ mice and the gemcabene calcium salt hydrate Crystal Form 1 (PSD90=52 μm)-treated 30 mg/kg mice.

Histological Analyses

For Hematoxylin and Eosin (H&E) staining, sections were cut from paraffin blocks of liver tissue prefixed in Bouin's solution and stained with Lillie-Mayer's Hematoxylin (Muto Pure Chemicals Co., Ltd., Japan) and eosin solution (Wako Pure Chemical Industries). NAFLD Activity score (NAS) was calculated according to the criteria of Kleiner, D E. Et al., *Hepatology,* 2005; 41:1313-1321. To visualize collagen deposition, Bouin's fixed liver sections were stained using picro-Sirius red solution (Waldeck, Germany). For Masson Trichrome staining, the sections were stained with Masson's Trichrome staining Kit (Sigma, USA) according to the manufacturer's instructions.

For quantitative analysis of fibrosis area, bright field images of Sirius red-stained sections were captured around the central vein using a digital camera (DFC295; Leica, Germany) at 200-fold magnification, and the positive areas in 5 fields/section were measured using ImageJ software (National Institute of Health, USA). Samples were analyzed in a blinded fashion.

Results

Figure 5A:
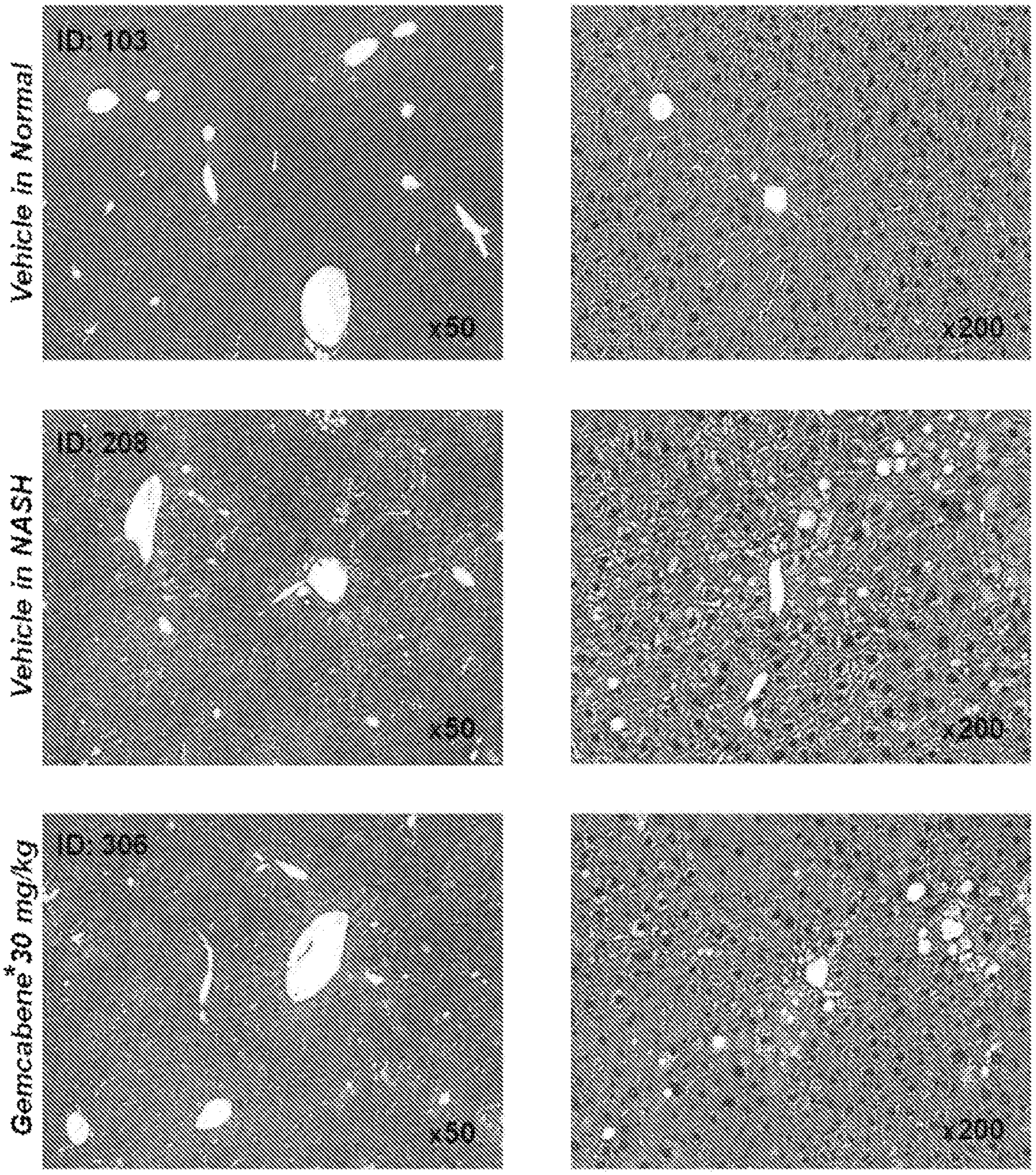
FIG. 5A shows photomicrographs of hematoxylin and eosin-stained liver sections of STAM™ model mice treated with gemcabene calcium salt hydrate Crystal Form 1 having a PSD90 of 52 μm as measured by laser light diffraction (ID: 306) or with vehicle (ID: 208) and photomicrographs of hematoxylin and eosin-stained liver sections of normal mice treated with vehicle (ID: 103).
Figure 5B:
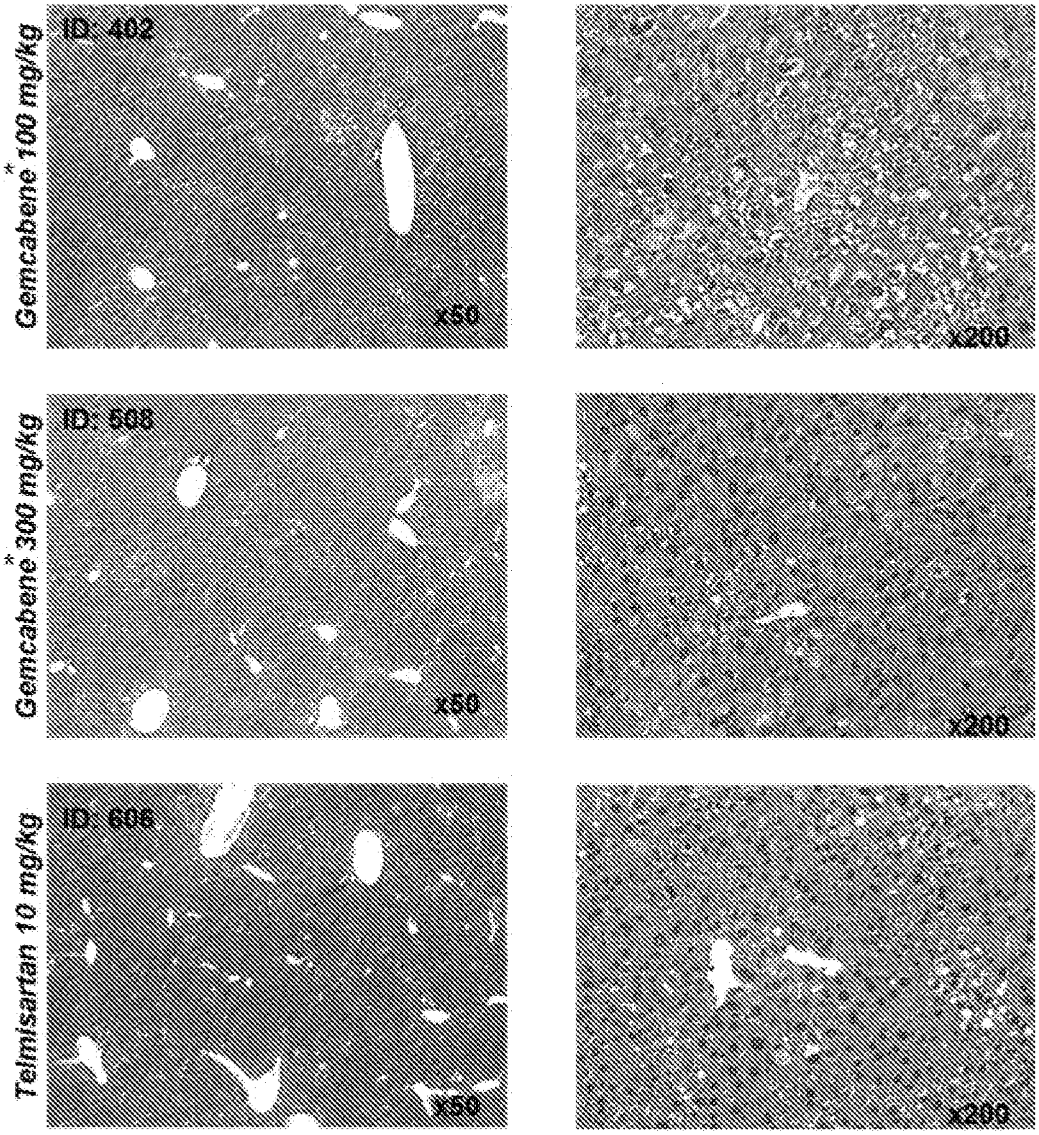
FIG. 5B shows photomicrographs of hematoxylin and eosin-stained liver sections of STAM™ model mice treated with gemcabene calcium salt hydrate Crystal Form 1 having a PSD90 of 52 μm as measured by laser light diffraction (ID: 402 and 508) and photomicrographs of hematoxylin and eosin-stained liver sections of STAM™ model mice treated with reference compound telmisartan.
Figure 6:
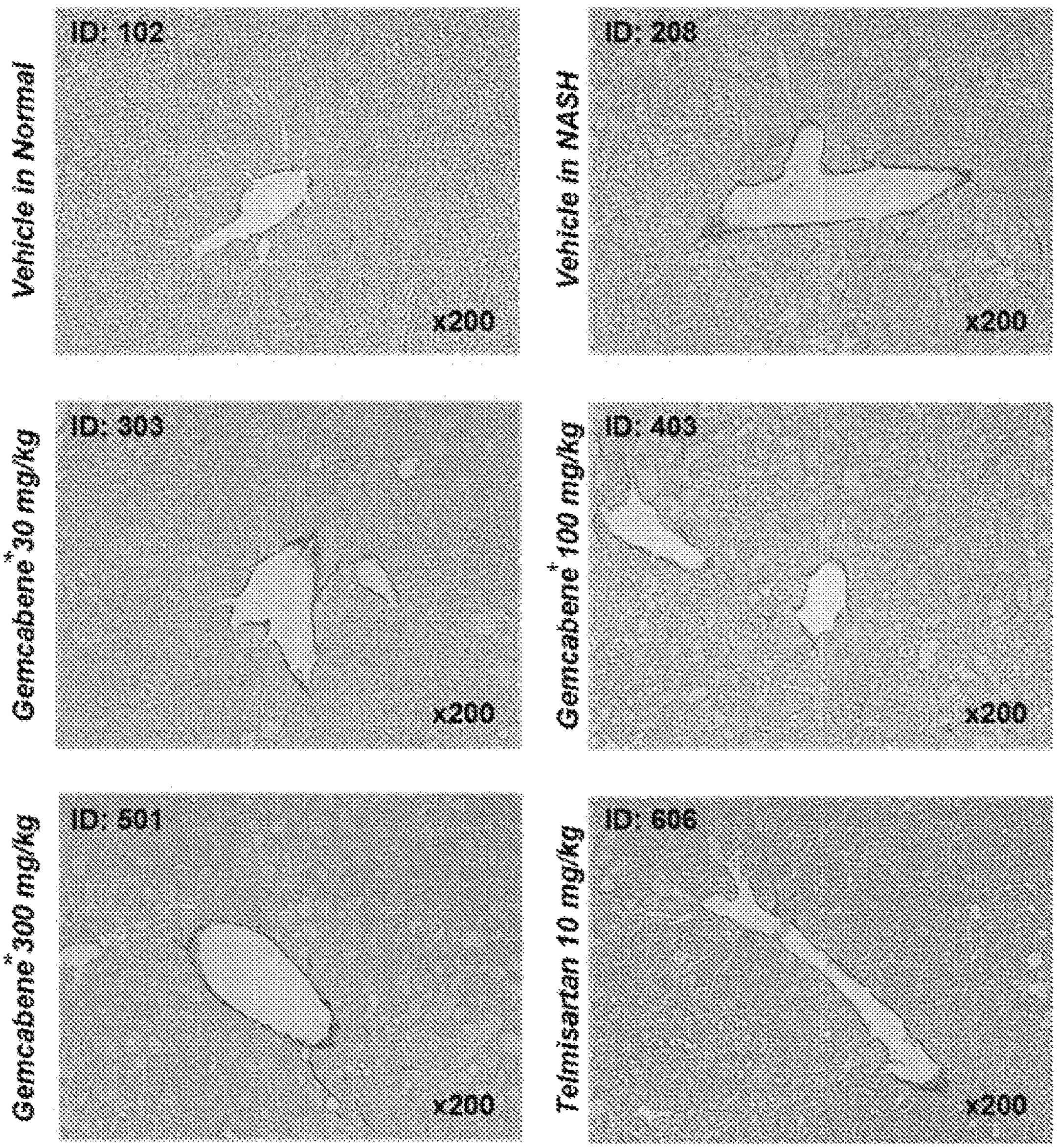
FIG. 6 shows photomicrographs of Sirius red-stained liver sections of STAM™ model mice treated with vehicle (ID: 208), treated with gemcabene calcium salt hydrate Crystal Form 1 having a PSD90 of 52 μm as measured by laser light diffraction (ID: 303, 403, 501), or treated with reference compound telmisartan (ID: 606) and photomicrographs of Sirius red-stained liver sections of normal mice treated with vehicle (ID: 102).
Figure 7:
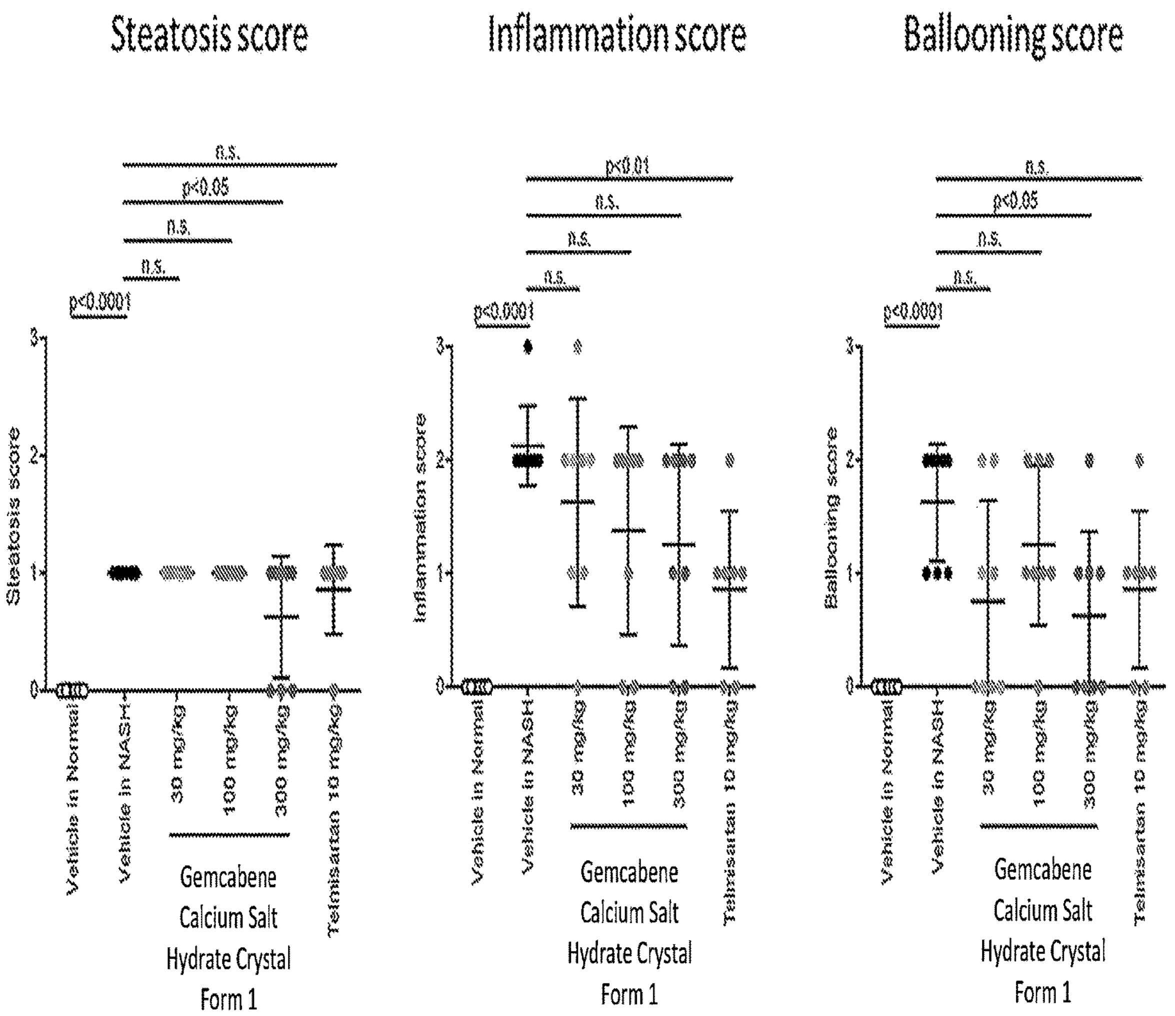
FIG. 7 shows graphs with components of the NAFLD Activity Score (NAS) of STAM™ model mice treated with vehicle, gemcabene calcium salt hydrate Crystal Form 1 having a PSD90 of 52 μm as measured by laser light diffraction or reference compound telmisartan and normal mice treated with vehicle.
Figure 8A:
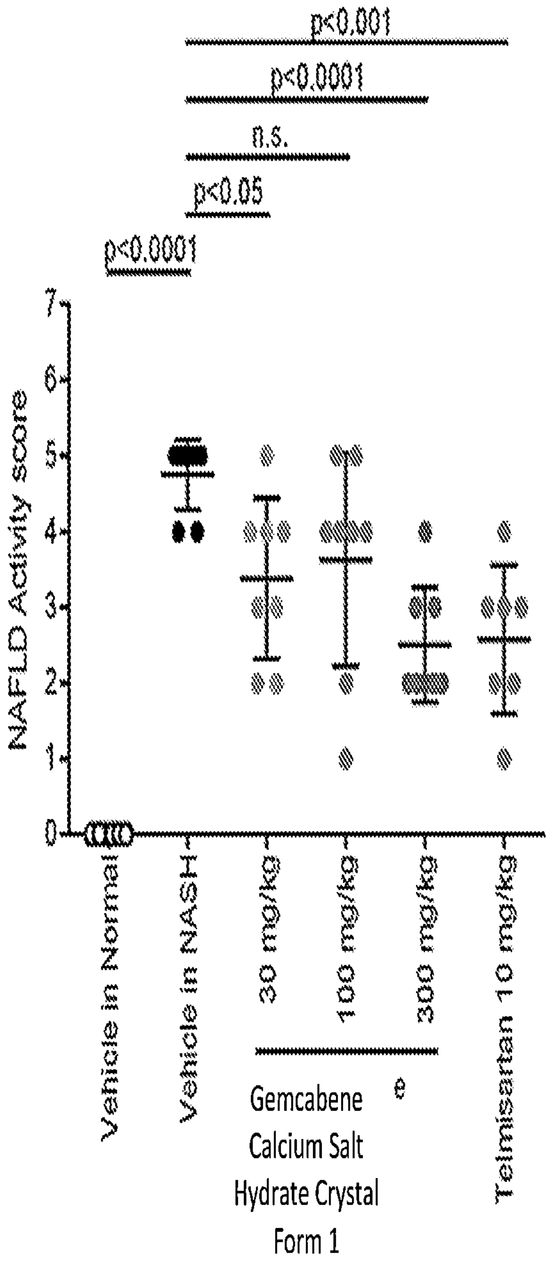
FIG. 8A shows a graph of the NAS in STAM™ model mice treated with (a) vehicle, gemcabene calcium salt hydrate Crystal Form 1 with a PSD90 of 52 μm as measured by laser light diffraction or reference compound telmisartan.
Figure 8B:
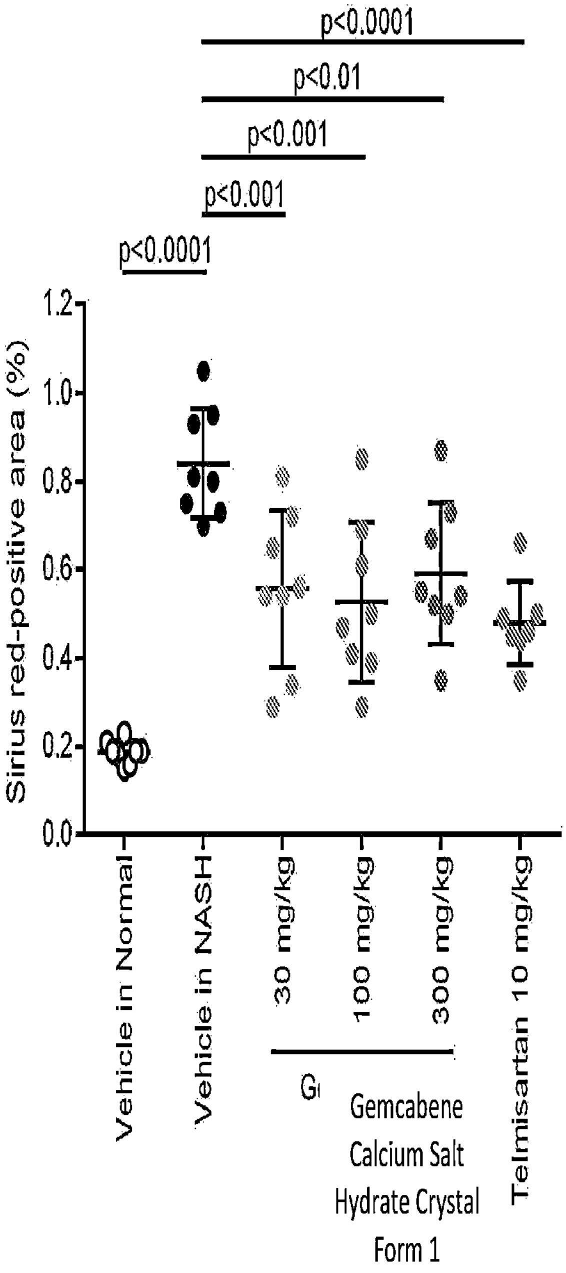
FIG. 8B shows a graph of the liver Sirius-red positive area (the fibrosis area) in STAM™ model mice treated with vehicle, gemcabene calcium salt hydrate Crystal Form 1 having a PSD90 of 52 μm as measured by laser light diffraction or reference compound telmisartan.

Effects of gemcabene calcium salt hydrate Crystal Form 1 (PSD90=52 μm) on various NASH parameters were analyzed and are summarized below. Relevant parameters for gemcabene calcium salt hydrate Crystal Form 1 (PSD90=52 μm) efficacy are related to liver disease and displayed as follows: hepatic pathology (FIGS. 5 and 6), NAFLD score (NAS, composite of steatosis, lobular inflammation, and hepatocellular ballooning (Table 19, FIGS. 7 and 8A), and fibrosis (FIG. 8B). In FIG. 7, the score is an unweighted sum of the scores for liver steatosis, lobular inflammation and ballooning degeneration.

Gemcabene calcium salt hydrate Crystal Form 1 (PSD90=52 μm) diminished micro- and macro-vesicular hepatic fat deposition, hepatocellular ballooning and inflammatory cell infiltration. Representative photomicrographs of hematoxylin and eosin (H&E)-stained liver sections are presented in FIG. 5A and FIG. 5B. H&E-stained liver sections from the vehicle-treated STAM™ mice exhibited micro- and macrovesicular fat deposition, hepatocellular ballooning (degeneration of liver cells and nuclei) and inflammatory cell infiltration compared to the vehicle-treated normal mice. Gemcabene calcium salt hydrate Crystal Form 1 (PSD90=52 μm)-treated (30 and 300 mg/kg) and telmisartan-treated mice showed less steatosis than the vehicle-treated STAM™ mice (see FIGS. 5A and 5B).

Gemcabene calcium salt hydrate Crystal Form 1 (PSD90=52 μm)-treated (30 and 300 mg/kg) and telmisartan-treated mice showed lower lobular inflammation and ballooning (degeneration of liver cells and nuclei) scores in general than the vehicle-treated STAM™ mice (FIG. 5A, FIG. 5B, FIG. 7, Table 19, top), and showed significant reduction in the NAS (FIG. 8A) compared with the vehicle-treated STAM™ mice. The steatosis score and the ballooning score at 300 mg/kg showed a significant decrease as compared to vehicle-treated STAM™ mice (FIG. 8A, Table 19, bottom). Although trending lower, there was no significant difference in NAS between the gemcabene calcium salt hydrate Crystal Form 1 (PSD90=52 μm)-treated (100 mg/kg) and the vehicle-treated STAM™ mice.

Gemcabene calcium salt hydrate Crystal Form 1 (PSD90=52 μm) significantly reduced the fibrosis area. Sirius Red stained liver sections (FIG. 6) from the vehicle-treated STAM™ mice showed increased collagen deposition in the hepatic lobule pericentral region compared with the vehicle-treated normal mice. All gemcabene calcium salt hydrate Crystal Form 1 and telmisartan-treated groups showed significant decreases in fibrosis area compared to the vehicle-treated STAM™ mice (FIG. 6).

TABLE 19

Overview of the NAFLD Activity Score (NAS)

| | | Score | | | | | | | | | | | |
|---|---|---|---|---|---|---|---|---|---|---|---|---|---|
| | | Steatosis | | | | Lobular Inflammation | | | | Hepatocyte Ballooning | | | NAS (mean ± SD) |
| Group | n | 0 | 1 | 2 | 3 | 0 | 1 | 2 | 3 | 0 | 1 | 2 | (P values) |
| Vehicle in Normal | 8 | 8 | — | — | — | 8 | — | — | — | 8 | — | — | 0.0 ± 0.0 |
| Vehicle in NASH | 8 | — | 8 | — | — | — | — | 7 | 1 | — | 3 | 5 | 4.8 ± 0.5 ($p < 0.0001$)[a] |
| Gemcabene[1] 30 mg/kg | 8 | — | 8 | — | — | 1 | 2 | 4 | 1 | 4 | 2 | 2 | 3.4 ± 1.1 ($p < 0.05$)[b] |
| Gemcabene[1] 100 mg/kg | 8 | — | 8 | — | — | 2 | 1 | 5 | — | 1 | 4 | 3 | 3.6 ± 1.4 (ns)b |
| Gemcabene[1] 300 mg/kg | 8 | 3 | 5 | — | — | 2 | 2 | 4 | — | 4 | 3 | 1 | 2.5 ± 0.8 ($p < 0.0001$)[b] |
| Telmisartan 10 mg/kg | 7 | 1 | 6 | — | — | 2 | 4 | 1 | — | 2 | 4 | 1 | 2.6 ± 1.0 ($p < 0.001$)[b] |

| Item | Score | Extent |
|---|---|---|
| Steatosis | 0 | <5% |
| | 1 | 5-33% |
| | 2 | >33-66% |
| | 3 | >66% |

TABLE 19-continued

| Overview of the NAFLD Activity Score (NAS) | | |
|---|---|---|
| Lobular Inflammation | 0 | No foci |
| | 1 | <2 foci/200x |
| | 2 | 2-4 foci/200x |
| | 3 | >4 foci/200x |
| Hepatocyte Ballooning | 0 | None |
| | 1 | Few balloon cells |
| | 2 | Many cells/prominent ballooning |

| | | Vehicle in NASH | Gemcabene[1] | | | Telmisartan |
|---|---|---|---|---|---|---|
| | | (vs. Vehicle in Normal) | 30 mg/kg | 100 mg/kg (vs. Vehicle in NASH) (P values) | 300 mg/kg | 10 mg/kg |
| Histological analyses | NAFLD Activity score | ▲ ($p < 0.0001$) | ▼ ($p < 0.05$) | (NS) | ▼ ($p < 0.0001$) | ▼ ($p < 0.001$) |
| | Steatosis score | ▲ ($p < 0.0001$) | (NS) | (NS) | ▼ ($p < 0.05$) | (NS) |
| | Inflammation score | ▲ ($p < 0.0001$) | (NS) | (NS) | (NS) | ▼ ($p < 0.01$) |
| | Ballooning score | ▲ ($p < 0.0001$) | (NS) | (NS) | ▼ ($p < 0.05$) | (NS) |
| | Fibrosis area | ▲ ($p < 0.0001$) | ▼ ($p < 0.001$) | ▼ ($p < 0.001$) | ▼ ($p < 0.01$) | ▼ ($p < 0.0001$) |

[1]Gemcabene calcium salt hydrate Crystal Form 1 (PSD90 = 52 μm)
— no significant difference;
▲ significant increase;
▼ significant decrease
[a]Compared to Vehicle Normal;
[b]Compared to Vehicle NASH Quantitative RT-PCR Various gene expression markers of liver metabolism were evaluated by Real-Time PCR (RT-PCR) in all mouse groups. Total RNA was extracted from liver samples using RNAiso (Takara Bio, Japan) according to the manufacturer's instructions. One μg of RNA was reverse-transcribed using a reaction mixture containing 4.4 mM $MgCl_2$ (F. Hoffmann-La Roche, Switzerland), 40 U RNase inhibitor (Toyobo, Japan), 0.5 mM dNTP (Promega, USA), 6.28 μM random hexamer (Promega), 5× first strand buffer (Promega), 10 mM dithiothreitol (Invitrogen, USA) and 200 U MMLV-RT (Invitrogen) in a final volume of 20 μL. The reaction was carried out for 1 hour at 37° C., followed by 5 minutes at 99° C. Real-time PCR was performed using real-time PCR DICE and SYBR premix Taq (Takara Bio). To calculate the relative mRNA expression level, the expression of each gene was normalized to that of reference gene 36B4 (gene symbol: Rplp0). Information of PCR-primer sets is described in Tables 20A-20C. Statistical analyses were performed using the Bonferroni Multiple Comparison Test on GraphPad Prism 6 (GraphPad Software Inc., USA). P values<0.05 were considered statistically significant. Results are expressed as mean±SD.

TABLE 20A

Quantitative RT-PCR Primers

| Gene | Set ID | | Sequence |
|---|---|---|---|
| 36B4 | MA057856 | forward | 5'-TTCCAGGCTTTGGGCATCA-3' (SEQ ID NO: 1) |
| | | reverse | 5'-ATGTTCAGCATGTTCAGCAGTGTG-3' (SEQ ID NO: 2) |
| TNF-α | MA117190 | forward | 5'-TATGGCCCAGACCCTCACA-3' (SEQ ID NO: 3) |
| | | reverse | 5'-GGAGTAGACAAGGTACAACCCATC-3' (SEQ ID NO: 4) |
| MCP-1 | MA066003 | forward | 5'-GCATCCACGTGTTGGCTCA-3' (SEQ ID NO: 5) |
| | | reverse | 5'-CTCCAGCCTACTCATTGGGATCA-3' (SEQ ID NO: 6) |
| Alpha-SMA | MA057911 | forward | 5'-AAGAGCATCCGACACTGCTGAC-3' (SEQ ID NO: 7) |
| | | reverse | 5'-AGCACAGCCTGAATAGCCACATAC-3' (SEQ ID NO: 8) |
| TIMP-1 | MA098519 | forward | 5'-TGAGCCCTGCTCAGCAAAGA-3' (SEQ ID NO: 9) |
| | | reverse | 5'-GAGGACCTGATCCGTCCACAA-3' (SEQ ID NO: 10) |
| SREBP-1 | MA096955 | forward | 5'-GGGACAGCTTAGCCTCTACACCAA-3' (SEQ ID NO: 11) |
| | | reverse | 5'-GACTGGTACGGGCCACAAGAA-3' (SEQ ID NO: 12) |
| MIP-1β | MA112918 | forward | 5'-GAGACCAGCAGTCTTTGCTCCA-3' (SEQ ID NO: 13) |
| | | reverse | 5'-GGAGCTGCTCAGTTCAACTCCA-3' (SEQ ID NO: 14) |

TABLE 20A-continued

| Quantitative RT-PCR Primers | | |
|---|---|---|
| Gene | Set ID | Sequence |
| CCR5 | MA173758 | forward 5'-ACCGCTGGGTTCCTGAAAG-3' (SEQ ID NO: 15)<br>reverse 5'-TCAGGCACATCCATAGACAGCA-3' (SEQ ID NO: 16) |
| CCR2 | MA028237 | forward 5'-GCAAGTTCAGCTGCCTGCAA-3' (SEQ ID NO: 17)<br>reverse 5'-ATGCCGTGGATGAACTGAGGTAA-3' (SEQ ID NO: 18) |
| NF-κB | MA128217 | forward 5'-ACCACTGCTCAGGTCCACTGTC-3' (SEQ ID NO: 19)<br>reverse 5'-GCTGTCACTATCCCGGAGTTCA-3' (SEQ ID NO: 20) |

36B4: Ribosomal protein, large, P0 (Rplp0)
TNF-α: Tumor necrosis factor (Tnf)
MCP-1: Chemokine (C—C motif) ligand 2 (Ccl2)
Alpha-SMA: Actin, alpha 2, smooth muscle, aorta (Acta2)
TIMP-1: Tissue inhibitor of metalloproteinase 1 (Timp1)
SREBP-1: Sterol regulatory element binding transcription factor 1 (Srebf1)
MIP-1β: Chemokine (C—C motif) ligand 4 (Ccl4)
CCR5: Chemokine (C—C motif) receptor 5 (Ccr5)
CCR2: Chemokine (C—C motif) receptor 2 (Ccr2)
NF-κB: Nuclear factor of kappa light polypeptide gene enhancer in B cells 1, p105 (Nfkb1)

TABLE 20B

| Quantitative RT-PCR Primers | | |
|---|---|---|
| Gene | Set ID | Sequence |
| CRP | MA095073 | forward 5'-ATGTGGGACTTTGTGCTATCTCCAG-3' (SEQ ID NO: 21)<br>reverse 5'-AGTTCAGTGCCCGCCAGTTC-3' (SEQ ID NO: 22) |
| LDL receptor | MA133540 | forward 5'-TGACCTTCATCCCAGAGCCTTC-3' (SEQ ID NO: 23)<br>reverse 5'-GGCATGAGCGGGTATCCATC-3' (SEQ ID NO: 24) |
| ACC1 | MA082176 | forward 5'-GGATGACAGGCTTGCAGCTATG-3' (SEQ ID NO: 25)<br>reverse 5'-GGAACGTAAGTCGCCGGATG-3' (SEQ ID NO: 26) |
| ACC2 | MA093896 | forward 5'-GAAGCGGGACTCTGTCCTCAAG-3' (SEQ ID NO: 27)<br>reverse 5'-CAGCAGCTGAGCCACCTGTATC-3' (SEQ ID NO: 28) |
| ApoC-III | MA165386 | forward 5'-CTAAGTAGCGTGCAGGAGTCCGATA-3' (SEQ ID NO: 29)<br>reverse 5'-CAGAAGCCGGTGAACTTGTCAGTA-3' (SEQ ID NO: 30) |
| Sulf-2 | MA133987 | forward 5'-GGTGCTTGAGGACCATAAATGAGA-3' (SEQ ID NO: 31)<br>reverse 5'-GCACGTGCAGTTGGTTAAGGAC-3' (SEQ ID NO: 32) |
| PNPLA3 | MA120996 | forward 5'-GTGACCTCATTGCCTGTGACC-3' (SEQ ID NO: 33)<br>reverse 5'-TTAAGCACCAGACTTCACCCAGAC-3' (SEQ ID NO: 34) |
| MMP-2 | MA079820 | forward 5'-GATAACCTGGATGCCGTCGTG-3' (SEQ ID NO: 35)<br>reverse 5'-CTTCACGCTCTTGAGACTTTGGTTC-3' (SEQ ID NO: 36) |
| ADH4 | MA088910 | forward 5'-TGGACGTTATATTGGGCCGTTC-3' (SEQ ID NO: 37)<br>reverse 5'-GTAGGGCATGGGTCACCAGTAAG-3' (SEQ ID NO: 38) |

CRP: C-reactive protein, pentraxin-related (Crp)
LDL receptor: Low-density lipoprotein receptor (Ldlr)
ACC1: Acetyl-Coenzyme A carboxylase alpha (Acaca)
ACC2: Acetyl-Coenzyme A carboxylase beta (Acacb)
ApoC-III: Apolipoprotein C-III (Apoc3)
Sulf-2: Sulfatase 2 (Sulf2)
PNPLA3: Patatin-like phospholipase domain containing 3 (Pnpla3)
MMP-2: Matrix metallopeptidase 2 (Mmp2)
ADH4: Alcohol dehydrogenase 4 (class II), pi polypeptide (Adh4)

TABLE 20C

| Quantitative RT-PCR Primers | | |
|---|---|---|
| Gene | Set ID | Sequence |
| 36B4 | MA057856 | forward 5'-TTCCAGGCTTTGGGCATCA-3' (SEQ ID NO: 39)<br>reverse 5'-ATGTTCAGCATGTTCAGCAGTGTG-3' (SEQ. ID NO: 40) |
| IL-6 | MA152279 | forward 5'-CAACGATGATGCACTTGCAGA-3' (SEQ ID NO: 41)<br>reverse 5'-CTCCAGGTAGCTATGGTACTCCAGA-3' (SEQ ID NO: 42) |
| IL-1β | MA025939 | forward 5'-TCCAGGATGAGGACATGAGCAC-3' (SEQ ID NO: 43)<br>reverse 5'-GAACGTCACACACCAGCAGGTTA-3' (SEQ ID NO: 44) |
| CXCL1/ KC | MA104685 | forward 5'-TGCACCCAAACCGAAGTC-3' (SEQ ID NO: 45)<br>reverse 5'-GTCAGAAGCCAGCGTTCACC-3' (SEQ ID NO: 46) |
| CXCL2/ MIP-2 | MA152904 | forward 5'-GCCAAGGGTTGACTTCAAGAACA-3' (SEQ. ID NO: 47)<br>reverse 5'-AGGCTCCTCCTTTCCAGGTCA-3' (SEQ ID NO: 48) |
| SCD | MA027072 | forward 5'-GCCTGTACGGGATCATACTGGTTC-3' (SEQ ID NO: 49)<br>reverse 5'-CCAGAGCGCTGGTCATGTAGTAGA-3' (SEQ ID NO: 50) |
| LPL | MA106741 | forward 5'-AGAGGCTATAGCTGGGAGCAGAAAC-3' (SEQ ID NO: 51)<br>reverse 5'-GCAAGGGCTAACATTCCAGCA-3' (SEQ ID NO: 52) |
| ANGPTL3 | MA109144 | forward 5'-AAAGACTGGTATTCAAGAACCCTCA-3' (SEQ ID NO: 53)<br>reverse 5'-CCTCTGTTATAAACGGCAGAGCA-3' (SEQ ID NO: 54) |
| ANGPTL4 | MA128743 | forward 5'-CTCTACTTGGGACCAAGACCATGA-3' (SEQ ID NO: 55)<br>reverse 5'-CCATTGAGATTGGAATGGCTACAG-3' (SEQ ID NO: 56) |
| ANGPTL8 | MA077126 | forward 5'-CGGGACACTGTACGGAGACTACAA-3' (SEQ ID NO: 57)<br>reverse 5'-GTGGCCAGTGAGAGCCCATAA-3' (SEQ ID NO: 58) |
| Fetuin-A | MA164631 | forward 5'-TGTGACTTCCACATCCTGAAACAA-3' (SEQ ID NO: 59)<br>reverse 5'-GCACCGTGGGCACAACTTAC-3' (SEQ ID NO: 60) |

36B4: Ribosomal protein, large, P0 (Rplp0)
IL-6: Interleukin 6 (Il6)
IL-1β: Interleukin 1 beta (Il1b)
CXCL1/KC: Chemokine (C—X—C motif) ligand 1 (Cxcl1)
CXCL2/MIP-2: Chemokine (C—X—C motif) ligand 2 (Cxcl2)
SCD: Stearoyl-Coenzyme A desaturase 1 (Scd1)
LPL: Lipoprotein lipase (Lpl)
ANGPTL3: Angiopoietin-like 3 (Angptl3)
ANGPTL4: Angiopoietin-like 4 (Angptl4)
ANGPTL8: Angiopoietin-like 8 (Angptl8)
Fetuin-A: Alpha-2-HS-glycoprotein (Ahsg)

In order to calculate the relative mRNA expression level, the expression of each gene was normalized to that of the reference gene 36B4 (gene symbol: Rplp0). The gene expression levels were measured by quantitative RT-PCR. Results were normalized with values for the vehicle-treated normal group. Gene expression analysis showed downregulation of many inflammatory, fibrosis, cell signaling and cancer genes by gemcabene calcium salt hydrate Crystal Form 1 (PSD90=52 μm) treatment. Gemcabene calcium salt hydrate Crystal Form 1 (PSD90=52 μm) modulated the mRNA expression of many hepatic genes that play a significant role in the liver homeostasis and injury.

Table 21 presents the results of the gene expression RT-PCR measurements normalized to the non-treated group and summaries of the gene functions. Table 22 summarizes the gene expression results. FIGS. 10 and 11-27 display the plots of the relative gene expression data.

Gene expression of inflammatory, fibrosis, cell signaling and cancer genes. Gemcabene calcium salt hydrate Crystal Form 1 (PSD90=52 μm) modulated the mRNA expression of many hepatic genes that play a significant role in the liver homeostasis and injury (Bertola, A. et al. *PLOS One* 5, e13577, doi:10.1371/journal.pone.0013577 (2010)). Table 21 presents the results of the gene expression RT-PCR measurements normalized to the non-treated group and summaries of the gene functions.

Gemcabene calcium salt hydrate Crystal Form 1-treated 100 and 300 mg/kg groups significantly suppressed TNF-α mRNA expression (2.0±0.8 and 1.9±0.7, respectively), while the vehicle-treated STAM™ mice showed a significant up-regulation in TNF-α mRNA levels (3.6±1.0) compared to the vehicle-treated normal mice. There were no significant differences in TNF-α mRNA levels between the vehicle-treated STAM™ mice and any other treatment groups Similarly, NF-κB mRNA levels were slightly up-regulated in vehicle-treated STAM™ mice (1.1±0.1) compared to vehicle-treated normal mice. Gemcabene calcium salt hydrate Crystal Form 1 100 and 300 mg/kg down-regulated NF-κB mRNA expression levels (0.9±0.1 and 0.8±0.1, respectively) compared to the vehicle-treated STAM™ mice.

Gemcabene calcium salt hydrate Crystal Form 1 (PSD90=52 μm) 100 and 300 mg/kg treated groups showed significant reduction in CRP mRNA levels (0.6±0.1 and 0.5±0.1, respectively) compared with the vehicle-treated STAM™ group (1.0±0.2), consistent with the observed clinical reduction of plasma with gemcabene calcium salt hydrate Crystal Form 1 tablets (Stein, E. et al., *J Clin Lipidol* 10, 1212-1222, doi:10.1016/j.jacl.2016.08.002 (2016)). No significant differences in CRP mRNA levels were observed for other treatment groups, particularly telmisartan.

The monocyte chemoattractant protein-1 (MCP-1/CCL2) mRNA in the vehicle-treated STAM™ mice was significantly up-regulated compared with the vehicle-treated normal mice. Gemcabene calcium salt hydrate Crystal Form 1 (PSD90=52 μm) 100 and 300 mg/kg treated mice significantly down-regulated MCP-1 mRNA expression levels compared with the vehicle-treated STAM™ mice (1.7±0.7 and 1.6±0.7, respectively, versus 3.6±1.7), and higher than telmisartan (2.1±1.0).

Expression of fibrotic genes showed similar patterns. TNF-α induction in hepatic stellar cells results in the expression and deposition of smooth muscle α-actin (α-SMA). A significant increase in α-SMA mRNA expression was observed in the vehicle-treated STAM™ mice (3.1±0.9) compared with the vehicle-treated normal mice (1.0±0.3). The α-SMA mRNA expression levels of all other treatment groups were down-regulated.

The SREBP-1 gene is associated with lipogenesis, and its levels are indirectly regulated by cholesterol, insulin and other endogenous molecules. In this experiment, there were no differences in the SREBP-1 mRNA levels between the vehicle-treated STAM™ mice and any other treatment groups.

Matrix metalloproteinase-2 (MMP-2) mRNA levels were up-regulated in vehicle-treated STAM™ mice (1.9±0.7), while gemcabene calcium salt hydrate Crystal Form 1 (PSD90=52 μm)-treated mice at 100 and 300 mg/kg doses significantly down-regulated the MMP-2 mRNA expression levels (0.5±0.2 and 0.9±0.2, respectively).

Tissue inhibitor of metalloproteinase 1 (TIMP-1) mRNA levels were significantly up-regulated in the vehicle-treated STAM™ mice (12.9±9.0) compared to the vehicle-treated normal mice. Gemcabene calcium salt hydrate Crystal Form 1 (PSD90=52 μm) 100 and 300 mg/kg treated groups significantly down-regulated TIMP-1 mRNA expression (3.8±1.6 and 4.4±2.1, respectively).

Chemokine (C—C motif) ligand 4, CCL4, also known as macrophage inflammatory protein-1β (MIP-1β) is known to be elevated in NAFLD. Hepatic MIP-1β mRNA levels were significantly higher in the vehicle-treated STAM™ mice (5.6±2.0) compared with vehicle-treated normal mice. Gemcabene calcium salt hydrate Crystal Form 1 (PSD90=52 μm) 100 and 300 mg/kg treated mice and telmisartan, showed significant down-regulation of MIP-1β mRNA levels (2.3±0.9, 2.8±1.4, and 3.9±1.5, respectively).

Sulf-2 is one of the sulfatases that modulates the sulfation status of heparan sulfate proteoglycans (HSPGs), particularly Syndecan-1, in the extracellular hepatic matrix, and regulate a number of critical signaling pathways. Its up-regulation is associated with hepatic carcinogenesis, Rosen, S. D. & Lemjabbar-Alaoui, H. *Expert Opin Ther Targets* 14, 935-949, doi:10.1517/14728222.2010.504718 (2010). In the current study, vehicle-treated STAM™ mice showed a significant up-regulation of Sulf-2 mRNA levels (5.2±1.2) compared with the vehicle-treated normal group. Gemcabene calcium salt hydrate Crystal Form 1 (PSD90=52 μm) 100 and 300 mg/kg-treated mice significantly down-regulated Sulf-2 mRNA expression levels (3.8 f 0.7 and 3.3±0.9, respectively).

Expression of CCR2 and CCR5 mRNA. Interactions between C—C chemokine receptor types 2 (CCR2) and its ligand, CCL2, mediate fibrogenesis by promoting monocyte/macrophage recruitment and tissue infiltration, as well as hepatic stellate cell activation (Lefebvre, E. et al., *PLOS One* 11, e0158156, doi:10.1371/journal.pone.0158156 (2016)). Vehicle-treated STAM™ mice showed significant up-regulation in CCR2 mRNA expression levels (3.5±1.7) compared with the vehicle-treated normal mice. Gemcabene calcium salt hydrate Crystal Form 1 (PSD90=52 μm) 100 and 300 mg/kg treated groups showed significant down-regulation in CCR2 mRNA expression levels (1.6±0.4 and 1.7±0.7, respectively) to a greater extent when compared to telmisartan (2.4±0.8).

The chemokine CCL5/RANTES and its receptor, CCR5, play important roles in the progression of hepatic inflammation and fibrosis (Lefebvre, E. et al. *PLOS One* 11, e0158156, doi:10.1371/journal.pone.0158156 (2016)). The vehicle-treated NASH group showed a significant increase in CCR5 mRNA levels (2.3±0). Gemcabene calcium salt hydrate Crystal Form 1 100 and 300 mg/kg and Telmisartan-treated groups significantly down-regulated CCR5 mRNA expression levels (1.4±0.3, 1.3±0.3, and 1.5±0.3, respectively).

Genes of lipogenesis and lipid metabolism: ACC-1, ApoC-III, and PNPLA3. Both Acetyl CoA carboxylases 1 and 2 (ACC-1 and ACC-2) catalyze the synthesis of malonyl-CoA, the substrate for fatty acid synthesis and the regulator of fatty acid oxidation, major players in the NAFLD pathogenesis (Savage, D. B. et al., *J Clin Invest* 116, 817-824, doi:10.1172/JCI27300 (2006)). Gemcabene calcium salt hydrate Crystal Form 1 (PSD90=52 μm) 100 mg/kg and telmisartan-treated mice down-regulated ACC-1 mRNA expression levels compared to the vehicle-treated STAM™ mice (0.7±0.1 compared to 0.9±0.2).

Patatin-like phospholipase domain-containing protein 3 (PNPLA3) mRNA expression Hazlehurst, J. M. et al., *Metabolism* 65, 1096-1108, doi:10.1016/j.metabol.2016.01.001 (2016), (Speliotes, E. K. et al. *Hepatology* 52, 904-912, doi:10.1002/hep.23768 (2010) was significantly down-regulated in the vehicle-treated STAM™ mice compared to the vehicle-treated normal mice. However, there were no significant differences in PNPLA3 mRNA expression levels between the vehicle-treated STAM™ mice and any of the treatment groups.

In this model, gemcabene calcium salt hydrate Crystal Form 1 (PSD90=52 μm) and telmisartan showed no effect on the LDL receptor gene expression.

Regulation of the human alcohol dehydrogenase 4 (ADH-4) gene. ADH-4, associated with NAFLD, contributes to ethanol metabolism at moderate and high concentrations (Baker, S. S. et al., *PLOS One* 5, e9570, doi:10.1371/journal.pone.0009570 (2010). Induction of NASH in the STAM™ mice had no significant effect on ADH-4 mRNA levels (vehicle-treated NASH and vehicle-treated normal groups have similar values). However, gemcabene calcium salt hydrate Crystal Form 1 (PSD90=52 μm) 100 and 300 mg/kg and telmisartan-treated groups down-regulated ADH-4 mRNA expression levels compared to the vehicle-treated STAM™ group (0.6±0.1, 0.5±0.1 and 0.6±0.2, respectively, compared to 0.9±0.3).

TABLE 21

Gene Expression Analysis

| | Parameter (mean ± SD) | | | | | | |
|---|---|---|---|---|---|---|---|
| | Vehicle in Normal (n = 8) | [a]Vehicle in NASH (n = 8) | [b]Gemcabene[1] 30 mg/kg (n = 8) | [b]Gemcabene[1] 100 mg/kg (n = 8) | [b]Gemcabene[1] 300 mg/kg (n = 8) | [b]Telmisartan 10 mg/kg (n = 7) | Function |
| TNF-α | 1.0 ± 0.3 | 3.6 ± 1.0 (p < 0.0001) | 4.0 ± 1.8 (NS) | 2.0 ± 0.8 (p < 0.05) | 1.9 ± 0.7 (p < 0.05) | 3.0 ± 1.2 (NS) | Inflammation - ↑ in NAFLD |
| NF-κB | 1.0 ± 0.1 | 1.3 ± 0.2 (p < 0.001) | 1.3 ± 0.2 (NS) | 0.9 ± 0.1 (p < 0.0001) | 0.8 ± 0.1 (p < 0.0001) | 1.1 ± 0.1 (p < 0.05) | ↑ Proinflammatory genes (cytokines, chemokines, and adhesion molecules) |
| CRP | 1.0 ± 0.2 | 1.0 ± 0.2 (NS) | 0.9 ± 0.2 (NS) | 0.6 ± 0.1 (p < 0.0001) | 0.5 ± 0.1 (p < 0.0001) | 0.9 ± 0.1 (p < 0.0001) | Surrogate marker of hepatic inflammation in NASH |
| MCP-1 | 1.0 ± 0.4 | 3.6 ± 1.7 (p < 0.001) | 3.2 ± 1.5 (NS) | 1.7 ± 0.7 (p < 0.01) | 1.6 ± 0.7 (p < 0.01) | 2.1 ± 1.0 (p < 0.05) | ↑ Chemokine following inflammation in stellate cells NAFLD |
| α-SMA | 1.0 ± 0.3 | 3.1 ± 0.9 (p < 0.0001) | 2.6 ± 0.6 (NS) | 2.4 ± 0.9 (NS) | 2.5 ± 0.7 (NS) | 2.3 ± 0.7 (NS) | ↑TNF-α ↑expression and deposition of α-SMA |
| SREBP-1 | 1.0 ± 0.3 | 0.9 ± 0.2 (NS) | 0.9 ± 0.2 (NS) | 0.9 ± 0.2 (NS) | 0.7 ± 0.1 (NS) | 0.7 ± 0.2 (NS) | Regulates genes required for lipogenesis; ↑ de novo C synthesis and uptake and FA synthesis |
| MMP-2 | 1.0 ± 0.2 | 1.9 ± 0.7 (p < 0.01) | 1.7 ± 0.5 (NS) | 0.5 ± 0.2 (p < 0.0001) | 0.9 ± 0.2 (p < 0.001) | 1.4 ± 0.7 (NS) | Degrades type-IV collagen; involved in NAFLD pathogenesis |
| TIMP-1 | 1.0 ± 0.3 | 12.9 ± 9.0 (p < 0.0001) | 9.9 ± 4.9 (NS) | 3.8 ± 1.6 (p < 0.01) | 4.4 ± 2.1 (p < 0.01) | 8.6 ± 5.1 (NS) | ↓ collagenase activity |
| MIP-1β | 1.0 ± 0.2 | 5.6 ± 2.0 (p < 0.0001) | 5.4 ± 3.2 (NS) | 2.3 ± 0.9 (p < 0.01) | 2.8 ± 1.4 (p < 0.05) | 3.9 ± 1.5 (NS) | ↑ Pyrogenic, mitogenic, induce the synthesis and release of pro-inflammatory cytokines such as IL-1, IL-6 and TNF-α from fibroblasts and macrophages |
| Sulf-2 | 1.0 ± 0.3 | 5.2 ± 1.2 (p < 0.001) | 5.1 ± 1.1 (NS) | 3.8 ± 0.7 (p < 0.05) | 3.3 ± 0.9 (p < 0.001) | 3.9 ± 0.9 (NS) | Sulfation of heparan sulfate proteoglycans (HSPGs), (i.e., Syndecan-1), in the extracellular hepatic matrix, critical signaling pathway |
| CCR5 | 1.0 ± 0.2 | 2.3 ± 0.7 (p < 0.0001) | 2.4 ± 0.9 (NS) | 1.4 ± 0.3 (p < 0.01) | 1.3 ± 0.3 (p < 0.01) | 1.5 ± 0.3 (p < 0.05) | Progression of hepatic inflammation and fibrosis |
| CCR2 | 1.0 ± 0.2 | 3.5 ± 1.7 (p < 0.0001) | 3.3 ± 1.0 (NS) | 1.6 ± 0.4 (p < 0.001) | 1.7 ± 0.7 (p < 0.01) | 2.4 ± 0.8 (NS) | Monocyte/macrophage recruitment and tissue infiltration, hepatic stellate cell activation |
| ACC1 | 1.0 ± 0.2 | 0.9 ± 0.2 (NS) | 1.0 ± 0.1 (NS) | 0.7 ± 0.1 (p < 0.05) | 0.8 ± 0.1 (NS) | 0.7 ± 0.1 (p < 0.01) | Hepatic lipogenesis (CoA synthesis, FFA synthesis and oxidation) |
| ACC2 | 1.0 ± 0.2 | 0.5 ± 0.1 (p < 0.0001) | 0.6 ± 0.2 (NS) | 0.4 ± 0.1 (NS) | 0.5 ± 0.1 (NS) | 0.3 ± 0.1 (p < 0.05) | |
| ApoC-III | 1.0 ± 0.2 | 0.7 ± 0.1 (p < 0.001) | 0.7 ± 0.1 (NS) | 0.5 ± 0.0 (p < 0.01) | 0.4 ± 0.1 (p < 0.0001) | 0.8 ± 0.2 (NS) | Clearance of triglyceride-rich lipoproteins |
| PNPLA3 | 1.0 ± 0.4 | 0.3 ± 0.1 (p < 0.0001) | 0.3 ± 0.1 (NS) | 0.2 ± 0.1 (NS) | 0.2 ± 0.2 (NS) | 0.1 ± 0.0 (NS) | Isomorphs associated with insulin resistance and NASH |
| ADH-4 | 1.0 ± 0.2 | 0.9 ± 0.3 (NS) | 0.8 ± 0.2 (NS) | 0.6 ± 0.1 (p < 0.05) | 0.5 ± 0.1 (p < 0.001) | 0.6 ± 0.2 (p < 0.01) | Oxidation of ethanol to aldehydes and ketones; reduces NAD to NADH |
| LDL receptor | 1.0 ± 0.1 | 0.9 ± 0.2 (NS) | 0.9 ± 0.2 (NS) | 0.9 ± 0.2 (NS) | 0.8 ± 0.1 (NS) | 0.7 ± 0.3 (NS) | C homeostasis, cell signaling |
| IL-6 | 1.0 ± 0.6 | 5.3 ± 5.4 | 4.6 ± 4.7 | 0.9 ± 0.3 | 0.6 ± 0.2 | 0.8 ± 0.4 | Cytokine associated with increased inflammation |
| IL-1β | 1.0 ± 0.3 | 0.9 ± 0.4 | 1.0 ± 0.5 | 1.1 ± 0.5 | 0.7 ± 0.3 | 0.7 ± 0.2 | Cytokine associated with increased inflammation |
| CXCL1/KC | 1.0 ± 1.3 | 0.7 ± 0.3 | 0.8 ± 0.4 | 0.2 ± 0.1 | 0.2 ± 0.1 | 0.6 ± 0.3 | Cytokine expressed in macrophages, neutrophils and epithelial cells that has neutrophil attractant activity, associated with inflammation angiogenesis, wound healing and tumor growth |
| CXCL2/MIP-2 | — | — | — | — | — | — | Cytokine secreted by monocytes and macrophages and is a chemoattractant for polymorphonuclear leukocytes and hematopoietic stem cells |
| SCD1 | 1.0 ± 0.2 | 0.2 ± 0.1 | 0.2 ± 0.1 | 0.3 ± 0.1 | 0.4 ± 0.2 | 0.1 ± 0.0 | Enzyme in de novo fatty acid synthesis that introduces double bond in palmitoyl-CoA and stearitoyl-CoA |
| LPL | 1.0 ± 0.2 | 2.2 ± 0.4 | 3.8 ± 0.9 | 7.4 ± 0.9 | 6.9 ± 1.1 | 2.4 ± 0.5 | Cell membrane bound protein that hydrolysis TG in VLDL and VLDL remnants to release FA for tissue delivery |
| ANGPTL3 | 1.0 ± 0.1 | 0.6 ± 0.1 | 0.7 ± 0.2 | 0.4 ± 0.1 | 0.4 ± 0.1 | 0.7 ± 0.2 | Protein in plasma that inhibits LPL activity |
| ANGPTL4 | 1.0 ± 0.5 | 2.8 ± 0.3 | 2.9 ± 0.5 | 1.6 ± 0.3 | 1.7 ± 0.3 | 2.1 ± 0.3 | Protein in plasma that inhibits LPL activity |
| ANGPTL8 | 1.0 ± 0.6 | 0.3 ± 0.1 | 0.3 ± 0.1 | 0.4 ± 0.1 | 0.2 ± 0.1 | 0.3 ± 0.1 | Protein in plasma that inhibits LPL activity |

TABLE 21-continued

Gene Expression Analysis

| | Parameter (mean ± SD) | | | | | | |
|---|---|---|---|---|---|---|---|
| | Vehicle in Normal (n = 8) | [a]Vehicle in NASH (n = 8) | [b]Gemcabene[1] 30 mg/kg (n = 8) | [b]Gemcabene[1] 100 mg/kg (n = 8) | [b]Gemcabene[1] 300 mg/kg (n = 8) | [b]Telmisartan 10 mg/kg (n = 7) | Function |
| Fetuin-A | 1.0 ± 0.1 | 1.0 ± 0.1 | 1.1 ± 0.4 | 0.7 ± 0.1 | 0.7 ± 0.1 | 1.0 ± 0.1 | An inhibitor of systemic calcification. Enhances fatty acid induced insulin resistance. It is also associated with NASH due to its pro-inflammatory activity, however, in contrast has also been associated with anti-inflammatory activity. Also a negative acute phase - reactant- may be protective in sepsis, endotoxemia, promote wound healing and maybe neuroprotective. |

[1]Gemcabene calcium salt hydrate Crystal Form 1 (PSD90 = 52 μm)

[a]Compared to Vehicle Normal;

[b]Compared to Vehicle NASH

Abbreviations: ACC = Acetyl-CoA carboxylase; ADH = Alcohol dehydrogenase; C = cholesterol; CCR = C-C chemokine receptor; CRP = C-reactive protein; FA = Fatty acid; FFA = free fatty acid; HSPGs = heparan sulfate proteoglycans; LDL = low-density lipoprotein; MCoA = Malonyl-CoA; MCP = Monocyte chemotactic protein; MMP = Matrix metalloproteinase; MIP = Macrophage inflammatory protein; NAD = nicotinamide adenine dinucleotide; NF-κB = Nuclear factor-kappa B; PNPLA = Patatin-like phospholipase-containing domain; SMA = Smooth muscle actin; SPF = Specific pathogen-free; SREBP = Sterol regulatory element-binding protein; Sulf = Sulfatase; TIMP = Tissue inhibitor of metalloproteinase; TNF = Tumor necrosis factor.

TABLE 22

Gene Expression Summary

| | | Vehicle in NASH | Gemcabene[1] | | | Telmisartan |
|---|---|---|---|---|---|---|
| | | (vs Vehicle in Normal) | 30 mg/kg | 100 mg/kg (vs Vehicle in NASH) | 300 mg/kg | 10 mg/kg |
| Gene Expression Analyses | TNF-alpha | ▲ ($p < 0.0001$) | NS | ▼ ($p < 0.05$) | ▼ ($p < 0.05$) | NS |
| | MCP-1 | ▲ ($p < 0.001$) | NS | ▼ ($p < 0.01$) | ▼ ($p < 0.01$) | ▼ ($p < 0.05$) |
| | Alpha-SMA | ▲ ($p < 0.0001$) | NS | NS | NS | NS |
| | TIMP-1 | ▲ ($p < 0.0001$) | NS | ▼ ($p < 0.01$) | ▼ ($p < 0.01$) | NS |
| | SREBP-1 | NS | NS | NS | NS | NS |
| | MIP-1Beta | ▲ ($p < 0.0001$) | NS | ▼ ($p < 0.01$) | ▼ ($p < 0.05$) | NS |
| | CCR5 | ▲ ($p < 0.0001$) | NS | ▼ ($p < 0.01$) | ▼ ($p < 0.01$) | ▼ ($p < 0.05$) |
| | CCR2 | ▲ ($p < 0.0001$) | NS | ▼ ($p < 0.001$) | ▼ ($p < 0.01$) | NS |
| | NF-κB | ▲ ($p < 0.001$) | NS | ▼ ($p < 0.0001$) | ▼ ($p < 0.0001$) | ▼ ($p < 0.05$) |
| | CRP | NS | NS | ▼ ($p < 0.0001$) | ▼ ($p < 0.0001$) | ▼ ($p < 0.0001$) |
| | LDL receptor | NS | NS | NS | NS | NS |
| | ACC1 | NS | NS | ▼ ($p < 0.05$) | NS | ▼ ($p < 0.05$) |
| | ACC2 | ▼ ($p < 0.001$) | NS | NS | NS | ▼ ($p < 0.05$) |
| | ApoC-III | ▼ ($p < 0.001$) | NS | ▼ ($p < 0.01$) | ▼ ($p < 0.0001$) | NS |
| | Sulf-2 | ▲ ($p < 0.001$) | NS | ▼ ($p < 0.05$) | ▼ ($p < 0.001$) | NS |
| | PNPLA3 | ▼ ($p < 0.0001$) | NS | NS | NS | NS |
| | MMP-2 | ▲ ($p < 0.01$) | NS | ▼ ($p < 0.0001$) | ▼ ($p < 0.001$) | NS |
| | ADH4 | NS | NS | ▼ ($p < 0.05$) | ▼ ($p < 0.001$) | ▼ ($p < 0.01$) |
| Plasma and Liver Biochemical Anaylses | Plasma leptin | NS | NS | NS | NS | NS |
| | Plasma CRP | ▲ ($p < 0.001$) | NS | ▼ ($p < 0.0001$) | ▼ ($p < 0.0001$) | NS |
| | Plasma adiponectin | ▼ ($p < 0.0001$) | NS | NS | NS | ▲ ($p < 0.0001$) |
| | Liver triglceride | ▲ ($p < 0.0001$) | NS | NS | NS | ▼ ($p < 0.01$) |

TABLE 22-continued

Gene Expression Summary

| | | Vehicle in NASH | Gemcabene[1] | | | Telmisartan |
|---|---|---|---|---|---|---|
| | | (vs Vehicle in Normal) | 30 mg/kg | 100 mg/kg (vs Vehicle in NASH) | 300 mg/kg | 10 mg/kg |
| | Liver free fatty acid | ▲ ($p < 0.05$) | NS | NS | ▲ ($p < 0.0001$) | ▲ ($p < 0.0001$) |
| | Liver hydroxyproline | NS | NS | NS | NS | NS |
| Histological Analysis | NAFLS Activity Score | ▲ ($p < 0.0001$) | ▼ ($p < 0.05$) | NS | ▼ ($p < 0.0001$) | ▼ ($p < 0.001$) |
| | Steatosis Score | ▲ ($p < 0.0001$) | NS | NS | ▼ ($p < 0.05$) | NS |
| | Inflammation score | ▲ ($p < 0.0001$) | NS | NS | NS | ▼ ($p < 0.01$) |
| | Ballooning score | ▲ ($p < 0.0001$) | NS | NS | ▼ ($p < 0.05$) | NS |
| | Fibrosis score | ▲ ($p < 0.001$) | ▼ ($p < 0.001$) | ▼ ($p < 0.001$) | ▼ ($p < 0.01$) | ▼ ($p < 0.0001$) |
| | NAFLS Activity Score | 4.8 | 3.4 | 3.6 | 2.5 | 2.6 |
| | Sirius red-positive area | 0.84% | 0.56% | 0.53% | 0.59% | 0.48% |

NS = no significant difference;
▲ significant increase;
▼ significant decrease
[1]Gemcabene calcium salt hydrate Crystal Form 1 (PSD90 = 52 μm)

Figure 31:
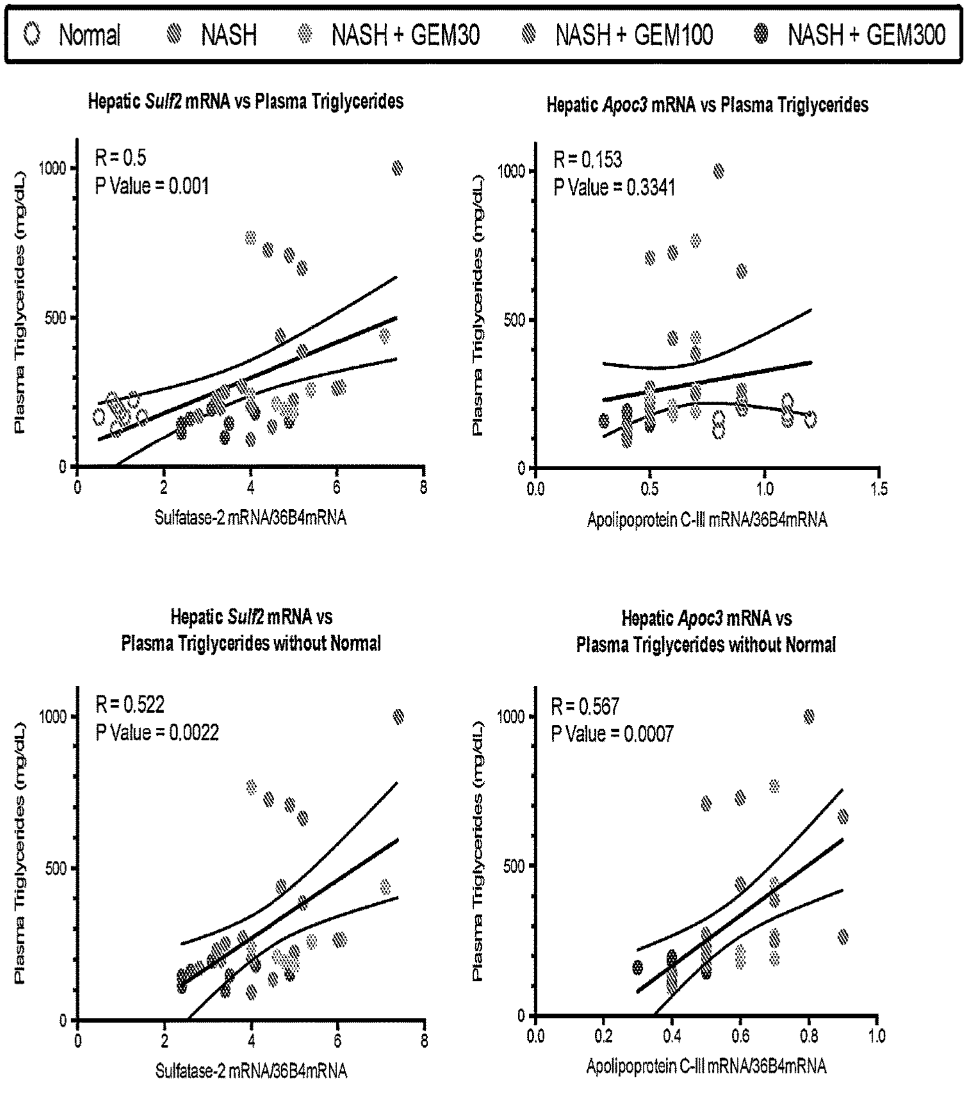
FIG. 31 shows the effect of gemcabene calcium salt hydrate Crystal Form 1 having a PSD90 of 52 μm as measured by laser light diffraction on the correlation between hepatic ApoC-III or hepatic Sulf-2 and plasma triglycerides in a diabetic mouse model.
Figure 32:
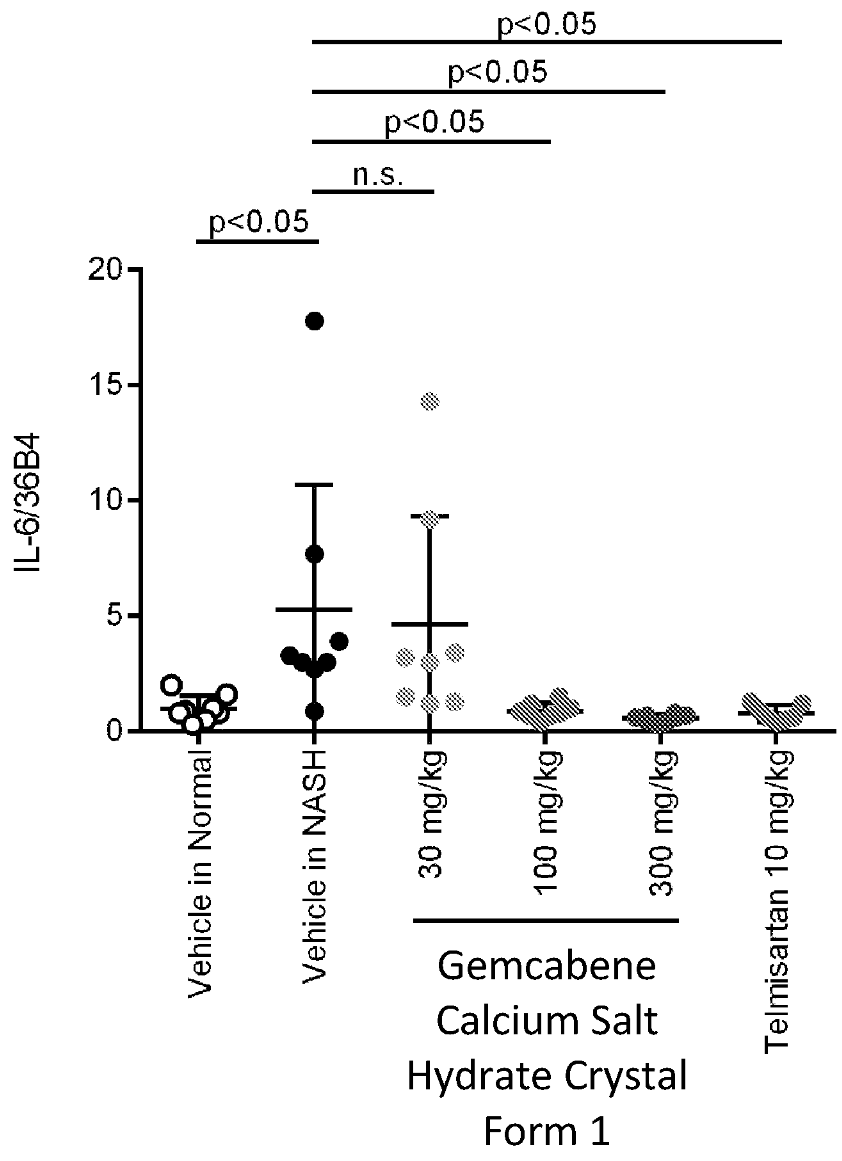
FIG. 32 is a graph showing hepatic gene expression levels for interleukin 6 (IL-6) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 33:
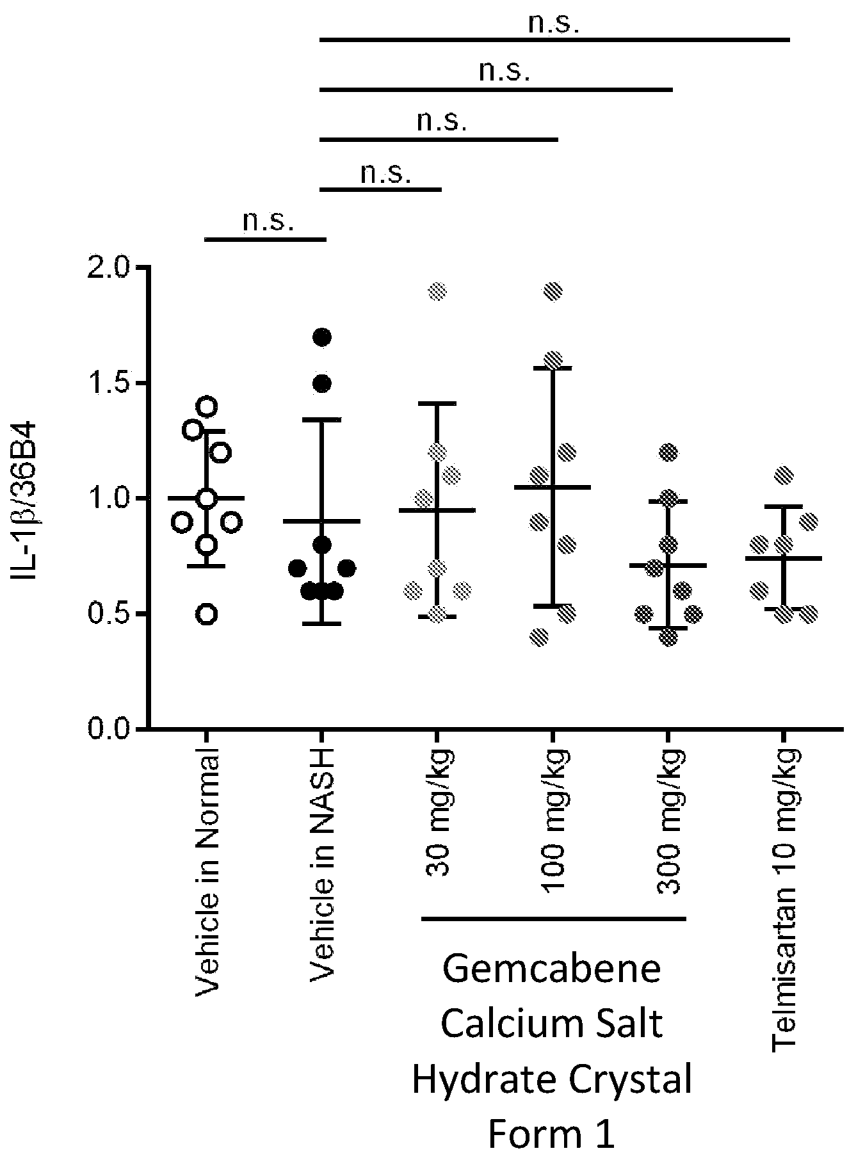
FIG. 33 is a graph showing hepatic gene expression levels for interleukin 1β (IL-1β) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 34:
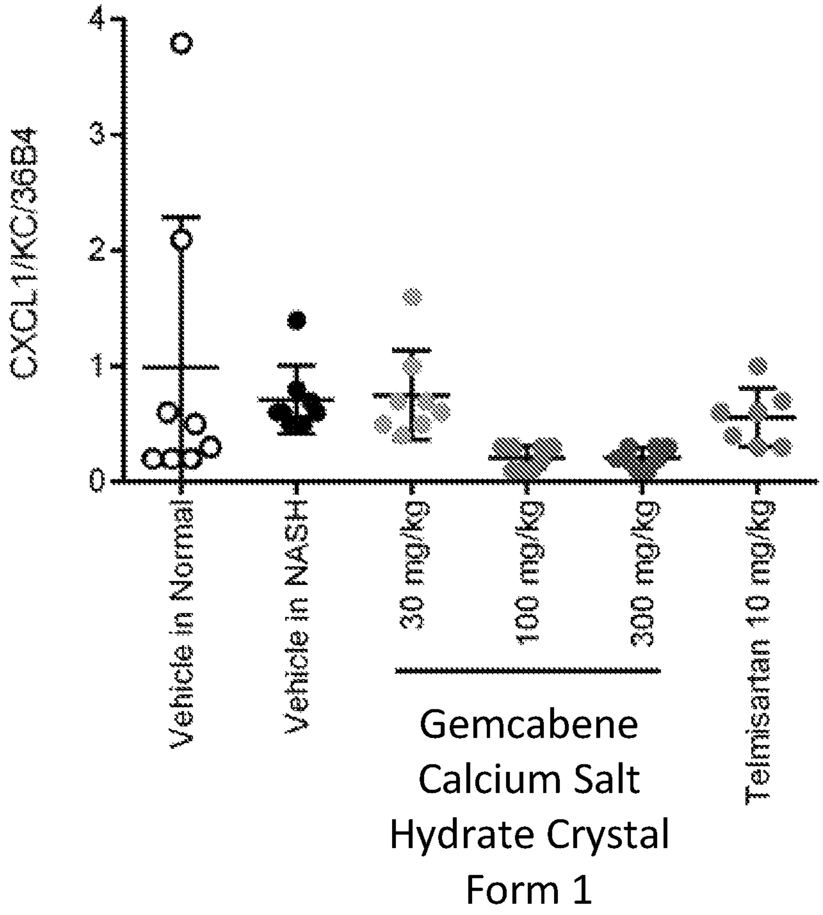
FIG. 34 is a graph showing hepatic gene expression levels for chemokine (C—X—C motif) ligand 1 (CXCL1/KC) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 35:
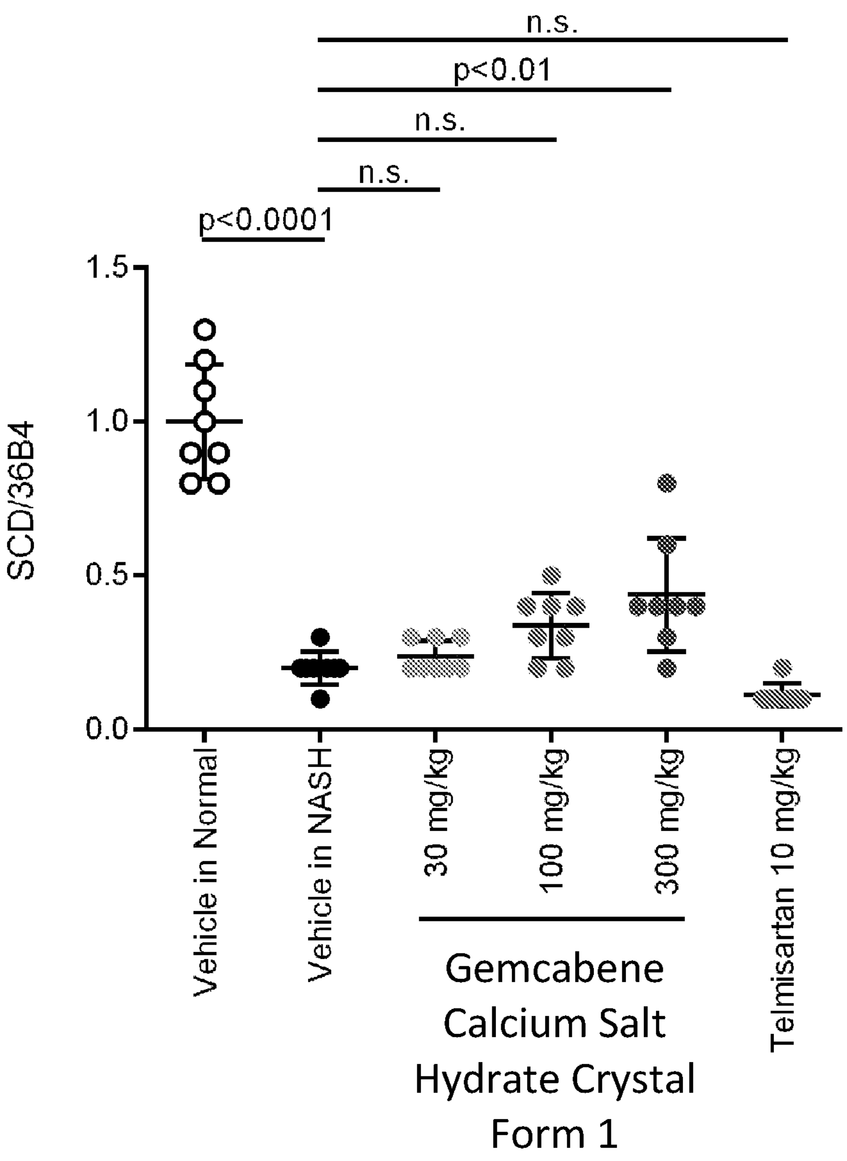
FIG. 35 is a graph showing hepatic gene expression levels for stearoyl-coenzyme A desaturase (SCD) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 36:
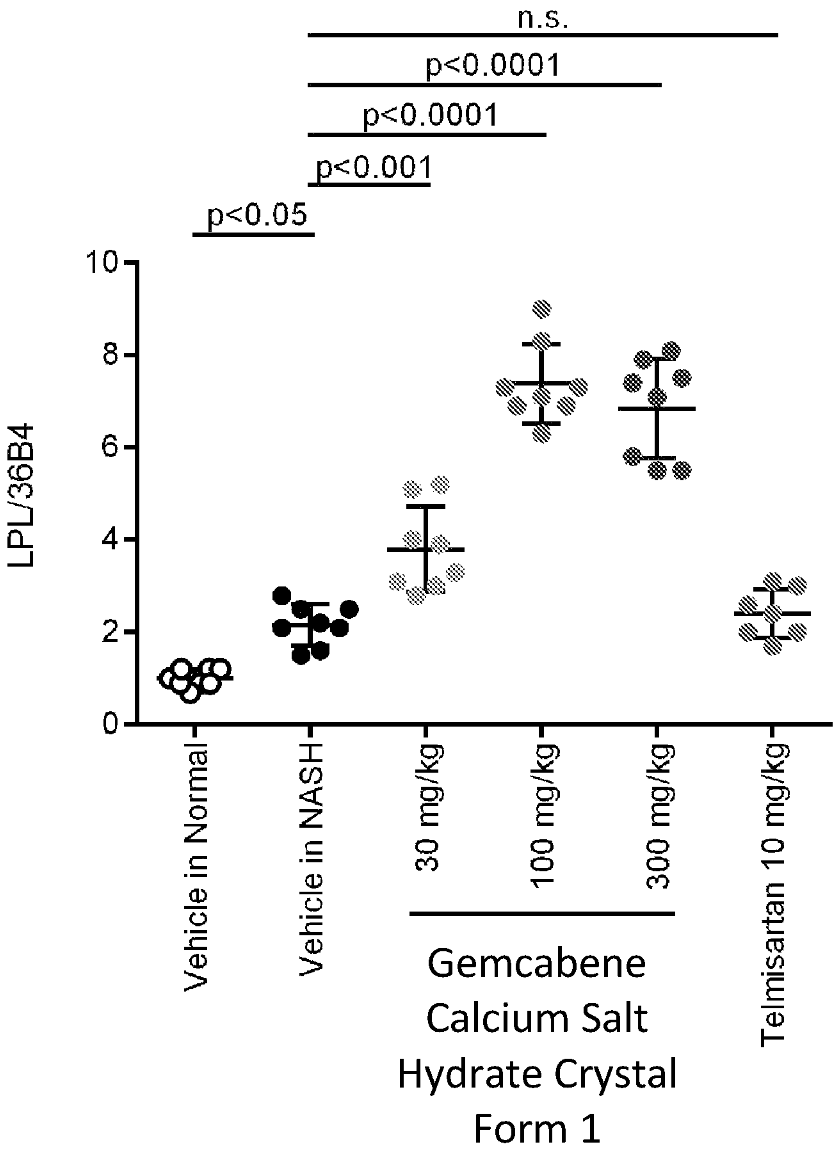
FIG. 36 is a graph showing hepatic gene expression levels for lipoprotein lipase (LPL) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 37:
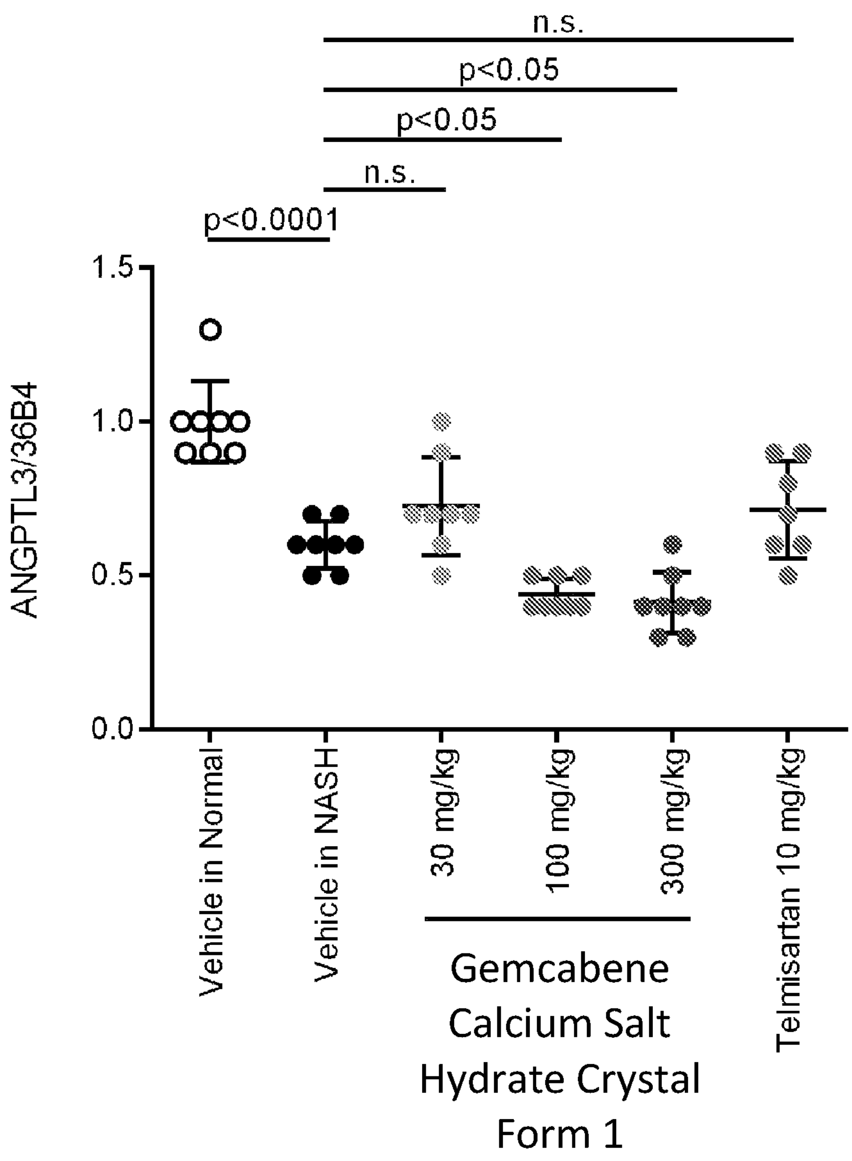
FIG. 37 is a graph showing hepatic gene expression levels for angiopoietin-like protein 3 (ANGPTL3) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 38:
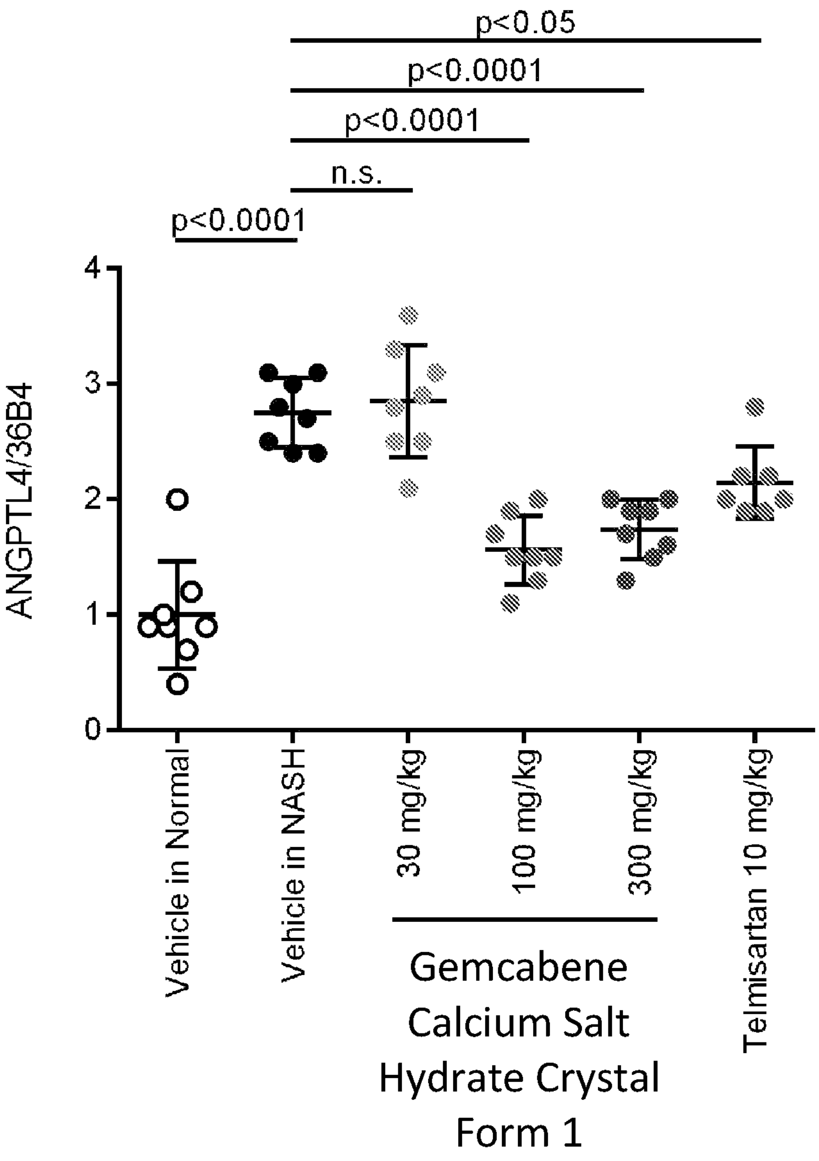
FIG. 38 is a graph showing hepatic gene expression levels for angiopoietin-like protein 4 (ANGPTL4) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 39:
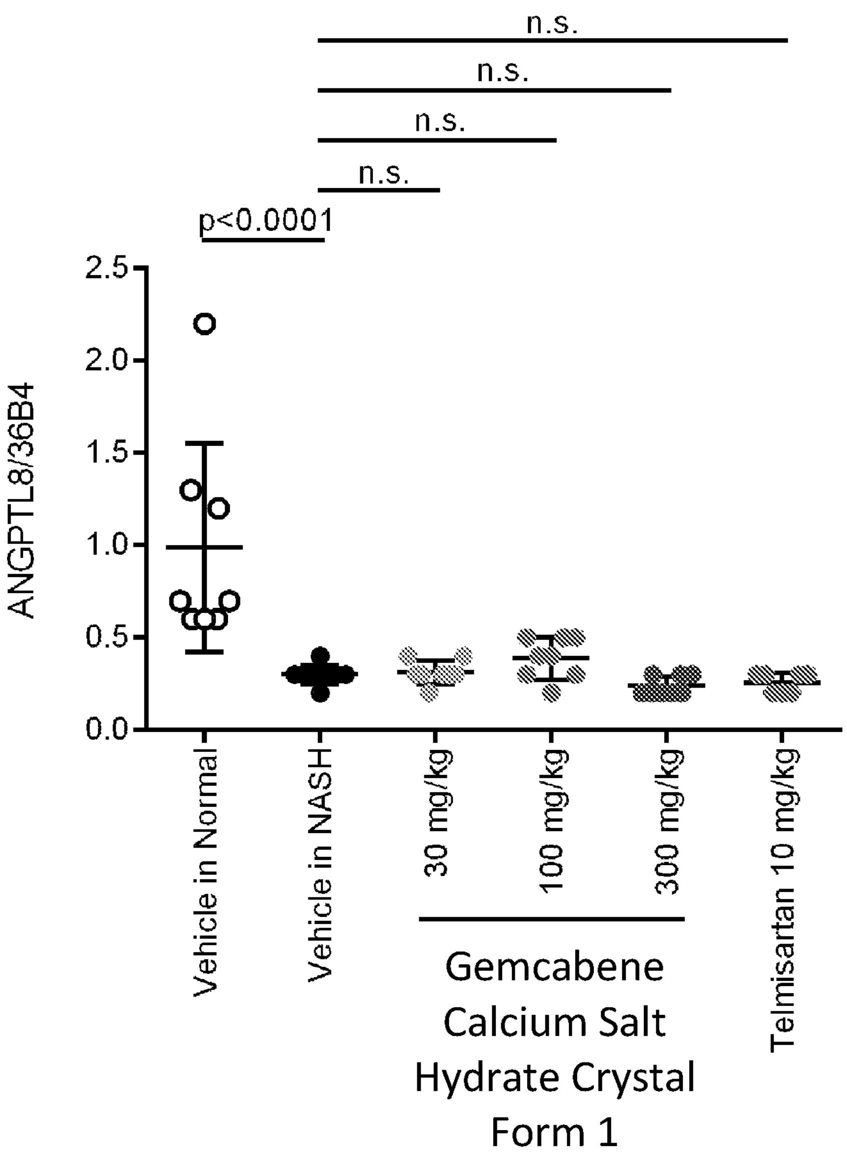
FIG. 39 is a graph showing hepatic gene expression levels for angiopoietin-like protein 8 (ANGPTL8) in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).
Figure 40:
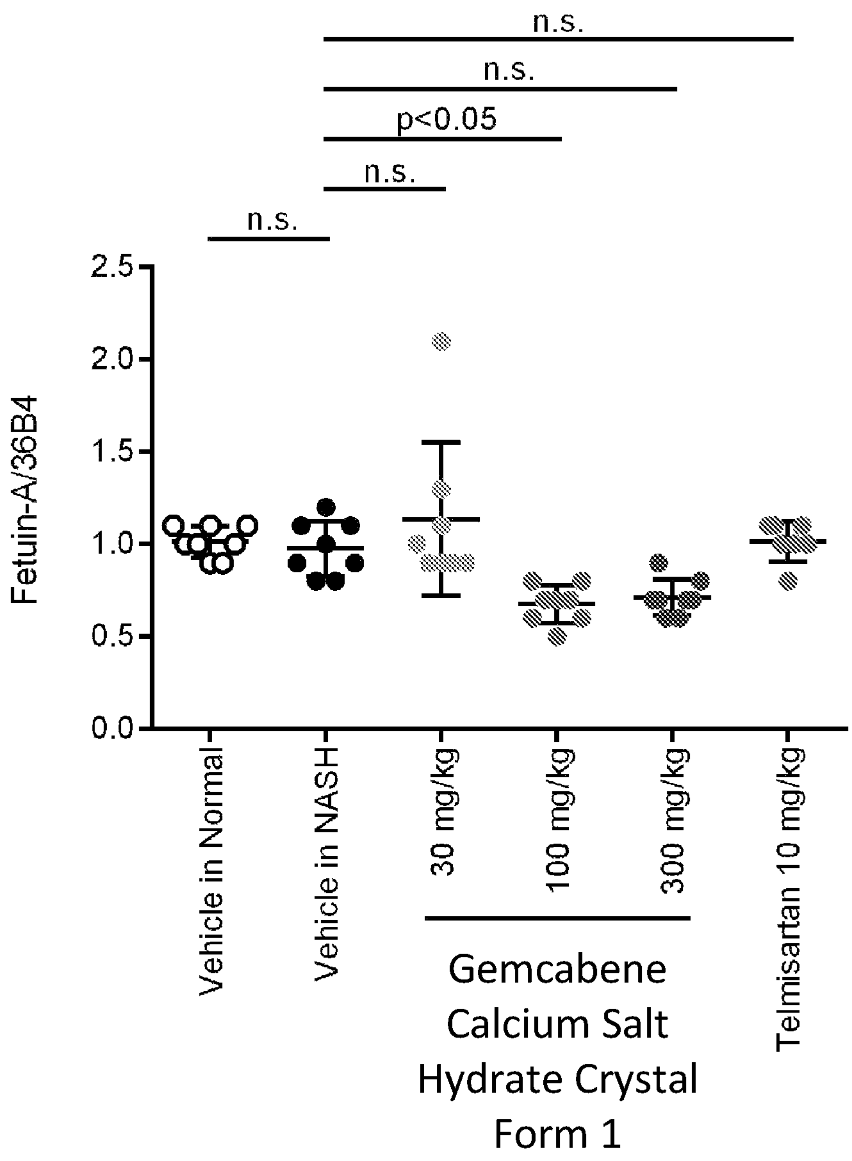
FIG. 40 is a graph showing hepatic gene expression levels for fetuin-A in normal mice treated with vehicle and NASH-induced mice treated for three weeks with vehicle, gemcabene calcium salt hydrate Crystal Form 1 having a PSD90 of 52 μm as measured by laser light diffraction (30, 100 or 300 mg/kg) or reference compound telmisartan (10 mg/kg).

The effect of gemcabene calcium salt hydrate Crystal Form 1 (PSD90=52 μm) on the correlation between hepatic ApoC-III or hepatic sulf-2 and plasma triglyceride concentration is shown in FIG. 31. In a diabetic mouse model, gemcabene calcium salt hydrate Crystal Form 1 showed decrease in sulf-2 mRNA level. Without bound to any theory, the decrease in Sulf-2 enzyme with gemcabene calcium salt hydrate Crystal Form 1 is indicative of rescuing or restoring Syndecan-1 activity, which regulates a number of critical signaling pathways. In the liver of a healthy subject, the Syndecan-1 receptor binds cholesterol-enriched triglyceride containing remnants with high capacity with an estimated internalization half-life of about 60 minutes, while the LDL-receptor binds these particles with low capacity, and an estimated half-life of about 10-minutes. However, in a diabetic subject, Syndecan-1 receptor is obstructed by high hepatic expression of Sulf-2.

Gemcabene calcium slat hydrate Crystal Form 1 (PSD90=52 μm)'s effect on the rescue of the remnant receptor is analogous to a PCSK9 inhibitor's rescue of the LDL-receptor. Thus, without bound to any theory, gemcabene calcium salt hydrate Crystal Form 1's effect on the reduction of C-TRLs may reduce residual risk for atherosclerotic cardiovascular disease (ASCVD) events.

Gemcabene calcium salt hydrate Crystal Form 1 significantly downregulated hepatic mRNA markers of inflammation (TNF-α, MCP-1, MIP-1β, CCR5, CCR2, NF-κB), lipogenesis and lipid modulation (ApoC-III, ACC1, ADH-4, Sulf-2), fibrosis (TIMP-1), and hepatic carcinogenesis (MMP-2). These effects demonstrate that administration of gemcabene calcium salt hydrate Crystal Form 1 is useful in the compositions and methods of the present invention, particularly for the treatment and prevention of steatosis, inflammation, and hepatocyte ballooning (i.e., NAS score reduction), and inhibition of fibrosis progression. Inhibitions of fibrosis progression were observed with gemcabene calcium salt hydrate Crystal Form 1 (PSD90=52 μm) treatments.

The Vehicle in NASH group showed a significant up-regulation in IL-6 mRNA expression level compared with the Vehicle in Normal group. The gemcabene calcium salt hydrate Crystal Form 1 (PSD90=52 μm)-treated 100 and 300 mg/kg groups and the Telmisartan group showed significant down-regulations in IL-6 mRNA expression level compared with the Vehicle in NASH group. There was no significant difference in IL-6 mRNA expression level between the Vehicle in NASH group and the gemcabene calcium salt hydrate Crystal Form 1 (PSD90=52 μm)-treated 30 mg/kg group.

There was no significant difference in IL-1β mRNA expression level between the Vehicle in Normal group and the Vehicle in NASH group. There were no significant differences in IL-1β mRNA expression level between the Vehicle in NASH group and the treatment groups.

The Vehicle in NASH group showed a down-regulation in CXCL1/KC mRNA expression level compared with the Vehicle in Normal group. The gemcabene calcium salt hydrate Crystal Form 1 (PSD90=52 μm)-treated 100 and 300 mg/kg groups showed marked down-regulation in CXCL1/KC mRNA expression levels compared with the Vehicle in NASH group. No amplification of CXCL2/MIP-2 mRNA was detected in the liver samples from STAM mice or normal mice. The reference gene 36B4 was amplified in both samples as expected. The CXCL2/MIP-2 amplification was detected in colon samples from the DSS-induced colitis model, suggesting that the RT-PCR system and the primer sets for CXCL2/MIP-2 had worked.

The Vehicle in NASH group showed a significant down-regulation in SCD mRNA expression level compared with the Vehicle in Normal group. The gemcabene calcium salt hydrate Crystal Form 1 (PSD90=52 μm)-treated 300 mg/kg group showed a significant up-regulation in SCD mRNA expression level compared with the Vehicle in NASH group. There were no significant differences in SCD mRNA expression levels between the Vehicle in NASH group and the other treatment groups.

The Vehicle in NASH group showed a significant up-regulation in hepatic LPL mRNA expression level compared with the Vehicle in Normal group. The gemcabene calcium salt hydrate Crystal Form 1 (PSD90=52 μm)-treated 30, 100 and 300 mg/kg groups showed significant up-regulations in hepatic LPL mRNA expression levels compared with the Vehicle in NASH group. There was no significant difference in hepatic LPL mRNA expression level between the Vehicle in NASH group and the Telmisartan group.

The Vehicle in NASH group showed a significant down-regulation in ANGPTL3 mRNA expression level compared with the Vehicle in Normal group. The gemcabene calcium salt hydrate Crystal Form 1 (PSD90=52 μm)-treated 100 and 300 mg/kg groups showed significant down-regulations in ANGPTL3 mRNA expression levels compared with the Vehicle in NASH group. There were no significant differences in ANGPTL3 mRNA expression level between the Vehicle in NASH group and the other treatment groups.

The Vehicle in NASH group showed a significant up-regulation in ANGPTL4 mRNA expression level compared with the Vehicle in Normal group. The gemcabene calcium salt hydrate Crystal Form 1 (PSD90=52 μm)-treated 100 and 300 mg/kg groups and the Telmisartan group showed significant down-regulations in ANGPTL4 mRNA expression levels compared with the Vehicle in NASH group. There was no significant difference in ANGPTL4 mRNA expression level between the Vehicle in NASH group and the gemcabene calcium salt hydrate Crystal Form 1 (PSD90=52 μm)-treated 30 mg/kg group.

The Vehicle in NASH group showed a significant down-regulation in ANGPTL8 mRNA expression level compared with the Vehicle in Normal group. There were no significant differences in ANGPTL8 mRNA expression levels between the Vehicle in NASH group and the treatment groups.

There was no significant difference in Fetuin-A mRNA expression level between the Vehicle in Normal group and the Vehicle in NASH group. The gemcabene calcium salt hydrate Crystal Form 1 (PSD90=52 μm)-treated 100 mg/kg group showed a significant down-regulation in Fetuin-A mRNA expression level compared with the Vehicle in NASH group. There were no significant differences in Fetuin-A mRNA expression levels between the Vehicle in NASH group and the other treatment groups. Elevated Fetuin-A mRNA expression is associated with increased insulin resistance and development of NASH.

The effect of gemcabene calcium salt hydrate Crystal Form 1 (PSD90=52 μm) on the liver histology and gene expression levels associated with inflammation supports the clinical evaluation of a pharmaceutically acceptable salt of gemcabene as a treatment for NAFLD/NASH. In the current study, gemcabene calcium salt hydrate Crystal Form 1 (PSD90=52 μm)-treated STAM™ mice demonstrated a significant histological reduction in both NAS and fibrosis progression. Further, analysis of hepatic expression of inflammation related genes TNF-α, MCP-1, MIP-1β, CCR5, CCR2, and NF-κB suggests a pharmaceutically acceptable salt of gemcabene hits multiple targets and has a hepatoprotective effect on liver pathology. Also, gemcabene calcium salt hydrate Crystal Form 1 reduced the mRNA expression levels of metabolism-related genes ACC1, ApoC-III, Sulf-2, and ADH4. Plasma CRP levels were also decreased by gemcabene calcium salt hydrate Crystal Form 1 treatment along with the down regulation of the CRP gene expression, which is in agreement with human data. Data from previous non-clinical and clinical studies have shown that gemcabene calcium salt hydrate Crystal Form 1 reduces plasma TG, apoC-III mRNA and plasma levels, and enhances VLDL clearance.

The STAM™ model was induced with STZ, with near complete loss of pancreatic insulin production, and, therefore, translation effects of drugs on insulin sensitization were not expected. However, this model demonstrated that pleiotropic drugs, such as a pharmaceutically acceptable salt of gemcabene and/or multi-modal combination therapy approaches may effectively guide treatments for NASH. The current nonclinical data corroborated with earlier clinical findings support the evaluation of pharmaceutically acceptable salts of gemcabene in the resolution of NASH in humans.

Example 16: Treatment of Hypercholesterolemia with Gemcabene Calcium Salt Hydrate Crystal Form 1

A study was performed to evaluate the efficacy of Tablet D in treating patients with familial hypercholesterolemia (FH) and who are on stable, lipid-lowering therapy. Male and female patients ≥17 years of age who had been diagnosed with FH by genetic confirmation or a clinical diagnosis based on either (1) a history of an untreated LDL-C concentration >500 mg/dl (12.92 mmol/L) together with either appearance of xanthoma before 10 years of age, or evidence of familial hypercholesterolemia in both parents or (2) LDL-C>300 mg/dl (7.76 mmol/L) on maximally tolerated lipid-lowering drug therapy were enrolled in the study. Patients had a fasting LDL-C value>130 mg/dl (3.36 mmol/L) and a triglyceride (TG) value≤400 mg/dl (4.52 mmol/L) while on a stable, low-fat, low-cholesterol diet in combination with a pre-existing lipid-lowering therapy (i.e., a statin, monoclonal antibody to PCSK9, a cholesterol-absorption inhibitor, a bile acid sequestrant, or nicotinic acid, or any combination thereof).

The study was a 3-period, 3-treatment study using successively escalating doses of 300 mg, 600 mg, and 900 mg gemcabene calcium salt hydrate Crystal Form 1 (PSD90=52 μm). All patients were on each of the successive doses for 4 weeks at a time. Patients remained on their stable, lipid-lowering therapy throughout the study.

Each patient received one 300 mg gemcabene calcium salt hydrate Crystal Form 1 tablet (Tablet D) orally QD (alternatively written as q.d.; meaning "once a day") for 4 weeks. The same patients then received 600 mg gemcabene calcium salt hydrate Crystal Form 1 orally QD for 4 weeks. The 600 mg dose consisted of two 300-mg tablets (Tablet D×2). Finally, the same patients received 900 mg gemcabene calcium salt hydrate Crystal Form 1 orally QD for 4 weeks. The 900 mg dose consisted of three 300-mg tablets (Tablet D×3). There were no interruptions in gemcabene calcium salt hydrate Crystal Form 1 dosing when changing from the 300 mg to the 600 mg dose or when changing from the 600 mg to the 900 mg dose unless there were clinically significant safety issues resulting in the temporary or permanent discontinuation of gemcabene.

LDL-C values were measured after the patient had been administered Tablet D for 2 weeks for each dosing level and on the last day of each dose. For each escalated dose, percent change from baseline in LDL-C was calculated using the baseline LDL-C value and the final LDL-C value measured for each dose. Baseline was defined as the average of measurements taken at a screening visit occurring up to 14 days prior to Day 1 and Day 1 (pre-dose). Interim clinical trial data for LDL-C levels are shown in FIG. 3 and FIG. 4.

Figure 3:
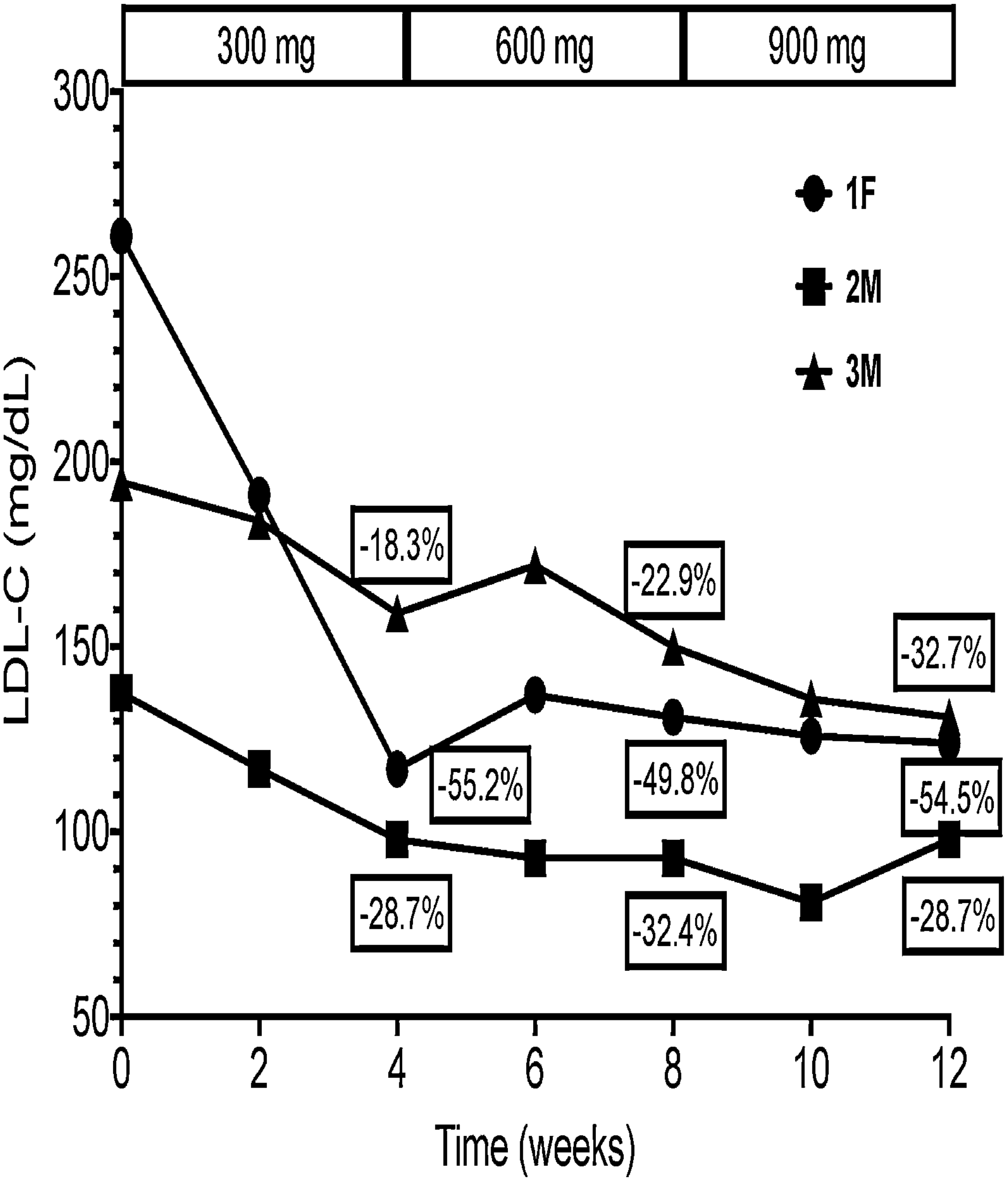
FIG. 3 is a line graph showing LDL-C concentrations of three familial hypercholesterolemia patients (1F, 2M and 3M) as measured during the course of their treatment with gemcabene calcium salt hydrate Crystal Form 1 having a particle size distribution characterized by a PSD90 of 52 μm as measured by laser light diffraction (gemcabene calcium salt hydrate Crystal Form 1, 300-mg strength film-coated tablet, Tablet D).
Figure 4:
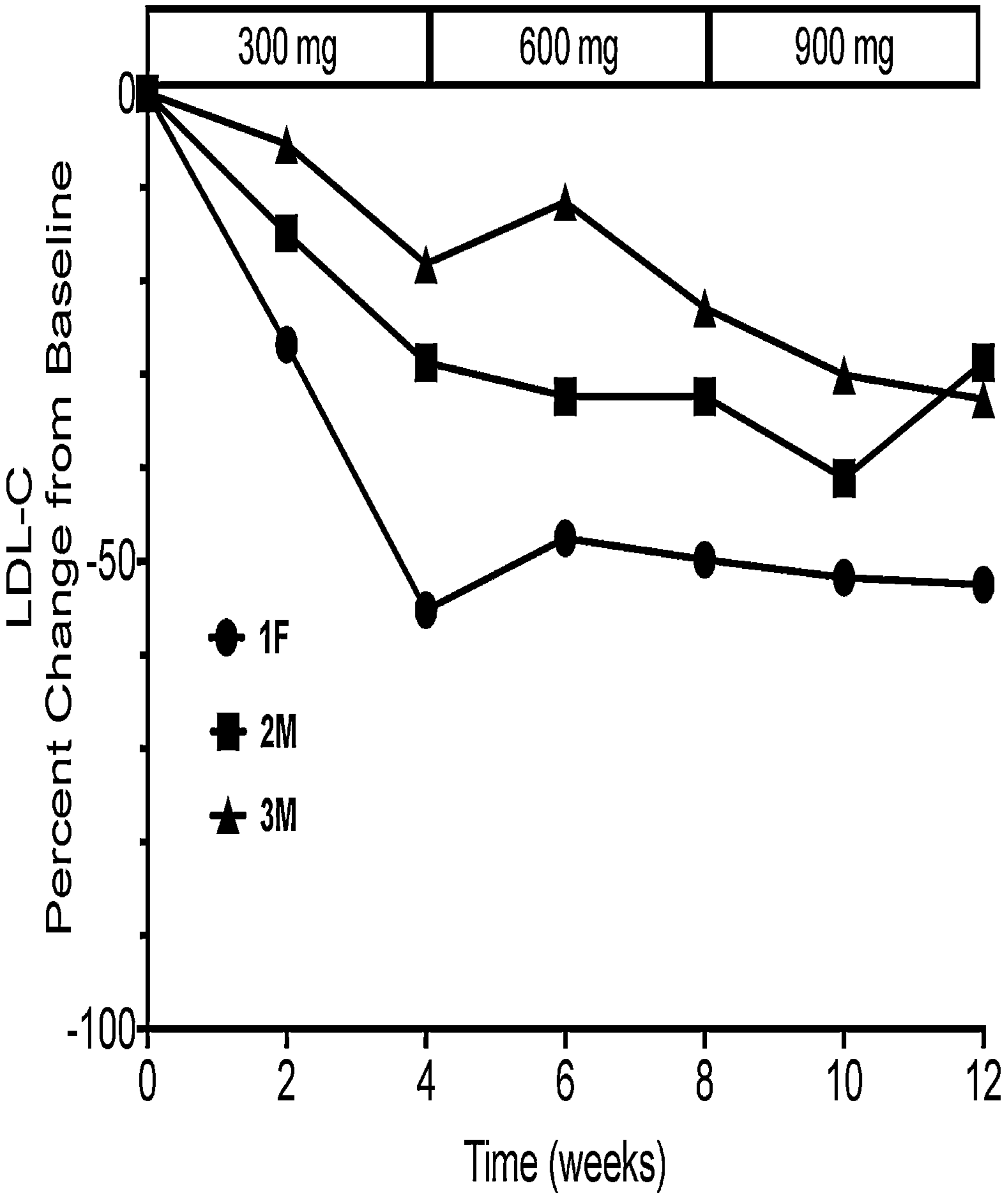
FIG. 4 is a line graph showing values for percent change from baseline of LDL-C concentrations of the three familial hypercholesterolemia patients (1F, 2M and 3M) shown in FIG. 3 as measured during the course of their treatment with gemcabene calcium salt hydrate Crystal Form 1 having a particle size distribution characterized by a PSD90 of 52 μm as measured by laser light diffraction (gemcabene calcium salt hydrate Crystal Form 1 300-mg strength film-coated tablet, Tablet D).

FIG. 3 shows LDL-C concentrations of three patients (1F, 2M and 3M) as measured during the course of the study. FIG. 4 shows values for the LDL-C concentration percent change from baseline for the same three patients.

All patients were on their maximal tolerated cholesterol lowering therapy before the rising dose treatments with Tablet D. Patient 1F was statin intolerant her cholesterol lowering therapy included Zetia 10 mg, Cholestyramine 4 g, and krill oil 350 mg. Patient 2M's cholesterol lowering therapy included Crestor 40 mg. Patient 3M's cholesterol lowering therapy included atorvastatin 80 mg and Zetia 10 mg. Each of the three patients showed a significant LDL-C reduction compared to their individual baselines following each 4-week dose interval of Tablet D oral QD treatment. Patient 1F showed an LDL-C reduction of 55.2% (4 weeks), 49.8% (8 weeks) and 54.5% (12 weeks) following treatment with 300 mg, 600 mg, and 900 mg, oral QD gemcabene calcium salt hydrate Crystal Form 1, respectively. Patient 2M showed an LDL-C reduction of 28.7% (4 weeks), 32.4% (8 weeks) and 28.7% (12 weeks) following treatment with 300 mg, 600 mg, and 900 mg, oral QD Tablet D, respectively. Patient 3M showed an LDL-C reduction of 18.3% (4 weeks), 22.9% (8 weeks) and 32.7% (12 weeks) following treatment with 300 mg, 600 mg, and 900 mg, oral QD Tablet D, respectively. The LDL-C reduction was sustained for the duration of the 12-week intervention (FIGS. 3 and 4).

Example 17: Pharmacokinetics and Safety Study for Gemcabene Calcium Salt Hydrate Crystal Form 1 300-mg Tablets An open-label, non-randomized study to evaluate the pharmacokinetics, safety, and tolerability of oral gemcabene in patients with varying degrees of renal impairment and healthy matched control subjects with normal renal function was conducted with 300 mg compressed film-coated tablets prepared with gemcabene calcium salt hydrate Crystal Form 1 having a PSD90 of 52 μm (Tablet F). The rationale of the study was to explore the potential use of gemcabene in healthy male and female subjects with normal renal function, and those with varying degrees of renal impairment (RI), by assessing the pharmacokinetics (PK), and safety and tolerability, of a single, 600 mg oral dose (Tablet F×2). The single 600 mg dose level represents low exposure to gemcabene as tested in human subjects and has been shown to be safe and well tolerated based on all available data.

The PK assessments can be used to provide appropriate dosing recommendations for patients with RI. The primary objective of this study was to evaluate the PK profile of gemcabene following oral administration in patients with varying degrees of RI compared to healthy matched control subjects with normal renal function. The secondary objective of this study was to evaluate the safety and tolerability of oral gemcabene in patients with varying degrees of renal function.

All subjects in the study were male or female, between 18 and 75 years of age, inclusive, with a body mass index between 18 and 35 kg/m$^2$, inclusive. Eight subjects in Cohort 1 was healthy, based on medical and surgical history review, a defined complete physical examination, as well as vital sign measurements, ECGs, and laboratory test results, have an estimated creatine clearance (CLcr)≥90 mL/min at the time of screening, were non-smokers, and were matched demographically (gender, BMI±20%, age±10 years) with a subject in Cohort 2 (severe RI). Patients in Cohorts 2-4 had mild, moderate, or severe RI, and were nonsmokers or light smokers (smoke fewer than 10 cigarettes per day). Cohort 1 subjects received a single oral dose of 600 mg gemcabene on Day 1 and were followed for 11 days (240 hours) for PK and safety assessments. For PK collection timepoints up to and including 12 hours (i.e., 0 [predose], 1, 2, 3, 6, 12 hours), the window was ±5 minutes of the indicated nominal time. For PK collection timepoints at 24, 48, 72, and 96 hours, the window was ±10 minutes of the indicated nominal time. For later timepoints (i.e. 120, 144, 192, 240, and 336 hours postdose) the window was ±60 minutes of the indicated nominal time.

Cohort 2 consisted of 8 patients with severe renal impairment (RI) (estimated glomerular filtration rate (eGFR<30 mL/min/1.73 m$^2$ based on the isotope dilution mass spectrometry (IDMS) traceable Modification of Diet in Renal Disease (MDRD) equation). Cohort 2 patients received a single dose of 600 mg gemcabene calcium salt hydrate Crystal Form 1 having a PSD90 of 52 μm (Tablet F×2) on Day 1 and were followed for 15 days (336 hours) for PK and safety assessments.

Cohort 3 consisted of 6 patients with mild RI (eGFR≥60 to <90 mL/min/1.73 m$^2$ based on the IDMS traceable MDRD equation). These patients received a single oral dose of 600 mg gemcabene calcium salt hydrate Crystal Form 1 having a PSD90 of 52 μm on Day 1 and were followed for 15 days (336 hours) for PK and safety assessments.

Cohort 4 consisted of 6 patients with moderate renal impairment (eGFR≥30 to <60 mL/min/1.73 m$^2$ based on the IDMS traceable MDRD equation). These patients received a single oral dose of 600 mg gemcabene calcium salt hydrate Crystal Form 1 having a PSD90 of 52 μm on Day 1 and were followed for 15 days (336 hours) for PK and safety assessments.

Gemcabene calcium salt hydrate Crystal Form 1 (PSD90=52 μm) was administered orally as a single dose of 600 mg, given as two 300 mg tablets (Tablet F) (with 240 mL of water) following an overnight, 28 hour fast. Subjects remained fasted (with no water for 1 hour before and after dosing) for 4 hours after dosing. Administration of each dose of study drug were supervised, verified, and documented.

The 300-mg film-coated gemcabene calcium salt hydrate Crystal Form 1 (PSD90=52 μm) tablets used in this study had a dissolution value in pH 5.0 potassium acetate buffer at 37° C.±5° C. as measured by high-performance liquid chromatography using detection wavelength of 210 nm as shown in Table 23 (see Example 13).

TABLE 23

Dissolution of 300-mg film-coated tablets prepared with gemcabene calcium salt hydrate Crystal Form 1 having a PSD90 of 52 μm (Tablet F)

| | Mean (N = 6) % Dissolved in: |
|---|---|
| 10 minutes | 23 |
| 20 minutes | 53 |

TABLE 23-continued

| Dissolution of 300-mg film-coated tablets prepared with gemcabene calcium salt hydrate Crystal Form 1 having a PSD90 of 52 μm (Tablet F) | |
|---|---|
| | Mean (N = 6) % Dissolved in: |
| 30 minutes | 76 |
| 45 minutes | 93 |

The following pharmacokinetic parameters were calculated using noncompartmental methods, whenever possible, based on plasma gemcabene concentrations: maximum concentration ($C_{max}$), time to maximum concentration ($t_{max}$), area under the concentration-time curve from time 0 to 48 hours postdose $AUC_{(0-48)}$, area under the concentration-time curve from time 0 until the last quantifiable concentration $AUC_{last}$, area under the concentration-time curve extrapolated to infinity $AUC_{(0-\infty)}$, apparent terminal rate constant (λz), terminal phase half-life ($t_{1/2}$), apparent total body clearance (CL/F), apparent volume of distribution (Vz/F), unbound plasma concentration (Cu), fraction unbound in plasma (Fu), and fraction bound in plasma (Fb).

Table 24 shows pharmacokinetic variables of 2×300-mg compressed film-coated tablets (600 mg) containing gemcabene calcium salt hydrate Crystal Form 1 having a PSD90 of 52 μm (Tablet F).

TABLE 24

| Pharmacokinetic Variables for Cohort 1 | |
|---|---|
| Parameter | Tablet with Gemcabene Calcium Salt Hydrate Form 1 (PSD90 = 52 μm) Mean (±Standard Deviation) N = 8 |
| $C_{max}$ (μg/mL) | 64.2 (6.29) |
| $t_{max}$ (hr) | 1.4 (0.55) |
| $AUC_{last}$ (μg · hr/mL) | 2961 (599) |
| $AUC_{inf}$ (μg · hr/mL) | 3021 (640) |
| Half-life (hr) | 38.6 (10.1) |
| CL/F (mL/hr) | 207 (47.2) |
| Vz/F (mL) | 10990 (1354) |

Example 18: Steady-State Effects of Gemcabene Calcium Salt Hydrate Crystal Form 1 on Single-Dose An open-label, two-sequence, cross-over study to assess the steady-state effects of gerncabene on the single-dose pharmacokinetics (PK) of oral contraceptive tablets in healthy female subjects was conducted with 300 mg tablets containing gemcabene calcium salt hydrate Crystal Form 1 having PSD90 of 52 μm (Tablet F). Sixteen eligible female subjects were randomized in a 1:1 ratio of one of two treatment sequences, as presented in the Table 25.

TABLE 25

| Treatment Sequences | | | | |
|---|---|---|---|---|
| Treatment Sequence | Number of Subjects | Period 1 (Study Days 1-9) | | Period 2 (Study Days 22-30) |
| 1 | n = 8 | Treatment A - ON 1/35 (Study Day 7) (reference) | Washout (Study Days 10-21) | Treatment B - ON 1/35 (Study Day 28) and daily gemcabene 600 mg (Study Days 22-29) (test) |
| 2 | n = 8 | Treatment B - ON 1/35 (Study Day 7) and daily gemcabene 600 mg (Study Days 1-8) (test) | | Treatment A - ON 1/35 (Study Day 28) (reference) |

ON 1/35 = Ortho Novum 1/35.

The population for this study was generally healthy, adult female subjects of childbearing potential (≥18 to ≤535 years of age). This population supports the overall objective of the study to evaluate the effect of 600 mg of gemcabene calcium salt hydrate Crystal Form 1 having PSD90 of 52 μm at steady-state on the PK of a single dose of ON 1/35 (Ortho Novum 1/35; combined ethinyl estradiol/norethindrone oral contraceptive). The primary objective of this study was to assess the effect of daily 600 mg of gemcabene calcium salt hydrate Crystal Form 1 having PSD90 of 52 μm at steady-state on the pharmacokinetics (PK) of ON 1/35. The secondary objectives of this study were to assess the safety and tolerability of daily gemcabene 600 mg in combination with a single-dose ON 1/35 and to assess the steady-state PK of 600 mg of gemcabene calcium salt hydrate Crystal Form 1 having PSD90 of 52 μm (Tablet F×2).

Gemcabene calcium salt hydrate Crystal Form 1 having PSD90 of 52 μm was administered orally as a single dose of 600 mg, given as two 300 mg tablets (300-mg Tablet F×2) (with 240 mL of water). Gemcabene calcium salt hydrate Crystal Form 1 having PSD90 of 52 μm (600 mg) was administered at the same time each day.

Non-compartmental PK single-dose parameters were obtained, including $C_{max}$, time to the maximum observed plasma concentration ($T_{max}$), AUC from time 0 to time of last detectable concentration ($AUC_{last}$) and when possible, AUC extrapolated to infinite time ($AUC_{\infty}$), percent of $AUC_{\infty}$ obtained from forward extrapolation ($AUC_{extrap\ \%}$), apparent terminal rate constant (λz), apparent terminal half-life (tó), apparent total body clearance (CL/F), and apparent volume of distribution of the terminal phase (Vz/F) for ethinyl estradiol and norethindrone. Table 26 presents the ANOVA analysis results for the effect of daily

TABLE 26

Pharmacokinetic Parameters for Ethinyl Estradiol and Norethindrone

| PK Parameter (unit) | Ratio Geom. LS Mean (Treatment B/Treatment A) (%) | 90% CI Ratio (%) |
|---|---|---|
| | Ethinyl Estradiol | |
| $C_{max}$ (pg/mL) | 70.50 | 63.01, 78.89 |
| $AUC_{0-12}$ (h*pg/mL) | 78.54 | 70.63, 87.33 |
| $AUC_{last}$ (h*pg/mL) | 86.70 | 74.27, 101.22 |
| | Norethindrone | |
| $C_{max}$ (pg/mL) | 90.56 | 80.40, 102.01 |
| $AUC_{last}$ (h*pg/mL) | 85.94 | 75.87, 97.36 |
| $AUC_{inf}$ (h*pg/mL) | 86.33 | 75.77, 98.37 |

Treatment A = a single dose of ON 1/35 alone; Treatment B = a single dose of ON 1/35 and daily gemcabene 600 mg.
$AUC_{0-12}$ = area under the concentration-time curve from time 0 to 12 h; $AUC_{inf}$ = area under the concentration-time curve extrapolated to infinite time; $AUC_{last}$ = area under the concentration-time curve from time 0 to time of last measurable concentration; $C_{max}$ = maximum drug concentration; CI = confidence interval; Geom. = geometric mean; LS = least squares; ON 1/35 = Ortho Novum 1/35; PK = pharmacokinetic.

The geometric least square (LS) mean ratio indicated that a mild drug-drug interaction to the exposure to ethinyl estradiol and norethindrone slightly decreased in presence of gemcabene calcium salt hydrate Crystal Form 1. The lower bounds of the 90% confidence interval (CI) values for 5 of the 6 parameters fell below the pre-defined range of 80% to 125%, supporting reduction of exposure to ethinyl estradiol and norethindrone in presence of gemcabene calcium salt hydrate Crystal Form 1. The mean plasma gemcabene trough concentrations were 98.77 μg/mL, 106.37 μg/mL, and 104.27 μg/mL on Days 6, 7, and 8 during Treatment B. The steady-state plasma gemcabene PK parameters for the PK Parameter Analysis Set indicated a mean $C_{max,ss}$ of 177.73 μg/mL and Cian of 102.68 μg/mL.

Throughout the study, 2 (12.5%) subjects in Treatment A; 4 (26.7%) subjects during gemcabene alone treatment of Treatment B, and 3 (20%) subjects during gemcabene with ON 1/35 treatment of Treatment B, had treatment-emergent adverse events (TEAEs). Only 1 subject in gemcabene only treatment of Treatment B had a drug-related TEAE of gastrointestinal disorder of constipation. All TEAEs were considered to be mild or moderate in severity. There were no serious adverse events (SAEs) during the study. Overall, treatment with gemcabene with a single dose of ON 1/35 was well tolerated.

Example 19: Treatment Study with Gemcabene Calcium Salt Hydrate Crystal Form 1 Having PDS90 of 52 μm in Patients with Familial Hypercholesterolemia (FH) on Stable, Lipid Lowering Therapy This was an open-label, dose-finding, 3-period, 3-treatment study using successively escalating doses of 300 mg, 600 mg, and 900 mg gemcabene calcium salt hydrate Crystal Form 1 having PSD90 of 52 μm in patients clinically diagnosed with familial hypercholesterolemia (FH). The treatment plan was for each of 8 patients to receive each of the successive doses, daily, for 4 weeks at a time with no interruption in gemcabene calcium salt hydrate Crystal Form 1 dosing between the dose levels. That is, the 8 FH patients were administered daily oral doses of gemcabene calcium salt hydrate Crystal Form 1 having PSD90 of 52 μm at 300 mg/day on Days 1-28, 600 mg/day on Days 29-56, and 900 mg/day on Days 57-84. Pharmacokinetic plasma samples were collected pre-dose and 0.5, 1, 2, 3, 5, and 12 hours post-dose on Day 28, Day 56, and Day 84. Additional (trough) samples were collected pre-dose on Day 14, Day 42, Day 70, and at the Early Termination Visit (if applicable). Plasma from these samples were analyzed for gemcabene concentrations and the data used for PK analysis. Plasma sample concentrations were available for pharmacokinetic analysis for all but 1 patient for whom no results were reported following the 900 mg dose on Day 84. Since there were no days off between dose levels, the starting plasma concentration for the 600 mg and 900 mg treatment periods was the steady state concentration for 300 mg and 600 mg, respectively.

During Days 1-28, patients received one 300-mg strength tablet containing gemcabene calcium salt hydrate Crystal Form 1 having PSD9A of 52 μm (Tablet D); during the Days 29-56, patients received two 300-mg strength tablets (2× Tablet D); and during the Days 57-84, patients received three 300-mg strength tablets (3× Tablet D) per day.

One of the objectives of this study was to determine the appropriate dose for use in clinical studies as assessed by efficacy, pharmacokinetic (PK), and safety data; and to evaluate trough plasma concentrations of gemcabene at doses 300 mg, 600 mg, and 900 mg of gemcabene calcium salt hydrate Crystal Form 1 having PSD90 of 52 μm. In some embodiments, an effective dose is defined as a dose that achieves a 15% mean reduction in low-density lipoprotein cholesterol LDL-C after 4 weeks of treatment.

Table 27 shows the demographics of the 8 patients in this study. Each patient's stable, lipid lowering therapy concurrently administered is as indicated in Table 27.

TABLE 27

Patient Demographics

| Age | Gender | Race | Post-Treatment Genetic Assessment | Concomitant Lipid Lowering Medication |
|---|---|---|---|---|
| 58 | Male | Caucasian | HeFH | Atorvastatin 80 mg<br>Ezetimibe 10 mg |
| 71 | Female | Caucasian | HeFH | Ezetimibe 10 mg<br>Cholestyramine 4 g<br>Krill oil 350 mg |
| 56 | Male | Caucasian | HeFH | Rosuvastatin 40 mg |
| 47 | Male | Caucasian | HoFH (LDL-C Receptor Deficient) | Atorvastatin 80 mg |
| 42 | Male | Caucasian | HoFH (LDL-C Receptor Deficient) | Atorvastatin 80 mg<br>Ezetimibe 10 mg<br>Evolocumab 140 mg |
| 59 | Female | Caucasian | HeFH | Evolocumab 140 mg |
| 25 | Male | Caucasian | HoFH (LDL-C Receptor Deficient) | Atorvastatin 80 mg<br>Ezetimibe 10 mg<br>Evetol 100 mg |
| 65 | Female | Caucasian | HeFH | Ezetimibe 10 mg |

Pharmacokinetics (PK)

PK parameter estimates were derived by standard non-compartmental analysis methods using a validated installation of Phoenix® WinNonlin® version 6.4. The actual sampling times were used in the PK parameter calculations.

All plasma concentrations reported as missing were treated as missing. Steady state was assumed following QD administration for 28 days and therefore, plasma gemcabene concentrations at 24 hours post-dose were used as the pre-dose concentrations.

The following gemcabene PK parameters were calculated for each patient from the plasma concentration-time data:

| | |
|---|---|
| $C_{max}$ | Maximum observed plasma concentration |
| $T_{max}$ | Time to maximum observed plasma concentration |
| $AUC_{last}$ | Area under the concentration-time curve from time zero to the time of the last quantifiable concentration after dosing |
| $AUC_{(0-24)}$ | Area under the concentration-time curve from time zero to the 24-h time point |
| CL/Fss | Apparent oral clearance at steady state |
| $T_{last}$ | Time at which the last quantifiable sample occurred |

$AUC_{last}$ and $AUC_{(0-24)}$ were calculated by numeric integration using the trapezoidal rule with linear up and log down interpolation. Gemcabene half-life and apparent volume of distribution were not estimated because a terminal phase could not be accurately estimated from these data.

Statistical Methods

Summary statistics were generated using WinNonlin. All missing plasma concentrations were treated as missing.

Dose proportionality was assessed using GraphPad Prism® v6.07 (LaJolla, CA), by estimating the slope and 95% confidence intervals (CI) from linear regressions of log ($C_{max}$), log ($AUC_{last}$sa), and log ($AUC_{0-24}$) on log (dose). The criterion for dose proportionality is 95% CI around the slope containing the value "1".

Data Displays

The individual patient and gemcabene concentration-time data are listed using the number of significant digits or decimal places provided by the bioanalytical lab and nominal sample times, and summarized descriptively in tabular formats by dose level, and visit (for trough samples). PK analysis results were rounded to 3 significant figures except for $T_{max}$ which was rounded to 2 significant figures, and the results from the dose proportionality analysis which are displayed to 4 significant figures. All summary statistics are rounded to 3 significant figures except for $T_{max}$ (2 significant figures).

Plots of gemcabene plasma concentrations vs time were generated using GraphPad Prism using nominal sample times and displayed on both linear and semi-log axes, except for plots of trough concentrations which are shown on linear axes only.

Results

Figure 41A:
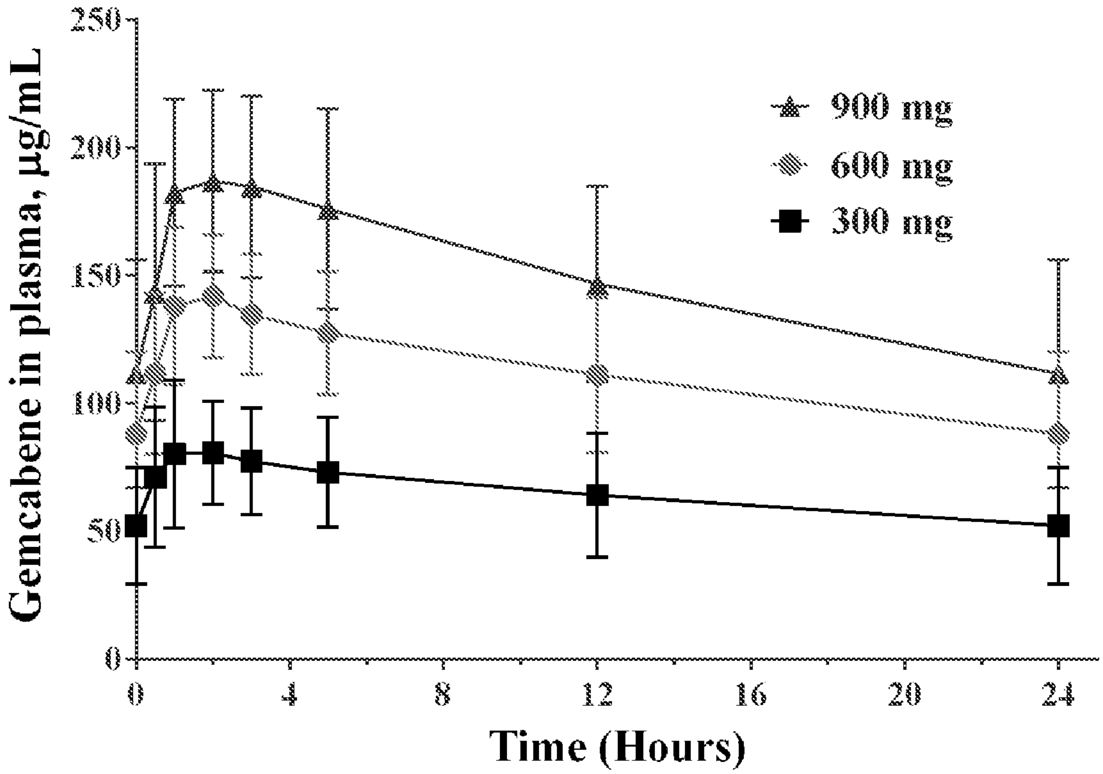
FIG. 41A shows arithmetic-mean concentration of gemcabene (±SD) versus time, overlaid by dose for the time points collected 0-24 h post-dose displayed on linear axes.
Figure 41B:
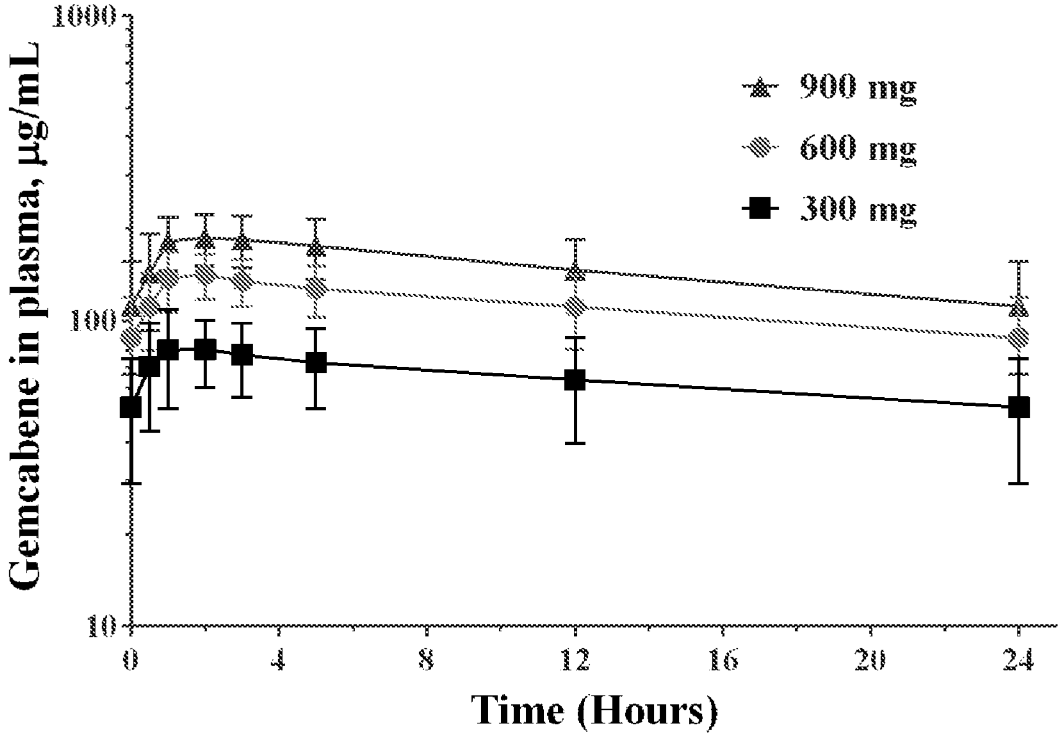
FIG. 41B shows arithmetic-mean concentration of gemcabene (±SD) versus time, overlaid by dose for the time points collected 0-24 h post-dose displayed on semi-log axes.

According to patient records, the eight patients in the study had an average of 98% compliance with all patients at least 93% compliance at each dose level with the exception of patient 006-001 who stopped taking 900 mg (Tablet D×3) prior to the Day 84 visit. This patient was removed from the 900 mg dose study analysis. Plots of arithmetic-mean gemcabene concentrations (±SD) versus time, overlaid by dose for the time points collects 0-24 h post dose are displayed in FIGS. 41A and 41B and for trough samples in FIG. 42.

There were no Day 84 plasma sample concentrations reported for one patient (006-001). One trough sample was missing: patient 004-004, Visit 3 (Day 14), 300 mg/day treatment period. Omission of these results is not expected to have impacted the PK results of this study. There were unexpectedly low gemcabene plasma concentrations reported for one patient (006-003) on Day 84, but records confirmed dosing per protocol for this patient, so the data has been retained in all analyses.

Key PK parameters for gemcabene are summarized for each dose level in Table 28. Following 28 daily oral doses, gemcabene was rapidly absorbed, appearing in plasma at the first sample time point (0.5 h) and maximum plasma concentrations were achieved in most patients 1 to 2 h post-dose. Median $T_{max}$ (min-max) was 1.6 h (1.0-2.0 h), 1.5 h (0.93-3.0 h), and 1.9 h (0.98-3.0 h), for the 300 mg, 600 mg, and 900 mg dose levels, respectively. Although the median value was slightly increased at the 900 mg/day dose, there was no consistent increase in $T_{max}$ with dose in individual patients. Quantifiable gemcabene plasma concentrations were reported out through the 24 h post-dose nominal sampling period for all patients dosed at each level. The calculation for $AUC_{0-24}$ and $AUC_{last}$ differ in that the $AUC_{0-24}$ may extrapolate or interpolate between time points to estimate the concentration at time 24 hours postdose, thus creating a slight difference between parameter values.

TABLE 28

Summary of PK Parameters

| Dose (mg) | | $C_{max}$ (μg/mL) | $T_{max}$[a] (h) | $AUC_{last}$ (μg · h/mL) | $AUC_{0-24}$ (μg · h/mL) | CL/Fss (L/h) | $T_{last}$[a] (h) |
|---|---|---|---|---|---|---|---|
| 300 | n | 8 | 8 | 8 | 8 | 8 | 8 |
| | Mean | 84.8 | 1.6 | 1590 | 1550 | 0.213 | 25.2 |
| | SD | 23.0 | 1.0-2.0 | 556 | 551 | 0.0653 | 22.3-25.7 |
| 600 | n | 8 | 8 | 8 | 8 | 8 | 8 |
| | Mean | 149 | 1.5 | 2700 | 2680 | 0.234 | 24.6 |
| | SD | 21.8 | 0.93-3.0 | 597 | 667 | 0.0445 | 22.3-25.9 |
| 900 | n | 7 | 7 | 7 | 7 | 7 | 7 |
| | Mean | 195 | 1.9 | 3490 | 3530 | 0.271 | 23.8 |
| | SD | 35.4 | 0.98-3.0 | 849 | 945 | 0.0749 | 22.4-25.7 |

[a]Median and min-max.

Figure 42A:
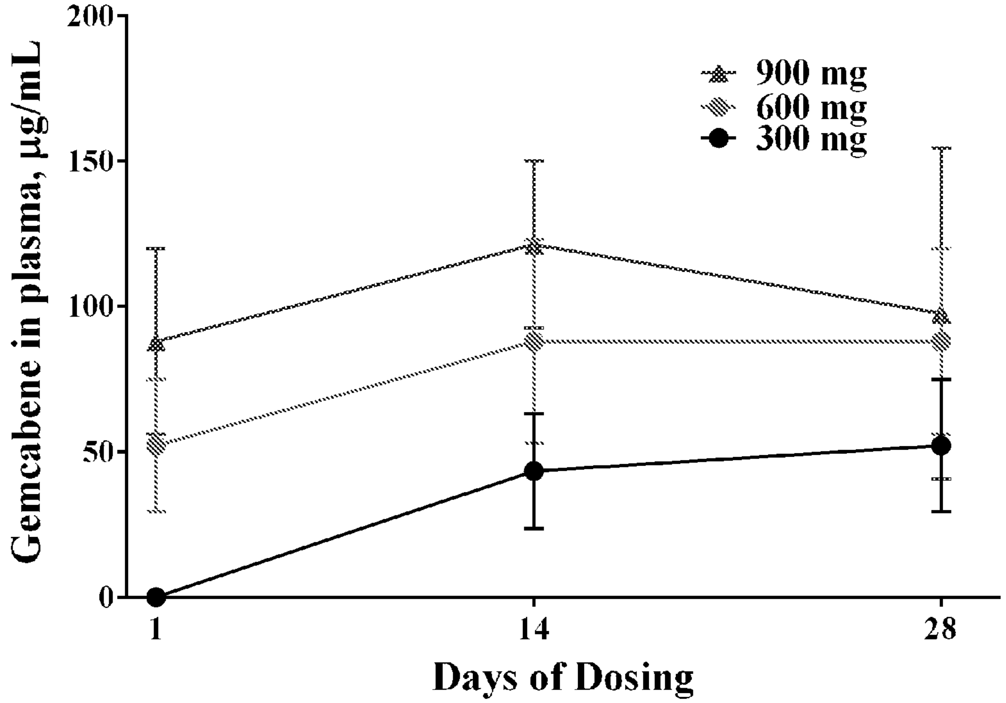
FIG. 42A shows arithmetic-mean predose ($C_{trough}$) concentration of gemcabene (±SD) versus time, overlaid by dose.
Figure 42B:
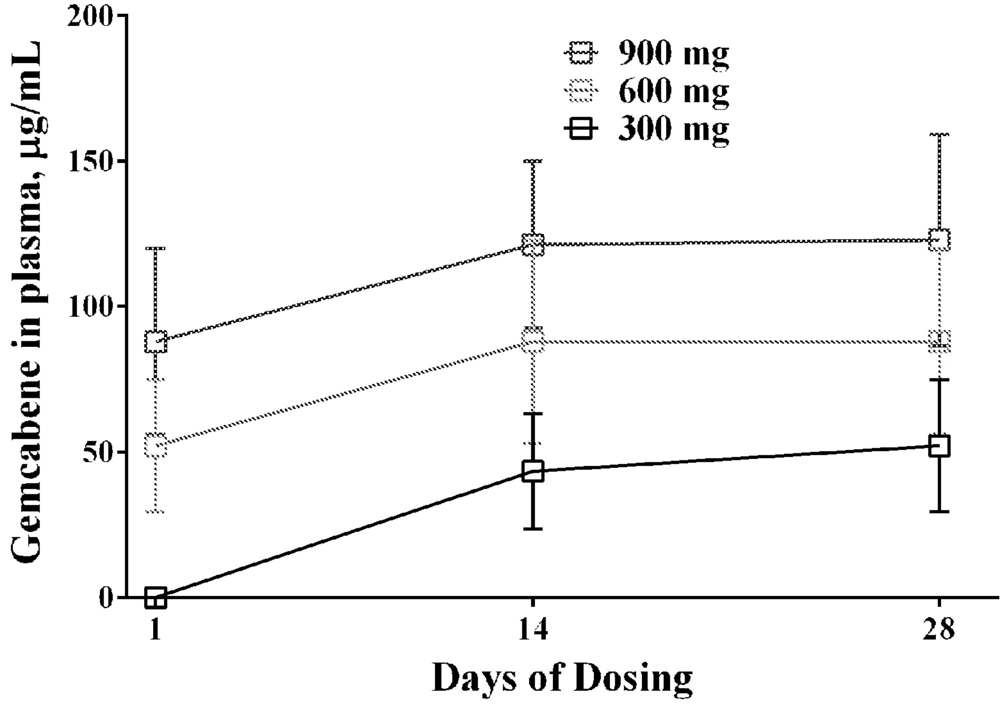
FIG. 42B shows arithmetic-mean predose ($C_{trough}$) concentration of gemcabene (±SD) versus time, overlaid by dose with the 900 mg Day 28 trough concentration from patient 006-003 excluded.

Mean gemcabene trough plasma concentrations were increased following both 14 and 28 daily doses of Tablet D within the 300 mg/day and 600 mg/day treatment periods as well as between the 300 mg/day and 600 mg/day dose levels. Mean trough concentrations were also increased for the 900 mg/day compared to the lower dose levels but decreased between Day 14 and Day 28 of the 900 mg/day treatment period (FIG. 42A). This was largely due to the Day 28 trough value for 1 patient (006-003), which decreased from 122 μg/mL on Day 14 to 43.5 μg/mL on Day 28 (FIG. 42B).

Inspection of individual patient trough gemcabene plasma concentrations revealed that steady state was generally attained within 14 days of daily gemcabene dosing, but not all patients showed a plateau in concentration from Days 14 to 28.

In general, gemcabene $C_{max}$ and $AUC_{0-24}$ values increased with increasing Tablet D daily dose (Table 29). The 95% CI around the slope of log $AUC_{0-24}$ vs log dose include "1" as per statistical criteria. $C_{max}$ increase was slightly less than dose proportional; upper limits of the 95% CI for log $C_{max}$ and $AUC_{last}$ were 0.9767, and 0.9993, respectively.

TABLE 29

| Assessment of Dose Proportionality | | |
|---|---|---|
| Parameter | Slope (±SE) | 95% CI |
| $C_{max}$ | 0.7834 ± 0.09292 | 0.5902 to 0.9767 |
| $AUC_{last}$ | 0.7468 ± 0.1214 | 0.4944 to 0.9993 |
| $AUC_{(0-24)}$ | 0.7749 ± 0.1265 | 0.5118 to 1.038 |

The study demonstrated that gemcabene was rapidly absorbed and with median $T_{max}$ values that ranged from 1.5 to 1.9 h, which were independent of dose level.

The study also demonstrated that gemcabene $C_{max}$ and $AUC_{(0-24)}$ increased with increasing Tablet D daily dose. $AUC_{(0-24)}$ increased dose proportionally over the dose range 300 mg/day to 900 mg/day. The increase in $C_{max}$ was slightly less than dose proportional.

Figure 43:
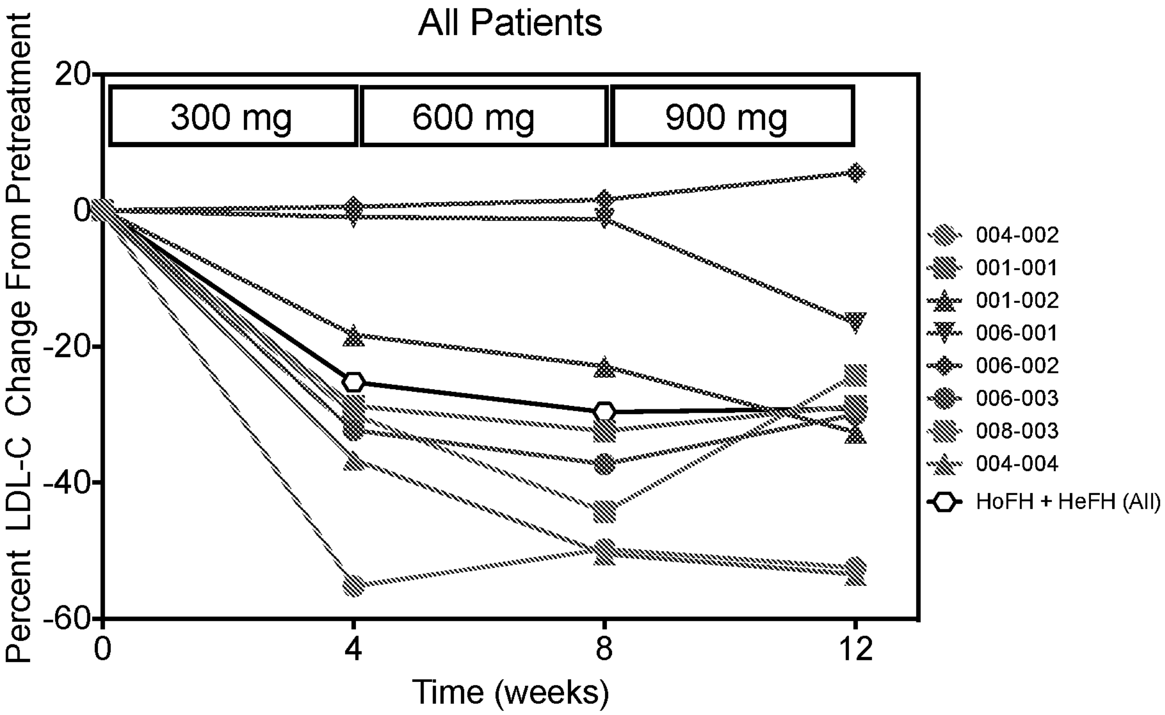
FIG. 43 is a line graph showing values for percent change from baseline of LDL-C concentrations of the eight familial hypercholesterolemia patients in Example 19 as measured during the course of their treatment with gemcabene calcium salt hydrate Crystal Form 1 having a particle size distribution characterized by a PSD90 of 52 μm as measured by laser light diffraction (gemcabene calcium salt hydrate Crystal Form 1 300-mg strength film-coated tablet, Tablet D).
Figure 44:
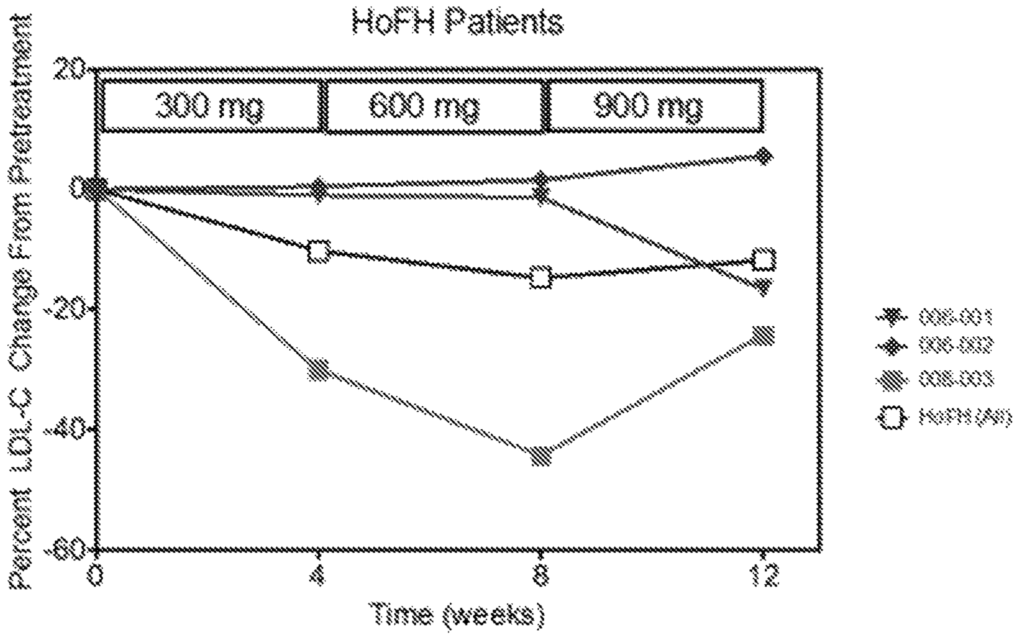
FIG. 44 is a line graph showing values for percent change from baseline of LDL-C concentrations of the three familial hypercholesterolemia patients, who were determined to have homozygous familial hypercholesterolemia (HoFH) genotype based on post-trial genetic assessment, as measured during the course of their treatment with gemcabene calcium salt hydrate Crystal Form 1 having a particle size distribution characterized by a PSD90 of 52 μm as measured by laser light diffraction (gemcabene calcium salt hydrate Crystal Form 1 300-mg strength film-coated tablet, Tablet D).
Figure 45:
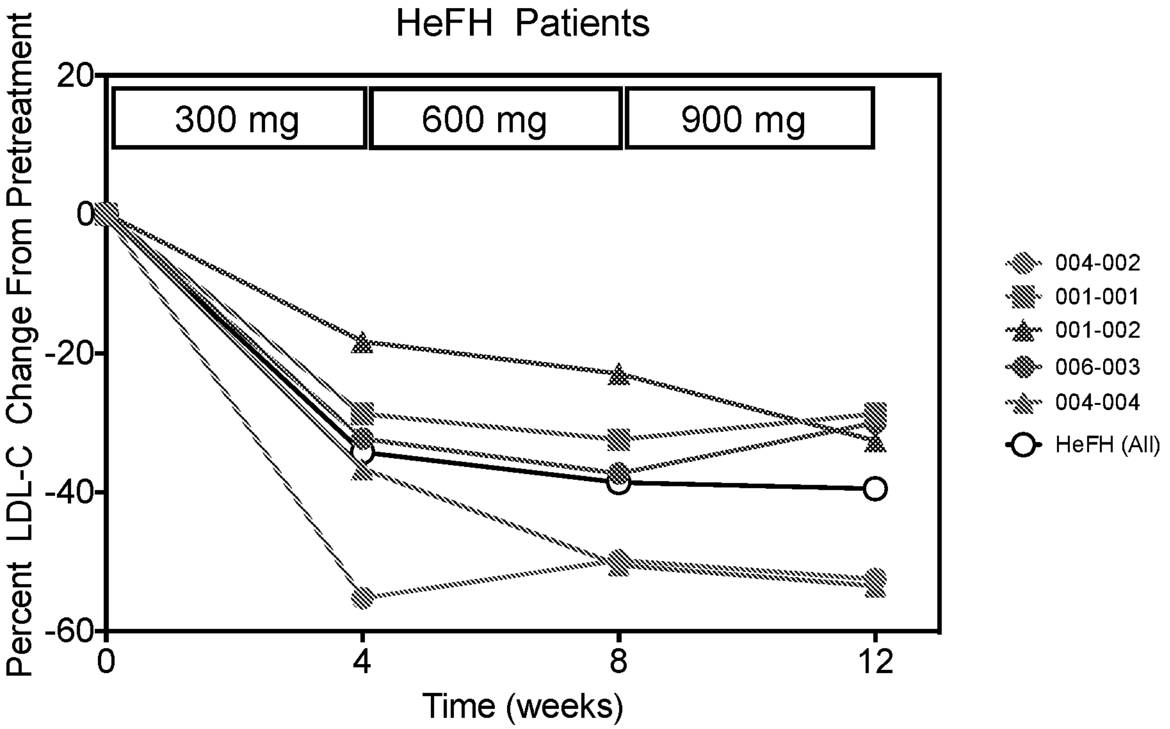
FIG. 45 is a line graph showing values for percent change from baseline of LDL-C concentrations of the three familial hypercholesterolemia patients, who were determined to have heterozygous familial hypercholesterolemia (HeFH) genotype based on post-trial genetic assessment, as measured during the course of their treatment with gemcabene calcium salt hydrate Crystal Form 1 having a particle size distribution characterized by a PSD90 of 52 μm as measured by laser light diffraction (gemcabene calcium salt hydrate Crystal Form 1 300-mg strength film-coated tablet, Tablet D).

After the study, the 8 patients were assessed by genetic confirmation where it was determined that 3 patients had homozygous familial hypercholesterolemia (HoFH) genotype and 5 patients had heterozygous familial hypercholesterolemia (HeFH) genotype (Table 27). The percent change from baseline of LDL-C concentrations of the 8 patients (FIG. 43) divided into HoFH and HeFH genotype groups as measured during the course of their treatment are shown in FIGS. 44 and 45.

Example 20. Treatment Study with Gemcabene Calcium Salt Hydrate Crystal Form 1 Having PDS90 of 52 μm in Patients with Hypercholesterolemia on Stable Moderate and High-Intensity Statins High-risk patients including some, but not all those with heterozygous familial hypercholesterolemia (HeFH) or atherosclerotic cardiovascular disease (ASCVD) on appropriate diet and stable statin therapy for at least 12 weeks and LDL-C≥100 mg/dL (2.59 mmol/L) and triglycerides <500 mg/dL (5.65 mmol/L) were randomized into a 12-week, placebo-controlled, parallel-group, double-blind study to assess the efficacy of gemcabene calcium salt hydrate Crystal Form 1 (PSD90=52 μm) 600 mg (300-mg Tablet D×2) QD on LDL-C and other lipoproteins and hsCRP (high-sensitivity C-reactive protein). Safety and tolerability were also evaluated. The patients were stratified by high- or moderate-intensity statin therapy, with or without ezetimibe, with a target of 52 patients (26 patients on 600 mg gemcabene calcium salt hydrate Crystal Form 1 as administered by 2× Tablet D and 26 patients on placebo ("placebo")) in each stratum. The study enrolled 105 patients (53% women, 77% Caucasian, mean age 61 years). Mean baseline LDL-C for all patients was approximately 134 mg/dL (3.48 mmol/L) with most patients in the high-intensity statin stratum on atorvastatin and most patients in the moderate-intensity stratum on either simvastatin or atorvastatin.

The aim of this study was to characterize gemcabene calcium salt hydrate Crystal Form 1's safety and tolerability and to determine gemcabene calcium salt hydrate Crystal Form 1's additive impact to statins on serum biomarker including atherogenic biomarkers (LDL-C, non-HDL-C, ApoB, ApoE, and triglyceride (TG)) and inflammatory biomarkers (hsCRP, serum amyloid A (SAA)).

Fifty patients (24 patients on 600 mg (Tablet D×2); 26 placebo) on baseline high-intensity (HI) statins received atorvastatin 40 mg or 80 mg QD; or rosuvastatin 20 mg or 40 mg QD. Fifty-five patients (29 patients on 600 mg GEM; 26 placebo) on baseline moderate-intensity (MI) statins received atorvastatin 10 mg or 20 mg QD; rosuvastatin 5 mg or 10 mg QD; or simvastatin 20 or 40 mg QD. Baseline LDL-C was 127 mg/dL and 134 mg/dL in the MI statin and HI statin stratum, respectively.

Overall, gemcabene calcium salt hydrate Form 1 was well tolerated. There were no serious adverse events (AEs) and no deaths reported in the study. 33 of 54 patients (61.1%) in the Tablet D group and 24 of 51 patients (47.1%) in the placebo group who reported at least one AE during the study. The most prevalent AEs were those associated with infections. Reported AEs were similar for the MI and HI statin stratums. There was no difference in myalgias between placebo and Tablet D patient groups. There were no transaminase elevations >3×ULN and no clinically significant CK elevations.

38% of HI statin patients receiving gemcabene were on highest doses of atorvastatin or rosuvastatin and 62% of MI statin patients receiving gemcabene were on highest atorvastatin, rosuvastatin or simvastatin dose for this stratum. Patient demographics are as shown in Table 30 and patient's baseline plasma lipid values are as shown in Table 31. The patient's baseline lipid values can be obtained in plasma or blood serum.

TABLE 30

| Patient demographics | | | |
|---|---|---|---|
| Characteristic | Tablet D × 2 N = 53 | Placebo N = 52 | Total N = 105 |
| Age | 62.7 | 59.0 | 60.8 |
| Female n (%) | 29 (55%) | 27 (52%) | 56 (53%) |
| BMI (kg/m2) | 30.2 | 31.0 | 30.6 |
| Moderate Intensity Statin Stratum n (%) | 29 (55%) | 26 (50%) | 55 (52%) |
| High Intensity Statin Stratum n (%) | 24 (45%) | 26 (50%) | 50 (48%) |
| Mixed Dyslipidemia TGs ≥200 mg/dL | 10 (19%) | 8 (15%) | 18 (17%) |

TABLE 31

| Patient Plasma Baseline Characteristics | | | | |
|---|---|---|---|---|
| Baseline Lipid Values | Tablet D × 2 N = 53 | Placebo N = 52 | Total N = 105 | Mixed Dyslipidemia N = 18 |
| LDL-C (mg/dL) | 134 | 126 | 130 | 146 |
| Non-HDL-C (mg/dL) | 162 | 154 | 158 | 193 |
| TC-C (mg/dL) | 217 | 206 | 211 | 238 |
| TG(mg/dL)* | 142 | 139 | 140 | 247 |
| VLDL-C (mg/dL) | 28 | 28 | 28 | 47 |
| HDL-C (mg/dL) | 55 | 52 | 53 | 46 |
| ApoB (mg/dL) | 108 | 100 | 104 | 127 |
| ApoE (mg/dL) | 4.3 | 4.2 | 4.3 | 4.6 |
| hsCRP(mg/L) | 1.5 | 1.7 | 1.7 | 3.9 |
| SAA(mg/L) | 5.1 | 5.8 | 5.8 | 6.5 |

*87 (83%) of subjects had baseline TGs <200 mg/dL. In prior studies, gemcabene was shown to significantly impact TG levels when above 200 mg/dL.

Figure 46:
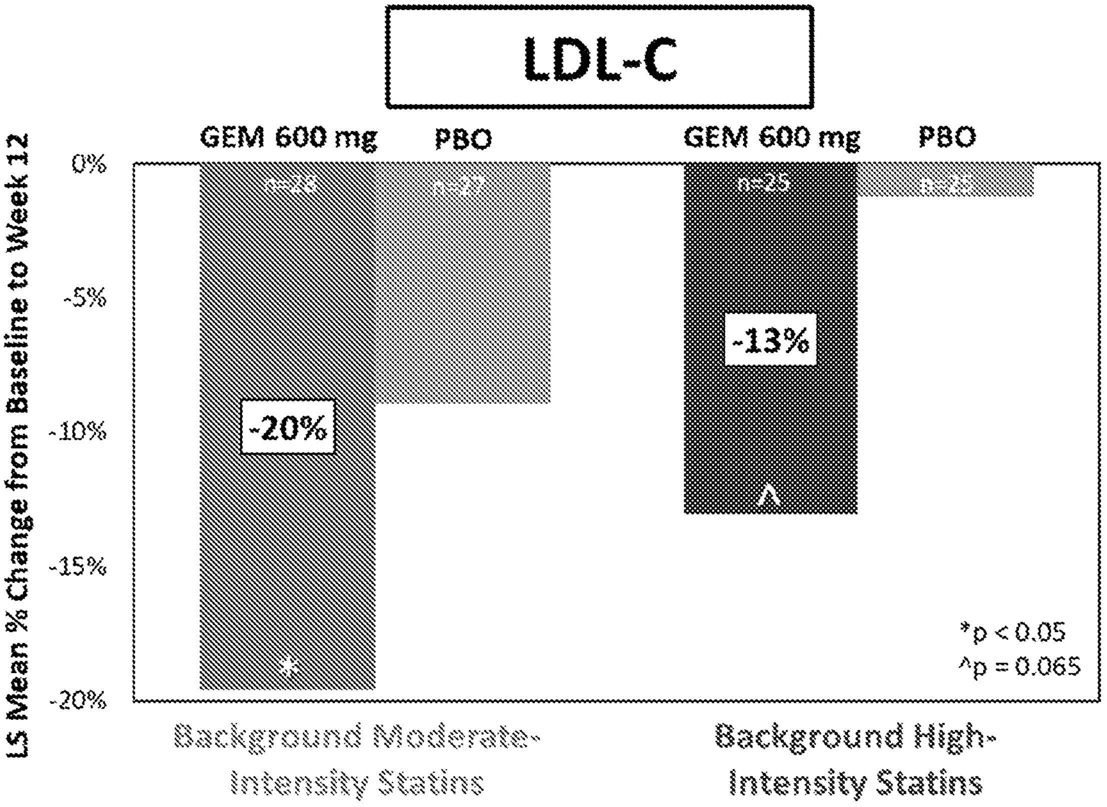
FIG. 46 shows least square (LS) mean % change in atherogenic biomarkers from baseline in hypercholesterolemia subjects on stable moderate and high intensity statins receiving gemcabene calcium salt hydrate Crystal Form 1 (PSD90=52 μm).
Figure 47:
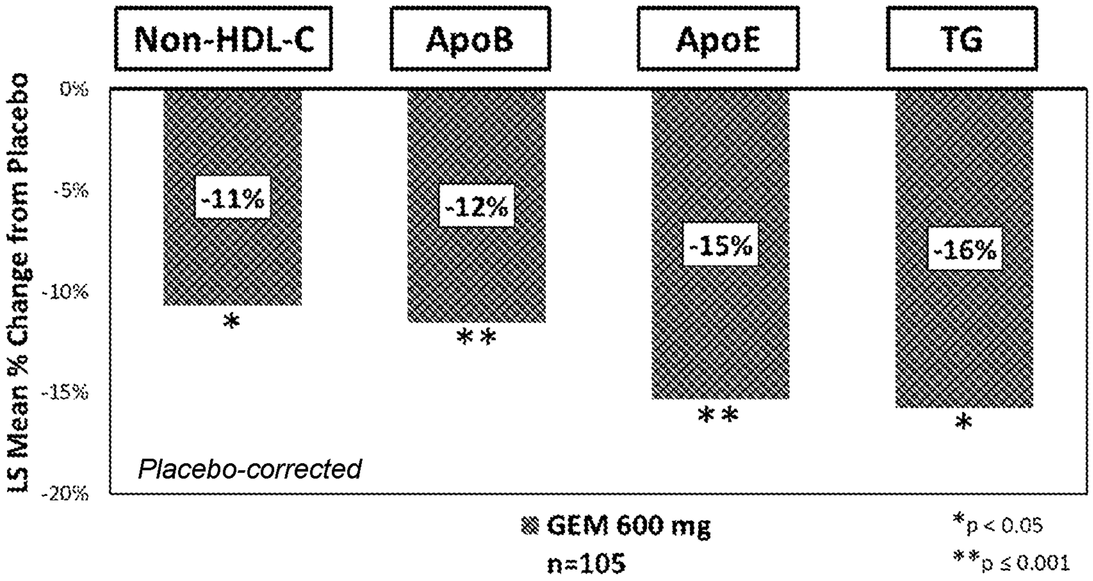
FIG. 47 shows least square (LS) mean % change in atherogenic biomarkers from placebo in hypercholesterolemia subjects on stable moderate and high intensity statins receiving gemcabene calcium salt hydrate Crystal Form 1 (PSD90=52 μm).
Figure 49:
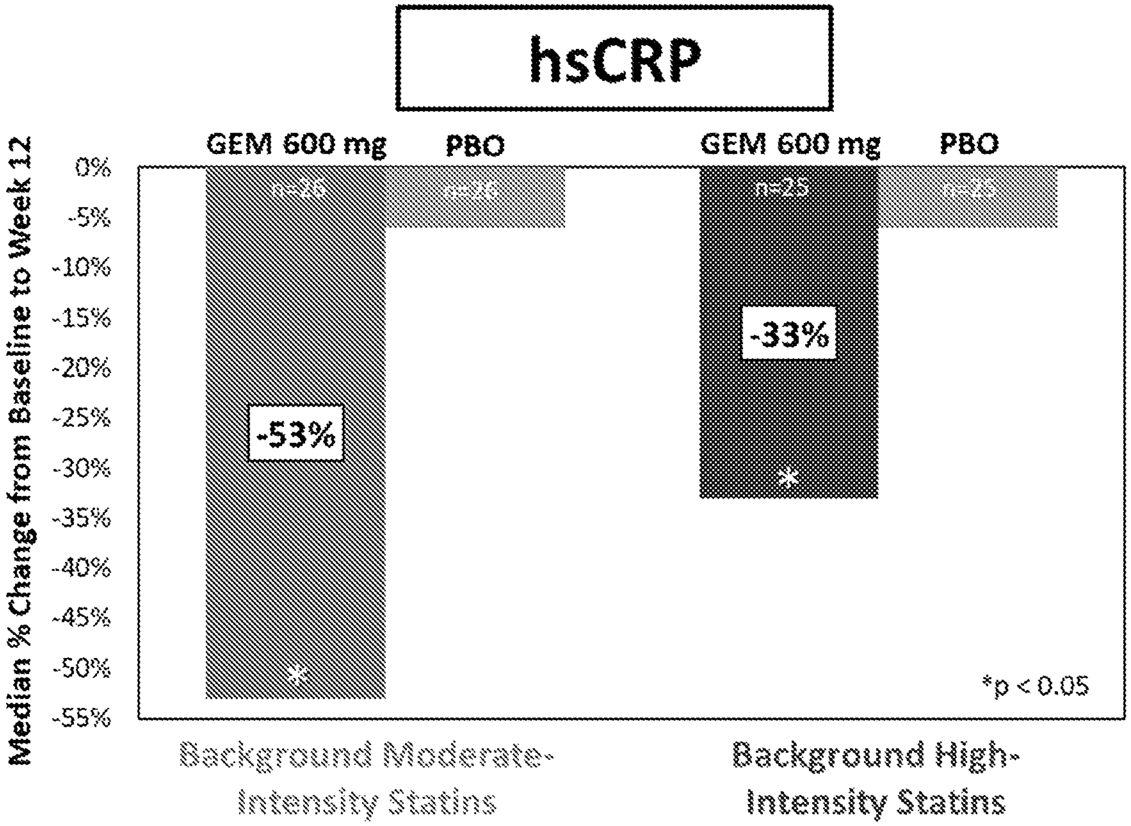
FIG. 49 shows least square (LS) mean % change in inflammatory markers from baseline in hypercholesterolemia subjects on stable moderate and high intensity statins receiving gemcabene calcium salt hydrate Crystal Form 1 (PSD90=52 μm).
Figure 50:
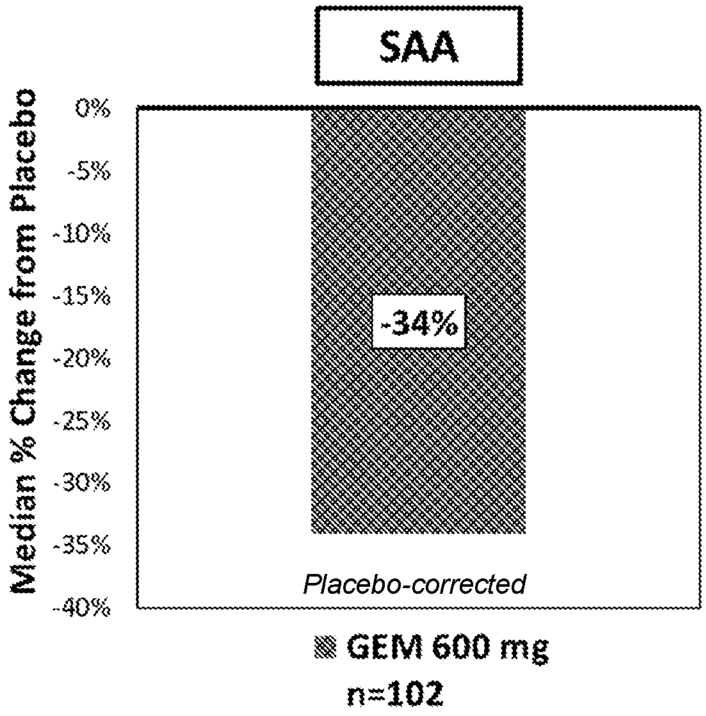
FIG. 50 shows least square (LS) mean % change in an inflammatory marker from placebo in hypercholesterolemia subjects on stable moderate and high intensity statins receiving gemcabene calcium salt hydrate Crystal Form 1 (PSD90=52 μm).
Figure 51:
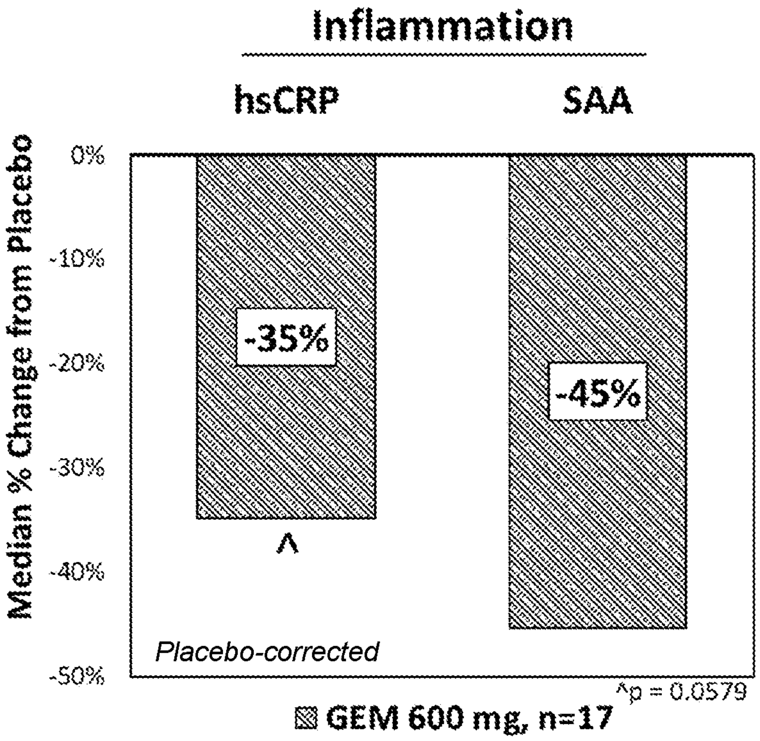
FIG. 51 shows least square (LS) mean % change in inflammatory markers from placebo in mixed dyslipidemia subjects (LDL-C≥100 mg/dL and triglycerides ≥200 and <500 mg/dL) on stable moderate and high intensity statins receiving gemcabene calcium salt hydrate Crystal Form 1 (PSD90=52 μm).

The administration of gemcabene calcium salt hydrate Crystal Form 1 (Tablet D×2) demonstrated to impact multiple atherogenic biomarkers (FIGS. 46 and 47) and inflammatory markers (FIGS. 49 and 50).

Figure 48:
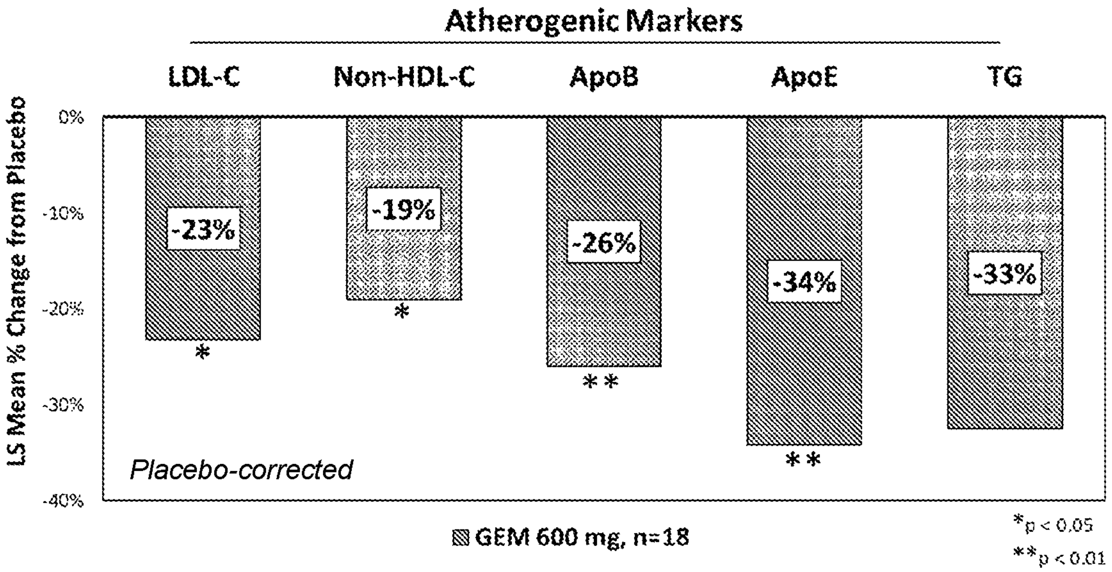
FIG. 48 shows least square (LS) mean % change in atherogenic biomarkers from placebo in mixed dyslipidemia subjects (LDL-C≥100 mg/dL and triglycerides≥200 and <500 mg/dL) on stable moderate and high intensity statins receiving gemcabene calcium salt hydrate Crystal Form 1 (PSD90=52 μm).

Within the study population, an analysis was performed in a subpopulation of patients having mixed dyslipidemia (LDL-C≥100 mg/dL and triglycerides ≥200 and <500 mg/dL). Eighteen patients (10 (Tablet D×2) patients and 8 placebo patients) having a baseline mean LDL-C level of 142 mg/dL, baseline mean triglyceride level of 247 mg/dL and BMI of 34 kg/$m^2$ were analyzed (FIG. 48). Although not measured in the subpopulation of this Example, some cardiometabolic patients could have elevated sulphatase-2 (Sulf-2) levels, which are believed to cause reduced Syndecan-1 (also known as "remnant receptor")-mediated clearance of atherogenic remnant lipoproteins. Without being bound by theory, the data shown in FIG. 48 support the inventors' belief that administration of Tablet D, which comprises a compound of the invention, rescues remnant receptor activity.

This study was designed to largely address the safety of gemcabene calcium salt hydrate Crystal Form 1 in patients on the highest doses of statins. In patients with hypercholesterolemia, despite being on MI and HI statins, gemcabene calcium salt hydrate Crystal Form 1 produced significant reductions in both atherogenic and inflammatory markers (FIGS. 46, 47, 49, and 50) without evidence of increased muscle or liver toxicities.

An integrated analysis of gemcabene calcium salt hydrate Crystal Form 1 efficacy, inclusive of all background therapies, from completed clinical studies, showed a mean LDL-C reduction of about 21%. Gemcabene calcium salt hydrate Crystal Form 1 given on top of steady-state statins has shown a statin-intensity dependent effect. Without bound to any theory, the statin-intensity dependent effect is related to three factors related to mechanism of action of pharmaceutically acceptable salts of gemcabene: 1) pharmaceutically acceptable salt of gemcabene enhances the clearance of VLDL remnants leading to reduced intravascular LDL-C formation; 2) reduction of intravascular LDL-C production would allow basal LDL receptor levels to more effectively remove an existing smaller LDL-C pool; and 3) pharmaceutically acceptable salts of gemcabene blocks hepatic cholesterol and triglyceride synthesis, likely reducing hepatic VLDL production. Statins inhibit cholesterol synthesis and upregulate LDL receptor expression to effect LDL-C reduction. The more potent the statin, the greater the effect on these processes.

Without bound to any theory, it is believed that the smaller percent reduction of LDL-C lowering when statin intensity increases may be due to a lesser effect that pharmaceutically acceptable salt of gemcabene can have on reducing hepatic cholesterol production. Low-intensity statins have not optimized the effects on hepatic cholesterol synthesis and LDL receptor expression, and therefore, pharmaceutically acceptable salt of gemcabene shows greater LDL-C lowering by enhancing the clearance of atherogenic precursors via the remnant receptor as well as adding additional inhibition of hepatic cholesterol synthesis. At the highest statin levels, as in this example, cholesterol synthesis is already markedly inhibited, thus, without bound to any theory, the LDL receptor is highly expressed and pharmaceutically acceptable salt of gemcabene would have limited additional hepatic cholesterol synthesis effects but would still maintain the ability to reduce intravascular LDL-C production.

This study supports that other atherogenic lipoproteins beyond LDL-C can impact the residual cardiovascular (CV) risk of patients and that lowering of ApoB and non-HDL-C can be better correlate to improving CV outcomes. A recent Mendelian randomization analysis suggested that the clinical benefit of lowering LDL-C may be related to the reduction in ApoB-containing lipoprotein particles (Ference et al. JAMA 2017; 318 (10) 947-956). Consistent with the mechanism of action of pharmaceutically acceptable salt of gemcabene, patients with mixed dyslipidemia showed greater reductions in LDL-C, non-HDL-C, ApoB, ApoE and TG of 23%, 19%, 26%, 34% and 33%, respectively (FIG. 48).

The CANTOS study (Novartis) reported that canakinumab, when added to statins, further decreases hsCRP, without modulating LDL-C or other lipids which provides proof-of-concept for CV risk reduction by reducing inflammation. Thus, agents such as pharmaceutically acceptable salts of gemcabene, that reduce both atherogenic lipoproteins and hsCRP, without bound to any theory, can have a greater CV risk benefit than seen by lipid reduction alone.

In summary, gemcabene calcium salt hydrate Crystal Form 1 as an add-on therapy to the highest doses of background statins was well-tolerated and showed LDL-C reduction. No evidence of muscle or liver related toxicities were observed. Decreased atherogenic burden with mirrored lowering in non-HDL-C, apoB and apoE was observed. Decreased inflammation was observed with decreased serum hsCRP. Greater effects of gemcabene calcium salt hydrate Crystal Form 1 were observed in a cardiometabolic population, patients with mixed dyslipidemia, who have a particularly high atherogenic particle burden. Further, the safety, tolerability and efficacy on both atherogenic lipoproteins and hsCRP were supportive of continued clinical development.

What is claimed is:

1. A pharmaceutically acceptable salt of gemcabene, the pharmaceutically acceptable salt having a PSD90 ranging from 40 μm to about 75 μm as measured by laser light diffraction and providing a plasma gemcabene $AUC_{(0-24)}$ ranging from about 200 μg·hr/mL at steady state to about 6000 μg·hr/mL at steady state when administered to a human subject at a dose of about 50 mg to about 900 mg.

2. The pharmaceutically acceptable salt of claim 1, wherein the pharmaceutically acceptable salt has a dissolution profile characterized by a % dissolution value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm.

3. The pharmaceutically acceptable salt of claim 1, wherein the pharmaceutically acceptable salt is a calcium salt.

4. A pharmaceutically acceptable salt of gemcabene, the pharmaceutically acceptable salt having a PSD90 ranging from 40 μm to about 75 μm as measured by laser light diffraction and providing a plasma gemcabene $AUC_{last}$ ranging from about 50 μg·hr/mL to about 7500 μg·hr/mL after a single dose administration of about 50 mg to about 900 mg to a human subject.

5. The pharmaceutically acceptable salt of claim 4, wherein the pharmaceutically acceptable salt has a dissolution profile characterized by a % dissolution value of (1) at least 80% in pH 5.0 potassium acetate buffer at 37° C.±5° C. in no more than 45 minutes as measured by high-performance liquid chromatography using a detection wavelength of 210 nm or (2) at least 70% in pH 5.0 potassium acetate buffer at 37° C.±5° C. in no more than 30 minutes as measured by high-performance liquid chromatography using a detection wavelength of 210 nm.

6. The pharmaceutically acceptable salt of claim 4, wherein the pharmaceutically acceptable salt is a calcium salt.

7. A composition comprising an effective amount of the pharmaceutically acceptable salt of claim 1 and a pharmaceutically acceptable carrier or vehicle.

8. A composition comprising an effective amount of the pharmaceutically acceptable salt of claim 4 and a pharmaceutically acceptable carrier or vehicle.

* * * * *